US007217572B2

(12) United States Patent
Ward et al.

(10) Patent No.: US 7,217,572 B2
(45) Date of Patent: May 15, 2007

(54) MODULATION OF HIF1α AND HIF2α EXPRESSION

(75) Inventors: Donna T. Ward, Murrieta, CA (US); Kenneth W. Dobie, Del Mar, CA (US); Eric G. Marcusson, San Diego, CA (US); Susan M. Freier, San Diego, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 379 days.

(21) Appl. No.: 10/719,370

(22) Filed: Nov. 21, 2003

(65) Prior Publication Data

US 2004/0220393 A1 Nov. 4, 2004

Related U.S. Application Data

(63) Continuation-in-part of application No. 10/304,126, filed on Nov. 23, 2002, now Pat. No. 7,144,999.

(51) Int. Cl.

*C12N 15/58* (2006.01)
*C12Q 1/68* (2006.01)
*C12P 19/34* (2006.01)
*C07H 21/02* (2006.01)
*C07H 21/04* (2006.01)

(52) U.S. Cl. ........................ 435/458; 435/6; 435/91.1; 435/91.31; 435/455; 536/23.1; 536/24.5

(58) Field of Classification Search .................... 435/6, 435/91.1, 91.31, 455, 458, 375; 536/23.1, 536/24.5; 514/44

See application file for complete search history.

(56) References Cited

U.S. PATENT DOCUMENTS

| | | | | |
|---|---|---|---|---|
| 5,695,963 | A | 12/1997 | McKnight et al. | 435/69.1 |
| 5,882,914 | A | 3/1999 | Semenza | 435/252.3 |
| 6,133,246 | A | 10/2000 | McKay et al. | |
| 6,395,548 | B1 | 5/2002 | Lee et al. | 435/455 |
| 6,432,927 | B1 | 8/2002 | Gregory et al. | 514/44 |
| 6,958,240 | B1 * | 10/2005 | Baird et al. | 435/375 |
| 2003/0045686 | A1 | 3/2003 | Kaelin, Jr. et al. | 530/350 |
| 2004/0086498 | A9 | 5/2004 | Krissansen et al. | |
| 2004/0152655 | A1 | 8/2004 | Yoon et al. | 514/44 |
| 2004/0180357 | A1 | 9/2004 | Reich et al. | |
| 2005/0070474 | A1 | 3/2005 | Krissansen et al. | |
| 2005/0148496 | A1 | 7/2005 | Defranoux et al. | |
| 2005/0163781 | A1 | 7/2005 | Koninckx et al. | |

FOREIGN PATENT DOCUMENTS

| | | | |
|---|---|---|---|
| EP | 0147819 | * | 7/1985 |
| WO | WO 99/48916 | | 9/1999 |
| WO | WO 00/09657 | | 2/2000 |
| WO | WO 01/62965 | A2 | 8/2001 |
| WO | WO 02/34291 | A2 | 5/2002 |
| WO | WO 02/068466 | A2 | 9/2002 |
| WO | WO 02/086497 | A2 | 10/2002 |
| WO | WO 02/094862 | A2 | 11/2002 |
| WO | WO 03/040366 | | 5/2003 |
| WO | WO 03/085110 | A2 | 10/2003 |
| WO | WO 2005/035759 | * | 4/2005 |

OTHER PUBLICATIONS

Chirila, T.V. et al., Biomaterials, vol. 23, pp. 321-342 (2002).*
Crooke, S.T., Antisense Research & Application, Chapter 1, pp. 1-50, Ed. by S.T. Crooke, Publi. by Springer-Verlag (1998).*
Agrawal, S. et al., Molecular Med. Today, vol. 6, pp. 72-81 (2000).*
Peracchi, A., Rev. Med. virol., vol. 14, pp. 47-64 (2004).*
Branch, A.D., Trends in Biochem. Sci., vol. 23, pates 45-50 (1998).*
Opalinska, J.B. et al., Nature Rev., vol. 1, pp. 503-514 (2002).*
Andrew, A.S. et al., "Nickel requires hypoxia-inducible factor-1α, not redox signaling, to induce plasminogen activator inhibitor-1" *Am. J. Physiol. Lung Cell Mol. Physiol.*, 2001, 281, L607-L615.
Caniggia, I. et al., "Hypoxia-inducible factor-1 mediates the biological effects of oxygen on human trophoblast differentiation through TGF$\beta_3$," *J. Clin. Investigation*, 2000, 105(5), 577-587.
Caniggia, I. et al., "Oxygen and Placental Development During the First Trimester: Implications for the Pathophysiology of Pre-eclampsia," *Placenta*, 2000, 21 Suppl. A, 14, S25-S30.
Drutel, G. et al., "Two splice variants of the hypoxia-inducible factor HIF-1α as potential dimerization partners of ARNT2 in neurons," *European N. Neurosc.*, 2000, 12, 3701-3708.
Furuta, G.T. et al., "Hypoxia-inducible Factor 1-dependent Induction of Intestinal Trefoil Factor Protects Barrier Function during Hypoxia," *J. Exp. Med.*, 2001, 193(9), 1027-1034.
Huang, L.E., et al., "Regulation of hypoxia-inducible factor 1α is mediated by an $O_2$-dependent degradation domain via the ubiquitin-proteasome pathway," *Proc. Natl. Acad. Sci. USA*, 1998, 95, 7987-7992.
Iyer, N.V. et al., "Cellular and developmental control of $O_2$ homeostasis by hypoxia-inducible factor 1α," *Genes & Development*, 1998, 12, 149-162.
Kakinuma, Y. et al., "Novel Molecular Mechanism of Increased Myocardial Endothelin-1 Expression in the Failing Heart Involving the Transcriptional Factor Hypoxia-Inducible Factor-1α Induced for Impaired Myocardial Energy Metabolism," *Circulation*, 2001, 103, 2387-2394.
Maxwell et al., "Insights into the role of the von Hippel-Lindau gene product. A key player in hypoxic regulation," *Exp. Nephrol.*, 2001, 9, 235-240.
Minchenko, A. et al., "Hypoxia-inducible factor-1 (HIF-1) mediated expression of the 6-phosphofructo-2-kinase/fructose-2,6-bisphosphatase-3 (PFKBF3) gene: its possible role in the Warburg effect," *J. Biol. Chem.*, 2001, 14, 21 pages.

(Continued)

*Primary Examiner*—Jane Zara
(74) *Attorney, Agent, or Firm*—Isis Pharmaceuticals, Inc. Patent Department; Knobbe, Martens, Olson and Bear, LLP

(57) ABSTRACT

Compounds, compositions and methods are provided for modulating the expression of HIF1α and/or HIF2α. The compositions comprise oligonucleotides, targeted to nucleic acid encoding HIF1α and HIF2α. Methods of using these compounds for modulation of HIF1α and/or HIF2α expression and for diagnosis and treatment of disease associated with expression of HIF1α and/or HIF2α are provided.

18 Claims, No Drawings

OTHER PUBLICATIONS

Narravula, S. et al., "Hypoxia-Inducible Factor 1-Mediated Inhibition of Peroxisome Proliferator-Activated Receptor α Expression During Hypoxia," *J. Immunol.*, 2001, 166, 7543-7548.

Ravi, R. et al., "Regulation of tumor angiogenesis by p53-induced degradation of hypoxia-inducible factor 1α," *Genes & Development*, 2000, 14, 43-44.

Ryan, H.E. et al., "HIF-1α is required for solid tumor formation and embryonic vascularization," *EMBO J.*, 1998, 17(11), 3005-3015.

Semenza, G.L., "HIF-1 and human disease: one highly involved factor," *Genes & Development*, 2000, 14, 1983-1991.

Semenza, G.L., "Hypoxia-Inducible Factor 1: Control of Oxygen Homeostasis in Health and Disease," *Pediatr. Res.*, 2001, 49(5), 614-617.

Sun, X. et al., "Gene transfer of antisense hypoxia inducible factor-1 α enhances the therapeutic efficacy of cancer immunotherapy," *Gene Therapy*, 2001, 8, 638-645.

Sutter, C.H. et al., "Hypoxia-inducible factor 1α protein expression is controlled by oxygen-regulated ubiquitination that is disrupted by deletions and missense mutations," *Proc. Natl. Acad. Sci. USA*, 2000, 97(9), 4748-4753.

Thrash-Bingham, C.A. et al., "aHIF: a Natural Antisense Transcript Overexpressed in Human Renal Cancer and During Hypoxia," *J. Natl. Cancer Inst.*, 1999, 91(2), 143-151.

Wang, G.L. et al., "Hypoxia-inducible factor 1 is a basic-helix-loop-helix-PAS heterodimer regulated by cellular $O_2$ tension," *Proc. Natl. Acad. Sci. USA*, 1995, 92, 5510-5514.

Wang, G.L. et al., "Purification and Characterization of Hypoxia-inducible Factor 1," *J. Biol. Chem.*, 1995, 270(3), 1230-1237.

Yu, A.Y. et al., "Impaired physiological responses to chronic hypoxia in mice partially deficient for hypoxia-inducible factor 1α," *J. Clin. Investigation*, 1999, 103(5), 691-696.

Zagzag, D. et al., "Expression of Hypoxia-Inducible Factor 1α in Brain Tumors," *Cancer*, 2000, 88(11), 2606-2618.

Cockman, M.E. et al., "Hypoxia Inducible Factor-α Binding and Ubiquitylation by the von Hippel-Lindau Tumor Suppressor Protein," *J. Biol. Chem.*, 2000, 275(33), 25733-25741.

Conrad, P.W. et al., "The molecular basis of $O_2$-sensing and hypoxia tolerance in pheochromocytoma cells," *Comparative Biochem. Physiol.*, 2001, Part B, 128, 187-204.

Conrad, W.P. et al., "EPAS1 *trans*-Activation during Hypoxia Requires p42/p44 MAPK," *J. Biol. Chem.*, 1999, 274(47), 33709-33713.

Ema, M. et al., "A novel bHLH-PAS factor with close sequence similarity to hypoxia-inducible factor 1α regulates the *VEGF* expression and is potentially involved in lung and vascular development," *Proc. Natl. Acad. Sci. USA*, 1997, 94, 4273-4278.

Favier, J. et al., "Angiogenesis and Vascular Architecture in Pheochromocytomas," *Am. J. Pathology*, 2002, 161(4), 1235-1246.

Flamme, I. et al., "Up-Regulation of Vascular Endothelial Growth Factor in Stromal Cells of Hemangioblastomas is Correlated with Up-Regulation of the Transcription Factor HRF/HIF-2α," *Am. J. Pathology*, 1998, 153(1), 25-29.

Flamme, I. et al., "HRF, a putative basic helix-loop-helix-PAS-domain transcription factor is closely related to hypoxia-inducible factor-1α and developmentally expressed in blood vessels," *Mechan. Develop.*, 1997, 63, 51-60.

Giatromanolaki, A. et al., "Relation of hypoxia inducible factor 1α and 2α in operable non-small cell lung cancer to angiogenic/molecular profile of tumours and survival," *British J. Cancer*, 2001, 85(6), 881-890.

Giatromanolaki, A. et al., "Hypoxia inducible factor 1α and 2α overexpression in inflammatory bowel disease," *J. Clin. Pathol.*, 2003, 56, 209-213.

Harris, A.L., "Hypoxia—A Key Regulatory Factor in Tumour Growth," *Nature Reviews*, 2002, 2, 38-47.

Hirsila, M. et al., "Characterization of the Human Prolyl 4-Hydroxylases That Modify the Hypoxia-inducible Factor," *J. Biol. Chem.*, 2003, 278(33), 30772-30780.

Hogenesch, J.B. et al., "Characterization of s Subset of the Basic-Helix-Loop-Helix-PAS Superfamily That Interacts with Components of the Dioxin Signaling Pathway," *J. Biol. Chem.*, 1997, 272(13), 8581-8593.

Koukourakis, M.I. et al., "Hypoxia-Inducible Factor (HIF1A and HIF2A), Angiogenesis, and Chemoradiotherapy Outcome of Squamous Cell Head-and-Neck Cancer," *Int. J. Radiation Oncology Biol. Phys.*, 2002, 53(5), 1192-1202.

Leek, R.D. et al., "Relation of Hypoxia-inducible Factor-2α (HIF-2α) Expression in Tumor-infiltrative Macrophages to Tumor Angiogenesis and the Oxidative Thymidine Phosphorylase Pathway in Human Breast Cancer," *Cancer Res.*, 2002, 62, 1326-1329.

Liang, Y et al., "Activation of Vascular Endothelial Growth Factor A Transcription in Tumorigenic Glioblastoma Cell Lines by an Enhancer with Cell Type-specific DNase I Accessibility," *J. Biol. Chem.*, 2002, 277(22), 20087-20094.

Liu, M.Y., "Up-Regulation of Hypoxia-inducible Factor 2α in Renal Cell Carcinoma Associated with Loss of Tsc-2 Tumor Suppressor Gene," *Cancer Res.*, 2003, 63, 2675-2680.

Maemura, K. et al., "Generation of a Dominant-negative Mutant of Endothelial PAS Domain Protein 1 by Deletion of a Potent C-terminal Transactivation Domain," *J. Biol. Chem.*, 1999, 274(44), 31565-31570.

Maxwell, P.H., "Activation of the HIF pathway in cancer," *Curr. Opin. Genetics & Develop.*, 2001, 11, 293-299.

Maxwell, P.H., "The tumour suppressor protein VHL targets hypoxia-inducible factors for oxygen-dependent proteolysis," *Nature*, 1999, 399, 271-275.

Ohh, M. et al., "Ubiquitination of hypoxia-inducible factor requires direct binding to the β-domain of the von Hippel-Lindau protein," *Nature Cell Biology*, 2000, 2, 423-427.

Pugh, C.W. et al., "The von Hippel-Lindau tumor suppressor, hypoxia-inducible factor-1 (HIF-1) degradation, and cancer pathogenesis," *Seminars in Cancer Biol.*, 2003, 13, 83-89.

Rajakumar, A. et al., "Expression, Ontogeny, and Regulation of Hypoxia-Inducible Transcription Factors in the Human Placenta," *Biol. Reproduction*, 2000, 63, 559-569.

Rajakumar, A. et al., "Selective Overexpression of the Hypoxia-Inducible Transcription Factor, HIF-2α, in Placentas from Women with Preeclampsia," *Biol. Reproduction*, 2001, 64, 499-506.

Safran, M. et al., "HIF hydroxylation and the mammalian oxygen-sensing pathway," *J. Clin. Investigation*, 2003, 111(6), 779-783.

Sato, M. et al., "Inducible Expression of Endothelial PAS Domain Protein-1 by Hypoxia in Human Lung Adenocarcinoma A549 Cells: Role of Src Family Kinases-dependent Pathway," *Am. J. Respir. Cell Miol. Biol.*, 2002, 26, 127-134.

Semenza, G.L., "Hypoxia-inducible factor 1: oxygen homeostasis and disease pathophysiology," *Trends in Mol. Med.*, 2001, 7(8), 345-350.

Sowter, H.M. et al., "Predominant Role of Hypoxia-Inducible Transcription Factor (Hif)-1α versus Hif-2α in Regulation of the Transcriptional Response to Hypoxia," *Cancer Res*, 2003, 63, 6130-6134.

Talks, K.L. et al., "The Expression and Distribution of the Hypoxia-Inducible Factors HIF-1α and HIF-2α in Normal Human Tissues, Cancers, and Tumor-Associated Macrophages," *Am. J. Pathology*, 2000, 157(2), 411-421.

Tanaka, T. et al., "Endothelial PAS Domain Protein 1 (EPAS1) Induces Adrenomedullin Gene Expression in Cardiac Myocytes: Role of EPAS1 in an Inflammatory Response in Cardiac Myocytes," *J. Mol. Cell Cardiol.*, 2002, 34, 739-748.

Tian, H. et al., "Endothelial PAS domain protein 1 (EPAS1), a transcription factor selectively expressed in endothelial cells," *Genes & Development*, 1997, 11, 72-82.

Tian, H. et al., "The hypoxia-responsive transcription factor EPAS1 is essential for catecholamine homeostasis and protection against heart failure during embryonic development," *Genes & Development*, 1998, 12, 3320-3324.

Wiesener, M.S. et al., "Induction of Endothelial PAS Domain Protein-1 by Hypoxia: Characterization and Comparison with Hypoxia-Inducible Factor-1α," *Blood*, 1998, 92(7), 2260-2268.

Xia, G. et al., "Regulation of Vascular Endotelial Growth Factor Transcription by Endothelial PAS Domain Protein 1 (EPAS1) and Possible Involvement of EPAS1 in the Angiogenesis of Renal Cell Carcinoma," *Cancer*, 2001, 91(8), 1429-1436.
Xia, G. et al., "Positive Expression of HIF-2α/EPAS1 in Invasive Bladder Cancer," *Urology*, 2002, 5, 774-778.
Kang L. et al. "An antisense oligonucleotide that inhibits the expression of hypoxia-induced factor-1alpha alters hypoxia-induced changes in proliferation and viability of human cardiac fibroblasts" Circulation, American Heart Association, vol. 104, Oct. 23, 2001.
Comerford, K. M. et al. "Hypoxia-inducible factor-1-dependent regulation of the multidrug resistance (MDR1) gene" Cancer Research, vol. 62, Jun. 15, 2002.
Synnestvedt, K. et al. "Ecto-5-nucleotide (CD73) regulation by hypoxia-inducible factor-1 mediates permeability changes in intestinal epithelia" Journal of Clinical Investigtion, vol. 110, Oct. 1, 2002.

* cited by examiner

SEQUENCE LISTING

```
<160> NUMBER OF SEQ ID NOS: 458

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(3)
<223> OTHER INFORMATION: 2'-O-methoxyethyl with phosphorothioate
      backbone
<220> FEATURE:
<221> NAME/KEY: misc_feature
<222> LOCATION: (13)..(20)
<223> OTHER INFORMATION: 2'-O-methoxyethyl with phosphorothioate
      backbone

<400> SEQUENCE: 1

tccgtcatcg ctcctcaggg                                          20


<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(5)
<223> OTHER INFORMATION: 2'-O-methoxyethyl with phosphorothioate
      backbone
<220> FEATURE:
<221> NAME/KEY: misc_feature
<222> LOCATION: (16)..(20)
<223> OTHER INFORMATION: 2'-O-methoxyethyl with phosphorothioate
      backbone

<400> SEQUENCE: 2

gtgcgcgcga gcccgaaatc                                          20
```

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(5)
<223> OTHER INFORMATION: 2'-O-methoxyethyl with phosphorioate backbone
<220> FEATURE:
<221> NAME/KEY: misc_feature
<222> LOCATION: (16)..(20)
<223> OTHER INFORMATION: 2'-O-methoxyethyl with phosphorioate backbone

<400> SEQUENCE: 3
atgcattctg cccccaagga                                             20

<210> SEQ ID NO 4
<211> LENGTH: 3933
<212> TYPE: DNA
<213> ORGANISM: Homo sapiens
<220> FEATURE:
<221> NAME/KEY: misc_feature
<222> LOCATION: (265)..(2745)
<223> OTHER INFORMATION: CDS
<300> PUBLICATION INFORMATION:
<301> AUTHORS: Hogenesch et al.
<302> TITLE: Characterization of a subset of the basic-helix-loop-helix-PAS superfamily that interacts with components of the dioxin signaling pathway
<303> JOURNAL: J. Biol. Chem
<304> VOLUME: 272
<305> ISSUE: 13
<306> PAGES: 8581-8593
<307> DATE: 1997
<308> DATABASE ACCESSION NUMBER: U29165.1
<309> DATABASE ENTRY DATE: 1997-04-11
<313> RELEVANT RESIDUES: (1)..(3933)

<400> SEQUENCE: 4
cacgaggcag cactctcttc gtcgcttcgg ccagtgtgtc gggctgggcc ctgacaagcc    60
acctgaggag aggctcggag ccgggcccgg accccggcga ttgccgcccg cttctctcta   120
gtctcacgag gggtttcccg cctcgcaccc ccacctctgg acttgccttt ccttctcttc   180
tccgcgtgtg gagggagcca gcgcttaggc cggagcgagc ctgggggccg cccgccgtga   240
agacatcgcg gggaccgatt caccatggag ggcgccggcg gcgcgaacga caagaaaaag   300
ataagttctg aacgtcgaaa agaaaagtct cgagatgcag ccagatctcg gcgaagtaaa   360
gaatctgaag ttttttatga gcttgctcat cagttgccac ttccacataa tgtgagttcg   420
catcttgata aggcctctgt gatgaggctt accatcagct atttgcgtgt gaggaaactt   480
ctggatgctg gtgatttgga tattgaagat gacatgaaag cacagatgaa ttgcttttat   540
ttgaaagcct tggatggttt tgttatggtt ctcacagatg atggtgacat gatttacatt   600
tctgataatg tgaacaaata catgggatta actcagtttg aactaactgg acacagtgtg   660
tttgatttta ctcatccatg tgaccatgag gaaatgagag aaatgcttac acacagaaat   720
ggccttgtga aaaagggtaa agaacaaaac acacagcgaa gcttttttct cagaatgaag   780
tgtaccctaa ctagccgagg aagaactatg aacataaagt ctgcaacatg gaaggtattg   840
cactgcacag gccacattca cgtatatgat accaacagta accaacctca gtgtgggtat   900
aagaaaccac ctatgacctg cttggtgctg atttgtgaac ccattcctca cccatcaaat   960
attgaaattc ctttagatag caagactttc ctcagtcgac acagcctgga tatgaaattt  1020

-continued

```
tcttattgtg atgaaagaat taccgaattg atgggatatg agccagaaga acttttaggc   1080
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtg ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgtttttat gtggatagtg atatggtcaa tgaattcaag   1860
ttggaattgg tagaaaaact tttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aaatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580
ttaataccct ctgatttagc atgtagactg ctggggcaat caatggatga aagtggatta   2640
ccacagctga ccagttatga ttgtgaagtt aatgctccta tacaaggcag cagaaaccta   2700
ctgcagggtg aagaattact cagagctttg gatcaagtta actgagcttt ttcttaattt   2760
cattcctttt tttggacact ggtggctcac tacctaaagc agtctattta tattttctac   2820
atctaatttt agaagcctgg ctacaatact gcacaaactt ggttagttca atttttgatc   2880
ccctttctac ttaatttaca ttaatgctct tttttagtat gttctttaat gctggatcac   2940
agacagctca ttttctcagt tttttggtat ttaaaccatt gcattgcagt agcatcattt   3000
taaaaaatgc accttttat ttatttattt ttggctaggg agtttatccc tttttcgaat   3060
tatttttaag aagatgccaa tataattttt gtaagaaggc agtaaccttt catcatgatc   3120
ataggcagtt gaaaaatttt tacacctttt ttttcacatt ttacataaat aataatgctt   3180
tgccagcagt acgtggtagc cacaattgca caatatattt tcttaaaaaa taccagcagt   3240
tactcatgga atatattctg cgtttataaa actagttttt aagaagaaat ttttttggc   3300
ctatgaaatt gttaaacctg gaacatgaca ttgttaatca tataataatg attcttaaat   3360
```

-continued

```
gctgtatggt ttattattta aatgggtaaa gccatttaca taatatagaa agatatgcat   3420

atatctagaa ggtatgtggc atttatttgg ataaaattct caattcagag aaatcatctg   3480

atgtttctat agtcactttg ccagctcaaa agaaaacaat accctatgta gttgtggaag   3540

tttatgctaa tattgtgtaa ctgatattaa acctaaatgt tctgcctacc ctgttggtat   3600

aaagatattt tgagcagact gtaaacaaga aaaaaaaaat catgcattct tagcaaaatt   3660

gcctagtatg ttaatttgct caaaatacaa tgtttgattt tatgcacttt gtcgctatta   3720

acatcctttt tttcatgtag atttcaataa ttgagtaatt ttagaagcat tattttagga   3780

atatatagtt gtcacagtaa atatcttgtt ttttctatgt acattgtaca aatttttcat   3840

tccttttgct ctttgtggtt ggatctaaca ctaactgtat tgttttgtta catcaaataa   3900

acatcttctg tggaaaaaaa aaaaaaaaaa aaa                                 3933


<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5

ccagttacgt tccttcgatc agt                                             23


<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6

tttgaggact tgcgctttca                                                 20


<210> SEQ ID NO 7
<211> LENGTH: 28
<212> TYPE: DNA
<213> ORGANISM: Artificial Sequence
<220> FEATURE:
<223> OTHER INFORMATION: PCR Primer

<400> SEQUENCE: 7

tcaccattag aaagcagttc cgcaagcc                                        28


<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8

gaaggtgaag gtcggagtc                                                  19


<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9

gaagatggtg atgggatttc                                                 20
```

-continued

<210> SEQ ID NO 10
<211> LENGTH: 20
<212> TYPE: DNA
<213> ORGANISM: Artificial Sequence
<220> FEATURE:
<223> OTHER INFORMATION: PCR Primer

<400> SEQUENCE: 10
caagcttccc gttctcagcc 20

<210> SEQ ID NO 11
<211> LENGTH: 57500
<212> TYPE: DNA
<213> ORGANISM: Homo sapiens
<220> FEATURE:
<221> NAME/KEY: misc_feature
<222> LOCATION: (1)..(57500)
<223> OTHER INFORMATION: positions 82000 to 139500 of the sequence with GenBank Accession No. AL137129.4
<300> PUBLICATION INFORMATION:
<308> DATABASE ACCESSION NUMBER: AL137129.4
<309> DATABASE ENTRY DATE: 2001-04-30
<313> RELEVANT RESIDUES: (1)..(57500)

<400> SEQUENCE: 11
taaaatttta tcctatatga aattttcctt tttggtgtct gttatttaat aggattgttt 60
gaattagggg atactatttg gtgcctttgt aactatatga aaattagttg gttgaatatt 120
actgctttcc atgttcatat ttatatttgt atagacatat atatatatac acatatacta 180
ctttcctttc cattttcata tttatatttg tgtatacaca tatacataaa catatatttt 240
atacattttt gaaaaggaaa attaacttaa gggcatattt aatgaatatt caaaaatttt 300
tttgctgatc aaattatcat tctgctttaa acttttgaaa tgatccaaaa aaattttaaa 360
tgacttagat ttactgttac aaaatgcttg tcttttgatg tcacaaacat tatatactat 420
aatcactggc cagagataat tgctataagt ataatgaaaa gggaaatgat ggaagatctc 480
tgcagctatc ctcataaatg agggtgggaa cacgatgggc agttccaaag ttgaaaatag 540
agaatatatg tggatttata ttaacataat tggtattctt ggatagttaa aaatggctaa 600
actgtaggag aagcccgagt aattactgtt aacagaggaa taaatttgag ggcaataata 660
atgatgatag gccaggcact gtggctcatg cctgtaatcc cagcactttg ggaacccgag 720
gcgagcggac cacctgaggt caggagttcg agagcagcct ggccaacatg gtgaaacctc 780
gtctctacta aaaatagaaa aattatccga gtgtggtggt gcgtgcctgt aatcccagct 840
acttgggagg ctgaggcagg agaatcactt gtacctggga ggcggagttg cagtgagccg 900
aaatcgcgcc actgcgctcc agcctgtggg ccagagcgag actccgcctc agaataataa 960
taatgataat aataataacg ccaccaacaa tactaagagc taacatttac tgagtgctta 1020
ctatgcacca gatattgttc taagtataca tttattatct catttaacca tccataatac 1080
tgtggtatag acacttttat atccatttta taaataagta aactgagtta tggagagatt 1140
aaacgacttg ccagtaagat tcaaagcctg tgtacaagct cacgcttgat tctggagcca 1200
gtgttcttaa cacagtatct tgagaatgtt aaactaaaaa gtttttaatt tacagtattc 1260
tttccacaat taaaaaagaa attatgagta attattttta gttctttctt ctcttcaggc 1320
atttcccatg gttcttttca agacataata catatcattt agtgttgtag atctgaaaaa 1380
acaaaagtag cgtgaagatc aaaaattttc taaagagacg gagtctcgct acgttcccta 1440

-continued ggctggaaca cccaggcttc tccagcctca cacctctgag tagctggaac caccctgtcc 1500
gctaaggtca atgtttaatc gtatctttgt aggtctactg accagttaaa aagaggtgct 1560
gtatacattg gttgttgtct tgtcagagtt tgatgcttct atatagacca ttgtttttac 1620
atgctaatac aattgaaagc cactacagat atttatattt acaacccaaa gctaggtttt 1680
aacaagaaac tcataaggca aaggtgagaa gtaaaataat ttagcgccaa gtggagatat 1740
atgtgcaatg ctactttgtt gggctcaaaa catatttttc ttttagaaga ctgacaggct 1800
tgaagtttat gcctccaaag acaaaagtga ttatgttttg tttagtagct tgcaaagttg 1860
ccaaaggcca ttttttctac tctttccctg aaattggttt atatgcttat taaagtcatt 1920
tatacctatt tgcaaatgct taacatagtt tcagatttta agatttccct gcaactttat 1980
ttcccttgaa gtttacagca acaggagttc atttttattt ttaattgcat ttattcagta 2040
agtaaactcc gccacagaaa aacttagtag acaaggtgag ttcccctgtg ctccgtggca 2100
aagagtgcgg tgggtgacat tgacccatgg ttaggtaatc tggtaaggaa agaccccgtt 2160
gtaacacatc tgagcaacga gaccaaagga agggcttgct gccacgaggc gaagtctgct 2220
tttttgaaca gagagcccag cagagttggg cggcaatcgt gcccagcact gaggccgagg 2280
agaaagagag caggagcatt acattactgc accaagagta ggaaaatatg atgcatgttt 2340
gggaccaggc aaccgaaatc ccttctcagc agcgcctccc aaagccgggc accgccttcc 2400
ttcggagaag gcgcagagtc cccagactcg ggctgagccg cacccccatc tcctttctct 2460
ttcctccgcc gctaaacaca gacgagcacg tgagcgtcgc agcccgtccc agctgtgcct 2520
cagctgaccg cctcctgatt ggctgagagc ggcgtgggct ggggtgggga cttgccgcct 2580
gcgtcgctcg ccattggatc tcgaggaacc cgcctccacc tcaggtgagg cgggcttgcg 2640
ggagcgcgcg ccggcctggg caggcgagcg ggcgcgctcc cgccccctct cccctccccg 2700
cgcgcccgag cgcgcctccg cccttgcccg ccccctgacg ctgcctcagc tcctcagtgc 2760
acagtgctgc ctcgtctgag gggacaggag gatcaccctc ttcgtcgctt cggccagtgt 2820
gtcgggctgg gccctgacaa gccacctgag gagaggctcg gagccgggcc cggaccccgg 2880
cgattgccgc ccgcttctct ctagtctcac gaggggtttc ccgcctcgca cccccacctc 2940
tggacttgcc tttccttctc ttctccgcgt gtggagggag ccagcgctta ggccggagcg 3000
agcctggggg ccgcccgccg tgaagacatc gcggggaccg attcaccatg gagggcgccg 3060
gcggcgcgaa cgacaagaaa aagtaagccc attccctcgg cccgccgcct tctcccccgg 3120
cgaccccgcc cgcctgcccg ccctgggctc ctgggccggc ctcggcgtta atgggattgg 3180
gggggcagc ctttttgttt ctgctgctgc tcccctcccc tctcttcccc caacctcgcc 3240
ggccgggctc ccccgctgtc cacgtcgcca tcttgtcgtg gggggtggga gacgcctcga 3300
aagtgctttc aggggccggg gtctgagccc tgcttgccct ccccgccggc cgtgggggcc 3360
tcgcgccgcc cacctacccg cctcaaaaac ccagcctgct ctgtggcccc atccggaggg 3420
gactttaccc agcctgaaaa ccccgggaag agaaatgagc tgcagctcgg tagccgcggt 3480
ttgcacccgg agcttccgct ccttcccgcc cccatcctct ccagttccat tgaaaactcg 3540
gccctggggc ggaccctgca cgctggtcct ggctttccag tggacttggg gccttgagtt 3600
cccgactgag ggactcgcgt ggtcggatgc gatcttgtcc tgtagttgtc cagccgtcgc 3660
gggtgtcttt gcctttgtgc attagggatt tgccgcgatg gccttaagat gcgaactttt 3720
tagtttgcac gtgcaggttt tgtttcgttt taatcgcctt gaaaaacttg cctagactga 3780
gagtcagagt aatgggaatt tagggaaatg gcaacatttt aaagagaact tcagaattgg 3840

-continued atacttgagt tcatatcacc tgtcacgaga acgcagatat tataaatgaa tatatgcctc 3900
attcattctt caaataatga aaatgtaggg gctggttaaa tttaggcagt tttaatgata 3960
ctgaaaaaag tatatgatga gtgaatgaaa tgcggcacta aaatgttgca aaaattttcg 4020
aactctgtct cattttcctg aaattgaagt atattaaagg aaaaccgtca acatatatct 4080
aaagtaagta atcactcggt tagaacttaa tgcaagtttt ataaatcacc ttgaagtttg 4140
agtctaaggg gtacattaga gattaagaat tgtgagttgg accagtggtg ttaagagcgg 4200
actcccccat cccccaacac acacacaatt ttgcccactt tggcatttta acttttaagg 4260
aaatcactta aggaattgaa gatttagagt aagagttttg gttagtagac tggctttgct 4320
gttaaatcct tccactcttc tggcagagag attaatttcc ctaatcagta tcagcagaag 4380
ataaacttgt ttatattcct gctgttttgt agatcccttc tcctggtcct tcttcaatag 4440
aatattaaat tcttagtttg tatacagcag agaaggtcac ttataaaatt caaaaagtga 4500
gcaaacaggt ctagattaat tccaagagtt accaggaatt aattgcagtt tattttgcgg 4560
aggtgattac agtgcttttg atgaaatgat aaagctgcta tattgtaaac ctaaggcaga 4620
ttacctctgt gtagtgccag ttttctatcc ttattatata ttgaatcata cttaatacaa 4680
tgcattaaat tatgtaccac tttttttata tacagtatcg aactcattgt tttgccattc 4740
atccgttcag aatatcagaa gcagttttga aacgaattaa taaattagct actgttcatc 4800
agccccaatt ctaaataagc tcttagattt tcctcagccc atctgttact ttcaaaattt 4860
tctcatttga aaacttggca accttggatt ggatggattc atatttctta gtatagaagt 4920
tcttgatata actgaaaaat taagttaaac acttaataag tggtggttac tcagcacttt 4980
tagatgctgt ttataataga tgaccttttc taactaattt acagtttttt gaaagataac 5040
tgagaggttg agggacggag attttcttca agcaattttt tttttcattt taaatgagct 5100
cccaatgtcg gagtttggaa aacaaatttg tctttttaaa agaaggtcta ggaaactcaa 5160
aacctgaaga attggaagaa atcagaatag aaaatgggta tggttatgat actgtagatt 5220
taacgcagga catttcatgt tgttcctagt tatagggget gaacttattt aatagcacgt 5280
gcattttgat ttttagattt ttaagggaat gtcaagagag taatgattct gtttcaggct 5340
tcaggccaga ctccttcaga gttttccaaa acaaataatt actgaatcat taaagtaaaa 5400
tttctgagaa tagatattcc ttaatttcct tcattaactt tggccattaa aagtcaagaa 5460
gctctctcat ttattagcaa acttttctcc ttatgattct attttgattg tccttttgtt 5520
tgaggaagca gcatatggtg gttaagagca taggatctag aggcagatac ctctgagtta 5580
agggtcccag cccttcactt gtgagcttga gcaagttact gaatgcctct gagcctcttt 5640
cctccttttg aaatgatgat aagaatagca gccatctgag cagttattgt aaaggttaaa 5700
tgagataatg cttgtgaagc acttagccca ttgcaggagt cttgatgaca ctgtgtactt 5760
gaaaatagat gttacctgtt aaaattcttg tttaaacttc cacaactctt aaaactcttt 5820
tttgctagtc cttccagctg tttcctttag tttcttttct gtgtcttcat gcatcttttc 5880
tatctcctga aagtgaaaag actaacattg gatccagagc ttgaaaagcg tttttttcct 5940
gttacaatgg gcaaaagagt acatccttgg gttatattgg cacctagtat cagttatttt 6000
tcttgagcat ctgatctgct ctctactcta gtggaggcct cctgcttcac aattgctcac 6060
ccctgtgttt tctccccaaa tagaatactg agtttactct ggactctaga gtcaaacata 6120
cacagtattc tagtcttact gttcatttaa gcaagatatg tgcaagacac tgcattctta 6180

-continued

```
gtactggcag taagttaaaa catttttcgt cttgatgcca aagtttagac aattttataa   6240
aaattaacct ttgtaaaaga taatgagttg ataaaatatt ctcagtaaag cagctacgtg   6300
gtagaaaaac tgtcctttgc ttatgagttt ctccagagtt aagaccattg ggttccatct   6360
gaaggcaaga cttcaagctt gtcttactgg tctgttttgt ggctcaattt gtatgaagtc   6420
tatgcactct tccacacgtg tgtatttact gaactatcga gttattttag actgagaaag   6480
tattggagtt cattcctacg gtccactgca gagcaccttg tgcagtttgg agaatgtcaa   6540
cttttctacc tgttaacttc cattgtcttt acttttaacg ccattgtctg tgactctaat   6600
ggtgtcacgg ctcagggttt agattttgtg gttacattct attcttgtat gtcaagagtg   6660
gtgtatagaa agctgagggg gattatttag tctcttgact gatttttttt ttttttctga   6720
agaactcagt ttattatgtt tggtggtgaa ataaaaattg atgtgcatgg atgttaaaga   6780
tttgggttaa attgtgtgtt catagatgcc ttctcttagt atataatttt ttaaatttag   6840
atacttaaaa tactgtatcc ctttatctaa gattaacata agtctgtttc ttaaccagga   6900
taaaaaaatc taaatttaaa tgtgatgttg gatgagtttc caatcaagaa attgattttt   6960
taaactttgt gactagttat ccagtgggtg gatttaccc agtgtgtgta tgtgttttct   7020
gcttaactct ggaaggttag aaagagaatt tgaaactaag acaagccaag cttcttgttg   7080
ctcagtattt ttggtaaaaa tatggtcaga ttgtttaaat taactatagg ctttggaatt   7140
ttaaaaataa ttatatctct tggtctcttg acacatcaag aattaactgt tttgtatatg   7200
cgttgagtat taatgttcat gttttctgca gtagaaattt ataaaccctt atttatttgc   7260
cagacatgat ccctttagag aaatctagta tctaaaacct gaatttttaa aacaaaattt   7320
aaaatttttg tttcataaaa acaaaaatgt gattacctca tggctttttt cttatagctt   7380
ttgattgttt tttaaaatcg tagttcaaaa acattaacct aaaatttacc atcttaacca   7440
tttctaagta ctgttcagta gtgttaagta tattcacatt gtgccactaa cttccagaac   7500
tttttcatct tgcaaagctg aaatcttacc cattaaacaa ctcccaattt ccccctctcc   7560
tcagcctctg gcaaccacca ttttactttc tgtttctgca aatttaacta ctctagatgc   7620
ctcatataaa tagaattata gggttttaat atttttgtga tgggcttatt tcactttgtg   7680
taatgtcctc aaggttcatc catgttgtag catgtgtcag aatttccttc ctttttgagt   7740
ctgagcaata ttccattata tgttccatat tttgtttctc cattcatcca gcaacggaca   7800
cttgggttgc ttccacatct tggttattgt gctgctctga acatgagtct gcaaatctct   7860
ctttgaagct ttcacttttt ttggatacat atccagaaga gggatgctgg atcatatggt   7920
aacccttttt aattttcaag gaaccaccat attgttttct atagcagttg caccagttta   7980
cattcccacc aacagtgcac aagggttcct atttctccac atccttctaa acacttgttt   8040
tctttctttc cttccttctc ttctctttct ttcttagcca tctaatgtgg caaagtggta   8100
gccatctaat atgttgaagt gattgttttt aagggcttgt ttgtggataa ttaaccagct   8160
gaaagctaac tacagtttgc cagtggaagc tttaactgaa aggagagtaa gtacctctaa   8220
aaggagaatt caatttttct agtgacttag atttgttatg ccagtacttt ttcacagaaa   8280
cactttttgg gtaaaatagt gtacacctgt tctattgttg ataaagccca atttaattag   8340
gaaatttgtt ctctaagatt taaaacaata attgaaataa tgtattttta ttaaaaactg   8400
ttcccaagat gttagctttt agctgttctg gtgatctcaa ctgttattta tgagtgtttc   8460
tttattttaa aatttcacct taaccggtta cagttttaac cataaagatt atttcaacat   8520
atgattttga aaatttatta tcttgtaaat gggaaaatgt agtgatggaa catagtttac   8580
```

-continued

```
tgtatgtagt tcttcacttg tttgaaaagt cacaatatat ttaggcaaat taatttaaaa   8640
gtgtctagta tttaatattg caattttcac tcattaagga caggtccccc gtgtttcccc   8700
cttttttttt tccaagtagt ttgggaggat ttgtttttcc agctgaaaaa tactatggtt   8760
aaaaataagg tttaaaggcg aaagttgaag tctttgaggg ttgggatacg tttctgttct   8820
taagagtctt gtaaattcag atgctaagca aatttcttta aaatgatttc taccctcccc   8880
ctttccatta taaaactgga tatgtttcag tggaccaaat cccaagtagg ctgaatttga   8940
aatttgtggg ctgggcgcgg tggctcatgc ttgtaatccc agtactttgg gatgccgagg   9000
tgggtggatc acctgaggtc aggagttcga gaccagcctg gccaacatgg tgaaacccca   9060
tctctactaa aaataccaaa attagccagg cgtggtggcg ggtgcctgta atcccagcta   9120
cttaggaggc tgaggcagga gaattgcttg aacctgggag gcggaggttg cggtgagcca   9180
agatcgcccc attgcactcc agcctgggtg acagagcaag actgtgtttc aaaaaaatta   9240
aaaaagaaat ctgtggtgtg aatactggta cgtggtgtac acagtgagct cttaataagt   9300
atttgaatta acaaatgaga caatgattga ataattggat gaacaaagag aatgcaggtt   9360
tttaaaaggt ttctttagaa atattgtcgg cccggcacgg tggctcctgc ctgtaatccc   9420
accattttgg gaggccgggg caggtgaatc acctgaggtc aggagttcaa gacaagcctg   9480
accaacttgg agaaaccccg tctctactaa aaatacaaaa aaaaaaaaaa aaaaatagca   9540
ggatgtggtg gcacatgcct gtaatcccag ctactcggag gctgaggcag gagaatcgct   9600
tgaacctggg aagcagaggt tgcagtgagc caagatcgcg ccactgcact ccagcctgat   9660
gacagtgtga gatgctgtct ccaaaaaaaa aaaaaaaaaa ttaaaaagaa tgttttaatt   9720
ctttagttcc ctgtctgaga ttcactgatt ggtaagaaga aagttaaaga atctcctttg   9780
acttttttttg atatagatat ttaaattcta ttactttata gtaaggttgg ggtttatttt   9840
ctttgcttta taatagaaga gcattgatta ttctctttgc tttataatag aataccattt   9900
aaataggagt tccctgagtg tgtttacaat catttgatct ggctaaacta ttttaatgtt   9960
aatgaaattt taaaattttg gaggaaaaaa tttaaaaact acacaggtgc acaaagaaat  10020
aaaaatcacc tgctttttca ctatgtagag accattgtct actatttctc aattctgtgt  10080
tacatctgta tgttaataac tgtaggatta gggactgagt actgttttta acctgctttt  10140
aaaaaattta catctacatt ttttcccatc taaatagtga ggaagagtat cagaattttg  10200
taggcttgtg gtgatggtta aattagataa tattaatgtt gggtacttaa cataatatat  10260
ggctcttaat actctccaga tttcagatat agtctgtttt accattactg ccttttttatc  10320
aaacctattc tcaaaaaagt gagaaaagtg ctgagattac aggcgtgagc caccatgccc  10380
ggcctcatgg ttctttctta ataataaatt agaagaagta gaattacagg gtcaaaaagt  10440
atccatttta aagctttcaa tgtaattgcc tgtttatctt ctagaaagtt tgacctagtt  10500
gtattttaga gtgtcatttt cttgaacttt atcatcatta aagttttaaa tttggaacac  10560
tggcaatttg ataagtatat taggattctt cttattgcaa gtagcaaaat acaactcaat  10620
ctagtttaag aggggaaaat gtagtcattg gctaacacaa tctaattttg gtttaagaga  10680
caaatctaga gtctcaaatg atctcagagt gtaataatcc ctgacttttg tcttgatatt  10740
acttggcttg tataccttttg ctctatttgc atgctggcct tactctgcca ctgacaggct  10800
gtctgtatgg tgtggaagag gacggctagc atccccatac ctgcatccat acagtttgta  10860
atataaaaaa aaaaaaagta aaaaaaactc cctctctctt ctagtgtcta tatatcagtt  10920
```

-continued

```
tcctagaaga aaacgttttg ccctacttgg ccatgtgaat ggagttccct gattacatga  10980
gtcaaatatg tcttattgta gcatatttga tggtcttctt gtagaatatt atcttactat  11040
acacagaact cttgaccagt aattaatggg ccatgagttt ttgttgcaag tcatttgaat  11100
tcatattcta tagttttcta ccaagtgtag tcattctgca agctgttctt gtcatgactt  11160
ttgggaagtt gagtatttct tctatgggtt agggttttca tctcaagaaa aagatgatcc  11220
ttttctctac taaatatgtg ttaagatcac acatttttct agatcgttta gctctactgt  11280
gtgatcttac acaaattgct ttattgggat gataagaata attgccttat aggattgtta  11340
tgagaatgaa atgatacatc aactcatatg aaacactcag aacagctctt ggcacaaagt  11400
aagggcttaa ttaagtagaa actatccata tattcataat attatagtat tggttaagtt  11460
gttttcaaca ttgtttagaa tcgctcaagc cttctttgtg ataatctgac gaaggctatt  11520
caccaccagt gagtaaataa tagtggcaga atagttactg atgcttttcc tttacttggt  11580
tttttttcca taaacatctg gcctttgcag actaaatact ggtttatgta tagacatgtt  11640
attctaaaat aattttccat agtggtaata ctaaaggaag aaaaatgttc tcaaagctat  11700
ttatttggga tgttaaagga gggggaaatt aagaaagcct acatttccat gtcctttgtg  11760
tccagaatct cattaaatgt cttttaactt gttagcagag gaaagttgga tattgcctgc  11820
ctttgtagct aacatagtta aaatatttaa atggttatag tgtcaaacca gtagtcaaag  11880
ccttcactgt gaatggatga agggatattt tcttgaataa tttaagttga cttatttcag  11940
tggttcaaaa aatttcttca acgcttaacc atgactcagg cacctaacta ttatactatg  12000
tcctgtaaca gattgttgtg cattcattta ttcaacaggt atttgtgcag ctaatttatt  12060
gagtacagca ttgaatcgtt gatggcttag gccacagttg aacattccat tttttatgtt  12120
cattcattca ttcatagcat attccatttt taaattttca gttcattgca ctttaaagtt  12180
tgaggttctt gcgaagtaca gacttttggg tttaagtttt gttatttaat gtcaaccacc  12240
acaggcgcat tggccagtct gcttttagaa ttttcagaca tacatacaca aaacattctc  12300
acaagacaat ctacttattt tcttttttat tcctgtgttt cttaacacag gattaatgtt  12360
cagatctctt ttggagcaaa ataatcctct gaatttttga gatgtaccca gtgacctcag  12420
tctgagtatg tatactgcat taaaaaatgt aaccttgttc cttttagtgg tcatttggta  12480
acagtttgat cataaacaaa tgcagcctca aacacagaag gcttgaggca agtatacaga  12540
actatggaga gatcatttag atgatgtaga atatgccttt tcttttttta caatgccacc  12600
aaaatgaaaa cacggtttta aaaattctca tagagtgtaa cttcaacact gctttaactc  12660
tattaaacaa agcactgcca tgttgtaatt cctatttatt actctctgga gttgtataaa  12720
ttaccaaatc cgccttttgt ttgatatcct tttcaaatat ctgagggtag ctatcatgtt  12780
tcttccttct attcttaaaa aatagtccca aatttcttga atcttttaat ttaaaaatta  12840
tatattgagc atctgatttg tggaaaggca taggccatat taaaaatggg gcttcatatt  12900
aaaatgggga aaagggtgga gattctcagg tggaatctga gatctgccac acactaatag  12960
tgttacctaa ccctttttaa agacaaagaa acaggatcag aaggtcactt tggaaaattt  13020
atttggtaat attggatagg atggattagt atagttggaa aacagagact cttgctttag  13080
gagagctgct cctttgtcat ttccagaatc ttaatcatgg tcaaggttta gagctaaata  13140
tttaatagaa gaagtcttta gggtatgctt tctattgtac acccttattt caatacatgt  13200
gttttttcct gttatgtaag tactttatta ttatttatgc atcttctatt aaagttaagc  13260
aaataattat ttcaaggaca cattcttcta catacacaca aagtttaggg tcactgacct  13320
```

-continued

```
tcttaggttc tagtcttaga tctgttacca tctaagagca tataaataag ggaaacagaa  13380
agaaaaggat ttacaagctg agaaggaagc aatgcagaga aagaagagtg atagagtagg  13440
taatttgggg aaagtcagtg atacacagct cttaaccatg aacagtgatt cttcactctt  13500
gaatgtttgt gacattcatg aaggtattaa aagctgactt ttaaaaaatt gtttcagaga  13560
actggaaaaa aattcagttg ccacattctt ccttaggtca tctttgaact ctactcatgc  13620
acttacgtgt ttaaggcaaa gttttactaa acgcacactt gttcttgctg gcttattgac  13680
ttttactgct agcttcttat tcttagcaat tatacctcac attacatagt attgtgaaac  13740
tcactatatt cagtgttttg cctgacaaac atggtatgtt ataggatgtg tattcagtta  13800
tagctaaaaa taaattattc tcgtttttca aaatttgctg gcctacctgt taagcttttg  13860
ctttaagacc tgctaatgtt tctcaaactt ctgtggttaa atcacctgag tgtctagttg  13920
ctctatggat tcccagggac ccattcgcca gagattctga tttggtaatt ttgggatgga  13980
actcagggat ctgtaaattt tacaagcact cagaaatgaa acatagactt taaacagcta  14040
agagtgctca tcaggattat gttgatatta ttttttaaac agatgtgcca agcctttaat  14100
ttgaatttcc agggttggga tttggccttc tatatttggg ggaaaaaagt tctattgatg  14160
attgtggata tataccacag gtcaaccatt gaatagtcta gtcagtgtag ttagtgtatt  14220
ttataattac taagttctaa gtatgtggtg tattaatgtc ttaggaggtg gatatatttc  14280
ctgtatttgt aaagcatttg ggtaggtttt ttaaagagaa aagtatgtaa caaactagtt  14340
ttgagcgttg ctcttttact tctttgggca tttttgaaga acacgttaag tatcttctta  14400
gagcagaggg gctcagagtg gtccccagat tatcatcatt ggtaacacct agttggtgca  14460
ttactaactt gttagaaatg cacattctca ggcgccattc agacttcata aatcagaaac  14520
tctggaagta aggctcagca ttctgtgttt ttttttcttt tattatactt taagttttag  14580
ggtacatgtg cacaacgtgc aggttagtta catatgtata catgtgccat gttggtgtgc  14640
tgcacccagt aactcgtcat ttaacattag gtatatctcc taatgctatc cctccccgct  14700
ccccccaccc cacaacaggc cccggcgtgt gatgttcccc ttcctgtgtc catgtgttct  14760
cattgttcag ttcctaccta tgagtgagaa cacgcggtgt ttggtttttt gtccttgcga  14820
tagtttgctg agaatgatgg tttccggctt catccatgtc cctacaaagg acatgaactc  14880
atcctttttt atggctgaat agtattccat ggtgtatatg tgccacattt tcttaatcca  14940
gtctatcatt attggacatt tgggttggtt ccaagtcttt gctattgtga atagtgccac  15000
aataaacata cgtgtgcatg tgtctttata gcagcatgat ttataatcct ttgggtatat  15060
acccagtaat gggatggctg ggtcaaatgg tatttctagt tctagatccc tgaggaatcg  15120
ccacactgac ttccacaatg gttgaactag tttacagtcc cactaacagt gtaaaagtgt  15180
tcctgtttct ccacatcctc tccagcacct gttgtttcct gactttttaa tgatcgccat  15240
tctaactggt gtgagatggt atctcattgt ggttttgatt tgcatttctc tgatggccag  15300
tgatgatgag catttttttca tgtgtctttt ggcagcataa atgtcgtctt ttgagaagtg  15360
tctgttcata tcgtttgccc actttttgat ggggttgttt ttttcttgta aatttgtttg  15420
agttcattgt agattctgga tactagccct ttgtcagatg agtagattgc aaaaattttc  15480
tcccattctg taggttgcct gttcactctg atggtagttt cttttgctgt gcagaagctc  15540
tttagtttaa ttagatccta tttgtcaatt ttggcttctg ttgccatggc ttttggtgtt  15600
ttaaacatga agtccttgcc catgcctatg tcctgaatgg tattgcctag gttttattct  15660
```

-continued

```
acggttttta tggttttagg tctaacattt aagtctttaa tccatcttga attaatttta  15720
gcataaggtg taaggaaggg atccagtttc agctttctgc atatggctag ccagttttcc  15780
cagcaccatt tattaaatag ggaatccttt ccccatttct tgtttttgtc aggtttgtca  15840
aagatcagat ggttgtagat aagcggcatt atttctgagg gctctgttct gttccattgg  15900
tctatatctc tgttttggta ccagtaccat gctgttttgg ttactgcatc cttgtagtat  15960
agtttgaagt caggtagtgt gatgcctcca gctttgttct tttggcttag gattgacttg  16020
gcaagcattc tgtgttttga gaattcttcc aggggactgt gatgaaaact gacgtttgag  16080
aaccttcatc ttagagtaaa aactttacat acacattttt gttgttttat ttatctagca  16140
caatacttct ttttttgaa atggagtttt gctcttgttg cccaggctgg agtgcaatgg  16200
tgtaatctca gctcaccaca acctccatct cccaggttca gttgattctc ctgcctcagc  16260
ctcccgagta gctggggtta caggcacgtg gcaacatgcc tagctaattt tgtattttta  16320
gtagagacgg ggtttctcca tgttggtcag gctggtctcg aactcccgac ctcaggtgat  16380
ccgcccacct cagcctccca aagtgctggg attacaggcg tgagccactg cacctggcac  16440
aataccttat atataatcag ggctcaaaga tttgttgaga ggctcaacac caattctgga  16500
ccaggaaaga ttttatttat atcactagtc aggaataatc taaaaacaaa aagcacattc  16560
ttcttacaag taatatttca atacacatta atgtaaacac atggaaaagt attagctact  16620
taataaatta acatgtaaat gaaaaattta cacattatgg ctatttcaga tgtgatatag  16680
atttcatttt cagaaggaac cctccaatgt aaaacagtga ttcttttccc cgtttatttt  16740
actgcattag aaaatcacat ttaaagtaag cattttggtg aggtttggaa ggtgaataaa  16800
tccatctttt ctttaattat ggatatttaa gagagatgtt gttgtgccgt ttagataata  16860
atgatctaaa ccaagaaatt tagttgcttt caaaaataaa ataagtgtat gcattctgaa  16920
catttttctt tagaaacaaa ccatttcatc tgttttttg aatttcaaat taattataca  16980
gaattttcaa aatttgaaaa ttaggttagc atgagaaact gaagatactg aattatattg  17040
cctgttcagt ctatactttt ctttaggata tacagtagga aagaaatatg atagttcaag  17100
ttagattact acttctttca gagtttttg acaaatgcag gtacagtgat agtgtcagtt  17160
catggtgaat ttttgttaaa ataaattaca aaaaatttgt gatcctggta tcttgaaact  17220
agttaatatt tgtaaacttt gctaacactg tatatcactg tattctggtt ttatctgtgc  17280
atctatgagt tatatgtgtg tatagctaca tatgtttata tttatacaca tacattacac  17340
acaggagtgg aatcatactc aatttttttt gtatagcctg ctctgttcat ataatactat  17400
attgtagcat ctagtataag caaagattaa tttttgtaga ctttgctttt atcctgaaat  17460
tttgtggtag ctggtttaat ggaaagacaa tttctgtgac gtgtttttgtc agttagggat  17520
tgaccctggt aaaatattgc tggataacaa caagcaatgt aaaaatacat ttgttccata  17580
agataacctc cgtgaaggta gagacttggt ctgttttgtt tattgcaccg tgtcctgttc  17640
tgggaagagt gttagactca tagaagatga tcaagaaata ttttttgaat acatcaataa  17700
cattctctaa catgtgggta tcctaaaggt ttatttttaa agtttattga ttagaattca  17760
gaagatattt tcccagataa aataatagat tgctagctgt cttgaaaatg taatttatat  17820
ttaatttgaa atgtcaggtt tttgctattt tttccattaa gtagagatag ggtttttaaa  17880
aattacatgt gatgttttaa gtattctggt tttgcaacaa ttactagata gaaaatgtaa  17940
caacagatcc tattaataat acttccaata atacatataa aatacttgtc taaaagtaac  18000
cctccttaaa aaaacaaagc tggccaggcg cggtggctca cgcctgtaat cccagcactt  18060
```

-continued

```
tgggaggctg aggcaggcgg atcaagaggt caggagttca agaccagcct ggccaacata  18120
gtgaaacccc atctctagta aaaatacaaa aaattagccg ggtgtggtgg caggcgcctg  18180
taaccccagc tactcaggaa aatcgcttga acctgggagg cggaggttgc agtgagcgga  18240
gatcgcacca ctgtacttca gccttgggca acagtgcgag actctgtctc aaaaaaaaaa  18300
aaaaaaaaag gcaataggat taggtatcaa cttaatgaaa acttcgtgac agcactttct  18360
tgaaaaagac tgtggaaacc aaagttagta aactcctgtt tctgcctggg ttcggaaaac  18420
ataaagatga taaagatgtt taagtattcc tttttttttt tttttttttt tttgagacag  18480
tgtcttgctc tgtctggagt gcagtggcac aatcacagct cactgcagcc ttgaactcct  18540
gggctcaaat aatcctcctg cctcagcctc ctgagtatct ggaactacag gagtgcacca  18600
ttacactcgg ctagtaattt gattggttaa gaacattaac tataactcac acattttcct  18660
gaccacattt gcttaggaca aaacagtaaa agacatgagt gtagatgaaa gcgataaggg  18720
aactaatctt aaacactgaa cctcttttca gcaaattggc tttctagttt ctcagctctc  18780
tctttacacc tctaaatctc tttcctggca agatcattta tttgccttgg tttatggtga  18840
tactcttcat tgttatactg gtgggtgatt gttttaattg atagctgttt ttttctactt  18900
caggaagatg acactgctgg ctctgctggc tctgatgttt accttgtggc taatgcctgt  18960
gtttgcctgt gttcacattt attccacgat tcatttgtta acatttacta agctgctttt  19020
ctgtgccagg aacttggcta gataaataaa tggttgtttt tgtacacaga attagctgtc  19080
ataatcagtt actgtagcat ttattcttgc aaaaatatat atttatactt caactagtga  19140
tcgaatctca acttattaat tcatacattc agccagcaca taattgaata cttcttatgt  19200
gtcagaaact gttctaggtg cttgggatgt tcattgaaca aaatagacaa aagtctccgc  19260
ctctatggaa cttactttcc agtgaaggtg tggattggtg ggatagaaaa taaaataatc  19320
aagtaagata tgtacttagg ctttcataaa aatacagcag ggcaagagga ccaagatgga  19380
ggcagtgatc agggaatctc aatgagggtg agactgcgac aaagacttga aaaaggtgga  19440
gaagcaagcc ttgtgggtat ttagggtagc agtagtccag gcaaggggaa caactagtgc  19500
aaaggctcta ggaggcaatg tgtttgaagt gttttaagaa cagtaaggag gctagtatgg  19560
ttagaacaga atgagcaaag ggggcaaagt ggtagaaggt gagatcaaag aggtaatgag  19620
gccattgtgg aggcccatat ggactattgg aagggctttg gcttttactc taaatgaggc  19680
aaaaaccatt ttaagcagag aggagtgata tgacttgatt tcttgttaaa aggattattc  19740
tagttgctgt tacagaaaaa gattacaggg gtgcaaagaa acagggagac aaaagaatat  19800
aagattttca ctgtaactta tatctagtat gcttgcttat acttgaaaat gcatatccag  19860
ataattgtag taaattcaaa tattatgttt atttaatagt actaacattg atatgctggt  19920
taattatgat taggagcact aataaagcac aaatcaggga ttcccaaaaa gaatgttgaa  19980
agggcagtca gcttttcctg tgccagaaat caaagtcata gcagatttgg ggcaaatatg  20040
tcaaagtcaa acttacgcac atcactactg agaagacaaa gatgaatgtg tgacagtttc  20100
ctgcccccaa gaatctttaa gcattgtgaa ggaagattaa tatagccaaa taactagagt  20160
gatcagttct accagagagg accagttttg gaagccagag gaaaaaaaaa aaaaacagaa  20220
acaaaatgat gtttgaatta aatctttaaa agtttctctt ataaatttac caagccacat  20280
attgggaatg gtaccccagg cagaaggagt agagtaagca agccagaaag gaaatactat  20340
ggtgcttttg agtaactgca gtgtggctga agaatgtgga aaatgatgag gataaagagg  20400
```

-continued

```
tggacaggga actaggtaag ggagggcttc cttttaaata attagacctt gtcctgtgta  20460
catttaatgg gattttaatc aggccataat gccaaatttc tttacttcgg aaggatcttt  20520
atggtgatgg tttcagaaag aaattaaagc agagtaacag tggttagcaa taatgatcag  20580
ctagtggttc ccaaacttac gtatcatatg catcttggaa gtttttaaaa actcagattt  20640
tgggatcctg acttagatct actgaatcag aatttacaga ttcaaattcc cagtgaggcc  20700
taggaatttg aaatgttgaa tgtccttcac gatgcagcta gacaagcatt tgggaataaa  20760
gcattaggtg actatttcag tagactaagg agtgggaggc catttaagct caaaggctat  20820
tctacttctc actatatttc tagtacctag cacagtgcat ggtacttgat agatgcatcc  20880
tttctcccat acctcgccct acacatctct tcatgtgtat ccttattaat atcctctatt  20940
ataaactggt aaacatgttt ccctgagttc tgtgagctgc tccagcaaag atgggtttgt  21000
gagaatccca acttttgaag cctgtcagtc agaagttcct gaggccagac ttgcaactcc  21060
tgttgagggg gcagtcttgg ggactgagcc ctcaacctga cactgtctcc aggtagatag  21120
tgttagaatt gaattgaagg acacccagtt ggtgtccgct gcagaactga ttgctcacct  21180
ggtggtggag agaacccctc ctctcccgat agggttgcag aagttgtctt ctgtgttgtt  21240
gattgctgtg gtgtgggagc agagggggga aaaaagctgt tggagagttt tttccaaaac  21300
aataggagat tatttagatt tataaaaata gaatcaaagt agattaactg agcacattgt  21360
gaaatataga gtagagctgt gtgtaaggag tatatcttaa tgtcaagctg acaccaaatt  21420
gaatgtttgc tggaacgttc aaaaatctaa gcttcccaaa tctgtgaaaa cactcaggtt  21480
agtaaacagt cttatgcaaa cagcaagaca atgctcaaag ccatttaagg aaaaagaaca  21540
gtaactgaat tctcttatgg aaatgtgaga tgttgtttta gtaagtactg atggtgttat  21600
actttttgtt tattcgtttg ctggtatttc agttcctaaa attccttcaa atatgctgca  21660
aaatacaaac caagaacttg gtggattttc catttgtttt cctgtgggaa atgatggaat  21720
taaaaacctt gaggattaga ccttgagagt taccttccag tgtttatgcc accattatac  21780
aaaattctgg aggacaaaac ccttcccact taaaaaccag ttagtttcag aaaatcacct  21840
catgttagga gactgcatca ttatagtatg tgtgttagct ttaggtatag atctaaaata  21900
tttttaatat tttaaaaact taagcctttc ttcattaatt tggcctaata caagttagaa  21960
taactttaaa aatgagtaca aacaacaagg aagggccagg cgcagtggct caacgcctgt  22020
aatccgaaca ctttgggagg ccaaggtggg cagatcacct gaggtcagga gttccagacc  22080
agcctggcca acataatgaa accccatctc tactaagaat acaaaaatta gctgggcgtg  22140
gtggcacacg cctgtaatcc cagctactcg ggaggctgag gcaggagaat tgcttgaacc  22200
caggaggcag aggttgcagt gagccgagat cgcgccattg cactccagtc tgggcaacaa  22260
gggtgaaatg ccgtctcagg aaaaaaaaaa acagtttctg tgactgctag acaaatgttg  22320
agcaagtaaa acaccaacaa tgttgaactt agatattgaa atagctgctc tgtacaaata  22380
aagtctactg ggagtataga ctgaattacc atcttttgac tctttcgcca taatgattgg  22440
cattaccgga agggattacc ttgctttgaa gagctgctgg acagtagagc agagagcatc  22500
tattaccatt gtaggtgcct ttcagttagg attttggatt tataagcaaa ctccaagaaa  22560
gagcctggtt ctgagtttct ctgaatagct taggtcaagt cctaaattct gaagccaact  22620
cctataattc cttctttatg tctttggcat gtgaagtagg caaatttcga actttataat  22680
aatagcctag acttacaaat acttgccttg gtaatcagga tgagtttttg agagacaaca  22740
tagtctagtg ttaatcgcgt ggacaccaga ctgcttgagt gaaatacagg ttctaccatt  22800
```

-continued tattaacgga gtaatgttgg gtaagctatt tagccagggt ccttatctgt aacatggtga 22860
taataataaa gattaaataa taggtgaaaa atgtttagaa taccactgtg ttattagtaa 22920
gcaccatgca taggtgtttg gatttaaaaa tactggcaaa ggccaggttg ggtggctcac 22980
acctataatc ctcgcacttt gggaggccaa ggcagaagga tcgctttagc ccaggagttc 23040
aggaccagtc gaggcaacat agattccgtc tctgcaaaaa atttaacaga attagttggg 23100
catggtagcg tgtgcctgta gctacttggg aggctgaggt agggaggggg aggattgctt 23160
gagcccacga tttcgaggct gcagtgagct tatgatcatg ccactgtact ccagcttggg 23220
tgacagagca agactctgtc tctaaaataa aatgaaaata aaactgcagg caaaaatgcc 23280
aactgaagag tgaacatgaa cttttctttg catttttctt gggcctgaga ctttaagaag 23340
tgcagggcag ttaaaatgat gagatataat tctcacctat cagctcagca gaaattaata 23400
agattaaaaa gatgcgtaat atataatatt gcagagtgca tgggggaatt gatatacaca 23460
ttcatgaact ggcagagaca aaaatgggca cagaaccatt tggaaagcta ttgtgtattt 23520
taaaaaattt cagtagcaca ttttttatat catgaaattt cacttcagaa tgtcagtcct 23580
gtagaaatac tgacgcaagt gcaaaaacaa caaaaaccaa cttgtacctt caaggccaga 23640
aagagttatt tcaccaaata acataattga ggtacattaa ctttattaga agtaaatctg 23700
ataatctgct cacattttaa atagttatgg tttaacttca gttcttgaag tcacatattt 23760
ttacaattag gaatgctaac aggctttttg tgcaatacga aaagatgact ttaaatgcct 23820
acaattattt tgtgtccttt tatttttttt taatttttac tgacctacta caaagcacta 23880
aatattttat gttcttaatc tgaagaacaa tagacattct ctataaaaca actcttgctt 23940
attcatgaac tttgtacaca agaagcttaa taagacgggc tcaaaattat ttttctaaat 24000
atatttccta tacaaaataa tttcaagata taattgttac ttttgtgtct aatactgtat 24060
gttaaataat aaaatggtaa gcatgtaaaa actacaatac cacaaagatt gagctatttt 24120
gccagtagta tactccaact ttagttctag aacagttgta gaaatgggta aacaaactgt 24180
tttaactgta ctcttaactg aaatatagta ccttatgcag tagcagaaca tatcagcaga 24240
agaacttcac ttgacctgta cttaaaaaca aaacagatgc aatttataaa atttagagaa 24300
atatagtgac cttatttgca tgtggaaaat gtacttcttt ctgatctaca tatcttctgt 24360
tgtgcaatgt aagcagtaaa acaaatagta caggattcat ctctgtggga cctagacccc 24420
ctggtctaac aaataattct tggtcagtac tgtaattctg tggtataaaa ctgataaaat 24480
tagccttcct gtgactagac aagaagccgg gcagtttaaa tgctgaaact cacaagaact 24540
tcagaagctt tagctttaag ctttaagctt acttagaaat gttataagac ctccagtagt 24600
cacatatgaa gaatatcatg aagatttttc cattaaatct ttattataga tcccttgatt 24660
ggtttctgtc tagactcatt gtgtgataaa ggacataata atttttatca ccttcatcta 24720
atataggttt gtcaactcta tattagttgt tttcttgaag gctggttttc ttccaaaatt 24780
cagtcttatt ttcagtctac actagctttt aaatatactg tcctttagat gctttatcta 24840
acctcaaatt tctaatggat ttgtcttaga cacttattgc cactccttag atagtcattg 24900
ctatctttga agttctggac gatacgtgta ttacagagga actggagaca ttccatcacc 24960
atagttagct tgattggata ccctttaaaa gcatatactc gcgcctgtaa tcccagcact 25020
ttgggaggcc gaggcgggtg gatcacttga ggtctggagt ttgagacaag cctggccaac 25080
atggtgaaac ctgtctgtac taaaaataca aaaattagcc tggcatggta ccacatgcct 25140

-continued

```
gtaatcccag ctactcagga ggctgaggca ggagaattgc ttgaacctgg gaagtggagg  25200
ttgcagtgaa ccaagatctt gccattgcac tccagcctgg gtgacaagag cagaactcca  25260
ttaaaaaaaa aaaaaagcat atatagcaca tattataagg ttttcaattt tttcaccaag  25320
tgtttcattt gggtagtcat ttattggtag tttacatcag ttgagtggtt cagaaaaaat  25380
acagtaagtt gcttataaaa ttctgaacac tttggccagg cacaatggct caagcctgta  25440
atttgagccc tttgtgaggc tgaggcagga gaattgcttg agcttaggcg ttcaagacca  25500
gcctaggtaa caaagaacgc ctggaatgat tgtggcattt gaactaatat tcaggtttaa  25560
caagagataa ttgaccatca ctctatttta gaggctttat ttgaaccaga tagaaatcta  25620
tttcccacag ctatcactgc ctgtcaccta caacttaagg gggttgggga ggaagtgaga  25680
gattttctgt tagggccaat agggacctgc tagataccccc cccatcctgg gaatggtgta  25740
tggaactcca gtgtatgctg gagttattat catcatactt gtttttttat tttactcttc  25800
tgcttataca gatcaagtct tacgttttat ttttaagttt aaattgaaaa catttacaga  25860
gaacaatgca gtgaaatgaa aaaattacag actgctggca tttgcatttt catgtagcct  25920
cagtgactaa ttttttttta ttgtacagca ttgagaaaat cctagttcat ataactagtt  25980
atagttcata tagattcata taactagttt taagtgataa tagtttcttc cttttttttcc  26040
tccaccatct aaccagatga agataatagt ttttaatagc tcaccgtaaa tttcaaggta  26100
ctcaagttaa attgatctag atgcttgagt tgaaattttt ctatcaaagt tcaataacat  26160
gcttacattc cttattaaag tataaaagtc ctataaacac acaaacttga gtaagtacta  26220
aaactagtat cagtattgtc acaatacaac atgttatatt gtaacaagag catttgctga  26280
gaactgtgct tgttactcca gaatgttgct tctatggttg tacctttcaa ctttgcagat  26340
catttggaag gaggagagat ttggggtgga gacaattcgg tacttcattc acaggatgta  26400
aggaggatta agtaaaataa tgctggctaa aagtccttat ttagcatact gcccaatgct  26460
cactaaatca taatagctgt ttttaacatt tggtgaagaa tctatttaac aggagtgagt  26520
tgaggggcat aggagatcat gtgagtgttt aaagtagaag cagcattccc cattaagaag  26580
agaaatactg tggaagagca aagactttaa aacacctggg ttcaaatcct atttgctaca  26640
taatggctac ttttaaccta ttgaacgcca gttccctcat ttgtaaaata gggacaatat  26700
ttaacctatt tacaggttgt gagagaacta ggcacctagt acagggtaat gttggcacat  26760
ggtaaccttt aataaactgt tgctattcaa caagctatta gatgtcacta ggcagttaag  26820
caaaggaaga cagcttttgc ttggtgtgac aatgaaaatc tttctgattt ccttcttgga  26880
agagttccct gaagatatgt cattgtattg acacctttat ttttgctaac ctatccctct  26940
aaattctgga tattgtgtgt gccacagctt tttttcttcc atattcctgc atttatttgg  27000
cacctgttgt gccagtaata gataaggggc tgctaaggga ggaggcaacc tgcactggct  27060
tatagctgct aatgtcagtt cctatagctt atcgtcagtg ttattcatgt ggtaaaaggg  27120
tgagaaagta ctggagtcta aagaaacaag tagaaatcag tttgtagcta ttaccgttct  27180
acctgctaac aactcctgtt ttcaagttat tatgtacaac tttaggtagt ttctctagcc  27240
ttaatcgtgg tttctctgta ttgagactac ttttgaattc tatgaagtac agccttagat  27300
gtacaggcta ctttaaattt ttgcctaaaa taaaaacatt ctctccaatt acatatgctg  27360
gggaggaaac acctgcttcc gacaggttta aagcttggtt ttggactttt tgtgagagtt  27420
ccttatgtgt gcagtaatcc aaaatttgta tagttgccct ttataaaagt acattaatct  27480
agtagacaaa tctccatgta acttaattac atggcatctt ctaatccttc tgtgataagc  27540
```

-continued

```
agaaatgtaa agttttattc aagttaaggc aaactaactt gtatacactt tccatctcgt  27600
gtttttcttg ttgttgttaa gtaggataag ttctgaacgt cgaaaagaaa agtctcgaga  27660
tgcagccaga tctcggcgaa gtaaagaatc tgaagttttt tatgagcttg ctcatcagtt  27720
gccacttcca cataatgtga gttcgcatct tgataaggcc tctgtgatga ggcttaccat  27780
cagctatttg cgtgtgagga aacttctgga tgctggtgag ttattttaca agggtataaa  27840
taggcctgaa aattagaagt tagaagtaaa tagaaattat ttttagaagg tggtcgcaat  27900
gttttgattt tgtatacctc tttatattgt gatatgtaca cgtttaaaaa tttttctgta  27960
attctcacta tttttatcaa gcttcatttt tttctcatca gttattcttt gaaataatca  28020
ttctttatgc acataatttg ttttgcttta ttctcttaaa catactctca attcttttct  28080
aatataacat cctttttatt acctgctttt aaagctttag tcaggaataa gatactggct  28140
tttcccctcc cccttttttc tcctgttcca tctacctttc ttcctttaaa aaacatgact  28200
caggccgggc gcggtggctc acgcctgtaa tcccagaact ttgggatgct gaggcgggtg  28260
gatcatgagg tcaggagttc aagaccagcc tggccaagat ggtgaaaccc catatatacc  28320
aaaaatataa aaaattagat gggcacgctg gtaggtgcct gtaatctcag ctactaggga  28380
ggctgaggca ggagaattgc ttaaactcag agggcggagc ttgcagtaag ccgagatcaa  28440
gccactgcac tccagcctgg gcggcagagt gagactccat ctcaaaaata ataaaataaa  28500
taaataaata aaaaacatta ctcttctttc ttcttctatg gtttgctttg ctgcattact  28560
ttaatcatga aaagcagctg gcacatctaa ttatagtttt tctagcttct ggcctgcact  28620
tttctgtgtt gaaatggctg tatatattaa ataaagtgtc tgcgagaaaa ctttgtaaaa  28680
acatctaaat attatatcat ttaagtacaa ctttttaact aattattttc ctcttcttgt  28740
gccctttttta ggtgatttgg atattgaaga tgacatgaaa gcacagatga attgctttta  28800
tttgaaagcc ttggatggtt ttgttatggt tctcacagat gatggtgaca tgatttacat  28860
ttctgataat gtgaacaaat acatgggatt aactcaggta aaatgcacac atattaagag  28920
ctcttctata tgtttttatg attttatgat ctagccctaa tttttaaaaa tgtgtttaca  28980
gtttgaacta actggacaca gtgtgtttga ttttactcat ccatgtgacc atgaggaaat  29040
gagagaaatg cttacacaca gaaatggtaa gaaaagtctg ttgtttgatt taatgtgaca  29100
ggtggtttta cataataaga tactattgct aattattaaa ctttgctatt gtacttaccc  29160
aaggcaaaat gttatttcat gtttaataaa atgtctattc tttgttaaaa ctattatttt  29220
agtttttagg aatttcattt tgaaagccca cctaattgca taaataattg tgtgggtgtg  29280
agaaataaaa tggaaaagta aaatcatgac caagagagtt acaaataact tttttttttt  29340
ttttttaaga tggggtctcg ctcttttgcc catgctggag tgcagtggca caatcagctg  29400
actgcagcct tgaccgctgg gactcaagcg atcctcccac ctcagtctcc caagttagct  29460
gggaccacag acgcgtgcta ccatgcccag ctaaattttt aaaaattatt tgtagagaca  29520
aagtctcact atgctgctca ggctggtctt gaactactgg gcttaagcca tcctctcacc  29580
tcggcctctc aaagtgttgg gattacaggc atgagccacc acgcccaggc tacctttttt  29640
ttccttttct ttttaaattg tgataggggt tcttgctgta ttgcccaggc tggtcttaaa  29700
ctcctggact caagtgatcc tcctggctca gcctcccaaa gtgctaggat tataggcatg  29760
cgccaccaca cctggtggag ttaaaaatta aaatacacca ttaaggcaag gagaaattat  29820
aatacaaatg gcagataata ggactttaga cagtcattaa agttgaggtg ccagtttgag  29880
```

-continued

```
tctaaggccc aataaaaaaa gttcaccaga attttaagac aaacaactgc ttatttgact  29940
tctttggatg ttctcaataa ttcgagaccg tgtagttaga ttataaagta ttacattgtg  30000
gatgcccaca tattaacaaa aatagagagt aagacctcta attcttagga attaattgtt  30060
aaaaataatc aagtgttcca agattttttg gaaactacct cttgaattaa aaaattaaag  30120
tctttctaca tttttatctt gttaaacagt gtatactgat cataattatt taaaaaatca  30180
tgtgttctaa gatttttgga aagtacctct tgaattacaa aaacaagaaa gtctttccac  30240
atttgtgcct tcttaagcag tgtatactga tcataattga acttttcttc atgatggaaa  30300
gttaccacaa ggaaaatttc ttatgttctg ctgttctttg ttgctctcca atttaagtgc  30360
atacgtttgt ttgcttctat attataaaac ctcaaattta ctttttgtat aatttttgag  30420
gttttctttt tcatctcatt tattataata atagctaacc tccattgaga gaatgctgtg  30480
tgccaggaca ctgttcttcc tattttatat gcttttaact cctttattcc tcacaacaac  30540
cctgtgaagt taactgttag acaatttcta ttttactagg aaactgaggt acagagttac  30600
taagtaactt tcccaacatt atttggttag taaatggcag agcttgggct gaacttcagt  30660
agactggctt cagagtccac gctcattagt cctttggagc gcttttcata ttcttgaatt  30720
ctcacattct gtctttttc actctgtcag caggacctga ctcctgtttt taaatttcat  30780
attgtgtttt tactgttaat ttggaaaaca aatgcatact ttttagaatt ctgtataaag  30840
gaggagtaaa tatgctgtga acaaggacct aagtgggttg tcaatgagtt taatatatga  30900
gttctaatgt gcagagttga ggtttatatt gactgctcag tgcttccctg gggctagact  30960
ataaatggat ggatattagg aagtcttgtt ctgatttggt aatgatgtta atgcattatt  31020
ctaaatcaga tagtcttaat atagtttaaa tgtatgtttc gaaccaaatg ttcttttta  31080
aagcacacaa acattttgaa atcattacta atgtggttaa tgaattattg atgttccatt  31140
gggaaactaa aatgcagatt tttctctttt agaaatcagg gactattgca aagcatcaca  31200
ttttagtgat acactgagag ccagtggtgt gtttatacaa atagtcctat tttccaaata  31260
aattctagaa aaatgcttta gaatttataa attatacaaa atatgactta tttttagaga  31320
gtttaaaatt taggtttttt taatggtttg tttttgtttg tttgtttttt gttttttttt  31380
tcctcattag gaaaacacta gtacttttca gttaccttga tttttaaatt aatctgcagg  31440
tccccattca aaggccttgg gttcctttca aaggtcagta taattcaagc ttagtttatg  31500
aaggactgaa catacccaaa ggattttgca tgtggatctt tactgccact accacaacca  31560
tcaacaccta cacacacacg acacacacac attctctctc tctctctctc tctctctctc  31620
tctccccctc cctcccgcac tccttccctt ccccctcctt tgctctcatg gcatctttta  31680
aaaatatact cttaaatcct tccagggagg gcaaattcac ttcttaatct aagtaaaccc  31740
aaatggcatg catcagcacc aggactgccc atctttccta gttccattat tcatagagta  31800
taggctggaa ttcatcttgt tcctcaagag tccagcattt ctagttaacc atgcctacat  31860
ttaaacttac tctcatttct tttctacttt acagtgtttt ttcaatatac tagcattaca  31920
gtttccagat ttgatttctc tcctgtctta tttccatcag ttttcaagtc tattaagatt  31980
ctacctcttc atttgtcttt tgccaccatt cttttccctc atactctact ggctcagccc  32040
tctcattaca gtcacctaat tctaacatat atattgctgc taagttaatt ttccttaagt  32100
tactgattgt gcttttttaa agccccttgt tgaatattta ggcaggactc catgtggaca  32160
tccacagccc tccgtggtac agccctaacc ttcccttcta gctttgcctt actactcttc  32220
tacgtgtact ctacattgtg gacaaactac tatatgctgt ttttcaaaca tgtcctattt  32280
```

-continued ttcctacctc tgtgcttttc attctcttac ttctccttgg aatacccttc taacccatct 32340
ctacttactg acattctaat gtctcttttt ctaagcaaga cttcttgatt tcccttgact 32400
agaaattatc ttctaagctc tccctatcct tctttaaagc atttttataa gtctcaagta 32460
ccaactctac attgtgtttt tgttgacctt actatatcta ctacattttt aacttcttca 32520
ggaaaggtgg cgtatcttac tcatctttgt attgcctaca atatctagtc caggttctga 32580
ataataaata tttttatatg tgttctgaag cacactgacc aatgaagata agaaatcaag 32640
aggctagttc cttatttttt ttaatttttt tttttgagac agtgtctcac tttgtcaccc 32700
aggctggagt gcagtggcac aatctcagtt cactacaacc tctgcctccc gggttcaagt 32760
gattctcacg cctcaacctc ccaagtagct gggattatag gcatgtgcca ccacacctag 32820
ctgatattta tatttttagt agagatgggg ttttgccatg atggccagca tggtctcaaa 32880
cttctgtcct caagtgatct tcctgcctca gcctcccaaa gtgctgggat tacaggcatg 32940
aggcataagc cactgcgccc agcaagatgc tcttttctca gtcacctaaa tataatctca 33000
tttttagtta tagaaggttt gaaattggag tgaatagact ttacttaatt ctgactttat 33060
ttctgtagct tttttttttt gagatggatt ctcgctctat atcccaggtt ggagtgcagt 33120
ggcacagtct cagctcactg caacctctgc ctcccacgtt cgagtgattc ccctgcctca 33180
gtctcccaag tagctgggat tacaggcacc cactatcaca cccagctaat ttttgtattt 33240
ttagtagaga cagggtttca ccatgttggc caggccggtt tcgaactcct gacctcaagt 33300
gatcctcttg cctcagcctc ccaaagtgct gggattacag gcatgagcca ccgtgccctg 33360
cctatttctg taacttttga taagtcattt gatctgttgt tgttgttttc tcatagtaac 33420
aaagtagaag taattttctg cctgctttac tagataaatt aaggggaaaa aaataagata 33480
cgtaaaaatg ttatttgtta ttaaaaagaa agttgttatt ttaaaggttc tataaagaca 33540
tagagtgctt attagaaatt gagctaacac attcaggaaa ggataggaag agtttgctga 33600
agttctttct ttagggattc ttgtgtaccg atagcacagt taaagagcaa actcatacca 33660
tttttatatt tctgtgtatt tgactaagct tactggcttc aatgattaac tgttatccca 33720
aatatggatt atctttcagc caactcaggg aatcacagct actgagtagt gtgtgtcaga 33780
tctcttgggt gtgctggagt gagtaaaagg ggaatgaatt actgtgttca tgctgagact 33840
taattgaacg ggtattcagt tgatctaggt gatgggcact ttgttacttt tattgtaaca 33900
aatttgtata tttagttgct ttaaaacttt atttcatgct ttcattaggc cttgtgaaaa 33960
agggtaaaga acaaaacaca cagcgaagct tttttctcag aatgaagtgt accctaacta 34020
gccgaggaag aactatgaac ataaagtctg caacatggaa ggtaagtgaa aattatttgt 34080
gattgattat acactttatt tatacataga cattgtagta ttaagataac tttagaattg 34140
tgagggaagg tttacagttc catggtgttt ggttatgtaa catttatatc ttcaactcat 34200
ttgcatgtga tctccaaaat gcagaaccgt gtagtaattt gccaatttga ggcacaaact 34260
taaattacgt gaattgtggc actggtgttc caggcttaat cagttggctt tgccagccac 34320
acaatatttg aatcctgata gggcttaatt ttctattaat catggtttta tatctttgtt 34380
caatgttgaa acatagtcat cagtgcaaga aataactatc aaacagccat gatgatgaga 34440
tgaatgaaaa agcagcctag actttatacg aggggaattt tttaaagagt aatgtatagg 34500
ccctgggcag gaagtaggtc ataggtggta tcataggaaa aatgttcatt gattttcaaa 34560
aacgtgatta atccactagt gacagtaaat tttatcaaag cttactggcc atgtcagact 34620

-continued

```
caactactta tctctgcttt ttttttccct agcattgtaa atattttttt taactgcttt  34680
gttcttcata cacaggtatt gcactgcaca ggccacattc acgtatatga taccaacagt  34740
aaccaacctc agtgtgggta taagaaacca cctatgacct gcttggtgct gatttgtgaa  34800
cccattcctc acccatcaaa tattgaaatt cctttagata gcaagacttt cctcagtcga  34860
cacagcctgg atatgaaatt ttcttattgt gatgaaaggt aaattagatc taaaatgtga  34920
atttgaaatt tttaattagt ctacagcatt actgaatatt caccatagca aagattcagc  34980
gctggccatg catggtggct cacacctgta atcccagcac tttggaaggc tgaggcaagc  35040
ggggggtgga tcatctgagg tcaggagatt gagaccagcc tggccaatgt ggtgaaaccc  35100
catctctact aaaaaataca aaaattagtg ggacgtggtg gcaggcacta ctcaggaggc  35160
tgaggcagga gaatcgcttg aacctgggag gtggatgttg tggtgagctg agctcacacc  35220
accacactgc aagcctggat gacagagcaa gactcccatt tcaaaaaaaa aaaaaaaaat  35280
tactcaatgt taaactatac tttccactaa attgaacaga atgatacatc ctataatatt  35340
agattaactt tgtaaattaa ttcagccaca tttattgaac atttactctg tactatgaac  35400
acttacttta ctaggtgcta tccagaagtt aagatgagtc tttttttccc caataggggc  35460
tctacttact tagagaattt caaagatatg cagtgtgtat tttgagcaaa gatagattac  35520
cttaggttgg ggactagaaa gccaagtgtt tgtacatctc ttcatcctac atattttccc  35580
tgagaagctt caaccttgcc catggtttct attactattt cccacatttc ttcctgtaac  35640
taattctatt taattgccaa cttaatattt ctatctggat attcttctgt attgtaaact  35700
aagtattact gtaacaactg tactactact gcccccaaac aacatcatca tcaaaaactg  35760
cctttcttcc tataatgctt attgtggttt aatacaccac catacacaca tgactccagc  35820
aaaactttgg aagtcatctg taacttttct tttacattca ttggctacat acagttggtg  35880
tctaaatctt acagatttac tatctacata tatctcttga tccatttcct cctttccatc  35940
cttgcactcc tgccattgaa ttcattagct cattattact cttgacttga gttgttggca  36000
tagctgcctt tttgccaaca gatttgtacc cttataatct ttcatctaag ttgccagaaa  36060
gtgggtgtcc taatgtgaaa atcagatcat gtcattctgt tgttgaaaat gcctcaaatg  36120
cttccctcca tctttgcaca caaaaatatt ttgtttataa aaatactaga tgagggaagt  36180
aaatttttca tttatcaaaa gaagatgtgt attttagaag actgaaaaaa aatagaccta  36240
cacaatacaa tctaaactta gcatggcaaa caaagatatt tatgctctgg ccctaactct  36300
gtctttggaa tcagatgtta gattcactca tggcttgcag ctctgatact tacaatgtgg  36360
ccttggcctt ggtacttaac tgttgtaaaa ttcacattcc ttatctataa aataagaatc  36420
atggctgggt ggggtggctc atgcctataa tcctagcact gtgggaggcc gaggtgggtg  36480
gatcacctga ggtcaggagt ttgaaaccag cctggccaac atggtaaaac cccatctcta  36540
ctaaaaatac aaaaattagc tgggtatggg ggcacatgtc cgtaatccca gctacttggg  36600
aggctgaggt aggagaattg cttgaatcca ggaggcggag gttgcagtga accaagcttg  36660
caccactgca ctccggcctg ggagacggag tgagactcca tctcaaaaaa caaaaacaaa  36720
acaaaaaaaa gacctcagaa ggatgttgtc aggattaaag gagtccattg agtgcctagt  36780
acagatagtg aatgcttcac tactggtgtc aactttaaga aaatgaatat agaaaagcta  36840
agaattattt taaggtgttt actactagca tgtaaatgta tgatgggaca gagatttcca  36900
tcctattttg aggaattatt ttttattttt ttgaaaactt aaggtaacaa agtagagagg  36960
aggccaggga gaaaggaagg tagtggagca aaaatgagaa agggagtgac attcccctct  37020
```

-continued agttatagca gaaaattagc aaaatgatca tgacaggagg taacagtaaa gacagccagc 37080
tcatatatca accaagacag ttttgagttt gaccagcaga ctgttatttt ctggtttaga 37140
gctctttcca ggaacttctt gcatctataa cccctgagaa ccaagctatg gaaaaaattt 37200
tgctcaattt taagaaaatc taacatatca agctcctcaa ctccaaaata ttccacaaat 37260
agctgctatt tactatactg agtaataatc atttaaaatt attcaacact ttatttgagc 37320
atctactatg ttcatggcac taaagtagaa atgaagatga acagttcctg cctcaaaata 37380
aatgagtagt atactgcttt agatcatggg tttcctagtc cattaaaaac actttttggt 37440
catattttct ggacaccccg accctttttgg tatagaatat aacctatgta attctctaaa 37500
gttaaattaa cctcactttt cttgctctaa tatgtgtaaa actgaccttc taggaaagca 37560
tatacagttt atatttttga cttcttggta tcttttagtg atagacatac ctcagattga 37620
gaagcactga ttgacattag attaaatcag agcttcctat gacaatataa acaatacctt 37680
cattaatctg atccccctac ctacttcttc agcatcatct catatctgtc tccactaatc 37740
atattataga atctttgtta cctgcaccat gttaagcatt tttaaaaatc ttttgtttat 37800
accatacctt tttcctgaaa gcggttttgc ctttcctttg tctctagtca taagtctcct 37860
ataagaggct gttcctcatt ctaccattcc tttgcatgga taggattcca tggaatagat 37920
tctcatcact gcatttatca cattatttcc taagtagtac agtacatcta ctggaagatt 37980
agccacgtat tgagttttgt ctttgcattt tcatgcctag aataatgccg ggcacacata 38040
ggcatattaa gatttgaata gtgaaaaagt ttttaattcc atggggattt tatttaaaca 38100
gaaaaatata agaccaatta gaattatttt taaagcataa tttcaagaaa tatgactgat 38160
tttgtttaaa aacatgtttt cctttataat gctgccacct ggtgttgctg tgtttagaga 38220
tgtccctttg taaagaattg agggtttgag ttgagtttgg tttggttttt ggcaaatcag 38280
cttttccttt gtatatttat tttgtaataa actatggaag atcttgcctt taagtgtgag 38340
aacacaagca atgttacttt tataccttta tagaatatct tgcctatgtc cttcctgtag 38400
ttaggtaggg tttttttttt gacacacagc atgttatata aggtttgctt gcacctcggt 38460
aggaaagtcc tctgaaatct aaaggctgag aatctaaaag cttaactcat gttttgctcc 38520
tagaaagact tgagaagaga gtatttctgt tcagcatggt actaagaaga cagctttctc 38580
ttcctcatgt catggttgcc atttcatact gcttacagag aataagatct agtctctgtc 38640
ttaaataaag gtctactctc tgccagcgag ctagataggg taattggatt gttttccaat 38700
ctattttcat ttgaaatatt gttttatctg aaattactcc cataatttca tgtaatgcca 38760
aaaactaaac taagtacaag agcatcttca aaaaccaaca taattccttt agttcccatt 38820
tagtgtagat gctctttggt tgatgatatt agaattgtgt aatggctatt gatctctcaa 38880
agtgaggtgt tgcctagggg cttaaaagtt actacataaa gaatttggct ttatgaagaa 38940
atgttacaga ttttatctat attttaaaat aagtgtaagt gactaccttt ataactttta 39000
ccatgtagtt tagtagtatt tcttatctgt ttattaatac cctgccttgt taccaaaagt 39060
atgtataatg agatgtaata agaataggta acaagtaggc tgggcacgtt ggctcatgcc 39120
tgtaatccca gtactttggg aggccaaggc gggtgaatta cctgagttca ggagttcaag 39180
acgagcctga ccaacatgga gaaaccccat ccctactaaa aatacaaaat tagctgggca 39240
tggtggcaca tgcctgtaat cccagctact tgggaggctg aggcagggga atcgcttgaa 39300
cctaggaggt ggaggttgcg gtgagccaag atcacacctc attgtgctct ccagcctgag 39360

-continued

```
caacacgagg gaaactcttg tctcaaaaaa aaagaccagg taacaagttt gggtgaacag  39420
gattaaagag ttaaataaca ggaggaatct agaggactta aagaaatgtg tggtgttgga  39480
tttaataact gtagttgcca aaggtgaggt gtaaatttat tctaagcaaa ggaggatgct  39540
catttttgaa aattcacttg tccataagat taatgcctat cagttaactt gggaggagaa  39600
aaatttttct ttatcagtgt ctccctttt tttcttaaat cttgtatttt ttactaacag  39660
aattaccgaa ttgatgggat atgagccaga agaactttta ggccgctcaa tttatgaata  39720
ttatcatgct ttggactctg atcatctgac caaaactcat catgatagta agtacaatgg  39780
aagaactcag agatattcta attacttaac tgttgcaacc tctgtacagt ttggctaccc  39840
atctaattct ctggttaaaa gttctagact aaatgtgtta acaggcctat tcagtagaga  39900
tcttgaccat tttgtgtttt gtatgtgttg caacaaatat cagtaaaaat agaatcattt  39960
aatcatagaa aaaacttcct ggcattttaa atacaaagac ttttgaaaat ccaaatatta  40020
tagagtattg aatagcataa ttttcagaat tcacataaat actcagaaca gtggttggta  40080
tgtaaaaggc actcagaaag tatttgtaca atcaatgaat gtgaaggtgg tgaacatcac  40140
ctttggtaat aagtaccatt ttaaaaaatg cttataagtg catagttagg tatttatatt  40200
tatgggttca tgaaatattt tgatataggc atgcagtgca taaggataaa tggagtacct  40260
atcacctcaa gcattatctt gtgtgacaaa caatccagtt atactctttt ggttattttt  40320
attttatttt attttatttt tttcttttga gacaggatct cactctcgcc caggctggag  40380
tgcagtggag caatctcagc tcactgcaac cccgcctac cgggttcaag agattctcct  40440
gcctcatcct cccaagtagc tgggattata agcatgtacc accatgcctg gctaattttt  40500
gtatttttag tatagacagg gttttgccat gttggccagg ctggtctcga actcctgacc  40560
tcaggttatc cacctgcctt ggcacccggc ctcttttagt ttctttaaaa tgtacaatta  40620
aattattttt tactatagtc acccaaaaca agtacctttg acataagatt tgattctgaa  40680
ttttactcaa atgaatgtta agatccccaa gataagttaa actttggact atctcacctg  40740
tttaatctgt acctatgcat gacttcccac tgtgcttgag gatacctgaa tatcactgag  40800
tttgtgtgac tgatcagcct tgaactcaag agtaaatcca agtctgcagt caggacaccc  40860
caatcctcaa aataatacca tcattagcat ttatttagta ctttctccca aatcagtatt  40920
taatttaaat tgccaaaaga cttacaatgt ggtatcaatt tatatttaaa tatgctacat  40980
atagcttttt aaagcatctt tggttctctg gaaaccatag tcagaattta aggaagttat  41040
tgtggcacca ttttcttgaa aaaggctatt gattattctc taatctgaca ccaacctaag  41100
tcattaaagg aattttagtt actgaagatt gtatattcat gaactcttca cttagctcac  41160
tggcagcaaa ggagttttat ttagggggtt tgaaaaagga aatgggtaca ttttcagcta  41220
ttctgggacg cactgtcaga atgtaagcag ttacaactga ttccactaaa taaacatttg  41280
ttttccaaaa caatgatgaa cattcagcat ctgttcattt aattgaaaat tcaaagttaa  41340
aatattttct ctgcatgatt ctttttcttt tccccctag tgtttactaa aggacaagtc  41400
accacaggac agtacaggat gcttgccaaa agaggtggat atgtctgggt tgaaactcaa  41460
gcaactgtca tatataacac caagaattct caaccacagt gcattgtatg tgtgaattac  41520
gttgtgaggt aagtaagttt gagaaataaa catttttggg gaacaaatag taattctttt  41580
tggatactct gttcatttat aggaagataa gataataaat attaactaaa ttttaattct  41640
tttacatcgc taccaaatta ttattttcta tactctgacc taggtttcca gtccagctat  41700
tccacagtga tgctgctaaa cactgtcagt agttgtctat ccccatacct tcactcctat  41760
```

-continued

```
ttttaaaaag accatgaaaa aaataccaga tccattgatt ggtttggtct aattatacag  41820
atatcggcat atactatctc aagacagctg tgttcttttt gtaggaagaa tcctggccta  41880
gatttgtatc atagctctac cactcattag ctccctgacc ttggggaagt ctcttcattt  41940
ttctgaattt catctatgta gataatcctt cagaaggtta taatgaaaat taaatgaaat  42000
tctatgagat tagggagggg ggagggatag cattaggaga tatacttaat gtgaatgatg  42060
agttaatgga tgtagcacac caacatggca catgtataca tatgtaacaa acctgcacgt  42120
tgtgcacatg caccctagaa cttaaagtat aatttaaaaa agaaaagaaa ttctatgaga  42180
ttaataagct atatgatgta atacatggct cttgtatatt catgaactct tcacttagct  42240
ctttggcttg tgaatattat gtacatcaaa atttaatttt tcatttgatc tattttacta  42300
gactcctgcc ccatctagtc tacctgtcca cattattacc acattctagt ccatcttgcc  42360
cattactacc aggctaagct ttctagtgtg gatatgtcat catcttattt tccttagaat  42420
tttagcgatc tttttatcat ttccaagata aacacttgcc taggtgtaca gcatccttgt  42480
ttaccatcat actcacgcat tagagattta gccttccctt taaaatctag ggtcactcct  42540
cttaggaaga ctttgggcag tttttatttt tgctacttct gacaccatcc tttaatgttt  42600
taatattagt gccacagagt tcttttgtga ctttaccatt atgtaagaat cttccacttg  42660
gaatgtcttt ctcttcctca caccccagtc tgcctagcaa atgccacttg atcccaagta  42720
tcagcttgtt agcttctcag tgaagcaagc cttctctatt ttagcagtta tcacagtgta  42780
ttttaattgt ttacatatct actttcacaa tgggttataa atttcttaag gtcaagggtt  42840
ggctatttta atctttgcat tatcagttca tttcagatag tgaacattta atacgttaat  42900
taaaggaata atttacattt aagccaaacg tgaagataaa ctattgctca tcatccctct  42960
tcagccgtat cctgtaggtg gtatcacctt atattcttac caccaaagaa aatatggccc  43020
ctctcttaga aagatcttaa tcatttatct gtgtatcttt aggactatcc ttagatcatg  43080
cctcacatat tgatgccaaa gagttctttt gtgccaattt cataatgtgt gtcagcacaa  43140
caattctgaa gatttgttgg tgtctttcat gtacttgact acaaattgcc ttgccattac  43200
tactcttctc aaaggatatc tgaaattctt tttttctttt ttttttttga gatggagtct  43260
cactgtcacc caggctggag tgcagtggcg tgatcttggc tcactccatt tcccgagctc  43320
aagtgattct catgcctcag cctcccaagt agctgggact acaggtgtgc accaccacac  43380
cgggctaatt ttttgtattt ttagtagaga cagggttttg ccatgttggc caggctcttg  43440
aactcccagg ctcaagcgat ccacccgcct cagcctccca aagtcctggg attacaggca  43500
tgagccacca cgcccagcct ggatatctga aattcttaac tgaaattagt caaattatct  43560
tgtactgggg attttttttt taatttcaac ttttattttt gattcagggg atacatgcat  43620
aggtttgtta catgggtata tcatgtgatg ctgaggtttg gggtacaatt gatcctgtca  43680
cccaggtagt gagcataata cccaacagtt gttcaaccct tgcccctctc ccctagtagt  43740
cctcagtgtc tattgatgcc atctttatgt ccacaagtaa cccagtgttt agctccccact 43800
tacaagtgag aacatgcagc atttggtttt ctgttcctgg gttatctcac ttaggataat  43860
ggtctctgga tgcatccatg ttgctgcaaa ggacattatt tcattctttt ttatggttgc  43920
atactgtgga ttttattggg tctttatttt gtattagcat tttaaaaccc taaatgtgac  43980
acagtacgca tgagtgatca tgcatctcaa gaaatcttga aatgttcctg tccataaagc  44040
agaatttttt aagagaccat ttcacagtct cccttcccct cactgtatca agtgctcatt  44100
```

-continued

```
tgtgaattac caatttctct tgttttgaca gtggtattat tcagcacgac ttgattttct  44160
cccttcaaca aacagaatgt gtccttaaac cggttgaatc ttcagatatg aaaatgactc  44220
agctattcac caaagttgaa tcagaagata caagtagcct ctttgacaaa cttaagaagg  44280
aacctgatgc tttaactttg ctggccccag ccgctggaga cacaatcata tctttagatt  44340
ttggcagcaa cggtgagtag ttatttttgt taatccccta aattgtgtct gttgctacaa  44400
gccccatttc aactaaacat tactttacgg tttttgttgg taatcatttg gacattacaa  44460
gctaatatat gtttatagtt ttcttaaatg tatttgctta aatatttttg cccccgtaat  44520
ttcttaccat tcttgctttt ttatactgtt ggaaattgtg cttcaaagtg tccttaaggt  44580
atttcttctt cccacataaa tttttcctgg ctactctatt tctgtatcct gctgtcagat  44640
tttctccaca gtttagcaga gttatatgga agtaggcatt gttgcattaa aggataaaaa  44700
agtagtcata ctataacatc aagcattgaa gatgaaaact gcaattttaa agtagagaac  44760
atttaatgt ataaaaaggt tggtattgcc ttttgtcttt tatgccatag agattaagac  44820
gcggtatcaa tagtggattg taaaggtaac tcagacttat ggttatacta tactattgta  44880
tgtaaacttt ctgatgaagg aaaatttggt gacattttgt tgtttgatga attagacaaa  44940
ccttttgtga aaaagaacat aaattttta tatgtgaaaa tccttgtggc cgggcgcagt  45000
ggctcacgcc tgtaatccca gcactttggg aggccgaggc gggtggatca cttgaggtta  45060
ggagttcgag accagcctgg ccaccatggt gaaaccccgt ctctaccaaa aatacaaaag  45120
ttagctgggc gtggtggtgt gcgcctgtaa tcccagctac ttgggaggct gaggcagggg  45180
aattgcttga acctgggagg cagaggttgc agtgagccaa gattgcgcca ttgcactcca  45240
gcctgggcaa cagagcaaga ctctgtcttg ggtaaaaaaa aaaaaaaatc cttctatact  45300
ttagattgac tcatattttt tccccacaga cacagaaact gatgaccagc aacttgagga  45360
agtaccatta tataatgatg taatgctccc ctcacccaac gaaaaattac agaatataaa  45420
tttggcaatg tctccattac ccaccgctga aacgccaaag ccacttcgaa gtagtgctga  45480
ccctgcactc aatcaagaag ttgcattaaa attagaacca aatccagagt cactggaact  45540
ttcttttacc atgccccaga ttcaggatca gacacctagt ccttccgatg gaagcactag  45600
acaaagttca cctgaggtag gtgtcatgat ataatcagaa agggacaact ttcagatttt  45660
aacattcaag aatgtattta taagtttgat tcaaacactt atttgaacca caaattacat  45720
ttgtgtgtgt gtttgaattt tagcacttta aaattattgc aagagctact gcctaaccta  45780
gacctgagca catgttttag gctcaaagat agtcaggaac atgggaagaa actagcttaa  45840
tataaaccaa aaggtgaaac gtacattgtt tctctattat ttatatcagt aggacaaaaa  45900
catcttgaat ttggacattt aaagagaata gtactaagtg tgctcaaggt agctacagcc  45960
tatacctgtt accccttta gtttgtttta ttgtgttttg ttttgttttg agaaagagtc  46020
tcactatcac ccaggctgga gtgcagtggt gcaatcacag cctcaacctc ccaggctcaa  46080
atgattctcc cacctcagcc tcccaagtag ctgggactac aggcctgcat caccatgcct  46140
ggctaatttt ttaacctttt tttgtgtgtg tgtgtggagt tggggttctc actatgttgc  46200
tcaggctggt tttaaactcc tgggctcaag cgatcctcct gccttggcct cccaaagtac  46260
taggattaca ggcgtgagct accatgcctg gcccattacc cctttgagtt ggagaactgt  46320
ctggtagcaa tagacttacg agggtttaaa tgggaaagga ccttataaat tctttgccca  46380
atttagtcta atttccatca ctattttgaa attttgggta agtataatat gaaaataaca  46440
agtgttacat aaaataaata cttagtaact ggtctttttt attctggatc tgtcttgata  46500
```

-continued

```
ttaattgtcc tatgaacaca aaaataatct ttaaaggcta ggctggccaa gacttagaga  46560
tatcacacag ggctctattt ctaaatctag aatgattcca ttttagggct tcctacatct  46620
aaaaatatgc tcaggagtag ggcaacttag atctgaacat tataacttga taaatgaggc  46680
ataaataagc tttaataagt ggtaaataat tctacattag gtatttgttg aataaaactg  46740
acaagctaag agtaggggat ttgacatctc acagccttgt gttgaatgaa tatatatcct  46800
atgctctggt tgcttaattt acccagaaaa aaaaatgttt gattcatctt ggtttttatc  46860
taacaaaagt aaatctaaca aaaacgttag aatgaggaaa gcaaaatttc ttgtttagaa  46920
tacacagcta tagtttttg ttaaacttct tgcccagaac tcttaaaata gtaataatgt  46980
acattcgttc aggtatatgc aggtaaaata acttaggttt ctactcccac ccccgacagt  47040
aacagtgaga tttttaggta gctcagtcac cacaggagtg tgccttctca gttcaaaggt  47100
aaattccagt gaatgtagca tctagttaat tggtcaatta ggtaccattg tgggatgtga  47160
attaccaaat aggttttatt ctttagaata aggtgtttct tttcatctca atttgtaaa  47220
tgatgttata ttacatagtc agaaatatat atattggcaa aattagttac cagtataagc  47280
ttcaaaatgt cactattttc acaaattttt tttttttttt tttttttga catggagtct  47340
cactctgtcg ccaggctgga gtgcagtggc atgatcttgg ctcactgcaa cctctgcctc  47400
ccaggttcaa gtgattctcc tgcctcagcc tcctgagtag ctgggattac aggcgtttgc  47460
caccatgcct agctaatttt tgtattttta gtagagacga ggtttcacca tgttggccag  47520
gatggtctcg atctcttgac ctcattatcc ctccaccttg gcttcccaaa gtgctgggat  47580
tacaggcgtg agccactgag cccggcctag ttaaataaaa tttgataaac acgatggact  47640
tggttgtgtg ttttctggtt tttctgagat ctagtttgaa aattctgaca actagcaaag  47700
tatatggaag cttcttcagg aaatagtaaa catatttctt tttacagcct aatagtccca  47760
gtgaatattg tttttatgtg gatagtgata tggtcaatga attcaagttg gaattggtag  47820
aaaaactttt tgctgaagac acagaagcaa agaacccatt ttctactcag gtatatgaac  47880
ttatttgttt tatattaaat ttcattaatt tttagtctga agtgactttg agtttcactt  47940
gtttttttatt tataaggtgt ggccattgta aaaactcatg tatttgctgt tttaaaggac  48000
acagatttag acttggagat gttagctccc tatatcccaa tggatgatga cttccagtta  48060
cgttccttcg atcagttgtc accattagaa agcagttccg caagccctga aagcgcaagt  48120
cctcaaagca cagttacagt attccagcag actcaaatac aagaacctac tgctaatgcc  48180
accactacca ctgccaccac tgatgaatta aaaacagtga caaaagaccg tatggaagac  48240
attaaaatat tgattgcatc tccatctcct acccacatac ataaagaaac tactagtgcc  48300
acatcatcac catatagaga tactcaaagt cggacagcct caccaaacag agcaggaaaa  48360
ggagtcatag aacagacaga aaaatctcat ccaagaagcc ctaacgtgtt atctgtcgct  48420
ttgagtcaaa ggtatttata tgtaacattc aagttatagt tcttttatta tttttgagat  48480
aaatgtatgt gatagtacat gatttttaaa cttatagcaa actttctgat atatatgccc  48540
taacgcaaat tcttgagaac tcaaaaaact ttctaaatta acctcatata ttttttcttt  48600
ttctttcttt tttttttttt tgagacagag tctcgctttg tcgcccaggc tggagtgcaa  48660
tggcatggca ccatctcagc tcacggcaac ctctgcctcc tgggtgcaag agattctcct  48720
gcctcagcct cccgagtagc tgggattaca ggcatgcacc accacgcccg gctgattttt  48780
ttggtatttt tcatagagac agggtttctc cacgttggtc aggctggtct caaactcccg  48840
```

-continued

```
acttcaggtg atccgcctgc ctcagcctcc gaaagagctg ggattacagg tgtgagccac  48900
catgcccgct cctatttttt ctaaaataat tataaattct aaaattacct atctaaatgg  48960
aggagggtct tctgacacct ttaaaataaa atccagctca gtactgtaaa tgtgtttaca  49020
gaacttgttt aaagttctta cagttgttta aatcagacta gttaactacc ctcactactt  49080
agatgcttcc atttcttaga gctctttttt aagcttatct gaagaaaagc ccttccaatt  49140
taagggttat ttccaattgc acattccaaa ttgagccttc catcttcagc attcaatata  49200
gatatttaca ggcccctctt ttaaaatttt attatagtta acttgtatta aagttgcttt  49260
tatttttcat tacgtatttg tagaacatta gctatatata tattgcaggc tacataggtt  49320
ttcaaactgt acaacaggaa tctaagcatg aattgttact tctatggagc tagttcaaac  49380
aaacatatgg acatgaccca atttttaagt tatactttct gtatataatt tgtaagggga  49440
tttcacatat tttaagtttg aggctatagc tagaagaaat taagttttat ctaataagtg  49500
tgtggaaaag ggaaatgatt ccttctctac tatgtctaga ctaagccaga tatcaatagc  49560
aataggaaag aaccactgtc gtagccagaa cacatagctt ttttccctgc ctaacattcc  49620
caccttgacc tagagtgctg ggagaggtct tttccctaag cttggaaaag acattggggc  49680
tttagatgaa ctcagaagta ctttacatta ctttatttac tgtgtcactt actcactttt  49740
gactctgagc tccacgaggg caatcacagt gtcttgggca ttttagtgat actaatactt  49800
agctcatgac ctaatgtgta gtacttcctc aataaatggt tgttgaggca gggcgcagtg  49860
gctcatcact gtaatctcag cactttggga ggctgaagcg ggtggatcac ctgaggccaa  49920
gagtttcaga ccagcctggc caacatggtg aaacccggtc tactaaaaat gcaaaaatta  49980
gctgggcgtg gtggcacgtg cctgtaatcc cagctacttt gggaggttga ggcaggagaa  50040
ttgcttgaac cctggaggtg gaggctgcag tgagccgaga tcgtgccatt gcactccagc  50100
ctgggcgaga agagtgaaac tcggtttcaa aaaaaaaaaa aaaaaaaaaa gttgttggac  50160
tgacagatgc atgaatacag tagtaaaaat gacaatcact tataagttac agtttactat  50220
cagctacaga ggatgggata tccagttttc tgaacaactg ttctcttgta cttgtcaaag  50280
ccaaagtgta acaacacatc aagtcacttt agcaatttat ttttgagacg gagttttgct  50340
cttgttgccc aggctggagt gcaatggcgt gatctcggat cttggctcac cgcaactgcc  50400
gcctcgctgg ttcaagcaaa tctcgtgcct cagcctcccg agtagctggg attacaggca  50460
tgcaccacca cacccagcta attttgtatt tttagtagag acagtgtttc tccaggttga  50520
tcaggctggt ctcaaactcc cgacctcagg tgatccacct gcctcagcct cccaaagtgc  50580
tgggatgaca gttgtgagcc actgtgccca gctagcaact gtttttaaac attagttcca  50640
atgtagtgta cactgaaaac ttttatgaaa ggaatttcaa aaattaagat aaaccattaa  50700
aaacgtaatt actaagtact actactacta caatgatatt tacataatag actgagttac  50760
atttcataaa gacaatatat ctgtataaga atttttaaac ttccctgtct atataataga  50820
agttttagag aaatttttta aaaaccaaag aaaactgcaa aataagatca cttacctatt  50880
tggcattctc aactgtctgg aacagcaagg agccattatg attatgcatt tggtttgtgg  50940
ggtgtcttga aaagtcaaaa taatgtaaca aagctgatgt actttactca ttagaacaat  51000
tcttcacaat ttaatattaa ttttagatat acatagttca tgtttgataa ccagatcaat  51060
actgagtgaa aaatagcata gtgggaagag caggggaggg gaggtaggga tctggagacc  51120
tagagtgtac ttccatattg caactagtga gcagtaggac tttgagaaag ttacccaata  51180
ggcctcaggg ttctaattta taaaatgggt atgatatgcc tgccttatct gtcttgggaa  51240
```

-continued cttaagtaag gttaaaatga actaatgaac ttgaaatgtt ttataaactg aaaatgctat 51300
acgaatgtga gattgatctt gtatttcaat agtcccaaca atatcactgc attgttatat 51360
taggtggaat aaaaggacaa tatttaactg ttttgactct acaatagtgt caatttagtt 51420
gtgttcagct ctattttata aaatagggat acgcatactg tagaaaattt cctgttaaat 51480
taagctttga cggccaggtg ctcacgcctg taatcccagc actttgggag gccaaggtgg 51540
gcagatcact tgcgctcagg agtttgagac cagcctgagc aacatagtga aatcctgtct 51600
ctacaaaaat atgtatatat aaattagtca taatcccagc tacttgagag gctgaggtgg 51660
gaggatcact tgattccaga ggcagggctt ggttgcagta agcagagatc acgtctctgc 51720
actccagcct ggctgacaga gtaagaccgt gtttcaccaa aaaaaaaaaa aaaaaattaa 51780
gcttttactt ttaagatgat aaactttagt gatcaggaaa gttatcttat gtatattata 51840
ttccttaata ttggagaact aaagaattat gtattttctt taaaagcgct cactggatat 51900
tttttttaaa aacgctatat tttcatttag aattttttttc ttttcagaac tacagttcct 51960
gaggaagaac taaatccaaa gatactagct ttgcagaatg ctcagagaaa gcgaaaaatg 52020
gaacatgatg gttcactttt tcaagcagta ggaattgtaa gtatgagtag taggttttgc 52080
ttttctagct aatgtgctat ttcgtgtgtg tgtgtgtgtg tgtgtgtgtg tgtgtgtttc 52140
cacgtttctt ccaaatagta aagttatatt ttcagaagtt atacattggg ttttttttact 52200
ctgtatgcac tggtttttaa aaatacaaat gtttaataca tacattcttg gtataaaaat 52260
tccaaacaat tccagtgtat tttgagttaa aaagtgaagt tctcccctta ctccaccctg 52320
aatatcacca ccaatctcat tctcttccct ttaagttact ttgccttatt aaaagaactg 52380
ctattggcca ggcacagtgc ctcacgcctg taatcccagc actttgggag gccaagatga 52440
ggatcacttg aggtcaggag ttcgagacca gcctggccaa cttggtgaaa ccctgtctct 52500
actaaaaata caaaaattag ccaggcgtgt tggtgcacaa ctataatccc agccactctg 52560
gaggctgagg caggagaata gcttgaaccc gggaggtgga ggttgcgatg agctgagatc 52620
aggccactgc actccagcct gggtaagaga gtgagagtcc atctcatatt taaaaaagaa 52680
ctgctatgtt ttggggtaag tcaatggtgg tataatacat tctgatattt tcaaactaaa 52740
ttaactggaa agtatttata gacagaatgg tcataatgga tgacaaataa cttaagaaag 52800
aattcaaaat aatttagggt agtatttaag aaactgccta taatgttatt aaatttacac 52860
caatttcaag gtttttggtt gtttaaaaaa aaaattcaac aaactaaact tgaaataact 52920
ttactgttta tagggaacat tattacagca gccagacgat catgcagcta ctacatcact 52980
ttcttggaaa cgtgtaaaag gatgcaaatc tagtgaacag aatggaatgg agcaaaagac 53040
aattatttta ataccctctg gttagtttat tctttttgac cttgaacatc acaaagacaa 53100
aatacatgaa acatttttat ttaggagctt taatctaagt gagaatgact ttggttcctt 53160
agcaagatta aaaagtaaag ttgtggctgg gcgcggtggc tcacacctgt aatcccagca 53220
ctttgggagg ccgaggcagc cagatcatct gaggtcagga gttggagacc agcctggcca 53280
ccatggtgaa accccgtctc tactaaaaat acaaaaatta gctgggcgtg gtggcgggcg 53340
cctgtaatcc cagctacttg ggaggctgag gcatgagaat tgcttgaacc cggaaggcag 53400
aggttgcagt gagccaagat ggcaccactg cactccagcc tgggcgacaa gggtgagact 53460
ctgcctcaaa aaaaaaaaaa aaaaaaagta cagttgtatt tcatgtgatg gtcttaatac 53520
agagattaac atttcaaggt ggagcttttc atttttagta attttctttg atttctctat 53580

-continued gtccatgtgc tgtcaatatt gatagaagct gaaatttgtg aacttttatg acttcttttt 53640
tttttttttt tttttttgag acagggtctc gctctgttgc ccaggcctgg agtgcagtgg 53700
catgatcata gctcactgca gtctcaaact cctgtgctca agctcaagca atcatcctac 53760
ctcagcctcc tgagtagctc gcactacaga catgcctcac cacacccggt tgctttttgt 53820
agagatgggg tctcactatg ttgcctaggc tggtttcaaa ctcctggcct caagtgatcc 53880
tcctgcctca gcctgtgcta ggattacagg catcagcttt gatgcccacc atatttatgc 53940
ctttttccaa attgttattt ctttgtgcct ttattgtatc ctgtaaacat ttctgacaca 54000
gcaacagtat cactggatta tacttacttt ttaacatagt tgtggttttg ccaggtaaac 54060
taaaaaccct tccagaattt tgctttattt tctatgatac ctaacacatt gtgggtgttt 54120
aataaatatt cattgactag atgaatgtat acttaggtat ctcttttgtt tttcagattt 54180
agcatgtaga ctgctggggc aatcaatgga tgaaagtgga ttaccacagc tgaccagtta 54240
tgattgtgaa gttaatgctc ctatacaagg cagcagaaac ctactgcagg gtgaagaatt 54300
actcagagct ttggatcaag ttaactgagc tttttcttaa tttcattcct ttttttggac 54360
actggtggct cattacctaa agcagtctat ttatattttc tacatctaat tttagaagcc 54420
tggctacaat actgcacaaa cttggttagt tcaattttga tccccttttct acttaattta 54480
cattaatgct ctttttttagt atgttcttta atgctggatc acagacagct cattttctca 54540
gttttttggt atttaaacca ttgcattgca gtagcatcat tttaaaaaat gcaccttttt 54600
atttatttat ttttggctag ggagtttatc cctttttcga attattttta agaagatgcc 54660
aatataattt ttgtaagaag gcagtaacct ttcatcatga tcataggcag ttgaaaaatt 54720
tttacacctt ttttttcaca ttttacataa ataataatgc tttgccagca gtacgtggta 54780
gccacaattg cacaatatat tttcttaaaa aataccagca gttactcatg gaatatattc 54840
tgcgtttata aaactagttt ttaagaagaa atttttttttg gcctatgaaa ttgttaaacc 54900
tggaacatga cattgttaat catataataa tgattcttaa atgctgtatg gtttattatt 54960
taaatgggta aagccattta cataatatag aaagatatgc atatatctag aaggtatgtg 55020
gcatttattt ggataaaatt ctcaattcag agaaatcatc tgatgtttct atagtcactt 55080
tgccagctca aaagaaaaca ataccctatg tagttgtgga agtttatgct aatattgtgt 55140
aactgatatt aaacctaaat gttctgccta ccctgttggt ataaagatat tttgagcaga 55200
ctgtaaacaa gaaaaaaaaa atcatgcatt cttagcaaaa ttgcctagta tgttaatttg 55260
ctcaaaatac aatgtttgat tttatgcact ttgtcgctat taacatcctt tttttcatgt 55320
agatttcaat aattgagtaa ttttagaagc attattttag gaatatatag ttgtcacagt 55380
aaatatcttg ttttttctat gtacattgta caaatttttc attccttttg ctctttgtgg 55440
ttggatctaa cactaactgt attgttttgt tacatcaaat aaacatcttc tgtggaccag 55500
gcccctttga tcagctttta tgttcaaata ttaataatat ttgcttcaac acctccaact 55560
cataaaattg tttaccaaca atttaagcac ttatgaaaat tacatggtac tggttatttc 55620
tacatttatc ttagtgccat caccttaatg tatgttgagt ccctaaatgt catgttaaat 55680
aataacaacc ataatatccc attgaaaaga gtatgttgtt agaaaagaaa catcattttt 55740
aagtttctga gcctattaaa atgctcaaac acaaaatatt agtattttta aaatatgaat 55800
gggatgagtg aagcagttct cagcattata gtcacaatgt tacaaaggct agagcttctc 55860
tgaagatttc taatctgttc ccattaacag attaataaat ttagacttca aatgaataat 55920
ttgcccaagc tttaaaagta atagatggca gaccaaaaat gtaagcttaa gtttcctgac 55980

-continued

```
tctaaagtca aacttagaac aaatttggtt tgtttttgtt ttaatgatac tgcgttttaa  56040

aacaaagtag ctttatcctt tttctcctgt atttttcttt tacaaaatag ctgtatttct  56100

tttatactga taatctcatt tttaaaaatc agacagtgta gaaagatatt ttttaaaaca  56160

gaaaaatcac tatgaatccc tgcacctaca ggtacagaaa attattttta tgaacaaatt  56220

atgtaggaag tgccagagcc ttaggtcctt taccctgagg tatatatact gaacaaaagg  56280

aactgagcca cagatctctt aggtagctct ttttatctta caatggagga cagtgattac  56340

aattatatga aaattttgga acaaaagtta atactaagat tcagtgcaaa atttgggggg  56400

gggggggca caggtatact taagcacaaa cactgtgacc caaagtgctt caacatttag  56460

ttacagatag tagtatacta gaagtggtat tttagaataa agtggttgct tagtattcac  56520

aggtcacaaa acaaaaaatt attcttgtat agcaaattag cttcagttga aaactatttg  56580

taaaagcaga ttatgtaatg accaggagtt caggaaaatg acttctgaaa gcattgagaa  56640

gggaaagcca cgttaaagga cagtacagct ggaaggaagc aagtacttac ccactgctca  56700

gtcactaaga caacaagctc cttggagtgc tttaagctac ggaatagcag aactggccct  56760

tcccaatttt atgcaccgtc acaaatttct tcataatggt tttgtccaag gcttataacc  56820

caaccctggc aactataatc cttactttat gaaacagctg tatttctttt atactcataa  56880

cccagaaaaa tgagaatgta tgttctgagt ataaaagaaa tgtagctatt ccataaaaat  56940

acaggagaaa aagaataaag ctattttaat ttttttaatg cagtatcatt aaaaaacaaa  57000

ccaagtttgt tctaagtttg actttagagt caggagactt aagcttacat ttctggtctg  57060

ccatctatta cttttagagc ttgggtaaat cttcatttga gatctaaatg ctatatatag  57120

ttcattcata gcagtaccag ataagggagg agtatatcta tacagtatat agtcttgaag  57180

aagtgatcta aggctcggag cttttgaggt ggccatgagt gactccaaag tccatggagc  57240

taaccaccct gcagtgctag ccaatccagt tgaacatacc cttttctcca ttgttaactg  57300

tttgtttaaa tagcaaacag aaggcggcaa tggaggtgtg gaaaactgag gatccgatgt  57360

cacttgaaag taatgagatc acataacatt gagggaatgt cctaagagga gtggcagggc  57420

ataaatagaa atgaataaaa gtgttttcaa gtgccattta gtgggttctg aatttgaact  57480

agagattgag atatccagtt                                              57500
```

<210> SEQ ID NO 12
<211> LENGTH: 754
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:

-continued

<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (694)..(694)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (748)..(748)
<223> OTHER INFORMATION: n is a, c, g, or t
<300> PUBLICATION INFORMATION:
<308> DATABASE ACCESSION NUMBER: AU123241
<309> DATABASE ENTRY DATE: 2000-10-23
<313> RELEVANT RESIDUES: (1)..(754)

<400> SEQUENCE: 12

```
ccctgacgct gcctcagctc ctcagtgcac agtgctgcct cgtctgaggg gacaggagga     60

tcaccctctt cgtcgcttcg gccagtgtgt cnggctgggc cctgacaagc cacctgagga    120

gaggctcgga gccgggcccg gaccccggcg attgccgccc gcttctctct agtctcacga    180

ngggtttccc gcctcgcacc cccacctctg gacttgcctt tccttctctt ctccgcgtgt    240

ggagggagcc agcgcttatg ccggagcgag cctgggggcc gcccgccgtg aagacatcgc    300

ggggaccgat tcaccatgga gggcgccggc ggcgcgaacg acaagaaaaa gataagttct    360

gaacgtcgaa aagaaaagtc tcgagatgca gccagatctc ggcgaagtaa agaatctgaa    420

gttttttatg agcttgctca tcagttgcca cttccacata atgtgagttc gcatcttgat    480

aaggcctctg tgatgaggct taccatcagc tatttgcgtg tgaggaaact tctggatgct    540

ggtgatttgg atattgaana tgacatgaaa gcacagatga attgctttta tttgaaancc    600

ttgggatggt tttgttatgg ttctcccnca tgatggtgac atgattttac atttcttgat    660

aatgttgaaa caaatacntt gggattnact tcanttttga aacttaactg ggaaacantg    720

tgttttgatt tttactccat cccatgtnaa ccat                                754
```

<210> SEQ ID NO 13
<211> LENGTH: 3551
<212> TYPE: DNA
<213> ORGANISM: Homo sapiens
<220> FEATURE:
<221> NAME/KEY: misc_feature
<222> LOCATION: (29)..(2236)
<223> OTHER INFORMATION: CDS
<300> PUBLICATION INFORMATION:
<308> DATABASE ACCESSION NUMBER: AB073325.1
<309> DATABASE ENTRY DATE: 2001-10-23
<313> RELEVANT RESIDUES: (1)..(3551)

<400> SEQUENCE: 13

```
gtgaagacat cgcggggacc gattcaccat ggagggcgcc ggcggcgcga acgacaagaa     60

aaagataagt tctgaacgtc gaaaagaaaa gtctcgagat gcagccagat ctcggcgaag    120

taaagaatct gaagtttttt atgagcttgc tcatcagttg ccacttccac ataatgtgag    180

ttcgcatctt gataaggcct ctgtgatgag gcttaccatc agctatttgc gtgtgaggaa    240

acttctggat gctggtgatt tggatattga agatgacatg aaagcacaga tgaattgctt    300

ttatttgaaa gccttggatg gttttgttat ggttctcaca gatgatggtg acatgattta    360
```

-continued

```
catttctgat aatgtgaaca aatacatggg attaactcag tttgaactaa ctggacacag    420
tgtgtttgat tttactcatc catgtgacca tgaggaaatg agagaaatgc ttacacacag    480
aaatggcctt gtgaaaaagg gtaaagaaca aaacacacag cgaagctttt ttctcagaat    540
gaagtgtacc ctaactagcc gaggaagaac tatgaacata aagtctgcaa catggaaggt    600
attgcactgc acaggccaca ttcacgtata tgataccaac agtaaccaac ctcagtgtgg    660
gtataagaaa ccacctatga cctgcttggt gctgatttgt gaacccattc ctcacccatc    720
aaatattgaa attcctttag atagcaagac tttcctcagt cgacacagcc tggatatgaa    780
attttcttat tgtgatgaaa gaattaccga attgatggga tatgagccag aagaactttt    840
aggccgctca atttatgaat attatcatgc tttggactct gatcatctga ccaaaactca    900
tcatgatatg tttactaaag gacaagtcac cacaggacag tacaggatgc ttgccaaaag    960
aggtggatat gtctgggttg aaactcaagc aactgtcata tataacacca agaattctca   1020
accacagtgc attgtatgtg tgaattacgt tgtgagtggt attattcagc acgacttgat   1080
tttctccctt caacaaacag aatgtgtcct taaaccggtt gaatcttcag atatgaaaat   1140
gactcagcta ttcaccaaag ttgaatcaga agatacaagt agcctctttg acaaacttaa   1200
gaaggaacct gatgctttaa ctttgctggc cccagccgct ggagacacaa tcatatcttt   1260
agattttggc agcaacgaca cagaaactga tgaccagcaa cttgaggaag taccattata   1320
taatgatgta atgctcccct cacccaacga aaaattacag aatataaatt tggcaatgtc   1380
tccattaccc accgctgaaa cgccaaagcc acttcgaagt agtgctgacc ctgcactcaa   1440
tcaagaagtt gcattaaaat tagaaccaaa tccagagtca ctggaacttt cttttaccat   1500
gccccagatt caggatcaga cacctagtcc ttccgatgga agcactagac aaagttcacc   1560
tgagcctaat agtcccagtg aatattgttt ttatgtggat agtgatatgg tcaatgaatt   1620
caagttggaa ttggtagaaa aactttttgc tgaagacaca gaagcaaaga acccattttc   1680
tactcaggac acagatttag acttggagat gttagctccc tatatcccaa tggatgatga   1740
cttccagtta cgttccttcg atcagttgtc accattagaa agcagttccg caagccctga   1800
aagcgcaagt cctcaaagca cagttacagt attccagcag actcaaatac aagaacctac   1860
tgctaatgcc accactacca ctgccaccac tgatgaatta aaaacagtga caaaagaccg   1920
tatggaagac attaaaatat tgattgcatc tccatctcct acccacatac ataaagaaac   1980
tactagtgcc acatcatcac catatagaga tactcaaagt cggacagcct caccaaacag   2040
agcaggaaaa ggagtcatag aacagacaga aaaatctcat ccaagaagcc ctaacgtgtt   2100
atctgtcgct ttgagtcaaa gaactacagt tcctgaggaa gaactaaatc caaagatact   2160
agctttgcag aatgctcaga gaaagcgaaa aatggaacat gatggttcac tttttcaagc   2220
agtaggaatt atttagcatg tagactgctg gggcaatcaa tggatgaaag tggattacca   2280
cagctgacca gttatgattg tgaagttaat gctcctatac aaggcagcag aaacctactg   2340
cagggtgaag aattactcag agctttggat caagttaact gagcttttc ttaatttcat   2400
tcctttttt ggacactggt ggctcactac ctaaagcagt ctatttatat tttctacatc   2460
taattttaga agcctggcta caatactgca caaacttggt tagttcaatt tttgatcccc   2520
tttctactta atttacatta atgctctttt ttagtatgtt ctttaatgct ggatcacaga   2580
cagctcattt tctcagtttt ttggtattta aaccattgca ttgcagtagc atcattttaa   2640
aaaatgcacc tttttattta tttatttttg gctagggagt ttatcccttt ttcgaattat   2700
```

-continued

```
ttttaagaag atgccaatat aatttttgta agaaggcagt aacctttcat catgatcata   2760

ggcagttgaa aaatttttac accttttttt tcacatttta cataaataat aatgctttgc   2820

cagcagtacg tggtagccac aattgcacaa tatattttct taaaaaatac cagcagttac   2880

tcatggaata tattctgcgt ttataaaact agtttttaag aagaaatttt ttttggccta   2940

tgaaattgtt aaacctggaa catgacattg ttaatcatat aataatgatt cttaaatgct   3000

gtatggttta ttatttaaat gggtaaagcc atttacataa tatagaaaga tatgcatata   3060

tctagaaggt atgtggcatt tatttggata aaattctcaa ttcagagaaa tcatctgatg   3120

tttctatagt cactttgcca gctcaaaaga aaacaatacc ctatgtagtt gtggaagttt   3180

atgctaatat tgtgtaactg atattaaacc taaatgttct gcctaccctg ttggtataaa   3240

gatattttga gcagactgta aacaagaaaa aaaaaatcat gcattcttag caaaattgcc   3300

tagtatgtta atttgctcaa aatacaatgt ttgattttat gcactttgtc gctattaaca   3360

tccttttttt catgtagatt tcaataattg agtaatttta gaagcattat tttaggaata   3420

tatagttgtc acagtaaata tcttgttttt tctatgtaca ttgtacaaat ttttcattcc   3480

ttttgctctt tgtggttgga tctaacacta actgtattgt tttgttacat caaataaaca   3540

tcttctgtgg a                                                        3551
```

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14

```
aaagtgatgt agtagctgca                                                 20
```

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 15

```
ggtatcatat acgtgaatgt                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 16

```
taccacgtac tgctggcaaa                                                 20
```

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 17

```
tgtgctttga ggacttgcgc                                                 20
```

-continued

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 18
gaaatgtaaa tcatgtcacc 20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 19
tcaaagaggc tacttgtatc 20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 20
ttaatgcaac ttcttgattg 20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 21
atcattatta tatgattaac 20

<210> SEQ ID NO 22
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 22
gaaaggcaag tccagaggtg 20

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 23
taaactccct agccaaaaat 20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 24
cattagcagt aggttcttgt 20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 25
gatcatgatg aaaggttact 20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26
aaatttcata tccaggctgt 20

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 27
agtttcctca cacgcaaata 20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 28
actgatcgaa ggaacgtaac 20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 29
cgctttctct gagcattctg 20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 30
aaatcaaaca cactgtgtcc 20

<210> SEQ ID NO 31
<211> LENGTH: 20

-continued

<212> TYPE: DNA
<213> ORGANISM: Artificial Sequence
<220> FEATURE:
<223> OTHER INFORMATION: Oligonucleotide primer

<400> SEQUENCE: 31
tcctttagta aacatatcat 20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 32
caaagttaaa gcatcaggtt 20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 33
ctagtgcttc catcggaagg 20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 34
aatgccacat accttctaga 20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 35
tcgtgagact agagagaagc 20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 36
atgaaaggtt actgccttct 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 37

-continued tcagcaccaa gcaggtcata 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 38
aagtttgtgc agtattgtag 20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
ctgagcattc tgcaaagcta 20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 40
ttcagattct ttacttcgcc 20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 41
gataacacgt tagggcttct 20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 42
tcaaagcgac agataacacg 20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 43
caaagcatga taatattcat 20

<210> SEQ ID NO 44
<211> LENGTH: 20
<212> TYPE: DNA
<213> ORGANISM: Artificial Sequence -continued
<220> FEATURE:
<223> OTHER INFORMATION: Oligonucleotide primer

<400> SEQUENCE: 44
ccatcatctg tgagaaccat 20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 45
atatggtgat gatgtggcac 20

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 46
ctcctcaggt ggcttgtcag 20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 47
tgagctgtct gtgatccagc 20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 48
agataacacg ttagggcttc 20

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 49
catggtgaat cggtccccgc 20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 50
tgttatatat gacagttgct 20

-continued

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 51
ccttatcaag atgcgaactc 20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 52
ccaaatcacc agcatccaga 20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 53
aactgagtta atcccatgta 20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 54
ttagttcaaa ctgagttaat 20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 55
aggccatttc tgtgtgtaag 20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 56
ctatctaaag gaatttcaat 20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 57
cccatcaatt cggtaattct 20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 58
tatcatgatg agttttggtc 20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 59
aataatacca ctcacaacgt 20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 60
caactttggt gaatagctga 20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 61
agtgactctg gatttggttc 20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 62
catctccaag tctaaatctg 20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 63
ctaatggtga caactgatcg 20

<210> SEQ ID NO 64

-continued

<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 64
cactgttttt aattcatcag 20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 65
ataatgttcc aattcctact 20

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 66
agaaaaagct cagttaactt 20

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 67
attgtagcca ggcttctaaa 20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 68
atcttcttaa aaataattcg 20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 69
tgtgcaattg tggctaccac 20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 70

-continued aacaatgtca tgttccaggt 20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 71
gctggcaaag tgactataga 20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 72
ttccacagaa gatgtttatt 20

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 73
tttttccaca gaagatgttt 20

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 74
tagagctaaa cgatctagaa 20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 75
taactctttc tggccttgaa 20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 76
attggcccta acagaaaatc 20

<210> SEQ ID NO 77
<211> LENGTH: 20
<212> TYPE: DNA

-continued

<213> ORGANISM: Artificial Sequence
<220> FEATURE:
<223> OTHER INFORMATION: Oligonucleotide primer

<400> SEQUENCE: 77
agaacttatc ctacttaaca 20

<210> SEQ ID NO 78
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 78
gtttccctcg tgttgctcag 20

<210> SEQ ID NO 79
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 79
ttgtacttac tatcatgatg 20

<210> SEQ ID NO 80
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 80
acttacttac ctcacaacgt 20

<210> SEQ ID NO 81
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 81
aatctgtgtc ctttaaaaca 20

<210> SEQ ID NO 82
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 82
tgtgcactga ggagctgagg 20

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 83
acgttcagaa cttatctttt 20

-continued

<210> SEQ ID NO 84
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 84
catgctaaat aattcctact 20

<210> SEQ ID NO 85
<211> LENGTH: 20
<212> TYPE: DNA
<213> ORGANISM: Homo sapiens

<400> SEQUENCE: 85
tgcagctact acatcacttt 20

<210> SEQ ID NO 86
<211> LENGTH: 20
<212> TYPE: DNA
<213> ORGANISM: Homo sapiens

<400> SEQUENCE: 86
acattcacgt atatgatacc 20

<210> SEQ ID NO 87
<211> LENGTH: 20
<212> TYPE: DNA
<213> ORGANISM: Homo sapiens

<400> SEQUENCE: 87
gcgcaagtcc tcaaagcaca 20

<210> SEQ ID NO 88
<211> LENGTH: 20
<212> TYPE: DNA
<213> ORGANISM: Homo sapiens

<400> SEQUENCE: 88
ggtgacatga tttacatttc 20

<210> SEQ ID NO 89
<211> LENGTH: 20
<212> TYPE: DNA
<213> ORGANISM: Homo sapiens

<400> SEQUENCE: 89
gatacaagta gcctctttga 20

<210> SEQ ID NO 90
<211> LENGTH: 20
<212> TYPE: DNA
<213> ORGANISM: Homo sapiens

<400> SEQUENCE: 90
caatcaagaa gttgcattaa 20

<210> SEQ ID NO 91
<211> LENGTH: 20
<212> TYPE: DNA
<213> ORGANISM: Homo sapiens -continued

<400> SEQUENCE: 91
gttaatcata taataatgat 20

<210> SEQ ID NO 92
<211> LENGTH: 20
<212> TYPE: DNA
<213> ORGANISM: Homo sapiens

<400> SEQUENCE: 92
cacctctgga cttgcctttc 20

<210> SEQ ID NO 93
<211> LENGTH: 20
<212> TYPE: DNA
<213> ORGANISM: Homo sapiens

<400> SEQUENCE: 93
atttttggct agggagttta 20

<210> SEQ ID NO 94
<211> LENGTH: 20
<212> TYPE: DNA
<213> ORGANISM: Homo sapiens

<400> SEQUENCE: 94
acaagaacct actgctaatg 20

<210> SEQ ID NO 95
<211> LENGTH: 20
<212> TYPE: DNA
<213> ORGANISM: Homo sapiens

<400> SEQUENCE: 95
agtaaccttt catcatgatc 20

<210> SEQ ID NO 96
<211> LENGTH: 20
<212> TYPE: DNA
<213> ORGANISM: Homo sapiens

<400> SEQUENCE: 96
acagcctgga tatgaaattt 20

<210> SEQ ID NO 97
<211> LENGTH: 20
<212> TYPE: DNA
<213> ORGANISM: Homo sapiens

<400> SEQUENCE: 97
gttacgttcc ttcgatcagt 20

<210> SEQ ID NO 98
<211> LENGTH: 20
<212> TYPE: DNA
<213> ORGANISM: Homo sapiens

<400> SEQUENCE: 98
cagaatgctc agagaaagcg 20

<210> SEQ ID NO 99
<211> LENGTH: 20
<212> TYPE: DNA
<213> ORGANISM: Homo sapiens -continued

<400> SEQUENCE: 99
ggacacagtg tgtttgattt 20

<210> SEQ ID NO 100
<211> LENGTH: 20
<212> TYPE: DNA
<213> ORGANISM: Homo sapiens

<400> SEQUENCE: 100
atgatatgtt tactaaagga 20

<210> SEQ ID NO 101
<211> LENGTH: 20
<212> TYPE: DNA
<213> ORGANISM: Homo sapiens

<400> SEQUENCE: 101
aacctgatgc tttaactttg 20

<210> SEQ ID NO 102
<211> LENGTH: 20
<212> TYPE: DNA
<213> ORGANISM: Homo sapiens

<400> SEQUENCE: 102
gcttctctct agtctcacga 20

<210> SEQ ID NO 103
<211> LENGTH: 20
<212> TYPE: DNA
<213> ORGANISM: Homo sapiens

<400> SEQUENCE: 103
agaaggcagt aacctttcat 20

<210> SEQ ID NO 104
<211> LENGTH: 20
<212> TYPE: DNA
<213> ORGANISM: Homo sapiens

<400> SEQUENCE: 104
ggcgaagtaa agaatctgaa 20

<210> SEQ ID NO 105
<211> LENGTH: 20
<212> TYPE: DNA
<213> ORGANISM: Homo sapiens

<400> SEQUENCE: 105
agaagcccta acgtgttatc 20

<210> SEQ ID NO 106
<211> LENGTH: 20
<212> TYPE: DNA
<213> ORGANISM: Homo sapiens

<400> SEQUENCE: 106
cgtgttatct gtcgctttga 20

<210> SEQ ID NO 107
<211> LENGTH: 20
<212> TYPE: DNA

-continued

<213> ORGANISM: Homo sapiens

<400> SEQUENCE: 107
atgaatatta tcatgctttg 20

<210> SEQ ID NO 108
<211> LENGTH: 20
<212> TYPE: DNA
<213> ORGANISM: Homo sapiens

<400> SEQUENCE: 108
atggttctca cagatgatgg 20

<210> SEQ ID NO 109
<211> LENGTH: 20
<212> TYPE: DNA
<213> ORGANISM: Homo sapiens

<400> SEQUENCE: 109
gtgccacatc atcaccatat 20

<210> SEQ ID NO 110
<211> LENGTH: 20
<212> TYPE: DNA
<213> ORGANISM: Homo sapiens

<400> SEQUENCE: 110
gctggatcac agacagctca 20

<210> SEQ ID NO 111
<211> LENGTH: 20
<212> TYPE: DNA
<213> ORGANISM: Homo sapiens

<400> SEQUENCE: 111
gaagccctaa cgtgttatct 20

<210> SEQ ID NO 112
<211> LENGTH: 20
<212> TYPE: DNA
<213> ORGANISM: Homo sapiens

<400> SEQUENCE: 112
gcggggaccg attcaccatg 20

<210> SEQ ID NO 113
<211> LENGTH: 20
<212> TYPE: DNA
<213> ORGANISM: Homo sapiens

<400> SEQUENCE: 113
agcaactgtc atatataaca 20

<210> SEQ ID NO 114
<211> LENGTH: 20
<212> TYPE: DNA
<213> ORGANISM: Homo sapiens

<400> SEQUENCE: 114
gagttcgcat cttgataagg 20

<210> SEQ ID NO 115
<211> LENGTH: 20

-continued

<212> TYPE: DNA
<213> ORGANISM: Homo sapiens

<400> SEQUENCE: 115
tacatgggat taactcagtt 20

<210> SEQ ID NO 116
<211> LENGTH: 20
<212> TYPE: DNA
<213> ORGANISM: Homo sapiens

<400> SEQUENCE: 116
cttacacaca gaaatggcct 20

<210> SEQ ID NO 117
<211> LENGTH: 20
<212> TYPE: DNA
<213> ORGANISM: Homo sapiens

<400> SEQUENCE: 117
agaattaccg aattgatggg 20

<210> SEQ ID NO 118
<211> LENGTH: 20
<212> TYPE: DNA
<213> ORGANISM: Homo sapiens

<400> SEQUENCE: 118
gaccaaaact catcatgata 20

<210> SEQ ID NO 119
<211> LENGTH: 20
<212> TYPE: DNA
<213> ORGANISM: Homo sapiens

<400> SEQUENCE: 119
acgttgtgag tggtattatt 20

<210> SEQ ID NO 120
<211> LENGTH: 20
<212> TYPE: DNA
<213> ORGANISM: Homo sapiens

<400> SEQUENCE: 120
tcagctattc accaaagttg 20

<210> SEQ ID NO 121
<211> LENGTH: 20
<212> TYPE: DNA
<213> ORGANISM: Homo sapiens

<400> SEQUENCE: 121
gaaccaaatc cagagtcact 20

<210> SEQ ID NO 122
<211> LENGTH: 20
<212> TYPE: DNA
<213> ORGANISM: Homo sapiens

<400> SEQUENCE: 122
cgatcagttg tcaccattag 20

<210> SEQ ID NO 123

-continued

<211> LENGTH: 20
<212> TYPE: DNA
<213> ORGANISM: Homo sapiens

<400> SEQUENCE: 123
ctgatgaatt aaaaacagtg 20

<210> SEQ ID NO 124
<211> LENGTH: 20
<212> TYPE: DNA
<213> ORGANISM: Homo sapiens

<400> SEQUENCE: 124
aagttaactg agctttttct 20

<210> SEQ ID NO 125
<211> LENGTH: 20
<212> TYPE: DNA
<213> ORGANISM: Homo sapiens

<400> SEQUENCE: 125
tttagaagcc tggctacaat 20

<210> SEQ ID NO 126
<211> LENGTH: 20
<212> TYPE: DNA
<213> ORGANISM: Homo sapiens

<400> SEQUENCE: 126
gtggtagcca caattgcaca 20

<210> SEQ ID NO 127
<211> LENGTH: 20
<212> TYPE: DNA
<213> ORGANISM: Homo sapiens

<400> SEQUENCE: 127
acctggaaca tgacattgtt 20

<210> SEQ ID NO 128
<211> LENGTH: 20
<212> TYPE: DNA
<213> ORGANISM: Homo sapiens

<400> SEQUENCE: 128
tctatagtca ctttgccagc 20

<210> SEQ ID NO 129
<211> LENGTH: 20
<212> TYPE: DNA
<213> ORGANISM: Homo sapiens

<400> SEQUENCE: 129
ttctagatcg tttagctcta 20

<210> SEQ ID NO 130
<211> LENGTH: 20
<212> TYPE: DNA
<213> ORGANISM: Homo sapiens

<400> SEQUENCE: 130
ttcaaggcca gaaagagtta 20

-continued

<210> SEQ ID NO 131
<211> LENGTH: 20
<212> TYPE: DNA
<213> ORGANISM: Homo sapiens

<400> SEQUENCE: 131
ctgagcaaca cgagggaaac 20

<210> SEQ ID NO 132
<211> LENGTH: 20
<212> TYPE: DNA
<213> ORGANISM: Homo sapiens

<400> SEQUENCE: 132
aaaagataag ttctgaacgt 20

<210> SEQ ID NO 133
<211> LENGTH: 3933
<212> TYPE: DNA
<213> ORGANISM: Homo Sapiens
<220> FEATURE:
<221> NAME/KEY: misc_feature
<222> LOCATION: (265)..(2745)
<223> OTHER INFORMATION: CDS
<300> PUBLICATION INFORMATION:
<301> AUTHORS: Hogenesch, et al.
<302> TITLE: Characterization Of A Subset Of The Basic-Helix-Loop-Helix-
PAS Superfamily That Interacts With Components Of The Dioxin
Signaling
<303> JOURNAL: J. Biol. Chem.
<304> VOLUME: 272
<305> ISSUE: 13
<306> PAGES: 8581-8593
<307> DATE: 1997
<308> DATABASE ACCESSION NUMBER: U29165.1
<309> DATABASE ENTRY DATE: 1997-04-11
<313> RELEVANT RESIDUES: (1)..(3933)

<400> SEQUENCE: 133
cacgaggcag cactctcttc gtcgcttcgg ccagtgtgtc gggctgggcc ctgacaagcc 60
acctgaggag aggctcggag ccgggcccgg accccggcga ttgccgcccg cttctctcta 120
gtctcacgag gggtttcccg cctcgcaccc ccacctctgg acttgccttt ccttctcttc 180
tccgcgtgtg gagggagcca gcgcttaggc cggagcgagc ctgggggccg cccgccgtga 240
agacatcgcg gggaccgatt caccatggag ggcgccggcg gcgcgaacga caagaaaaag 300
ataagttctg aacgtcgaaa agaaaagtct cgagatgcag ccagatctcg gcgaagtaaa 360
gaatctgaag ttttttatga gcttgctcat cagttgccac ttccacataa tgtgagttcg 420
catcttgata aggcctctgt gatgaggctt accatcagct atttgcgtgt gaggaaactt 480
ctggatgctg gtgatttgga tattgaagat gacatgaaag cacagatgaa ttgcttttat 540
ttgaaagcct tggatggttt tgttatggtt ctcacagatg atggtgacat gatttacatt 600
tctgataatg tgaacaaata catgggatta actcagtttg aactaactgg acacagtgtg 660
tttgatttta ctcatccatg tgaccatgag gaaatgagag aaatgcttac acacagaaat 720
ggccttgtga aaaagggtaa agaacaaaac acacagcgaa gcttttttct cagaatgaag 780
tgtaccctaa ctagccgagg aagaactatg aacataaagt ctgcaacatg gaaggtattg 840
cactgcacag gccacattca cgtatatgat accaacagta accaacctca gtgtgggtat 900
aagaaaccac ctatgacctg cttggtgctg atttgtgaac ccattcctca cccatcaaat 960
attgaaattc ctttagatag caagactttc ctcagtcgac acagcctgga tatgaaattt 1020
tcttattgtg atgaaagaat taccgaattg atgggatatg agccagaaga acttttaggc 1080

-continued

```
cgctcaattt atgaatatta tcatgctttg gactctgatc atctgaccaa aactcatcat   1140
gatatgttta ctaaaggaca agtcaccaca ggacagtaca ggatgcttgc caaaagaggt   1200
ggatatgtct gggttgaaac tcaagcaact gtcatatata acaccaagaa ttctcaacca   1260
cagtgcattg tatgtgtgaa ttacgttgtg agtggtatta ttcagcacga cttgattttc   1320
tcccttcaac aaacagaatg tgtccttaaa ccggttgaat cttcagatat gaaaatgact   1380
cagctattca ccaaagttga atcagaagat acaagtagcc tctttgacaa acttaagaag   1440
gaacctgatg ctttaacttt gctggcccca gccgctggag acacaatcat atctttagat   1500
tttggcagca acgacacaga aactgatgac cagcaacttg aggaagtacc attatataat   1560
gatgtaatgc tcccctcacc caacgaaaaa ttacagaata taaatttggc aatgtctcca   1620
ttacccaccg ctgaaacgcc aaagccactt cgaagtagtg ctgaccctgc actcaatcaa   1680
gaagttgcat taaaattaga accaaatcca gagtcactgg aactttcttt taccatgccc   1740
cagattcagg atcagacacc tagtccttcc gatggaagca ctagacaaag ttcacctgag   1800
cctaatagtc ccagtgaata ttgtttttat gtggatagtg atatggtcaa tgaattcaag   1860
ttggaattgg tagaaaaact ttttgctgaa gacacagaag caaagaaccc attttctact   1920
caggacacag atttagactt ggagatgtta gctccctata tcccaatgga tgatgacttc   1980
cagttacgtt ccttcgatca gttgtcacca ttagaaagca gttccgcaag ccctgaaagc   2040
gcaagtcctc aaagcacagt tacagtattc cagcagactc aaatacaaga acctactgct   2100
aatgccacca ctaccactgc caccactgat gaattaaaaa cagtgacaaa agaccgtatg   2160
gaagacatta aaatattgat tgcatctcca tctcctaccc acatacataa agaaactact   2220
agtgccacat catcaccata tagagatact caaagtcgga cagcctcacc aaacagagca   2280
ggaaaaggag tcatagaaca gacagaaaaa tctcatccaa gaagccctaa cgtgttatct   2340
gtcgctttga gtcaaagaac tacagttcct gaggaagaac taaatccaaa gatactagct   2400
ttgcagaatg ctcagagaaa gcgaaaaatg gaacatgatg gttcactttt tcaagcagta   2460
ggaattggaa cattattaca gcagccagac gatcatgcag ctactacatc actttcttgg   2520
aaacgtgtaa aaggatgcaa atctagtgaa cagaatggaa tggagcaaaa gacaattatt   2580
ttaataccct ctgatttagc atgtagactg ctggggcaat caatggatga aagtggatta   2640
ccacagctga ccagttatga ttgtgaagtt aatgctccta tacaaggcag cagaaaccta   2700
ctgcagggtg aagaattact cagagctttg gatcaagtta actgagcttt ttcttaattt   2760
cattcctttt tttggacact ggtggctcac tacctaaagc agtctattta tattttctac   2820
atctaatttt agaagcctgg ctacaatact gcacaaactt ggttagttca atttttgatc   2880
ccctttctac ttaatttaca ttaatgctct tttttagtat gttctttaat gctggatcac   2940
agacagctca ttttctcagt tttttggtat ttaaaccatt gcattgcagt agcatcattt   3000
taaaaaatgc acctttttat ttatttattt ttggctaggg agtttatccc tttttcgaat   3060
tatttttaag aagatgccaa tataattttt gtaagaaggc agtaaccttt catcatgatc   3120
ataggcagtt gaaaaatttt tacacctttt ttttcacatt ttacataaat aataatgctt   3180
tgccagcagt acgtggtagc cacaattgca caatatattt tcttaaaaaa taccagcagt   3240
tactcatgga atatattctg cgtttataaa actagttttt aagaagaaat ttttttggc   3300
ctatgaaatt gttaaacctg gaacatgaca ttgttaatca tataataatg attcttaaat   3360
gctgtatggt ttattattta aatgggtaaa gccatttaca taatatagaa agatatgcat   3420
```

-continued

```
atatctagaa ggtatgtggc atttatttgg ataaaattct caattcagag aaatcatctg   3480

atgtttctat agtcactttg ccagctcaaa agaaaacaat accctatgta gttgtggaag   3540

tttatgctaa tattgtgtaa ctgatattaa acctaaatgt tctgcctacc ctgttggtat   3600

aaagatattt tgagcagact gtaaacaaga aaaaaaaaat catgcattct tagcaaaatt   3660

gcctagtatg ttaatttgct caaaatacaa tgtttgattt tatgcacttt gtcgctatta   3720

acatcctttt tttcatgtag atttcaataa ttgagtaatt ttagaagcat tattttagga   3780

atatatagtt gtcacagtaa atatcttgtt ttttctatgt acattgtaca aatttttcat   3840

tccttttgct ctttgtggtt ggatctaaca ctaactgtat tgttttgtta catcaaataa   3900

acatcttctg tggaaaaaaa aaaaaaaaaa aaa                                 3933
```

```
<210> SEQ ID NO 134
<211> LENGTH: 20
<212> TYPE: DNA
<213> ORGANISM: Artificial Sequence
<220> FEATURE:
<223> OTHER INFORMATION: Synthetic Construct

<400> SEQUENCE: 134

tgatgagcaa gctcataaaa                                                 20


<210> SEQ ID NO 135
<211> LENGTH: 20
<212> TYPE: DNA
<213> ORGANISM: Artificial Sequence
<220> FEATURE:
<223> OTHER INFORMATION: Synthetic Construct

<400> SEQUENCE: 135

gcaactgatg agcaagctca                                                 20


<210> SEQ ID NO 136
<211> LENGTH: 20
<212> TYPE: DNA
<213> ORGANISM: Artificial Sequence
<220> FEATURE:
<223> OTHER INFORMATION: Synthetic Construct

<400> SEQUENCE: 136

ggaagtggca actgatgagc                                                 20


<210> SEQ ID NO 137
<211> LENGTH: 20
<212> TYPE: DNA
<213> ORGANISM: Artificial Sequence
<220> FEATURE:
<223> OTHER INFORMATION: Synthetic Construct

<400> SEQUENCE: 137

ccagttagtt caaactgagt                                                 20


<210> SEQ ID NO 138
<211> LENGTH: 20
<212> TYPE: DNA
<213> ORGANISM: Artificial Sequence
<220> FEATURE:
<223> OTHER INFORMATION: Synthetic Construct

<400> SEQUENCE: 138

tgtgtccagt tagttcaaac                                                 20
```

-continued

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct

<400> SEQUENCE: 139
cacactgtgt ccagttagtt 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct

<400> SEQUENCE: 140
cacatggatg agtaaaatca 20

<210> SEQ ID NO 141
<211> LENGTH: 20
<212> TYPE: DNA
<213> ORGANISM: Artificial Sequence
<220> FEATURE:
<223> OTHER INFORMATION: Synthetic Construct

<400> SEQUENCE: 141
tcctcatggt cacatggatg 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Construct

<400> SEQUENCE: 142
tctctcattt cctcatggtc 20

<210> SEQ ID NO 143
<211> LENGTH: 20
<212> TYPE: DNA
<213> ORGANISM: Artificial Sequence
<220> FEATURE:
<223> OTHER INFORMATION: Synthetic Construct

<400> SEQUENCE: 143
gcatttctct catttcctca 20

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct

<400> SEQUENCE: 144
gtgtgtaagc atttctctca 20

<210> SEQ ID NO 145
<211> LENGTH: 20
<212> TYPE: DNA
<213> ORGANISM: Artificial Sequence
<220> FEATURE:
<223> OTHER INFORMATION: Synthetic Construct -continued

<400> SEQUENCE: 145
ggccatttct gtgtgtaagc 20

<210> SEQ ID NO 146
<211> LENGTH: 20
<212> TYPE: DNA
<213> ORGANISM: Artificial Sequence
<220> FEATURE:
<223> OTHER INFORMATION: Synthetic Construct

<400> SEQUENCE: 146
tggttactgt tggtatcata 20

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct

<400> SEQUENCE: 147
tcacaaatca gcaccaagca 20

<210> SEQ ID NO 148
<211> LENGTH: 20
<212> TYPE: DNA
<213> ORGANISM: Artificial Sequence
<220> FEATURE:
<223> OTHER INFORMATION: Synthetic Construct

<400> SEQUENCE: 148
tgggttcaca aatcagcacc 20

<210> SEQ ID NO 149
<211> LENGTH: 20
<212> TYPE: DNA
<213> ORGANISM: Artificial Sequence
<220> FEATURE:
<223> OTHER INFORMATION: Synthetic Construct

<400> SEQUENCE: 149
tgaggaatgg gttcacaaat 20

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct

<400> SEQUENCE: 150
gtcttgctat ctaaaggaat 20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct

<400> SEQUENCE: 151
tattcataaa ttgagcggcc 20

<210> SEQ ID NO 152
<211> LENGTH: 20

-continued

<212> TYPE: DNA
<213> ORGANISM: Artificial Sequence
<220> FEATURE:
<223> OTHER INFORMATION: Synthetic Construct

<400> SEQUENCE: 152
tgataatatt cataaattga 20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct

<400> SEQUENCE: 153
tgagttttgg tcagatgatc 20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct

<400> SEQUENCE: 154
acttgtcctt tagtaaacat 20

<210> SEQ ID NO 155
<211> LENGTH: 20
<212> TYPE: DNA
<213> ORGANISM: Artificial Sequence
<220> FEATURE:
<223> OTHER INFORMATION: Synthetic Construct

<400> SEQUENCE: 155
tggtgacttg tcctttagta 20

<210> SEQ ID NO 156
<211> LENGTH: 20
<212> TYPE: DNA
<213> ORGANISM: Artificial Sequence
<220> FEATURE:
<223> OTHER INFORMATION: Synthetic Construct

<400> SEQUENCE: 156
tcctgtggtg acttgtcctt 20

<210> SEQ ID NO 157
<211> LENGTH: 20
<212> TYPE: DNA
<213> ORGANISM: Artificial Sequence
<220> FEATURE:
<223> OTHER INFORMATION: Synthetic Construct

<400> SEQUENCE: 157
tactgtcctg tggtgacttg 20

<210> SEQ ID NO 158
<211> LENGTH: 20
<212> TYPE: DNA
<213> ORGANISM: Artificial Sequence
<220> FEATURE:
<223> OTHER INFORMATION: Synthetic Construct

<400> SEQUENCE: 158

-continued tcctgtactg tcctgtggtg 20

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct

<400> SEQUENCE: 159
gcaagcatcc tgtactgtcc 20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct

<400> SEQUENCE: 160
cagacatatc cacctctttt 20

<210> SEQ ID NO 161
<211> LENGTH: 20
<212> TYPE: DNA
<213> ORGANISM: Artificial Sequence
<220> FEATURE:
<223> OTHER INFORMATION: Synthetic Construct

<400> SEQUENCE: 161
tcaacccaga catatccacc 20

<210> SEQ ID NO 162
<211> LENGTH: 20
<212> TYPE: DNA
<213> ORGANISM: Artificial Sequence
<220> FEATURE:
<223> OTHER INFORMATION: Synthetic Construct

<400> SEQUENCE: 162
tatgacagtt gcttgagttt 20

<210> SEQ ID NO 163
<211> LENGTH: 20
<212> TYPE: DNA
<213> ORGANISM: Artificial Sequence
<220> FEATURE:
<223> OTHER INFORMATION: Synthetic Construct

<400> SEQUENCE: 163
ttatatatga cagttgcttg 20

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct

<400> SEQUENCE: 164
gaagggagaa aatcaagtcg 20

<210> SEQ ID NO 165
<211> LENGTH: 20
<212> TYPE: DNA
<213> ORGANISM: Artificial Sequence -continued
<220> FEATURE:
<223> OTHER INFORMATION: Synthetic Construct

<400> SEQUENCE: 165
attctgtttg ttgaagggag 20

<210> SEQ ID NO 166
<211> LENGTH: 20
<212> TYPE: DNA
<213> ORGANISM: Artificial Sequence
<220> FEATURE:
<223> OTHER INFORMATION: Synthetic Construct

<400> SEQUENCE: 166
ttcatatctg aagattcaac 20

<210> SEQ ID NO 167
<211> LENGTH: 20
<212> TYPE: DNA
<213> ORGANISM: Artificial Sequence
<220> FEATURE:
<223> OTHER INFORMATION: Synthetic Construct

<400> SEQUENCE: 167
tctgattcaa ctttggtgaa 20

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct

<400> SEQUENCE: 168
attacatcat tatataatgg 20

<210> SEQ ID NO 169
<211> LENGTH: 20
<212> TYPE: DNA
<213> ORGANISM: Artificial Sequence
<220> FEATURE:
<223> OTHER INFORMATION: Synthetic Construct

<400> SEQUENCE: 169
ctacttcgaa gtggctttgg 20

<210> SEQ ID NO 170
<211> LENGTH: 20
<212> TYPE: DNA
<213> ORGANISM: Artificial Sequence
<220> FEATURE:
<223> OTHER INFORMATION: Synthetic Construct

<400> SEQUENCE: 170
tcagcactac ttcgaagtgg 20

<210> SEQ ID NO 171
<211> LENGTH: 20
<212> TYPE: DNA
<213> ORGANISM: Artificial Sequence
<220> FEATURE:
<223> OTHER INFORMATION: Synthetic Construct

<400> SEQUENCE: 171
ctttgtctag tgcttccatc 20

-continued

<210> SEQ ID NO 172
<211> LENGTH: 20
<212> TYPE: DNA
<213> ORGANISM: Artificial Sequence
<220> FEATURE:
<223> OTHER INFORMATION: Synthetic Construct

<400> SEQUENCE: 172
atcatccatt gggatatagg 20

<210> SEQ ID NO 173
<211> LENGTH: 20
<212> TYPE: DNA
<213> ORGANISM: Artificial Sequence
<220> FEATURE:
<223> OTHER INFORMATION: Synthetic Construct

<400> SEQUENCE: 173
tctaatggtg acaactgatc 20

<210> SEQ ID NO 174
<211> LENGTH: 20
<212> TYPE: DNA
<213> ORGANISM: Artificial Sequence
<220> FEATURE:
<223> OTHER INFORMATION: Synthetic Construct

<400> SEQUENCE: 174
catcatgttc catttttcgc 20

<210> SEQ ID NO 175
<211> LENGTH: 20
<212> TYPE: DNA
<213> ORGANISM: Artificial Sequence
<220> FEATURE:
<223> OTHER INFORMATION: Synthetic Construct

<400> SEQUENCE: 175
gtcagctgtg gtaatccact 20

<210> SEQ ID NO 176
<211> LENGTH: 20
<212> TYPE: DNA
<213> ORGANISM: Artificial Sequence
<220> FEATURE:
<223> OTHER INFORMATION: Synthetic Construct

<400> SEQUENCE: 176
taactggtca gctgtggtaa 20

<210> SEQ ID NO 177
<211> LENGTH: 20
<212> TYPE: DNA
<213> ORGANISM: Artificial Sequence
<220> FEATURE:
<223> OTHER INFORMATION: Synthetic Construct

<400> SEQUENCE: 177
ggagcattaa cttcacaatc 20

<210> SEQ ID NO 178
<211> LENGTH: 20
<212> TYPE: DNA
<213> ORGANISM: Artificial Sequence
<220> FEATURE:
<223> OTHER INFORMATION: Synthetic Construct -continued

<400> SEQUENCE: 178
aggtttctgc tgccttgtat 20

<210> SEQ ID NO 179
<211> LENGTH: 20
<212> TYPE: DNA
<213> ORGANISM: Artificial Sequence
<220> FEATURE:
<223> OTHER INFORMATION: Synthetic Construct

<400> SEQUENCE: 179
ccctgcagta ggtttctgct 20

<210> SEQ ID NO 180
<211> LENGTH: 20
<212> TYPE: DNA
<213> ORGANISM: Artificial Sequence
<220> FEATURE:
<223> OTHER INFORMATION: Synthetic Construct

<400> SEQUENCE: 180
cttcaccctg cagtaggttt 20

<210> SEQ ID NO 181
<211> LENGTH: 20
<212> TYPE: DNA
<213> ORGANISM: Artificial Sequence
<220> FEATURE:
<223> OTHER INFORMATION: Synthetic Construct

<400> SEQUENCE: 181
taattcttca ccctgcagta 20

<210> SEQ ID NO 182
<211> LENGTH: 20
<212> TYPE: DNA
<213> ORGANISM: Artificial Sequence
<220> FEATURE:
<223> OTHER INFORMATION: Synthetic Construct

<400> SEQUENCE: 182
ctgagtaatt cttcaccctg 20

<210> SEQ ID NO 183
<211> LENGTH: 20
<212> TYPE: DNA
<213> ORGANISM: Artificial Sequence
<220> FEATURE:
<223> OTHER INFORMATION: Synthetic Construct

<400> SEQUENCE: 183
aagctctgag taattcttca 20

<210> SEQ ID NO 184
<211> LENGTH: 20
<212> TYPE: DNA
<213> ORGANISM: Artificial Sequence
<220> FEATURE:
<223> OTHER INFORMATION: Synthetic Construct

<400> SEQUENCE: 184
atccaaagct ctgagtaatt 20

<210> SEQ ID NO 185

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 185

acttgatcca aagctctgag                                                    20

<210> SEQ ID NO 186
<211> LENGTH: 20
<212> TYPE: DNA
<213> ORGANISM: Artificial Sequence
<220> FEATURE:
<223> OTHER INFORMATION: Synthetic Construct

<400> SEQUENCE: 186

gctcagttaa cttgatccaa                                                    20

<210> SEQ ID NO 187
<211> LENGTH: 20
<212> TYPE: DNA
<213> ORGANISM: Artificial Sequence
<220> FEATURE:
<223> OTHER INFORMATION: Synthetic Construct

<400> SEQUENCE: 187

tgagccacca gtgtccaaaa                                                    20

<210> SEQ ID NO 188
<211> LENGTH: 20
<212> TYPE: DNA
<213> ORGANISM: Artificial Sequence
<220> FEATURE:
<223> OTHER INFORMATION: Synthetic Construct

<400> SEQUENCE: 188

ccaggcttct aaaattagat                                                    20

<210> SEQ ID NO 189
<211> LENGTH: 20
<212> TYPE: DNA
<213> ORGANISM: Artificial Sequence
<220> FEATURE:
<223> OTHER INFORMATION: Synthetic Construct

<400> SEQUENCE: 189

gtgcagtatt gtagccaggc                                                    20

<210> SEQ ID NO 190
<211> LENGTH: 20
<212> TYPE: DNA
<213> ORGANISM: Artificial Sequence
<220> FEATURE:
<223> OTHER INFORMATION: Synthetic Construct

<400> SEQUENCE: 190

agtttgtgca gtattgtagc                                                    20

<210> SEQ ID NO 191
<211> LENGTH: 20
<212> TYPE: DNA
<213> ORGANISM: Artificial Sequence
<220> FEATURE:
<223> OTHER INFORMATION: Synthetic Construct

<400> SEQUENCE: 191
```

-continued taaataaaaa ggtgcatttt 20

<210> SEQ ID NO 192
<211> LENGTH: 20
<212> TYPE: DNA
<213> ORGANISM: Artificial Sequence
<220> FEATURE:
<223> OTHER INFORMATION: Synthetic Construct

<400> SEQUENCE: 192
actgcctatg atcatgatga 20

<210> SEQ ID NO 193
<211> LENGTH: 20
<212> TYPE: DNA
<213> ORGANISM: Artificial Sequence
<220> FEATURE:
<223> OTHER INFORMATION: Synthetic Construct

<400> SEQUENCE: 193
ttgtgcaatt gtggctacca 20

<210> SEQ ID NO 194
<211> LENGTH: 20
<212> TYPE: DNA
<213> ORGANISM: Artificial Sequence
<220> FEATURE:
<223> OTHER INFORMATION: Synthetic Construct

<400> SEQUENCE: 194
atatattgtg caattgtggc 20

<210> SEQ ID NO 195
<211> LENGTH: 20
<212> TYPE: DNA
<213> ORGANISM: Artificial Sequence
<220> FEATURE:
<223> OTHER INFORMATION: Synthetic Construct

<400> SEQUENCE: 195
agaaaatata ttgtgcaatt 20

<210> SEQ ID NO 196
<211> LENGTH: 20
<212> TYPE: DNA
<213> ORGANISM: Artificial Sequence
<220> FEATURE:
<223> OTHER INFORMATION: Synthetic Construct

<400> SEQUENCE: 196
cttaaaaact agttttataa 20

<210> SEQ ID NO 197
<211> LENGTH: 20
<212> TYPE: DNA
<213> ORGANISM: Artificial Sequence
<220> FEATURE:
<223> OTHER INFORMATION: Synthetic Construct

<400> SEQUENCE: 197
atgtaaatgg ctttacccat 20

<210> SEQ ID NO 198
<211> LENGTH: 20
<212> TYPE: DNA

-continued

<213> ORGANISM: Artificial Sequence
<220> FEATURE:
<223> OTHER INFORMATION: Synthetic Construct

<400> SEQUENCE: 198
ttttatccaa ataaatgcca 20

<210> SEQ ID NO 199
<211> LENGTH: 20
<212> TYPE: DNA
<213> ORGANISM: Artificial Sequence
<220> FEATURE:
<223> OTHER INFORMATION: Synthetic Construct

<400> SEQUENCE: 199
tgagaatttt atccaaataa 20

<210> SEQ ID NO 200
<211> LENGTH: 20
<212> TYPE: DNA
<213> ORGANISM: Artificial Sequence
<220> FEATURE:
<223> OTHER INFORMATION: Synthetic Construct

<400> SEQUENCE: 200
taatagcgac aaagtgcata 20

<210> SEQ ID NO 201
<211> LENGTH: 20
<212> TYPE: DNA
<213> ORGANISM: Artificial Sequence
<220> FEATURE:
<223> OTHER INFORMATION: Synthetic Construct

<400> SEQUENCE: 201
gatgttaata gcgacaaagt 20

<210> SEQ ID NO 202
<211> LENGTH: 20
<212> TYPE: DNA
<213> ORGANISM: Artificial Sequence
<220> FEATURE:
<223> OTHER INFORMATION: Synthetic Construct

<400> SEQUENCE: 202
aaaaggatgt taatagcgac 20

<210> SEQ ID NO 203
<211> LENGTH: 20
<212> TYPE: DNA
<213> ORGANISM: Artificial Sequence
<220> FEATURE:
<223> OTHER INFORMATION: Synthetic Construct

<400> SEQUENCE: 203
aatgcttcta aaattactca 20

<210> SEQ ID NO 204
<211> LENGTH: 20
<212> TYPE: DNA
<213> ORGANISM: Artificial Sequence
<220> FEATURE:
<223> OTHER INFORMATION: Synthetic Construct

<400> SEQUENCE: 204
tatattccta aaataatgct 20

-continued

```
<210> SEQ ID NO 205
<211> LENGTH: 20
<212> TYPE: DNA
<213> ORGANISM: Artificial Sequence
<220> FEATURE:
<223> OTHER INFORMATION: Synthetic Construct

<400> SEQUENCE: 205

acagaagatg tttatttgat                                               20


<210> SEQ ID NO 206
<211> LENGTH: 3973
<212> TYPE: DNA
<213> ORGANISM: Mus muculus
<220> FEATURE:
<221> NAME/KEY: misc_feature
<222> LOCATION: (258)..(2768)
<223> OTHER INFORMATION: CDS
<300> PUBLICATION INFORMATION:
<308> DATABASE ACCESSION NUMBER: NM_010431.1
<309> DATABASE ENTRY DATE: 2003-12-20
<313> RELEVANT RESIDUES: (1)..(3973)

<400> SEQUENCE: 206

cgcgaggact gtcctcgccg ccgtcgcggg cagtgtctag ccaggccttg acaagctagc     60

cggaggagcg cctaggaacc cgagccggag ctcagcgagc gcagcctgca cgcccgcctc    120

gcgtcccggg ggggtcccgc ctcccacccc gcctctggac ttgtctcttt ccccgcgcgc    180

gcggacagag ccggcgttta ggcccgagcg agcccggggg ccgccggccg ggaagacaac    240

gcgggcaccg attcgccatg gagggcgccg gcggcgagaa cgagaagaaa aagatgagtt    300

ctgaacgtcg aaaagaaaag tctagagatg cagcaagatc tcggcgaagc aaagagtctg    360

aagtttttta tgagcttgct catcagttgc cacttcccca caatgtgagc tcacatcttg    420

ataaagcttc tgttatgagg ctcaccatca gttatttacg tgtgagaaaa cttctggatg    480

ccggtggtct agacagtgaa gatgagatga aggcacagat ggactgtttt tatctgaaag    540

ccctagatgg ctttgtgatg gtgctaacag atgacggcga catggtttac atttctgata    600

acgtgaacaa atacatgggg ttaactcagt ttgaactaac tggacacagt gtgtttgatt    660

ttactcatcc atgtgaccat gaggaaatga gagaaatgct tacacacaga aatggcccag    720

tgagaaaagg gaaagaacta aacacacagc ggagcttttt tctcagaatg aagtgcaccc    780

taacaagccg gggaggacg atgaacatca agtcagcaac gtggaaggtg cttcactgca     840

cgggccatat tcatgtctat gataccaaca gtaaccaacc tcagtgtggg tacaagaaac    900

cacccatgac gtgcttggtg ctgatttgtg aacccattcc tcatccgtca aatattgaaa    960

ttcctttaga tagcaagaca tttctcagtc gacacagcct cgatatgaaa ttttcttact   1020

gtgatgaaag aattactgag ttgatgggtt atgagccgga agaacttttg ggccgctcaa   1080

tttatgaata ttatcatgct ttggattctg atcatctgac caaaactcac catgatatgt   1140

ttactaaagg acaagtcacc acaggacagt acaggatgct tgccaaaaga ggtggatatg   1200

tctgggttga aactcaagca actgtcatat ataatacgaa gaactcccag ccacagtgca   1260

ttgtgtgtgt gaattatgtt gtaagtggta ttattcagca cgacttgatt ttctcccttc   1320

aacaaacaga atctgtgctc aaaccagttg aatcttcaga tatgaagatg actcagctgt   1380

tcaccaaagt tgaatcagag gatacaagct gcctttttga taagcttaag aaggagcctg   1440

atgctctcac tctgctggct ccagctgccg gcgacaccat catctctctg gattttggca   1500
```

-continued

```
gcgatgacac agaaactgaa gatcaacaac ttgaagatgt tccattatat aatgatgtaa   1560
tgtttccctc ttctaatgaa aaattaaata taaacctggc aatgtctcct ttaccttcat   1620
cggaaactcc aaagccactt cgaagtagtg ctgatcctgc actgaatcaa gaggttgcat   1680
taaaattaga atcaagtcca gagtcactgg gactttcttt taccatgccc cagattcaag   1740
atcagccagc aagtccttct gatggaagca ctagacaaag ttcacctgag agacttcttc   1800
aggaaaacgt aaacactcct aacttttccc agcctaacag tcccagtgaa tattgctttg   1860
atgtggatag cgatatggtc aatgtattca agttggaact ggtggaaaaa ctgtttgctg   1920
aagacacaga ggcaaagaat ccattttcaa ctcaggacac tgatttagat ttggagatgc   1980
tggctcccta tatcccaatg gatgatgatt tccagttacg ttcctttgat cagttgtcac   2040
cattagagag caattctcca agccctccaa gtatgagcac agttactggg ttccagcaga   2100
cccagttaca gaaacctacc atcactgcca ctgccaccac aactgccacc actgatgaat   2160
caaaaacaga gacgaaggac aataaagaag atattaaaat actgattgca tctccatctt   2220
ctacccaagt acctcaagaa acgaccactg ctaaggcatc agcatacagt ggcactcaca   2280
gtcggacagc ctcaccagac agagcaggaa agagagtcat agaacagaca gacaaagctc   2340
atccaaggag ccttaagctg tctgccactt tgaatcaaag aaatactgtt cctgaggaag   2400
aattaaaccc aaagacaata gcttcgcaga atgctcagag gaagcgaaaa atggaacatg   2460
atggctccct tttcaagca gcaggaattg gaacattatt gcagcaacca ggtgactgtg   2520
cacctactat gtcactttcc tggaaacgag tgaaaggatt catatctagt gaacagaatg   2580
gaacggagca aaagactatt attttaatac cctccgattt agcatgcaga ctgctggggc   2640
agtcaatgga tgagagtgga ttaccacagc tgaccagtta cgattgtgaa gttaatgctc   2700
ccatacaagg cagcagaaac ctactgcagg gtgaagaatt actcagagct ttggatcaag   2760
ttaactgagc gtttcctaat ctcattcctt ttgattgtta atgtttttgt tcagttgttg   2820
ttgtttgttg ggtttttgtt tctgttggtt atttttggac actggtggct cagcagtcta   2880
tttatatttt ctatatctaa ttttagaagc ctggctacaa tactgcacaa actcagatag   2940
tttagttttc atcccctttc tacttaattt tcattaatgc tctttttaat atgttctttt   3000
aatgccagat cacagcacat tcacagctcc tcagcatttc accattgcat tgctgtagtg   3060
tcatttaaaa tgcacctttt tatttattta tttttggtga gggagtttgt cccttattga   3120
attattttta atgaaatgcc aatataattt tttaagaaag cagtaaattc tcatcatgat   3180
cataggcagt tgaaaacttt ttactcattt ttttcatgtt ttacatgaaa ataatgcttt   3240
gtcagcagta catggtagcc acaattgcac aatatatttt ctttaaaaaa ccagcagtta   3300
ctcatgcaat atattctgca tttataaaac tagtttttaa gaaatttttt ttggcctatg   3360
gaattgttaa gcctggatca tgaagcgttg atcttataat gattcttaaa ctgtatggtt   3420
tctttatatg ggtaaagcca tttacatgat ataaagaaat atgcttatat ctggaaggta   3480
tgtggcattt atttggataa aattctcaat tcagagaagt tatctggtgt ttcttgactt   3540
taccaactca aaacagtccc tctgtagttg tggaagctta tgctaatatt gtgtaattga   3600
ttatgaaaca taaatgttct gcccaccctg ttggtataaa gacattttga gcatactgta   3660
aacaaacaaa caaaaaatca tgctttgtta gtaaaattgc ctagtatgtt gatttgttga   3720
aaatatgatg tttggtttta tgcactttgt cgctattaac atcctttttt catatagatt   3780
tcaataagtg agtaatttta gaagcattat tttaggaata tagagttgtc atagtaaaca   3840
tcttgttttt tctatgtaca ctgtataaat ttttcgttcc cttgctcttt gtggttgggt   3900
```

-continued ctaacactaa ctgtactgtt ttgttatatc aaataaacat cttctgtgga ccaggaaaaa 3960
aaaaaaaaaa aaa 3973

<210> SEQ ID NO 207
<211> LENGTH: 20
<212> TYPE: DNA
<213> ORGANISM: Artificial Sequence
<220> FEATURE:
<223> OTHER INFORMATION: Synthetic Construct

<400> SEQUENCE: 207
gatcatgatg agaatttact 20

<210> SEQ ID NO 208
<211> LENGTH: 2818
<212> TYPE: DNA
<213> ORGANISM: Homo sapiens
<220> FEATURE:
<221> NAME/KEY: misc_feature
<222> LOCATION: (150)..(2762)
<223> OTHER INFORMATION: CDS
<300> PUBLICATION INFORMATION:
<301> AUTHORS: Sang et al.
<302> TITLE: MAPK Signaling Up-Regulates The Activity Of Hypoxia-
      Inducible
      Factors By Its Effect on P300
<303> JOURNAL: J. Biol. Chem.
<304> VOLUME: 278
<305> ISSUE: 16
<306> PAGES: 14013-14019
<307> DATE: 2003
<308> DATABASE ACCESSION NUMBER: NM_001430.1
<309> DATABASE ENTRY DATE: 2003-10-06
<313> RELEVANT RESIDUES: (1)..(2818)

<400> SEQUENCE: 208
cctgactgcg cggggcgctc gggacctgcg cgcacctcgg accttcacca cccgcccggg 60
ccgcggggag cggacgaggg ccacagcccc ccacccgcca gggagcccag gtgctcggcg 120
tctgaacgtc tcaaagggcc acagcgacaa tgacagctga caaggagaag aaaaggagta 180
gctcggagag gaggaaggag aagtcccggg atgctgcgcg gtgccggcgg agcaaggaga 240
cggaggtgtt ctatgagctg gcccatgagc tgcctctgcc ccacagtgtg agctcccatc 300
tggacaaggc ctccatcatg cgactggaaa tcagcttcct gcgaacacac aagctcctct 360
cctcagtttg ctctgaaaac gagtccgaag ccgaagctga ccagcagatg gacaacttgt 420
acctgaaagc cttggagggt ttcattgccg tggtgaccca agatggcgac atgatctttc 480
tgtcagaaaa catcagcaag ttcatgggac ttacacaggt ggagctaaca ggacatagta 540
tctttgactt cactcatccc tgcgaccatg aggagattcg tgagaacctg agtctcaaaa 600
atggctctgg ttttgggaaa aaaagcaaag acatgtccac agagcgggac ttcttcatga 660
ggatgaagtg cacggtcacc aacagaggcc gtactgtcaa cctcaagtca gccacctgga 720
aggtcttgca ctgcacgggc caggtgaaag tctacaacaa ctgccctcct cacaatagtc 780
tgtgtggcta caaggagccc ctgctgtcct gcctcatcat catgtgtgaa ccaatccagc 840
acccatccca catggacatc cccctggata gcaagacctt cctgagccgc cacagcatgg 900
acatgaagtt cacctactgt gatgacagaa tcacagaact gattggttac caccctgagg 960
agctgcttgg ccgctcagcc tatgaattct accatgcgct agactccgag aacatgacca 1020
agagtcacca gaacttgtgc accaagggtc aggtagtaag tggccagtac cggatgctcg 1080
caaagcatgg gggctacgtg tggctggaga cccaggggac ggtcatctac aaccctcgca 1140

-continued

```
acctgcagcc ccagtgcatc atgtgtgtca actacgtcct gagtgagatt gagaagaatg   1200

acgtggtgtt ctccatggac cagactgaat ccctgttcaa gccccacctg atggccatga   1260

acagcatctt tgatagcagt ggcaaggggg ctgtgtctga gaagagtaac ttcctattca   1320

ccaagctaaa ggaggagccc gaggagctgg cccagctggc tcccacccca ggagacgcca   1380

tcatctctct ggatttcggg aatcagaact tcgaggagtc ctcagcctat ggcaaggcca   1440

tcctgccccc gagccagcca tgggccacgg agttgaggag ccacagcacc cagagcgagg   1500

ctgggagcct gcctgccttc accgtgcccc aggcagctgc cccgggcagc accacccccca   1560

gtgccaccag cagcagcagc agctgctcca cgcccaatag ccctgaagac tattacacat   1620

ctttggataa cgacctgaag attgaagtga ttgagaagct cttcgccatg gacacagagg   1680

ccaaggacca atgcagtacc cagacggatt tcaatgagct ggacttggag acactggcac   1740

cctatatccc catggacggg gaagacttcc agctaagccc catctgcccc gaggagcggc   1800

tcttggcgga gaacccacag tccacccccc agcactgctt cagtgccatg acaaacatct   1860

tccagccact ggcccctgta gccccgcaca gtcccttcct cctggacaag tttcagcagc   1920

agctggagag caagaagaca gagcccgagc accggcccat gtcctccatc ttctttgatg   1980

ccggaagcaa agcatccctg ccaccgtgct gtggccaggc cagcacccct ctctcttcca   2040

tggggggcag atccaatacc cagtggcccc cagatccacc attacatttt gggcccacaa   2100

agtgggccgt cggggatcag cgcacagagt tcttgggagc agcgccgttg gggccccctg   2160

tctctccacc ccatgtctcc accttcaaga caaggtctgc aaagggtttt ggggctcgag   2220

gcccagacgt gctgagtccg gccatggtag ccctctccaa caagctgaag ctgaagcgac   2280

agctggagta tgaagagcaa gccttccagg acctgagcgg gggggaccca cctggtggca   2340

gcacctcaca tttgatgtgg aaacggatga agaacctcag ggtgggagc tgccctttga    2400

tgccggacaa gccactgagc gcaaatgtac ccaatgataa gttcacccaa aaccccatga   2460

ggggcctggg ccatcccctg agacatctgc cgctgccaca gcctccatct gccatcagtc   2520

ccggggagaa cagcaagagc aggttccccc cacagtgcta cgccacccag taccaggact   2580

acagcctgtc gtcagcccac aaggtgtcag gcatggcaag ccggctgctc gggccctcat   2640

ttgagtccta cctgctgccc gaactgacca gatatgactg tgaggtgaac gtgcccgtgc   2700

tgggaagctc cacgctcctg caaggagggg acctcctcag agccctggac caggccacct   2760

gagccaggcc ttctacctgg gcagcacctc tgccgacgcc gtcccaccag cttcaccc     2818
```

```
<210> SEQ ID NO 209
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 209

aagccttgga gggtttcatt g                                               21


<210> SEQ ID NO 210
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 210
```

-continued

```
tgctgatgtt ttctgacaga aagat                                          25


<210> SEQ ID NO 211
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 211

cgtggtgacc caagatggcg aca                                            23


<210> SEQ ID NO 212
<211> LENGTH: 3415
<212> TYPE: DNA
<213> ORGANISM: Mus musculus
<220> FEATURE:
<221> NAME/KEY: misc_feature
<222> LOCATION: (184)..(2808)
<223> OTHER INFORMATION: CDS
<220> FEATURE:
<221> NAME/KEY: misc_feature
<222> LOCATION: (2965)..(2965)
<223> OTHER INFORMATION: n is a, c, g, or t
<220> FEATURE:
<221> NAME/KEY: misc_feature
<222> LOCATION: (2969)..(2969)
<223> OTHER INFORMATION: n is a, c, g, or t
<220> FEATURE:
<221> NAME/KEY: misc_feature
<222> LOCATION: (3022)..(3022)
<223> OTHER INFORMATION: n is a, c, g, or t
<220> FEATURE:
<221> NAME/KEY: misc_feature
<222> LOCATION: (3075)..(3075)
<223> OTHER INFORMATION: n is a, c, g, or t
<300> PUBLICATION INFORMATION:
<301> AUTHORS: Compernolle et al.
<302> TITLE: Loss of HIF-2 Alpha And Inhibition of VEGF Impair Fetal
      Lung Maturation, Whereas Treatment With VEGF Prevents Fatal
      Respiratory Distress In Premature Mice
<303> JOURNAL: Nat. Med.
<304> VOLUME: 8
<305> ISSUE: 7
<306> PAGES: 702-710
<307> DATE: 2002
<308> DATABASE ACCESSION NUMBER: NM_010137.1
<309> DATABASE ENTRY DATE: 2003-04-07
<313> RELEVANT RESIDUES: (1)..(3415)

<400> SEQUENCE: 212

ctagccagcc ctctgcaaac ttccacctga ttgagcggga ctctcggacc tgcgagcact     60

aaagaccttt cacacctgcc cgggcgacag agagctgcgg agggccacag caaagagagc    120

ggctgcagcc cctacggggt taaggaaccc aggtgctccg ggtctcggag ggccacggcg    180

acaatgacag ctgacaagga gaaaaaaagg agcagctcag agctgaggaa ggagaaatcc    240

cgtgatgccg cgaggtgccg gcgcagcaag gagacggagg tcttctatga gttggctcat    300

gagttgcccc tgcctcacag tgtgagctcc cacctggaca aagcctccat catgcgcctg    360

gccatcagct tccttcggac acataagctc ctgtcctcag tctgctctga aaatgaatct    420

gaagctgagg ccgaccagca aatggataac ttgtacctga aagccttgga gggtttcatt    480

gctgtggtga cccaagacgg tgacatgatc tttctgtcgg aaaacatcag caagttcatg    540

ggacttaccc aggtagaact aacaggacac agcatctttg acttcactca tccttgcgac    600

catgaggaga tccgtgagaa cctgactctc aaaaacggct ctggttttgg gaagaagagc    660

aaagacgtgt ccaccgagcg tgacttcttc atgaggatga agtgcacagt caccaacaga    720
```

-continued

```
ggccggactg tcaacctcaa gtcggccacc tggaaggtcc tgcactgcac cgggcaagtg    780
agagtctaca acaactgccc ccctcacagt agtctctgtg gctccaagga gcccctgctg    840
tcctgcctta tcatcatgtg tgagccaatc cagcacccat cccacatgga catccccctg    900
gacagcaaga ctttcctgag ccgccacagc atggacatga agttcaccta ctgtgacgac    960
agaatcttgg aactgattgg ttaccacccc gaggagctac ttggacgctc tgcctatgag   1020
ttctaccatg ccctggattc ggagaacatg accaaaagtc accagaactt gtgcaccaag   1080
gggcaggtgg tatctggcca gtaccggatg ctagccaaac acggaggata tgtgtggctg   1140
gagacccagg ggacggtcat ctacaacccc cgcaacctgc agcctcagtg tatcatgtgt   1200
gtcaactatg tgctgagtga gatcgagaag aacgacgtgg tgttctccat ggaccagacc   1260
gaatccctgt tcaagccaca cctgatggcc atgaacagca tctttgacag cagtgacgat   1320
gtggctgtaa ctgagaagag caactacctg ttcaccaaac tgaaggagga gcccgaggag   1380
ctggcccagt tggcccccac cccaggagat gccattattt ctctcgattt cggaagccag   1440
aacttcgatg aaccctcagc ctatggcaag gccatccttc ccccgggcca gccatgggcc   1500
gcggggctga ggagccacag tgcccagagc gagtccggga gcctgccagc cttcactgtg   1560
ccccaggcag gcaccccagg gaacactaca cccagtgctt caagcagcag tagctgctcc   1620
acgcccagca gccctgagga ctactattca tccttggaga atcccttgaa gatcgaagtg   1680
attgagaagc ttttcgccat ggacacggag ccgagggacc cgggcagtac ccagacggac   1740
ttcagtgaac tggatttgga gaccttggca ccctacatcc ctatggacgg cgaggacttc   1800
cagctgagcc ccatctgccc agaggagccg ctcatgccag agagccccca gcccaccccc   1860
cagcactgct tcagtaccat gaccagcatc ttccagccgc tcaccccggg ggccacccac   1920
ggccccttct tcctcgataa gtacccgcag cagttggaaa gcaggaagac agagtctgag   1980
cactggccca tgtcttccat cttctttgat gctgggagca aagggtccct gtctccatgc   2040
tgtggccagg ccagcacccc tctctcttct atggggggca gatccaacac gcagtggccc   2100
ccggatccac cattacattt cggccctact aagtggcctg tgggtgatca gagtgctgaa   2160
tccctgggag ccctgccggt ggggtcatcg cagttggaac ctccgagcgc cccgcctcat   2220
gtctccatgt tcaagatgag gtctgcaaag gacttcgggg cccgaggtcc atacatgatg   2280
agcccagcca tgatcgccct gtccaacaag ctgaagctaa agcggcagct ggagtatgag   2340
gagcaagctt tccaagaaac aagcgggggg gaccttccag gcaccagcag ttcacacttg   2400
atgtggaaac gtatgaagag cctcatgggc gggacctgtc ctttgatgcc tgacaagacc   2460
atcagtggga acatggcccc ggatgaattc acccaaaaat ctatgagagg cttgggccag   2520
ccattgagac acttgccact tccccagcca ccatttacca ggaactcagg ggagaacgcc   2580
aagactgggt tcccgccaca gtgctatgcc tcccagttcc aggactacgg tcctccagga   2640
gctcaaaagg tgtcaggcgt ggccagtcga ctgctggggc catcgttcga gccttacctg   2700
ttgccggaac tgaccagata tgactgtgag gtgaacgtgc ccgtgcctgg aagctccaca   2760
ctcctgcagg ggagagacct tctcagagct ctggaccagg ccacctgagc cagggcctct   2820
ggccgggcat gcccctgcct gccccgccgt cttgacctgc cagcttcact tccatctgtg   2880
ttgctattag gtatctctaa caccagcaca cttcttacga gatgtactca acctggccta   2940
ctggccaggt caccaagcag tggcntttnt ctgacatgct cactttatta tccatgtttt   3000
aaaaatacat agttgttgta cntgctatgt tttaccgttg atgaaagtgt tctgaaattt   3060
tataagattt ccccntcctt ccttcccttg aattacttct aatttatatt ccccaaaggt   3120
```

-continued ttttctctct ctcattcata tccatactaa caagcatggt ggctggtgcc tctccctagg 3180
aaagctttgg cgtcattcaa ctcaagtgtt cttgttcttg ttgccaaaga gaaaaggatt 3240
ttcctccact gtggattttc cctctccccc acccccacat acacacacac acacacacac 3300
acacccctac acacatatac acacatgcac gtatgcgtgc acacacacac acacacatat 3360
acacacacac acacacacac acacacaccc ctacacacat atacacacat gcacc 3415

<210> SEQ ID NO 213
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 213
ggccatcgtt cgagcctta 19

<210> SEQ ID NO 214
<211> LENGTH: 16
<212> TYPE: DNA
<213> ORGANISM: Artificial Sequence
<220> FEATURE:
<223> OTHER INFORMATION: Oligonucleotide primer

<400> SEQUENCE: 214
ggcacgggca cgttca 16

<210> SEQ ID NO 215
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 215
ctgttgccgg aactgaccag atatgactg 29

<210> SEQ ID NO 216
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 216
ggcaaattca acggcacagt 20

<210> SEQ ID NO 217
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 217
gggtctcgct cctggaagat 20

<210> SEQ ID NO 218
<211> LENGTH: 27
<212> TYPE: DNA
<213> ORGANISM: Artificial Sequence
<220> FEATURE:
<223> OTHER INFORMATION: Oligonucleotide primer -continued

<400> SEQUENCE: 218
aaggccgaga atgggaagct tgtcatc 27

<210> SEQ ID NO 219
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 219
gtcagctgtc attgtcgctg 20

<210> SEQ ID NO 220
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 220
ggcctggctc aggtggcctg 20

<210> SEQ ID NO 221
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 221
ggtcatgttc tcggagtcta 20

<210> SEQ ID NO 222
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 222
gtggagcagc tgctgctgct 20

<210> SEQ ID NO 223
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 223
ggtacatttg cgctcagtgg 20

<210> SEQ ID NO 224
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 224
tgggcctcga gccccaaaac 20

<210> SEQ ID NO 225
<211> LENGTH: 20

-continued

<212> TYPE: DNA
<213> ORGANISM: Artificial Sequence
<220> FEATURE:
<223> OTHER INFORMATION: Oligonucleotide primer

<400> SEQUENCE: 225
gaataggaag ttactcttct 20

<210> SEQ ID NO 226
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 226
tggaagtctt ccccgtccat 20

<210> SEQ ID NO 227
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 227
gcagctcctc agggtggtaa 20

<210> SEQ ID NO 228
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 228
catggtagaa ttcataggct 20

<210> SEQ ID NO 229
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 229
tcacttcaat cttcaggtcg 20

<210> SEQ ID NO 230
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 230
gagcttccca gcacgggcac 20

<210> SEQ ID NO 231
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 231

-continued tgaaggcagg caggctccca 20

<210> SEQ ID NO 232
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 232
ggtgctggcc tggccacagc 20

<210> SEQ ID NO 233
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 233
cgaatctcct catggtcgca 20

<210> SEQ ID NO 234
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 234
tgctgttcat ggccatcagg 20

<210> SEQ ID NO 235
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 235
tactgcattg gtccttggcc 20

<210> SEQ ID NO 236
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 236
ctcccagcct cgctctgggt 20

<210> SEQ ID NO 237
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 237
aggagcgtgg agcttcccag 20

<210> SEQ ID NO 238
<211> LENGTH: 20
<212> TYPE: DNA
<213> ORGANISM: Artificial Sequence -continued
<220> FEATURE:
<223> OTHER INFORMATION: Oligonucleotide primer

<400> SEQUENCE: 238
ctgtggacat gtctttgctt 20

<210> SEQ ID NO 239
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 239
agtgtctcca agtccagctc 20

<210> SEQ ID NO 240
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 240
ctattgtgag gagggcagtt 20

<210> SEQ ID NO 241
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 241
tcatagaaca cctccgtctc 20

<210> SEQ ID NO 242
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 242
aaatgtgagg tgctgccacc 20

<210> SEQ ID NO 243
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 243
ttgggcgtgg agcagctgct 20

<210> SEQ ID NO 244
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 244
gcgctgctcc caagaactct 20

-continued

<210> SEQ ID NO 245
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 245
gcagcaggta ggactcaaat 20

<210> SEQ ID NO 246
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 246
gtgctgccac caggtgggtc 20

<210> SEQ ID NO 247
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 247
tggtcatgtt ctcggagtct 20

<210> SEQ ID NO 248
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 248
tcagtctggt ccatggagaa 20

<210> SEQ ID NO 249
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 249
tctcacgaat ctcctcatgg 20

<210> SEQ ID NO 250
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 250
tcttcaggtc gttatccaaa 20

<210> SEQ ID NO 251
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 251
aggtcccctc cttgcaggag 20

<210> SEQ ID NO 252
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 252
tgggccagct catagaacac 20

<210> SEQ ID NO 253
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 253
tcaaatgtga ggtgctgcca 20

<210> SEQ ID NO 254
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 254
catctgctgg tcagcttcgg 20

<210> SEQ ID NO 255
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 255
acagggattc agtctggtcc 20

<210> SEQ ID NO 256
<211> LENGTH: 0
<212> TYPE: DNA
<213> ORGANISM: ...

<400> SEQUENCE: 256

000

<210> SEQ ID NO 257
<211> LENGTH: 78695
<212> TYPE: DNA
<213> ORGANISM: Mus musculus

<400> SEQUENCE: 257
aacaagtcgc agttctgcgg aaggaggagg aagggcaggc gggcgcccga ggagcgcagc 60
tccagagaaa ggggagggac ggggtcaggg cagaggctgt ggccgcgcct ccctattggc 120
cgggacacgg tgggaagtcg gggcaggcag ccagcgtgcg gggcggggct tctctggagc 180
cccgcccccg gcccgccccc agcccgatgt cccactcccg cgcccctcgc gccctcccgc 240

-continued

```
gggcgggccg tccgagtttt taaagtgggc tgacagccga ggaggccgga cattcgagag    300
cggccggtgt acagctccgg agtccgcagc gctccgctcc agctctcctg aggcggccgt    360
acaatcctcg gcagtgtcct gagactgtat ggtcatctca gcggccgcac tcgcttgccc    420
ccggattttt ttccaacttg ctctcttcga gccatttttt tttcttttttt tctttttctt    480
tttttctttt tcttttttgg ttggttggtt ttgatttgtc agatcccaga aaagtgactc    540
ctgttcgggg ctaaacggaa ctccaggtcc cttgtcgctg ctctctctct cttttggcgt    600
cttacaacct cctcccactc ctttccccgg ccccgcctcc tcctgcaggt tcctccccgt    660
caccccccctc ctccctcctc ctcctccgca cctagccagc cctctgcaaa cttccacctg    720
attgagcggg actctcggac ctgcgagcac taaagacctt tcacacctgc ccgggcgaca    780
gagagctgcg gagggccaca gcaaagagag cggctgcagc cctacgggg ttaaggaacc    840
caggtgctcc gggtctcgga gggccacggc gacaatgaca gctgacaagg agaaaaaaag    900
gtaagcggga gtcaaagctg gcgaccgact tggtcccagg cattggcgga actgcgcgtg    960
gcgggcgcga cccggggcag tcgggagagg ggtgcgagag ttctcggagg ctggaggacc   1020
gctgttgagg ggctttgagt aagcgagtcg gtgatgcctt tagggacaag gagctgcggt   1080
gtcgcagtag agttgcaaag cggatagttc cgagaccttg agacacggag agatggccct   1140
ggaggtcagg ggtgcttccg cggcgccttc caaagtctgt cgtccctgga gcaccaagct   1200
tccctagcga gtgttttgaa atgtttctgg gctgatgccc tcgactctta gggtttccat   1260
gctggagcag tagacacgcc tttcttttcc taagaccctc taggtctttc cgagagcgtt   1320
cctatgcggg ctttgcgccc caaactagca tggaacagag ggcaaagcgc aactctgggg   1380
tgcgccctga ccgagaagcc ggaacactgt caagggtcct gctccagacg gcacccaagt   1440
ttgttcaacc cccttaacct taccctacac ctagactccg gcagagagtg ggagtgagt    1500
gacctggatt gccctgcggg ggcaggtgct ctagtgtgca gagagaagac cgtgacaccc   1560
ggcggctccg agtgtctgat tcttaagacg aagggcagcc acgaaggttt gtcctcgcga   1620
acctttcggc actgggtgag aggcaactcg gggcaactcg cgctgccctc gagcctcctt   1680
caatccgccc cgcatctggt gacttgacac ccagctctag gagctgaggt gggaacacac   1740
tgtgaccccg ccgcagacct gggtacattc tcgtcgcctg caaaagttta tagctggccg   1800
cctggcactt tgctcctgtt tcgatcggtg cgtgccgtgg gttagagctt ccagcactgc   1860
gctccgtggc gacttagctg gggtgtccgg aatggtacgc gtgaccgcag aatggcgcga   1920
gctgccagag atccgtggcc agactggaaa agactggcgg tgaggaccca gccccgagca   1980
aacgggcttt ttgtttgggc ttccacttag ggacatgagc caggaactgt gtatcctctg   2040
gtcgaaagct gcagctccca cctcagggca ccgataagga gttgataaac tccagcgaat   2100
cgcacccgtc ctggcccggc gcccgcgccc tgcgctggcg gatctctaga gggggaaggt   2160
attgagtccg gttctagatt ccccattatc gcccaccaaa caactctgag gttctgtgta   2220
ctttgagggt agagaaggag aagcaagaga gagagagaga aaaaaaaaga ctaagattct   2280
agctcaaact gtaaaaccag ccagagggta atcacaaacc atcaaaaccg cgaagttgga   2340
cagcagagta gccaggagca cttattgaac actttattac tgccttgtct atgggtgact   2400
gtcgcgtttg tccgagatga gacctgacag taatcagtgt caagtgtcat cttgctctta   2460
ggtctatcaa tccttgggag agtcagggat cagtggggaa agctatttcc atacccagct   2520
tgcagagact ctttgccgag ggctggcagg gagtatagtc agagcctaga agaacgttgc   2580
ataatgacac tacaaattat ccacaacagc ggccacttta agaaccagtg tgacacagac   2640
```

-continued

```
tgtgaacctc ctaggaatct tcggcctgta gtgcagtgcc ccagtggtag ccaggcccgc   2700
agggtgtgtg tgtgtgtgtg tgtccaaaaa acagggcaag cagtgtaggt tcagtgtagg   2760
ttcagacttc caaagcctgt taggatagtg gttttgagat tctggttaaa ttgactgact   2820
tcttgggggc atcaatatgt agttgaaaat tgtgaagcag ggcatcaaaa gttaatgtcc   2880
cttaaatggc tgcccagagc tttccagagc gcttcaggaa atcaatgtga gcagcaaggg   2940
ttcccggatt ggtgatacca cccactagtg gttcaagggc cggttcttct ccagggcata   3000
actgagcatt tgtatggttc cttctggaaa cagcccttcc agaggccaga aggcttgttt   3060
tagtcccaaa catccttgtg tgggtggata tattccttca tgatagtcag gagccagtct   3120
tttatttgtt ggctggttag cagactgggg gagccacagc aagctctctt ggagttctca   3180
tcaacccagc aggattcctg attctaggaa gagccaagtg tggatgctct caagtgggga   3240
tttgtagaac aattaagata aatggaagtg aggtctttgg gtggccagga atccaagtcc   3300
aggcacaaag ctagactctg ggtccaagta cctttcagga gtgcttctgg tatttggtgc   3360
cagggcaaag atgggcaagg aattggagat agctggacct tcaagttttc taactgtggc   3420
tggcttctga tggcagcaga tttaattgtt cctctgttaa aataaaccca aggtccatca   3480
gttttcccag ccgaggagac aatgctggct gggcttcttg agtgaagctt atctcctaac   3540
tagtgttcct tcaacattg acaacagtct aacctggtag agcagtgctg tacgacacta    3600
tcagcctggc atttaaactg tactaaagat gactttctta gagttttggt ttttttgttt   3660
tgttttgttt tttgggtttt tttttttttt tttggttttt tgttgttgtt ttggtttttt   3720
gttgttgttg tttttttcag ttttattgtg aggcttgaag attattttat aagcaagtat   3780
gaaagccata aacatatttt ctctttctgg ataaggctca aggaaggtaa aataatccct   3840
ctcggtacaa ggaaaattag tgctgataag aatcagaaag ttggttcatt acaatcagtt   3900
agcatgtgaa cagcagagcc tcccacccca tcccccccac ccccccaccc cccccacccc   3960
cgccatggca tgcctcttgc cactgaggat ttccaaagga ttagtgcagc tcaccatcac   4020
catacctcca ccaccaccac caccagaccc ctgaaccttc aagacagagg tttactttcc   4080
tagataattg caagagcctt gttctgagct gaggcaggag agatgtcaac cagtcagtgg   4140
cgctgctctt ggtagttaaa aactttgggg aatcggaatc cattggttga gtacctttcc   4200
tttatttcag ttaggggaaa acaaaaaaca aaaaccaaac aaacaacaac aacaacaaaa   4260
gaccccaaca aaccctacta ctcgaggtat aaaataaaac caatgcaagc accctcctgg   4320
ttcctggatg tagcaagttg ctttgtgaag tagaggacat tccacagcta ctagattgtt   4380
gcctggtgtg attaggcaat tttgcaggga tgaaagcctg aactgaaaac aggctacttt   4440
gtttacgttg tcaacaaagc ctctctgctg ctgtttctct gcctctgtgc atgtgtgtgt   4500
ttacatggcc ctgcccaggg ttctaggaat ctatgttgtt tagagagaga aggaaccaag   4560
tagttaattc ctagtgctgt agggcttcag ccccctgggt ttgaaagtgc ctccttcaag   4620
gctgagcctt ttccatcttt gaggaaatct tttctgtgca gcatttactt gctttaaaaa   4680
ctgcaacaac aaagcaaaaa cggtcctgtc ctatctcaag ataatagggt cctccttcgt   4740
tttatcttga tgaatctttc cttagtccta aggaaagttt tgtggtacac aaactaccga   4800
gctttttacc aagttactga gtaagttctg ttttctccca gggccttatt attcagcttt   4860
gcacactcca gaaacatgct ggtgagtctc acaatgacat ctataccaag atactaacca   4920
gtgggtctgg aaaaacagtg ctgaaaacta agaaatgggg catctgttca ttactcccaa   4980
```

-continued

```
ttgcttggtc tgatgggggt cagggtgggg ggacaggacc acccaagaaa ccgttggggt   5040
atcagccact catgggtgtt ttctttggta gggttcaaat atttgaagct aaagaaaaga   5100
aattctgaat ggtatttcag ttggtaaccg tacaccatta ttgaaatgca ttcgtcattg   5160
aggaagctgg ctctgtgtcc ctgagataat aaacggtaga tgctggacac cagcataaac   5220
tggatctcag agagagtgtg gtggtagacg ttagaacttg gagatgatga acataaaaat   5280
acggatgctc cacaggcgtt ctgcaccatg aactttgaca catggacaaa atgactacca   5340
gttggttggt tttttttttt ttttaaagat ttatttatta ttatacctaa gttcactgta   5400
gctgacttca gacacaccag aagagggtgt cagatctcat tatgggtggt tgtgagccac   5460
catgtggttg ctgggatttg aactcaggac cttcggaaga gcagtcagtg ccctttacct   5520
gcccagccat ctcaccagcc cggctaccga gtttaactgc ttgatgtaca cacttgtttt   5580
gggtggagaa tttgcaggga ggacacttac tggcctccac agtgacaacc aaaggtttct   5640
gtttccactg aggacaacgg tggccttgac tgactccgtg aaggccgaga agggagggga   5700
gtacttttcc gggagccttg taaatgagct tccggggtag taatagatct ctaaaattct   5760
atagagtgta tgttttgttc tctgggtttt ttttttttta atgttaatct caatctcccc   5820
tcttcatgaa gagtgaaccc agagctttgc acgggctggg atagcattct ctaccactga   5880
gctggatcgc caccctttgt tcagctccta gtcgcctttc aaaggtggtg tgaagagaaa   5940
ataccttctt cctgcttgtc tgtctagcac ccaagagctc ccctccctga gttctaggct   6000
acaggctgcc tgttcctaca tttcaatgcc agcgtcttgt cttgtcctag ggagtgtcta   6060
taagacatgt tttccactat cccctgctat ctggagattc ttttgaacct tagaaatgga   6120
tgtgctcttg ggagaaatga gctacatagg cagaaggaca agatggaaag ctgagcgctc   6180
aatcttcccg tgccagcgct gtcctcagaa ctttccggat taactttgtt aatccttgta   6240
acaaccctgt gagataagcc ctgttattat ctccagttca ctgatgggaa ctcaggtgca   6300
gcaaggttgc tgcccgttgt cacaggcagt atatcttgga gctgagactc tccagagtcc   6360
acactctcac ccaccgttcc ttgcctcctg gccttaccta aaaggcctat aaagcattta   6420
ataccatgtc tgaatgtggt aagcactcta taaatgataa cttcttttgt tgctgtgttt   6480
ataattatta taatgacttt tctcgtgact catcccttgt atcaaacctc acacacacag   6540
gcaggaactg aagacccaaa ggctattcct gaattcctgg aattacttat ttttttttaat   6600
atatatatag atatttcctc agctaaagca ggggacagtt ctccactgcc cctggaagtt   6660
caaagctttc ttcccaccct ttgctggtgg caagacttca agaaccgttc agtcttcaga   6720
ctccattgtg cggagggacc tgttaggagc tcttcctctg tggctccttt gatcttttga   6780
aattgcaagc ataggaagga aaagatggat ggggggaggg gataaatagt agtttatgat   6840
tgtcgtgatc atatttttat agagtccttt ctctggtgag caccccaggc catataccaa   6900
gagccttgag atcttcttga gtttcctcgc ctcaaaccat gattgctttg gaacagttgt   6960
gggttgtggt atgggtttgg ggtggggcgg ggtgggatgg ggtggggtag ggtggggtgg   7020
ggtggggtgg ggtggggcat gtatgaatat atgcagctag caacacacag tttttcaagt   7080
agagtctatg tgcaattcac tgacattttt ctggtcctgt tactcaaaga cacagaacca   7140
atctgaacgt ccgagactga gagaaatgtg gaggttattt gagatcccca gaatcagaga   7200
taagcgtggc cgagaccaga gtgttatgtg cgtctgagtg gcctttcttt ccctaatagc   7260
tcaagaaata ctggtttgct tatggccttg ggctgtttcc agaggccacc agtacatcct   7320
ccaggctcct gggataaaga gtgttgcctg ccgagaagca caggattctt taaagttagg   7380
```

-continued agtggtctgt atgccagacc ctaggaagca gatactttct catacagaat gagatttcat 7440
gatgaatggc ttgttggtaa gtaaaacaaa cacatgaaaa cgtgtgtgtg tgtgtgtgtg 7500
tgtgtgtgtg tgtgtgtgtg tgatggctct gcacgtaaga gcatttgctg atcttataga 7560
agccctgagt ttgactccag cacccatgtg ctcataacta cccctcagta tagttcctag 7620
ggatctgaca cccagttccc acagccacgc agtcacatgt cacacactta aaaataacac 7680
acacacacac acacacacac acacacatgt atgtatgtat atccgtgtat acatctgaca 7740
tgttttaatt ccacaacatc atggaaatag acctttagaa ttttcctata tccccccag 7800
tggctcacta cattcaccat tctagtggca acttccgatg tcataggtaa gaatcagatg 7860
attcatgttt ttcatctggt tagactatgt acccaaacat gtatacacat acacacacac 7920
acacacacac acacacacac acacacggat ctactgtgct gccctattga ccatgatagt 7980
ctagagactg acccatgctg ttatattggc taccccccc ccctaaatgg caggctacag 8040
ccactggcaa ttttagatgt taatgagtag tgttagtggc ctcttttggt ctgcccttgg 8100
tttgaagtgc acagttagtt ggcctcttaa ctggaaagtc agtagtttgc taagaataag 8160
aggatacata ggctccatct aagaaagtta cgaatgcttt ataaatcatt taaaatacac 8220
cagctacagt atatggtttg gaactggcaa taatttaaag cactatgttg tgtgtctagc 8280
catgaagggt tctgtgtctt tggatggcat atcactgtta acaaacacac atgttactca 8340
taattgaaag cgctcagcct cttgtcacca tgtaaggttt gtcctgacct gcctgcctcc 8400
tggaggggcg ggaactggag gggctaaaga accaaacctc ttcatctgaa gccaaaccta 8460
ggcgtggaga ggctgggccc agaacaccat cttgggctcc tggtcttgtg ttgtgttgta 8520
ggaaggggcc atagccagga acctaaagga gcaacttagc tgcagcacta accccgctca 8580
ttactaatga gtaattacag caaatattta caggtctcct tcctaccttt atgacttcct 8640
gttgctgaag cactttggag tgttgagaaa gattgttctg gaacatacgt catacatggt 8700
tgtaggaaaa gagtgcctct aagcgcacac acacacacac acacacacac acacacgctt 8760
ggttttgttt atgaattcca tgtgggaata acaaaattac accttctaga agctgagaat 8820
tttacttttc aaaacaaggt ttaaaaatca attctcaact gctggtttta aagcaccaat 8880
aaggctattc atgttcataa agtaaaactt gaggttaaat cataggcatt gcctaaatac 8940
tttttaaagc actacaatgt tttatgaaac tgtgacccct cacagtgcct tctgagtgaa 9000
aacagaaaaa cctagtagaa taaatcaagg tctataaaac aagccatgtg ggcaattctc 9060
tgagttccag aagccctggt aatgtattta gggtttgttg ttgttgttgt tgtttgtttg 9120
tttgtttgtt tgttttttaa aatcggtcca gtgagtggct ttctcagtct gctcctgtga 9180
gccactgtgc cctgtgtttc tctctggtgt gtccagcagt tcccaggtgc tattttagaa 9240
tggcagcctt cgctccagcg ctggctgagg ttgatggagc taattttggt gtctagggta 9300
aagggagcga gaaagcctgt gcaggagtca aaaaggcttt cttgtcccgg gctgagagca 9360
gcgtggtgtt accagacaca ctacatttca cctttagaac ctttgtttgt gtacttgcac 9420
aacaaatgtt tacctagata ttaagataaa ggaaatatga aggtcccatt tcactggtga 9480
caagggagcg tctataattg taactgtatc accgtgtagc aagcaggagt cccttttact 9540
ctatagccag gtcttaaggg aattaatggt gggtgtggtg tacaagccaa ggcccttctc 9600
agtttctgtt tctggcttta ttgctgctac tatgttttct tggctcagcc aatgttttgc 9660
cccacccatt tggtgaaggc ctttgtggtg gtcaaggatt cagagggaat tctaaagcac 9720

-continued

```
tctgtggccc cactctggag tcatccgctg ttctatggaa accagttagc agaccctggc   9780
accatcactc ttttcctagg ctctcagaaa acgtttacat ggtaccaata cgaccttgtt   9840
tcaggccttc acgttgtctt ggaagcacag caaattttcc ttgtggcaag agggttccat   9900
gaggacttgg gggtttcttt gaagatcccc caaggattag ctaaatactc agtctgaaga   9960
tctaagaacc tcactcaagg gccttcccat agggaagcta cgaagcaggt gactgctgga  10020
aatgagggtc cccacactcc agctctctca tctgccccac tcagtcactt acggcacctc  10080
ctgagctccc cacaagccta ttcctctgcc acacaggtat tgtcacagta ctcgttcgtc  10140
tctggttctt agtccatgct tgaatgcttt ttccctcttt ctgcccaaat atctcacact  10200
ttgtcttatc atgaatgagc ctaagctctc tgcctttaac agaaacccat agcattccca  10260
ccctgccttt ccctccattt gctgttttat acttctttgt tgtctaaaga cattttattt  10320
gttcttgcct ttccacgttc gttcttgcac atggcacaag agcagggatg tctgattttc  10380
tgatgtggcc aataaatgct gatccttttc atttttctct gaaatcatgg ccattagaaa  10440
aataaataca gaatgacttt ggttttttgt tttgttttgt tttttcgaga cagggtttct  10500
ctgtatagcc cctggctgtc ctggaactca ctctgtagac caggctggcc tcgaactcag  10560
aaatctgcct gcctctgcct cccgagtgct gggattaaag gcgtgtgcca ccactgcccg  10620
gcttcgaatg actttgttga tgtcccactt tctcgggctc agctgtctcc atccacacga  10680
cttcccttca cctgtttctg tgaacaagaa aataattggg gttgggggag gggcaaggca  10740
cgggccaggt gagcattatt tgccatcaga tgcaaggatc aggcaggtag tatgccaatg  10800
ctgttgtgca tcaagaatgc atggtagtct aggtaaactc cccagcttaa ctccggagtt  10860
aacagctttc caggtgggaa attatgcaaa tgcatccgta tcagctgtcc caaagggtct  10920
ccctggaaag cagacctcct tcagtcagca gggcattgtg tagccctgta tccatctgat  10980
cttctgtctg aatttttaaa tttgcataat aagtttaaag cttgctttct atttccattt  11040
taggtgttct gtagttgtct gtaggtggaa ttcaggaata tggggacctt agttcaaagg  11100
gatggaaacc acaggcagaa acactgcctc agatcagctt acccatcctt atttgataat  11160
caccacgcag gtcagaagag gtttgtggta ctgctggcct cgagtataca tgcttacagg  11220
ttatttgctg atttggggac tgtgctgcac agagagatca caccaaggca tttgatgact  11280
ctggtctctt caaatgactc gtttaaacca gtatgtggca gtgtgtggca ccaaggcacc  11340
tggctgcatc tttaggatgt tgccatcttg gtgtggagta aaaactaggc cagatacagc  11400
acagagccag gagcagaaaa tggataggaa tcgagagctc tgagttgtat aaagttaaaa  11460
aggactgggc tggagaagac cagagctttg agagaagagc attaaataag acttcggtct  11520
tgaagattag aatttgggtt tgcacaggca gcaactgcag gctacgctgg ggatgggcga  11580
ggcagtgcag accgcgagac ggaaagaagc agagtgcgca ggacagggct tggggggtgc  11640
tcctttcttt caactcggaa tcagtagatc ttatattagc agagatggag cctgggcctg  11700
gactggagaa tctagggaca ggccctcttc gagcatgttt gatggaattc tcagcctgcc  11760
ttttttggag acattagaag ctatttagag caattttatt gtccttctcc cacaaactta  11820
gctagagtgt gcacacctag gagtgattgg cagaagccat gatggcctcc aaaacaatga  11880
cctcaaagcg ctgaacccat agatcttagg aaacccactg tcattccgtc aggtatgtat  11940
ttctttgtgg cttgcatagc tgcttgggag tgataaatac tagagttcta tcagaatggg  12000
aacctgaagg gggacggctt gctgttaccc taaaattgcc ttgcccttca ttcccatgtt  12060
ctcactagga ggccaaagcc tttgtcccct tggggacttg gtaaggtcat ttgtcatatc  12120
```

-continued ctttcttgcc atttctcctt agagaaggat aaggcttctt tcggcaccta gcacgtggag 12180
ggagttacac agccaaggct gagtcaaatc tttagtctct actggtagct cttcatccaa 12240
acccagccca gagcactccg gccaagccgt tctgtgacct tctctttaag acccagatct 12300
ggttgatgtt ctgagtctga ccatgccaga agagtggggg aaaaaaagaa tcctctttcg 12360
gagtcacctg ggtaggacag tcagagccct ttcctctcca caagcaggtg tgaccttttc 12420
cctggaggaa tttagaagca ctaaggtcac agttggtcaa agtgggccag gagttggtca 12480
aagatcccaa atccctggac aagagcccac atcagggaca gcagaggcca gcaactgatc 12540
ctagttacat gagtttaccc tgcccagtgg tacttcaagg gagggaacgg ctcctagatg 12600
gttttgtgtt aaactttaac ctcacaatga caactgtcat gtctcaactg ttagttctgt 12660
cccctgtggt tgtaggacgg aggaaccact gctcagttct ggcaggctgg ttaggccagt 12720
ggtttgctca ggttaaagcc tgagcccaga gaagagtctt ctggagccaa ggagccgtaa 12780
tcgcctgcca gaaccacata gggacagggg acagtggagc tttgcagcac agtacagact 12840
ggcccttatc caggagctaa ctgagacctc gggccatccc ttctggaagc ctcagggaag 12900
ctctaagaaa agccagaaac caagaccaga cctgaccaca catactcaga tctctccaca 12960
ttataaatgc gagtgtagca tctacattcc gatagcttct tacaggggtc aggaagggaa 13020
aaggaagatg tcttagccaa gtttgcctgt gactaaacac cagatagcta gctccatgtc 13080
tatgtatctg tgttttcttt cctaagtgtg tttcttaagg tttaaaaaga tgcatgtgta 13140
tgcccgggtg tttgtatgtg taacacatgt ctcaggtacc tgcagagacc agaagagggc 13200
gctggatctc ctgaagctgg aattacaagt ggttgtgagc catggatcat gggtacttgg 13260
aactgggcct gggccctctg tgctcttagc tgctaagcta tctaccccac cagcgtctgt 13320
gttcatgttc ttttccaaag taaaaggtcc ttaaaaaaac aacaaacgag caaacaaaca 13380
aacaaacaag caagcctttg cttctcctga actcatagca ggttcttcct ggccttggtc 13440
agtgaggggc taggcccggg catagctcaa gccagtgtgg ttctcatgtt ctctagctca 13500
ttccaggcta tggggagatc cagaggacta gcgcgctcct agtgagtgca ctctccatcc 13560
tgagccatct ctcaagcaca ttagattctt ttctctaaat cagtgggtgc attttagttc 13620
tggccacctg tagttgcttg tgtggggaca agggtggtga catcacctta attttcctgg 13680
ccttgggtcc ccggagccct tgtttatttc ggggagtgac aagctttcac ccacttgaat 13740
tccttcgcct ccaaatagcg tcagaatgac cacaagcctc ctgtgtttct tcgctttctc 13800
gggttttgcc agattctaaa tgccgtcagg gccactggct cttgttttat gtccctggca 13860
aagctggcct tcccatgaag ttcaaagccg ctttcaggca tcttgggagt ctgggagact 13920
gctttcgctt gctctctgct ttgtgcggac ctaggttgga gatgtcacct ctgtctgctg 13980
ctctctgaat acgaaccagg gaatgttcta gtaataccac gtgctttaaa tgtatatttt 14040
aaaagcacac tttgtgagta ttatcttaat ggaaagaact ttgaaaagta taaagtgcaa 14100
accttctagg cattgtcatt aaggagcaga gcaatatact cattaggtgt gttattacct 14160
cttaaaagtg aaccgcctgc agacaggagg aagccttgag agaggctaac aggagactct 14220
ggtctccagg ctcctaccgg tgggtccctc cgcctgggct tttgggtcct gtggattctt 14280
gccaatcgtg gcatttagtg gataccccaa gactgaggaa atctgaagaa agtcctgaca 14340
agcaccagat cccaacaccc ttctgcttgc tttgtttccc ctcacctgtg aagcaggaga 14400
gggcacagcc cagcactcac gtcaaggacg acacatcctt ccgtgtcgca caggaaccag 14460

-continued

```
ggctgcccag gccatagctg ctcgcctctt cctcgttcca ctattttatg ccaaagagag  14520
gcattgacaa cctagaaaca ggtgctactc taaagagacc ttggtctcct tgaatgcaga  14580
ggcctggctg tgcttatacc ctaaccagga gacttgaccg gtcactcagc tctggcctca  14640
gacctatcat caactgtaac acatctggac ttcttacctc tgagctctct cttccctcag  14700
ccccacccgg gagactggcc agctgacttc aagcggtcct tctcagctta aatatcacct  14760
cctcagggaa gcctttctcg acgtccttcc attgacctct aatcctgttc catttgtctt  14820
ctaaacattt tccacgtgta atttacatgt ttacttatgt ctaccatgcc cctcccctgc  14880
cagggtgaaa ctgaaggtat ggactccaca cgtgccttgt ttaccactga gggctcagcc  14940
tttagaatgg agcctgcatg cactgctgct ttttacagat gcgttcagcg aactcgttgc  15000
tccgatattg ctgggctcta cattaccacg gtttacaatt gtccagtgtt ttcctaaagc  15060
tgattttgtt tttgttttct gaggtagggt cccaggggct aggatttaca tgaatgcccc  15120
catacttgtt ctttccaaag ctcttggtgc taacaccaag gaattgtcac tttttagcat  15180
atggatgagg cagttgagac actagagtat aatgaccatg ccagggtctg gcagtaccta  15240
cctgaacacg ttcccagccc cagactattt gcaaagatcc acgctgcctc tcttggcccc  15300
atagttttct gttgtggcga tgttattgtt tgtcatattt ggcaatgttt accccagaga  15360
agtagggcca ttgtgtgctg gtagcgtctg ggaatgcaca gccaagtccc aggggaatgg  15420
ccactgctgt tcttaccaca attagaaatt gtcaagccag gagcagaagc agggtgggtg  15480
ctgccataca ctgctggttc tgcctctcca tggggctggg gtgagggtcc tagctccgca  15540
gccccgtgtg tctccttgtc ctggctctcc cactcacatc gaagtgtgga ccttctcctg  15600
cagggcgatg tgctatgctt agtgaatttc ctgagaagag gtaggcatta gctggctaga  15660
tgaccacctc tggcctcaat tattcaatta ttctaccctc tccaaaatga accagtagat  15720
gggaaccaga ccaggtaacc ccaaaactct ccaggttcta gctccgctct gaagggaatt  15780
tccaggggtc tggcctcctg tttgcagatg ctgactctgg aaagagcagg ggaagttgga  15840
ggttgttggc aggggctggc ggacctcttt ccatctcttt gtaactcttc ctctccaaaa  15900
agatattcca tcccatcagg agttgctgtt gggcctggtt cagtgcagca ggatgaacaa  15960
ccgcccccaa aagtcagctg aggtctgata tgtgatatgg tagaaagctc ccaaaaggag  16020
gccatgcctc catctccctg atgcaggctt ctggggtgtt ctgatgccat taacggacag  16080
gggtcagaca ccaagtgcct ctgtctaggc cttcgttttc atgtctggca ggtgactgtt  16140
ctgtgccctt caattgaaca aggctgcaca gatgtaaact gccacagagg aagggcacat  16200
tgctgctatg attcctgtgt acgaatgttt ctggcgtgct cacacctggt agtgacatga  16260
actgattgac acttgcagcc tgcaaatacg gtcctgcaac ctgaggcacc aagggagaag  16320
tcagctagga agcccgtgag gccttaagtt gttgaatgaa gtcatgctgc acagggtggg  16380
gggtggggt gaccgtgctg caggatagag gtgagtcaca gtgcaagact gttggggagt  16440
caccttgaat ctgagccaaa aaagcagaaa tattgggact cgtttatcag ccttctatca  16500
ggtacatcaa gttctggatg gccacccact ggccagcgac atgatgtgga cggctctgct  16560
ctaccgccct gggaaggctc tctgctggct cttgccccgc tgagcaaagt ccgcttgttc  16620
gctggagttc acacagactc cttgccaggc ctgcccagaa tcctgtctcc tctgacttcc  16680
tgtgttcttg cataatattt ccttgcctct tgaatggctg gccccagtgc gggggcagct  16740
cactggctct gctggattga gagtaggatg tggagggagg atgggtgata tttggatcta  16800
atccgtgggt gctccgcgtc ctggtggcag agcccctcaa actttttgat ggaagctttc  16860
```

-continued

```
agccagaagg gagtgagaga gcattgcaga ctgtatacac acactcgctc gtgcacatgc  16920
tccctggctt cttatattca tgaatcatct ccctgggaaa attgttgaag tagttcaatt  16980
gttttcttct ggtcataaaa atatgaatta ttcccatata gtcactgtat aagaagccta  17040
aaagtaaaat aaatatatat atatatataa ataaaaaaca aaaaaatgta ttattgaaag  17100
ataagttcca ttaacagtga atatagtttc tcctacgtca gaaaggctga tccccatggc  17160
tatgggatac cagcaatatt agctgtatta agttctgctt actgatgcat cttcatgaga  17220
ctcccattca ctacccgtcc aggctcaaaa agcaagtggt aactggccca acaattattt  17280
ccaaacctga aaagcaatgt ctcccctgaa gttctgacca gtatgctctg gagtcccaga  17340
aataactgca aaatcaaagg ctggtgcctg tgtgagcctt tctgtaggct tagagtaatt  17400
cccatgatta cacaggagaa ggctgcttcg atgacagctc tgagggctgg gcctggtctc  17460
actttgggga aaaaaaactc catctatcca cagggccgtg tgtgagttaa gccaggagcc  17520
cactggctgg cagagcaagt ttaactttgg ctttccagtg ctcaagattt cagggaggct  17580
ctatttaaat tttacttggc tgtcaccctt ctgaaaattt gtagcactat ccgtatcttt  17640
aaggaagtga cctttccccg tccttgtcct tgttagcatg acatgagaac ttggaagcgt  17700
ccatggtgac ctgcttccag tttgattatt gaaaacaaaa caaaaccatg catagatccg  17760
gggtttctga cttacctctg gaaactgtac tttctacagg gtggccatga gagtttgcag  17820
gccacctgct aaaagttgac aacctgagag tctgcagtag acaacacaca cagcatgctt  17880
ctgtgttgga tctgagtgtc tcctgcatct gtctgttttc tttgcttctc ctttaaactg  17940
ggttaaccat cctccatatt ggtactgggg atagatagca cccagggcct cacagattgc  18000
tagaaaagtg ctctaccaat gagcaacgtc ctctgctcaa tgagtgtgtg tgtgtgtgtg  18060
tgtgtgtgtg tgtgtgtgtg tgtgtgtgta aatatcagaa acttggttaa ataaatatat  18120
gtaacataca atatacttat ataatatatg tgtatatatt atatatctcc atcccaaagt  18180
tctctgtttg agactggact taatacttcc cgttgggaat tgcttataag gttttacttt  18240
ttagtaaaga aaagttgttt gtttcctaaa ctctctggct taaacttttt acttaagtca  18300
aaaagcaaga gaatacctct cggcttgaat acctttattt ttaaagctca agagtctttt  18360
ttaaaacaaa aacttgctac agaacttggc accaggggac tgcaaggatt taccttattt  18420
tgatgatagc tgcctgcaaa cgatctatta gaataatctg cataattgca gtctcccctt  18480
cagtttattc agcctgcact ccctagtcta gatttactgg ccagactgtt attacatcaa  18540
attccttgat gctgtattcc tgaggactga tggaactaag agttacagag aggaatcagc  18600
gacctttgtc tgcttttcag aattcttcag aacatactga tttagccagg ggcttttgcg  18660
attgctctcc ttactgggtc agtacctgat tttgctgggt ttctggccac acatgtgcgt  18720
ttgggaagca ggatagatag ggcgagaaac ctgaattggc agtcagagtt atgaaacagg  18780
actttgttac aattgatagg tctgtacagt ggacgcacag cagctgttgg catggtaact  18840
cctacgtggc agagtgcatg gagcccgcag atgactttag cagcgctccg tgttaatttg  18900
ataaatggct tttttaatag tagtttgtgg gctaatggaa agattgaagc gaaccctcgt  18960
taatggaagg gaggatggag attttgaagc cactgggtga agtcggagag tcccagccaa  19020
gtctccattt tcagctcagt gtctcttttc atgtgcctga agtgtggcaa accaaagtac  19080
agtagggagc ctgccttgag agtaggcatc ggccctgggc tccggcttac gagtgaagag  19140
gcttcagggt ccttattcaa tacagttgct ttgtgcaggg gcttagctta gggccactgt  19200
```

-continued

```
aagaagtcta cattgtgttt tctttttcct tagtggtaat ggggcagggg ttatggtggc  19260
cgacaggtct ggcatattta gccgtttggt tggttgtatt gtggttattt gggttctcag  19320
aggggttgtt tatttttgtc tctggtttgt ttgttgacat agggtctcgt aacccaggct  19380
ggcctcagat gccctacata tatatatctc tgaggatgac cctggacctc tgatccttct  19440
actgccagct ccagggtgct ggggtcatag gcgtgaacca ccttgcctag ctaatgtggt  19500
atcggggatt gaacacagag cttctgcctg ctagatgaca ctctatcaat taacggcatc  19560
tcctcctggt ttcggccatc tttcattgtg tgagaataca taatcacacc acactgctgg  19620
cccactcaag gagcctctct gcaacccaca ctgaagctct gcgttcctta tatagcgctc  19680
gacaaacacc tctgggggat ggatctcctc actgtgttgc caaagcaaaa cctggggttt  19740
tttgcctttc tggcaagttc ccaggagacg cggacattac cggttctcag tccacatgct  19800
gagaacttgg tgctttacac taatgcggag aaaattggga acaagacata aagaggccaa  19860
atgacttgca ccttaatggc taaggatgat ggagcttgaa cttgaacgtg gctagggcct  19920
ctaaggcacc tgctgtctct gtcttatcag caatggcaga agtgcagtgg ctggagcatc  19980
ccaagggtac cttctgccat cccaagggta cacggtgtat taatctgtca cagtcaagtt  20040
cagaggtggc ctcggaagcc tgctgctcac agccttctct gcgtgcgcat tggagttggt  20100
tttcccctgg gctaacctac aatggagaca gtaccaacaa acccaccaat gcagctgaaa  20160
caaaacaaga ctttatccgg gcattagtct aggccgccta ggagagaagt ggtttgtggc  20220
ttagatttgt aagggacgtg gcatctccag ttgttctagg ccagaacaga tcatcacagc  20280
tggagtcttt gttcagatct caggcaaccc agggtacttg agaagtttaa gacagatagc  20340
attactagag aggtttgttt ggttggcttg ctttttacat tttcatactt tttctcctta  20400
actcatactc caaacattcc attacatggc gctaggtgta gtgacggata ttaagatggt  20460
ggccagtgaa tacttgctaa gaaaagtagg ccaaaggcat ctgtgtccaa atatgctgaa  20520
ccgctcagcc caagagcggg agggatgatc aagacagaag gacaggtaac acctgggatt  20580
cacacaacac attggctctt aaagtcacat tttcaatgtc cttaaaaaac aaaatgcaca  20640
gacacagaca caattaaaat aagtcttaaa agaaaaaatt taaaaatgca aaaattatag  20700
tggctactgc tactgttctg tccccaggat gtcttccaca aagagggaat ggaagccaaa  20760
gcagggtttt gtgtgcgtcc ggagcctcct gaccaatagc tgtgattctt ctggctttag  20820
aaataaccca atgccatctc tccagtggct ttgccaaccc acatgatacc tatttctcat  20880
tacccccaat aacgaatatt tagtctgtga ctgttgtgta tacagggtga tctcgtctca  20940
ataactattt ataagcaact taaaagcaag ggtgggatta ggaggtatat atagctcgat  21000
ggtaaagtgt tctttagcat acccaaggcc ctgagtttga tccttagcat aggatcagag  21060
tgaaaggggc aagggcaagc aagatgtttg tggtggtgga ggtggtggtg gtggtagtgt  21120
gtgttactgt gtgttactgt gtgtgtgtgt ttctctctct ccatcatgtg tataatatgg  21180
catgtgtata gtaaatatta catgtaaata ttcaccatat taaaagctat ctgtaaatgc  21240
aaatttaatt tgtgaagaga taaagcttcc aggtccattg aagaggagag gtggctctaa  21300
ataggctgtt gcagacaaaa cagacaccgt caggagcaca gatgctctac tttggctgtg  21360
acacaccctg tggcagagaa gactggggtg agaatgaaaa atggacatcc ttgggcaact  21420
cccagatgcc atgggttttc cacatcacat ttgatcttat aggtaaaatt gtctttaatg  21480
ctggggatcc agtgcaaggc ctcacatata gtaagcaagg cttcttccac tgaccacatc  21540
catgacactc gctttttttg tttgtttgtt ttgttttgtt tttcaagaca gggtttctct  21600
```

-continued

```
gtgtagccct ggctgtcctg gaacacactt tgtagaccag cctggcctcg aactcagaaa  21660
tccgcctgcc tctgcctcct gagtgctggg attaaaggtg tgcgccacca caactggcga  21720
cactagcttt taaagtcata ttctaaaaac tactacataa gtgggtatct gcgcacagct  21780
tgtaacagac ttcacaagag gggcagagtc cgtgattcgg agttgttttg ttaaatgtca  21840
agaatacaga aacatagaac tggttaatat ttctgctttc gatgcaaatg ggttaggtta  21900
gagccaggct catggccttc cccggtctta ctctgcctca tgtagcttgg ctacaggcct  21960
tgggcatagt gttggattaa gcagagaggg tccctaatag gtatgttcag gaaataggta  22020
tgttaaataa aggaaatggg gtttggggtg ggctgaactt tcctgaagga gcaggaagat  22080
tttctctagt cagatctttg taagagcctc cttcttactt acaattaacc cccccccac  22140
acacacacac catggaagat gtcctgacac cctatggact cagggttcac tgcttagggc  22200
tctctgttct atatgcttaa gtcaggatct tagagataag ggttgtggaa accaattcct  22260
gagttacatc acaatactaa tatcctttgg aagtttttag gtcattacct taggaaggga  22320
agctattttg ctattcattg gagatgggag gaggaacata aagcaaaaat ttctgctgat  22380
gtgggtgttt gcttggggcc aaggtactgg gaggggcacc aagggtgtgc ttcctttatg  22440
tttgtaaaag ccctactagc ctctgtttaa gacggtcctg taggtaggtg caggagggca  22500
tgaatcattt tgtgctgcct tcctcttggt tcagcagagc ccagcaagtc agatgggtag  22560
aggtgaccta tctggcctgg tcaggctttc cattggtcag cagcaaaact gtgctctggg  22620
cactgatgat gccaggcccg tgctggggcc catgctggag gatgaggtcc acaagccagt  22680
tcctctgtac ctccaaggct tacaaaaccc cagccactgg gctgtgcaat ctcacttcaa  22740
atgagtgtta tgtccaccca tggccgtcac acatgagcat ttcagtggaa agagactgaa  22800
attctattgc catggacttt cagaactcat gctcgatgga gatagaaccc accagtgtat  22860
taggttcttg aaagctacct cctgcgcatc atttaaatcc taaaaagata atttccaatg  22920
aagagaaact gattattttt tgctagggac aggttggctt aaggtgggtg ctattcgaga  22980
tgtctgagac ctgagggatg accaggatga gaaggaaatg gtcctacact gggctaggtc  23040
ctccaggcaa cccccctaca gagagcagtc tcctgcccgg ggtggatttg ggaccttctg  23100
aaatctttgt ggtccaccag tagggaatca acttcttact acggagagca gctggagacg  23160
taagcataac gcctttccat tgtcccggcg tgtattctca agtgggtccc ggcttcctgg  23220
aacggcttcc cttgagtgtg agggctgaga tgagtctgcc gggtgatgaa tgggttcagg  23280
aaggagtggc tgcatcacct gcctgggggga tgagcaccca cgtgacttca tggttgtgca  23340
agaattgggc aacgtttggc cagggtggag aggtcttggc aaaggcagtt tcactcctaa  23400
cagattccta tctcctccat gggggaaaaa caactatcag gagatccatc tgtacagcat  23460
tggaggacgt tgatcgcttc ttcagctgtc tgtggccttt tatttgctaa gaactcatgg  23520
attgaagacc tcagaagatt aaggaagata ggcatccctt tccttcctgt ggcagctctg  23580
gagaagggga gggtgggtaa aaggaagaca aggtgggagg ccatcaatgg caggacgggg  23640
agaaatggtt ttagagcgtc tgcagagtag tcgcagagca gagtggtagg cttgcaggtt  23700
caagttgtgg atctacctct tagctgaggt atcttgataa agtactttaa accctctgta  23760
cctatgtgtt taaagtacaa gatggaaatc attgtagtat tgaatcagag ggtagggctt  23820
agtcatcatg aaggttggtc ctagttccaa gacactagac acaagtggaa gggctgaact  23880
aaacttgggt ttttgactta ccactcttca ggtctcaatt tcttcatctg tacagtaaag  23940
```

-continued agactagagc agattaatgc taaggttttg tgtattctaa atgatatgat tccatggttg 24000
aataactatt aagtgtctgc tgtatgttcc agcactgtac ggggcatgcg tgaataggga 24060
tctctttgtc cttaagatct tgtcttactg ggaatgttc actaatacac aggagaacat 24120
ttaattcaca aatcaactca caaattaaaa aacattagaa gccagacatg gtgacgcacg 24180
cctttaatcc cagcacttgg gaggcagagg caggtggatt tctgagtttg aggccagcgt 24240
ggtctacaga gtgagttcca ggacagctag ggctacacag agaaaccctg tctggaaaaa 24300
caaaaacaaa aacaaagcaa aacaaaaaaa aaacaaaaca aaaaaattag aaattgaaaa 24360
cttggagcat tttggctgga tagatggttc atctgtcaaa ggcacttggc tgctctttcg 24420
gaggacaggc atttaattcc cagcacccac atggctggtc acagttgcct gtaactccaa 24480
tttcaaggaa tctggtgccc ttttatggcc tccatgagca ccagttaggc atgtgatgca 24540
tatatatgca gacaaaagat ctatacagaa gtcaaaagta aataaattaa aaacccaaat 24600
gccgagtaat ggatctgaag aacattggaa taagaaattt cactgtggac cagagtaggg 24660
agacttgaca gcagctatgc accttgtcac atcccaggaa cactagcatt aatactgaag 24720
ctggagaaaa cagcctccta tttgaggctt agaccaaatt ttataagaag agtatagact 24780
gaaagtatga tgtggtccaa actggtttct catatattct tggatgttca tcctatcaga 24840
acaacgtatc tggcacacgt gagaattcac tttccaaagg ctgggaagat ctagggctct 24900
gcattgttag cttcagcagc acgtagtgtt ctcagccctg cctctagagg gtagcgcaca 24960
ggcaataccc atcacacaat acccatctta cctatagctt ggagaagagc tttgagtggc 25020
cttatgcttc ctgagccaga ttcttctaag ataaattctt ccagtgccta aactttgacg 25080
acattgtggg aggggaatat cgatacacac ccctgaagtc tctgcatcta catttggagg 25140
aaacttagca accccttcaa aggtgtttca taataaccaa accatagttc ctcatgcaaa 25200
ttggctgatc caggcaacaa gggaatattc ctaatggcca aagtagtgga gttcaggtca 25260
tctcagtgat agagctggga agaggcttac gcaggtcttg aaaagtaaga agaggccatt 25320
ttgggagata agatgggtaa ggcctcagct acctaccagt ttccaggcca cctctcccaa 25380
tgcacacatg cgcgcgcaca cacacacaca cacacacaca cacacacaca cgcactcttt 25440
ctcacacact cttttacaca tacattcttt cacacacaca ctcttacaca cacattcttt 25500
cacatacaca cacactcttt ctcacactct cttttacaca cacattcttt cacacacaca 25560
ctctttctca cacactcttt tacacacatt ctttcacaca cacactctct ttctcaaaca 25620
cactctttta cacacatatt ctttcacaca cacactcttt tacacacaca ttctttcaca 25680
cacacacttt ctcacacaca ctcttttgca cacacattct ttcacacaca cactctcttt 25740
tacacacaca ttctttcaca cacacacaca gacacacaca cagacacaca gacacacaca 25800
cacacacaca cacacacaca caccacattg caggtagtca gtgcatttgg atgtggttct 25860
ttatttccag acaggaagtg agatgtaaat gacagatgag gtgcatgaac tctctggcct 25920
cacccagaca ctgataattt cccatcatct cttgagcagt cagtgatggc ctggctcgat 25980
agggcggttc atgacaccct agcttcagat cagcagattg cagcttgttg ctgagactcc 26040
ttcctgttac agaccacaga aatcctggtg acatgcggcc cattttacct tgtgtaaagg 26100
cacaaggaca tgtcacgctt gccatgagaa cacccgttca cacaggcacc aaagcagtag 26160
gcaggccaga tggagtcaca gggttcagag aaggactgtg acataatgct gaagccccgt 26220
gttggggaca gatgtctctc tgccttccag gaggcggcag taagcgcttc ttttccaaac 26280
cctcctctca tcccggtccc ctccccttttt cgttcataaa aaagttattt tcttccaaat 26340

-continued

```
aagcaattcc aaaatatatg aaataaacgt tagttctaat gagcctctgg gaaagtgctc  26400
acctttgaac tcggccaagg attatgggga aaagaaaaag tcgtaggaac ttgatagagc  26460
gttagagctt cctgggtttt taagctgggt tatgtattgc atttctttgc cttaataagg  26520
acggttccag aactctgccc tggataattg ggccatgtct gatagtagag acccaggatt  26580
ggttactgga ttagggatta ttatctgggt gctaggcaac aattgggtag gaggccctgt  26640
ttctagaatg ttctttcttt ccaaggactc agaacctttt tttttttttg atggtccctg  26700
tggggagtct gagacctagg aagaaacaag aggatgttta taggaggccg actgctaaag  26760
gggagtaaca ctcaggaact gtcctgctga gacaagctta cccccccccac ttccccgaga  26820
cattgctgct tcaaataaca gaaatcattt tctgaaagac aggctttcag tctgggtcgc  26880
ctctggctgc ttgtatggac tcttcacatc tgaatttccc caccctcctc ccccagataa  26940
gaagtttact tccagccatt ggcacaaatc atccctaggg tgacttgaac ctgactaagg  27000
acagctctcg aaaatcctga taaggtctcc aaacttctat gccctgtagc agtaactaac  27060
cattcccctt tctttaaact cgtccatctt gctttcattg tagtgttttt cctcatgcct  27120
aagtcaaatg agctctgtgt ctcatcccta ccactctcga gggctgagca tcaccagtgg  27180
gctcctccta gggaccagag atctagaaac acagaggacc ttagctgagc tggaggtacc  27240
acttcacggc atgagctgtt tttcctcaat tttccttcct aggcctgcac agatttcttt  27300
actggatgga taggccccca tgcataccca gcctacctcc agcccagcac ctgctcagta  27360
cacttagcct gtaaatacag tcatcccaca aaggacattt tctctggtgg ctttaaggtt  27420
tgacggagag ttctctagac ttggcagctt agctgtgacc tcaggaatct cggtgctggc  27480
aaggctaggt ctttgcacta acgtggctca gtgcccatgg agataatctc ctcttgtaat  27540
gggtgcacaa tcattttatt gttgaagcaa taggaacgca aaaacagaag gaatcccaca  27600
acagagcttg cccgtggctc agtgagcctc tctgctcctg gctgagggca ccttgggaca  27660
cctcaagttc aatcccaacc gccaccctga aggtcagctg attcataagg tgtgggctta  27720
tggaggagcc tacacccaca gcctgagcct ccccaggcct ggcactgccc tgtgttctgg  27780
ctaacacctc ctgtttattg tttgaaactc aaaagacaaa accctccagc aacctcctcc  27840
ctttctactc tgagataggt accccctttt gtccctatta ccactgactt ctgcagtagc  27900
agcatttggc tccaacactt gagtgctcgg taggcatcag acacagttct gagcacgtta  27960
caagcgtttc ttccttccaa gtgctccatg gaacagagac ctgtaatgaa aactaaagta  28020
ggttgtccta gatcagagca tgcaagtgcc caggccctca ggcccaggct gcctgcttgt  28080
ctggctccca cactggcttc ctcacagagg cagtgttccc acctagtagg tctgcacttg  28140
tagtaagtac ctattcagta agtgaaggct tatggctcac aaatacctga tgggatttaa  28200
attccaaaga gctgtgcagc ttacaaagtt acataaatgc acaggaccac tgacttttta  28260
ttttagcaaa gtaagggtga tgcttatctg ttgttgttga ttttttttta actctgtgga  28320
gagagatgga gagagagtac accacagtgc acgcatggga gccagaagat aagccaaggg  28380
agccagtttt ctccttccat cctctgggtc cctgggatca aacgcctcac ggcttcagat  28440
tggcagcagg tgccttcacc tgcccaggga tgctctatga ctccagttgc tttggaacgg  28500
ttttttttcta ggtagcatag tcagagctgt gagatttggc agactgccac aggggaaagg  28560
acagtgtgtt tgtcagaata ctggcggcct ttagaagcga tttccatgaa gctgaagttg  28620
caactgacat tttaaaaata attaaggaaa gagagcaacc gaagtctgtc ccgggcggtt  28680
```

-continued ccaaagaggt tgtgtgtctg ctctccagcc atcagcaggg ctgggatatc cgagactaag 28740
tgacaactca ggcaagcctc cagggtcaca caacacagcc cctccactca ggtctcccca 28800
tgctggtaga atgtagcatg caagcctctg gggctgtagg gtctgagtgg gcctttggca 28860
gcctttctct gtggctctcc acacagtaga acgagagatc cggcctgaag gctacacagc 28920
tgtgtctgag gcagagctga gttgctaata tctcttcctg atggccaagg cagggatttt 28980
tacaggccta gaaatctagc cctgcttcgg tagctctggg aggaggtcct gggtgctcca 29040
actgcttggc caggggacag atggagcatt gagcctttca ccaggatctc atggaaagcc 29100
agtgtcctgt cacctgtcac ctgtcacctg tcacctgtca ccattaatag gcacaaagag 29160
tgttgcacag aaaaaaagta ccaacttgtt ttcttttcaa ctgctgggct gggtaatgat 29220
gtaaaaacga cattatccct aataaacgtg atttgcagag atcgttgaca accccagtag 29280
cagagacttg cattagcagg taaacagata agagaaacag ccggcttcac cagctcctgg 29340
cgtggcacgt gtgtctaggt ctggtatgaa ctgaaggttg ggggtggagt gtggagtttt 29400
aaaggcgaat cgggtgatgg agagagtttg tcttaaggtt ggccatccca taaatctact 29460
tctcgatttt taggttgtgg tttcagttgt atacatgttt gttttggtgg tatttttttt 29520
tcttaaggga tgggggcgtg cttatggggt gtgtggcttg tcctagtttc tcacctccat 29580
attacctcac caaaggaggt gggagccctg gtcaggccct agcaccgtcc ctgccaagtg 29640
actaaagagg gcagccacat ctgtggcata cagtctatgg gcctgcagcg agtggtagat 29700
tgctcgatta tgtcaaggag ttgggatcaa gacaggaact tccgcaggtg gggagagagt 29760
ggcttctgtc tggacctgtt cccctagtga gggctgactg gcagctggct ccctaaaaca 29820
cctgaatgta ggtagcaggc acaggtaccc atgtctgtgt gagaatagct tcaggatatg 29880
tgggtaagtt agttgaaccc ttgggtgtta aataacctgg atacagtcac cgttatttct 29940
ctttaccatt tttttttctt tgccagaaag cactaaagca ttaggactct ggcttcctgc 30000
tcctgaggct ggaggagtgt ggcttgtcta accttctcag cagctggcca cgtcacatct 30060
gaaagagcta cctgatgctg ttgttgcctc tgtgcgtgtg tgtgtgcgtg tgtgtgtgtg 30120
tgtgtgtgtg taattcataa gcttgccttc cacctgtccc tcagaggaga cccccccaag 30180
ataaggaata actgaaaggc cagaacctca cagctgagga tcaatcaagt ctcagtgctc 30240
aggcctgggc cggggaggag gcatccacat ggactgcgga gagtggctga gggagcctct 30300
gcagggtggc aggttatgct ggaccttaaa gcttggaagg tcagaaggaa gaagaccctc 30360
tactaaggca caactactag gacctcgctg gatggccggc aggatgtggc atgtggatct 30420
acatgtatgg ggggggggcg caaagggaca cagctggaag acaggggcaa acatctggaa 30480
ataaatgaaa tacccatgca gtctgccaag ggtatagcc tggttaagga attgttttca 30540
tcctgtgggt aacgtgtgac ctgtgcttca gcaagaagac cttgacaagg tctctgagga 30600
cccagccgga atacggccca cagcagccca gccgacacgg ctgtacttgg agcttttaac 30660
aaagacattc atttctcttg cctatggtgt caaaagagag attctcatat gtactgtcca 30720
gtgtggccaa agcttggcca acagaatggg ccgaatctaa ctggctgctg tgctgcctcc 30780
gatcacttgt ggggcagtgt gcacacttag tcaccccact ctgccttgcc acctttctcc 30840
tgcgctttgc tgtctcctga tcactggccc ctgtccttcc ctcagaggta tttgtgtcct 30900
ggcttcctgg cttccttccc tccacccact ctcccttcca attacctctc caagtctttc 30960
tgactttctc ctctcacact ctggtgttga ctggggagta aaccagtcct ccagaacaga 31020
acttctctgc aggctccctg aggtcagggg agccatctcc acttgtcact cttgctggaa 31080

-continued

```
gaccacacat ggaagaaggg aatcatgtct gtgcaatgag tgcagcgagt aagcccctgc  31140
tggggaagac agcctgatgt cctaggttgc tcagggttac catctgagag gaagcctttg  31200
gcatttcccg tggcttcgga tgacttcttt gcaaaggaat ggagtaaagc ttcctaaata  31260
tgcacagata ctcaattctc acagggacga agaagggaca aatttgggag aaaacaagag  31320
cctgccctgt ggccgtgaat cagacccaga aagccagaca tgtgaccatg taaacggggc  31380
acatatcggt gttcttgcag tagaaccagc aagattctct cagttggttc cttttctaaa  31440
aacagggtct catgctgccc aggctagact tggatttgct atataacggc gggtggcctt  31500
gggctcctgg tcatccttct gggtgcagag attactgtcc tgcgtcccca tgcatggctg  31560
ctgcaggaca ctcatctcgg gcttgaacat taggcgagca ctctaccaag gcgagctaac  31620
tcctcccaga gatcctgcag ggtttccccc ttgtctgtac gtgttcccaa acccgtgcca  31680
cagctctgac cctgaattgg attagaagag cacatcctga ggttcttcat cttaacttgt  31740
gaccaagcgc cagtcctgac gaaaagacca aaacactttc tgttcttctt aaaattaaag  31800
tgtctgaagt agagagaggc tcagccctta taattatgag aagtttccct cgcccaacac  31860
ccatctgctt aggatggctc cccacacctt tcctccttgt cctcttcctc ctcttccttt  31920
tctacatcct aatgtgtaac ccttgtaggg gactttctgc cccctt cttc ctgcgtatac  31980
ccagtgctgg ccgcagaggc agcccagctc tgttttctca tgatgcagtg attatttttg  32040
gcactgcgca tattttctct aatgttatta ttgcctcctc caccctt ctg ggtgccttct  32100
gaggagcact cagtttttgg caattccaca caaaatcaga gggttaattt tagttcagtg  32160
gtgaagacga ggcaaggaga gagggggatg ccttctcctt tcgcccccact gcagcatcct  32220
atgcccaccc caaaagggat gcgtttcccc atgcctactc ataaaagagc ttgcttgctt  32280
ccctggctct gtgttagcca ttcatccact gctgggcctg gggttgaggg taccgctctc  32340
cagaggtgac gtccttcggg ggctgcacct cagggctggc atcttaatga cttgacttgg  32400
cgggcttaga acagcctcat tcagaccgag ttcactccct gcgcagttgg cccactcagc  32460
ttctgtccat agagttctct tgttcaagct gcaggaggaa atggagattt ccaagtggga  32520
agcagccttc ccaatgcctt aactcttccc tgcagggaag aggagctaca gagagagagc  32580
aaaagaaaac ccaagaggca cagctgcagt tccctgggag agggggacag gggcggggtg  32640
gggagcagtg tggctggggg ctgaggctgg agccagcaca gctgggatca ctttccttcc  32700
tggggaggtg ggaaggaaga aagtggaggg cgcatttgaa ttgccctaca tcaattagca  32760
gatatttttc agtttgtcca gagctgaggc cctgagaaga acatgcaaaa gtagagaatg  32820
cagtgtctct gctgccacag tccttaaagc agtaggaaca tcacacagga aagccggtaa  32880
gatggggaca ttctctaata atgaatggcg ttagtaatgt gggcagaagt gccagaggga  32940
gccgggacca ggcatggcaa gaaatataca agtgaagctg attcttcctg acagaggaag  33000
tggtctgatc cgttacgtag taagtaccct tgaccaaaca tggcgttggg tagtggacac  33060
actgcacact gtctttggct tcaagatctt aaaggtcctg gaattctttc tgttgaaagt  33120
gtgaggtcat agaccagcag catcagcatc agcatctagg atggtgctag aaatgtagac  33180
cctcatgccc cggcccagcc ccgaacttaa aagtacagtg gatcaagttc cctaatgctc  33240
tgtgcactcg gaacagtgta ggtgatgtca tagactagat gatagcccag tgtttattca  33300
gagggatgga tcacatgctt gtgtgcacgt gggagcaaac acacacacac acttttacct  33360
atgagtgtca ctgtattaag aactgttccc gggtagaaac ttcttggtct aatcacgtgc  33420
```

-continued tgggttagaa ttcttaggga agattcaaac agtgagcagc attgaggaat ttacgcccca 33480
gaagtcactg aggtggtttt taatgccttc ctctggtact gcttgtgcct cagaggaagg 33540
actctgaggg aaccaagggt gggggccttc ccagaagaac atgtctgcat ggggtgaaat 33600
gaaagggaga acagcatgag gctgactctg cagcgtggaa tctctggagc aatgtgaaga 33660
ggtcagaaca ggcagggcct tcccggggaa aatggacacc tctggaggtg aacagaggag 33720
ctgtggaaca gagatagact aagatggtca agaggaacat tctggaaggc cgtggggagt 33780
gtcagtgcct agagctaaat cttccaggct acgtgggact ggtcagctgt tctccacacc 33840
tcggagcctt gcttcatgct agggagttca tgtcacacac cgatcagcct cttcttcctt 33900
ttttctgctg tgcgattttg ctagctctct ctgctgaaaa agaagtgctg tagggacggc 33960
ttgcacatgt gctgtggctt gagccaaatc acagatttgt gttgttgggt gcttgtgggg 34020
tccaaaagaa ggtgtctgag aggacacagg agccctaagg agaaacccca gaggccttca 34080
ggcaacagct taggcatggg gcttacgccc agacccaggg gaaaggcccg aaagaaacgg 34140
accagggaga aagacgcgct caccggagac atccattaca cctgcccacc acagtaagca 34200
tgctgtcccc aagtcactct atctctgctc aacccctgtg attctctcca ccagcccttt 34260
ctccatccct ccctccctcc tttctttttt tctcccttta acttcttgtc tttagatctc 34320
caaacaaaga tgatctcccc cttccctctg gcaagtttgc cccttgaagc aatggcctag 34380
agtagaaggt gatcctgctg tcccctctct tgccacttcc ttgatcaaga gagtgttttc 34440
aatggcttca aattcagtat tcttagaggg ctataccctc cgtgtgccca gttcagcgaa 34500
gccttctgag ctgcaagagg ggcctgttta ttggcatttg gagaaaattg cccaattaca 34560
acccaatgtg gcatgtgggc tgcgttgaca cagatgtgag agctaagcat gccaacttcc 34620
tccatctctg ggggctgctt cctcagggca cgtgacctgt cgccatactc tttccatgag 34680
atttgaggat taagtcaggc agtaggaatg gataagtgat ccttgttaag tgcaaagcac 34740
tgcccgtggt tatttgctag tttcagcagc ggcagcagca gcatttcaat ttgctgatac 34800
taattaaccc cttagctaga gtctgcacat tggcagaggt caggcagtaa agaacatcgg 34860
aggccagcaa agaacaacac ttagacagac aaatggccac tgctgcttgt tggcccttca 34920
ttacacgtaa acgtctacaa gtcttctcta gacctccatg tgtgaggaga gggacaacgg 34980
agagagagct agcttagagt gagggaagag gaattgttga cctgcaagat ggccatcatc 35040
ccggcactgg cttagagcca aaggcagcct cttcagatgc ttcaaaaaga tctaaggaaa 35100
agaggaaggc tgagaggaag gaagcctggg ggcggggcat gtagagccca ggaccaggca 35160
gaacatgagt ggttggtttt ccttccttct gcagactccc ctgcctcagg agtgaggcta 35220
cggatgttgc cactcaggtg aggggatgta agatggcagg gagttagata catgttacaa 35280
agcagtatgc agtgcagagg cctacatcat ggcactgttc acaacagcta agcgttgggg 35340
accccaactg agcaacatat ggggatcgcc aaatgcattg ggtctctgt tcacacaata 35400
cgctgtgact ggcttttagg aatattaaga aagaaatctg agcattatac gtaatgttaa 35460
gtaagaaagt caaggggaaa agccgtacgt tccgtgagag tcctttctgt aagcatctgt 35520
gtatttccca ggttaccctt gccgagtagg atttgggctg attctcggtt gcatgatgaa 35580
aggcctcctt ccaagcctag agctgcttgc cagcacactc ctcacgagtc cttgaaaata 35640
catccgagga gttccatcta cttccaccta tccctatttt ctaagcctca gttttcctca 35700
tctctaaaat ggacaactgg cagcagctgt tccttcgtgc tgtgaagtga gatttactta 35760
ctcttaaagt gccttataag gtgttgtgtg tgactcaaat gtaaagtagt attcactaat 35820

-continued

```
atgctagtgt ttacctattg ccacgggcca ttcagaatgc tgaagcaaaa gccataggcc  35880
gggaaacttt caaacagcag ggagtcattg cttgtgtgtt tgaagtctgg gcagcaaaga  35940
tcaaggtttg agcctgatct gttttgttta ttgaggatcc acattctgct tcacacagtg  36000
gggctggtgg aaggtgccag ggatccaact gggccttatc ttacccagag agagggctcc  36060
accctcactt tggaggcaag gatttcaaca ttaactttgg agacataaaa ctcagacctg  36120
ggcccttgct agaataaggc taggccaagg acagtttgtc acagctactc ctgtgcgtgg  36180
ccagctttcc tagcaggctg gggactccac atgtcctaag gtgatagaag ggtctgggtt  36240
cccagatgga ctgcttggta attaaatctg ttactgtctt ctgggaggct gcctggggca  36300
ggaggctcgt ccgataagca tctccagtcg gcccctgtgc agaattgacc attaaagggg  36360
caagtggagt gagccccaga cattacttac tgtcagctct gaacgtagtc caggcctgct  36420
gctctgggga tactgaccct cagagagggt cagcagctgg gggctaaact ccccatgaag  36480
gacggctggg ctgaaaggcc attataagga cttctcattg agacggggca tgagagccta  36540
gccctcattt cagccactcc tccctctgct actctgttgc tggcctcccc ttccaggaca  36600
gagaccacac tcttcataaa ctgtctgttt gtctgagtgc actgctgcct ctctgcctcg  36660
tccaggtctc agttcttcct gagttcttaa ctccgggtct tccattttga ctgacagctt  36720
ttccttccct ttgttttgca tgccctgact gaccactact gccttgggtc agaatgcttc  36780
cagaaagtgg ctcatcagaa cattgtctcc atagaccacg ttctcgctag cctttagaaa  36840
ttaccctctg agaaattctt gtgagttgtc ttgttctttt gagtgcctcc agttgtggca  36900
aaaaaaaaaa atatatcagt tgagagcaca ttttattctt tccaagaact atgagctgtc  36960
catagcctgg cctagtgact aaaagggtgg gtaagttggg gaacatacat agtcagttgg  37020
aatgatgtca ttgccattaa atgttgtaac tggtattctt ttgtggttcc aacattaatt  37080
cctaaatcac ctaccaaaat gttagagtag cagccgcctc agcaggataa gcctcagcct  37140
tctcctgaag tgactcttgt aatggccatc acctttttgt gatactcggt ataaatctct  37200
atgccattgt ttgggtccct tcctgtagct atagcatctg tagagcaatg gccccaccag  37260
ccctaacagt atctgttcag cctatgatag tgactttaaa tctgcttgac atgatggcca  37320
tgacaccgtg tgagggagag ggggagtgca tggtcagatc tcagaggtat ccgaggactt  37380
cctgcttttt gtgatgtata ataatgggtc ctgatgtctg tatcaataag aacgcaagtg  37440
attttgatat gagccaacat tgaaaatggc tgttttgcta aaatgacatc agtaacaata  37500
attccaatgt aaacatgggc caaaaaccaa aaacactcac tgaggaaaag ccctgcgccc  37560
caagctccat aaacgcaggt tttctttatt cctgagtgtt tgagaaaagg ggtaattgta  37620
tttccaacac atccttaatt ccagattaca tacatagtac acccccaaaa tcaacaaaag  37680
ggccctttaa aatcagacag ctttgtccag gtgtggtggc acacagacct ttaattccag  37740
ctcggaggca aagccaggtg gatctctgat tttgaggcta gcctggtcta cgaagcaagt  37800
tccaggatgg ccaggactat attacagaga aactctgtct cagaaagaaa aaaaaattga  37860
cagctgtgta acaatggtta gccctgggca cataagaaca gaattgggca ggagtcatgg  37920
tgtcctcaga taaatcaaat ctaaggtcag tccgagctgg gaccccagga tccatttttt  37980
ggggggtcg agacagggtt tctctgtgta gccctggctg tcctggaact cactctctag  38040
accaggctgg ctggccttga actcagaaat ccacctgcct ctgcgtccca agtgctggga  38100
ttaaaggcat gtgccaccac tgcccggccc caggatctac ttttaaggct tttccagtga  38160
```

-continued

```
gcaatcaaga tcaagaactc tgcagaggca tgggttctgc tgtgatttca tcagttgcgc  38220
aaacaactgc taagcttggg gtccagggac tcttgatttt ctccgggacc ctgagtaatt  38280
tttcttttta aaatatttat gtatttttat gttggatttt gtgttggctg tttcgctggc  38340
ctctgtgacc atgtaccatg tccacgcagc acccacaaag gaagaagata tcagaatcct  38400
taggactgga gttacagaca gttgtgagcc accatgtggg tgctgggaat tgaaccccag  38460
gtatggaaga acagtgtgtg ctcttaacca ctgagccatt tctagcctga agctgctatt  38520
tctttcacca ggcagctgtt gtctggcagc tccacaagct cactgaagag cccacctcct  38580
tcctgcttgc cttcacagtg ccctgtgatt tagcgtacgt ttagatccaa ccaacaggtt  38640
ggcccaagct ggtttagtga gcctcgcttg acctctcagc cacttaacct tatacggtag  38700
cagacatctg acttagatac ctgatgactg cagtcacagt aaaagttgag tctgctggag  38760
acagctaggc ttggacactc gcagatgaga aacaaggatt gggccgagag taggtcactg  38820
tgaatgagag catcgggacc cactgccaca cttacagtat cacgtgctct ggccaagctt  38880
tgcctgggtg agttttacct catagtctag gcttctggat cctttgattc tactaattag  38940
atctaaaata tttggaaaga aattatgaat gtggtgaata tatacagtct tttttttcta  39000
ttatcggccc ctaaataata cagcataata gctacttata gtgctcacat tctaggacgc  39060
attgtaagta atcaagtggt ttaaagtata gatgcagatg tgtgcaggtt ccacacaaac  39120
actacccctt aaggactgga gcatctttga ctttgtcttt gaggggtagc cagtcgtagc  39180
tgagcgagga acggttaccc ctggattgat gcttctggac agtcagttct gttttacctt  39240
tagcatgctg cttagaagag cttacctcct ttacctggga ttaaatcttt cagaatcatg  39300
tttgtttccc ctcagggaga gctactgtaa atgaatgtgg aaaagaaaat gctcccaccc  39360
ctagctgcag tgtggtagga aggactgtgc agtgtggtag ggaggactgt gcagtttggt  39420
aggaaggact gtgcagtgtg gtagggagga ctgtgcagtg tggtagggag gactgtgcag  39480
tgtggtaggg agcgtgcaag gctacttgat gttggacttg atcaaacaac acctcactgt  39540
aagtcagctc tacagcaacg gggctgtgt gcgtcctgcc ttcctgctcc tcccagtctg  39600
aactccaata ctggccttac tccttgggtc ctaggatgtc cctaaggtta ttgggtgctt  39660
ttccaaagac agagctgtcc aagccccaag gactgctttg cactgtgtct ttctaagtct  39720
caagcctcct ccctttccca tggtgtggat ggggatctga gttgtaggaa ggtctgtaac  39780
aacactggac atgtcagaac gatccaagag tttccttgct gcatggggag aaattggggt  39840
gttgggaccc agagaagcta ggattgagac aagtgattta gtctctgtag ctcctgtctt  39900
aaagagttat tatgaaactc aactgcagta aaatatgtaa aatatgtacc taagccgtta  39960
taagggcaac attgttatca ctcgcagtta gcagaatcct gcctcactgc ctttgctatt  40020
agcaggtttg tctctgatcc tctagctaag gactgcaggt gtaggtgacc ccctaactga  40080
ctgcttactt ctagagaagg aggcttgtgc tgtgaccaca ggggccagca tggtccccgc  40140
aggccaactt tggtgtgtgt aaggacaggc agccagaacc acatttaggt ggtgtgtttg  40200
gaacaccaca tatgatacag gccatctcgt gggaacagga gagggatggg aaccaaggat  40260
gggaaaggaa cttaggaaag aaaaccaacg tggagtaagg aagtaccaag tctctccgaa  40320
tcaagtattt agggtaggat atctttttaa gagaagccaa tggattctaa tatgtaaatt  40380
gtgggacaca ttcaataagg ataagcaaaa tgtggtcatt gtaggaccca tcttggaaga  40440
aaagtgttcc aggaaatgaa gcacattgtc ggcttaggaa gatgcccaga tataatatgc  40500
agagccagtc aagatcagcc cgtgtgccat agcctggtcc cctcagacag cctgcttagc  40560
```

-continued

```
gaggacggac aggtgccatg ccagagtcca gatgcagctg attctcaggg catcgatgcc  40620
cagggtagcc agacaatgga tcttcaatct gccccaatag ttttgattgc cagagaacct  40680
tctagggatt ctgcacccat tttatcctga taagacatgg agttttcttc ctactttaca  40740
gatgcaggaa ccagagccca gagaacgtgt tttcttcccc agattgagat gggtagatag  40800
cactgtggct tcgtacaagc tcgggcttct gttatctgtg ccttcatgat aattattctt  40860
tttcttcagg gttgctaatt aaatgatttc agtgttacag atttttgtct atttttccaa  40920
gagtcaacat tagacatctc tggactatgt caagattaac taggcaatct aattaaaatc  40980
aagctagttc tacagtggaa ctggaaaaaa aaggtagcta aagggagtgt acaacatttt  41040
aaaccaggga cctgcctcag ggtctcggcc atctaaatgt taaaatgttg aagttgcctc  41100
tttccagcta aggaaaggta ctgcctctta tgcgagtggg aggaggtaat gttttatcac  41160
tagctctgcc actaattagg taattgctct aagcacagaa cttaaccaaa ttgggtctca  41220
gtttccaagt ctctgaaatg gagacaatgg ttgcaaggat aaaattagtc agcctgtctg  41280
ctccctgact ggaagggcct atgtagctcc tggttgtaag accttgggaa aacggcatgg  41340
tatgttctgg gcctcagtgt tcctatctgt aaattgcaca atgtctaccg agccgtgtca  41400
gtaagaagag tataacgggg tgatatgtag ttgtcggcgc agtgactgaa cgtgtctgta  41460
tcagtaagtg tttatgtagc tgaaggagct tagccaaacc cagagctctt atgccaaaga  41520
gaacccagac tttagctagc ctgttcccca caactcagcc acgggggtag ggggcgcgga  41580
cgggagagct tgttcttggt atcgttgctg atacacggcc tgtggtgact gcttcacggc  41640
atagctgctc tggatgttaa caacgacggg atcaggcgct gaccctgctg ctgtccggaa  41700
gcgtgagggc tggtgctgag gaggggaatt caggatctcc tacttggacc tcaggagcca  41760
gagctgtggt actccagtgc agccattcct cctgtgagcc cttaaggtat cccaccctaa  41820
ggagctcagg attgagatat aaaatccagg gaccaataat ggcccttaaa gtctggtaga  41880
agatgcaaat tctcccaggg gtcaggttct gaggggtgag aagggtggga tagaaataga  41940
gaggtgtggg gtttctgaga gctgaaaggc agggaagggg gagaaaggga gacaaggaaa  42000
gccaagggga gaggggacaa gaaaacccat ttccctcttt cacaacttct cacaaggttc  42060
tgcctgacca tccatgttat gtggctcttc ctgcagtctg gtatccaatg gctaatccat  42120
ctgggggcct agatggcctg caaatgaagt gagctctgac gtcgaaaacg tcgaaacagg  42180
gcctctgcct caaatccgca cggggatgag aggcatgcca gcattccagg aatccccaag  42240
tagtgatgtt ctgtccagat aacgacatgc tcaaagacag gcagaaagga gagcaacccc  42300
taggactggc aacctcagag ggtaaggtgg catgagccag cctggagcta attggaagaa  42360
ggccttgaaa gccacaaagc acactggaca tctacagaag caaataccaa gttagtttct  42420
ttattaaaca agcaatatat gttatttata gaaaacacag gaaaatatcg ataaccactt  42480
ggtaggccag ggagggcgag ctccctaact aaccccatta ctctgcaact cttactaatg  42540
gctaagtgcc tagactctgg ggttgccctg ccaggggcag agttcaccta ccagctggca  42600
gtcacgggtg aattacttag cctccgtggg cctgttttct tatctgtata ttggagatgc  42660
taacagcagc tactctcaca acaatttgtg aaatttaaag atgctaacac tgtactgtct  42720
gaaagagtag ctgaactgta tcaaaaaacc tgtcaccatg acgctgtgac catcgtaaaa  42780
atgtttgcta cttaactgca ctccctgtgt agcacacagg aagtgctgtg tgggacctgc  42840
acagtgtttt gaggacatga ttgccctctg ttgcggatag gttgtctttt catggacaga  42900
```

-continued

```
ttgttgctaa tgtttcttta tagtggaatg tgcccaggac taaaagtttc acataaataa  42960
atggtcacag tatgtcctca cagttactgg ttactgatgc gacacttagg cagcttcatg  43020
gtagaatctg acgagttagc aggcagatac tctgactttt aaacttaccc gtgttagtac  43080
gtgatatgga ctttgtacga agaccgtgtt tctttaggat ctctggaaag aggcaggttt  43140
gggtgtcagt ttgtcctttc cttcccattc tgcaacaaag aagagtcagt ctggcacctc  43200
aggctggcaa ggatggcacc cactgcagct accacccttg gaggtctttg cttctggatt  43260
gcaaatggag gcgtgttgtc cgcctcatgt tctcttggcc tttactgatg tctccagact  43320
ctaacctgtc gtctctcaga tcagaaacag ggtcttaggt aagccagggc tggtctgacc  43380
gtagcttctt cgcccttctc tttccattgg tgccctttga ccctgtcctc aaactttgtt  43440
cattagttta attaaatctt tgctaacgct acccacgtga agcccagttc tggctcctgc  43500
aagaatacag aagaaagcaa tttgagaaga caccaatgcg caaaagcaga gtcaatacca  43560
aaaggtggct tgctcatagc tcccctgggc tgagccagat gggttcagtg ggagaattga  43620
ctcactgtgg gggtgagtgg gtcactaccg agagtgtgaa tggatgacgt ccacattcca  43680
ggactaaccc ctcgtttctt catgtaggag cagctcagag ctgaggaagg agaaatcccg  43740
tgatgccgcg aggtgccggc gcagcaagga gacggaggtc ttctatgagt tggctcatga  43800
gttgcccctg cctcacagtg tgagctccca cctggacaaa gcctccatca tgcgcctggc  43860
catcagcttc cttcggacac ataagctcct gtcctcaggt aaggcttgac aggtcctgcc  43920
ccaagctggc atctacctag gcctcgctcc aagacacatc tacaaatatc cactcacaga  43980
agctggcaca tggcctttag tgttacattt atttagttgc gtgtgagggt atgcatgtgg  44040
gtcagaggac agcctttggg agtccattct gttctcttct tccatcatct gggatctggg  44100
acttgaactt gggtcctcag gcttagcagc aaatgcctct agccactgga ccttcttgct  44160
ggccctgttc cttcatttta gcatctcccc tctggcaatg atcttctcat gagttcaccc  44220
agggaagaga ccaaggacag actcaagtga gagtgtgagg tgctcccaga gagtgtgagg  44280
tgctcccaga gagtgtgagg tgctccaagg ggttggagag ccgagagcag cttctcctgg  44340
aagcccatcc agtacctctg gacctctggc gagagtcccg ctccacactg tgttgactct  44400
gcaggaagcc ttttatcctt gtcttccagc tacatctcta ggacatcaga aatggtgatg  44460
tcccttgtga tctatctctc agaaccttgg tttccttgcc tacaaactgg aattagccag  44520
gcatactgcc tgggaggata ggggtaggaa atgggggggg gggattatta gggcactata  44580
ggaatgagtg gagacagcgg ctcagctgta ttcgttcttg ctgggctagc ccccgccata  44640
gaggacagcc tcgggcacct ctccctgctc agccgatgcg ttcttctttc ccgcatatct  44700
cttcaccaac aaacagttca taacgaatgc tttctttcct ttgtcagagt tacatccctc  44760
aaaaatcatt tcctgttagg cctcaccagg aagaggcagc ctggggtttc cactttcaca  44820
tcctatgtgc agtcttgtca gacttatcag ttctgtaagg aaactgggca gcatatagct  44880
gccaggctgg cactacagca gggcagtgtc cgaggcatga gcaagggagg caggcaggca  44940
agggggaaag agatcccgtg gctcattttg agttttcctg agtgagtgtg tcactctgga  45000
gatgactcct tacatggcta ttctgggaaa gagccccctg cacagagggg tccagaatga  45060
ggcggggaag ccagactagc ctgtgctatt ctgggcccct gtgcacagga aggatatatg  45120
ggaaagacct tcggaggtta gaatggctgc tcatcccatc gtcctcctct aaccccccagg  45180
ctggaggcta agcctgggct gcaaggctga ggtgaccgtg ctgttacaga aatgagcaga  45240
gagtggagaa agcaagggcg gagccgctgc acacacagca gggcaacagc aattactcag  45300
```

-continued atttagacgg tgaaaatggt tgagggaagc tcaggctaag gacttgtaaa gcctggactg 45360
ctaaataaaa aggcagactc ggaggtgtct cacccatgcc ccatgcatgc cttcatttta 45420
cagaggattg tcctcttgga gaaatgagga cgacagttcg gtgatttgta ggattttgca 45480
aagcctgtca ggcaaaaaaa aaaaaaaaaa aaaaaaaaaa aaaaaagaaa tgtagataag 45540
gggcagggag ccaatgtcca agtgaagcag ctagagcctg accaggacta gccaggagca 45600
gtgggtggcc aggaggttct gagagctgtg tcttgctgcc gtagcaggga cacattgtct 45660
gtgctcgccc acacagaagc ctgtgtgtct tcctcgatgg gtcgaggttg atttgcagag 45720
ggcttggcta gggttggatc ttccgagctt atctgccctc atgtgtcctg gtgcaacccc 45780
tcccgcactc cacgtactac acaaagccac agatacaaga gcagacacca cacggagcag 45840
acatctcagg agctctgagc cttgagaaca aggactgcct actctctaga cagcataagc 45900
acggacagac cagaaccctt ggcgcgtcag ctatggggct cccaggcctg aagaaagaaa 45960
agttagagat tgataaacaa gttttggtca tctggtcctg gtgaccttaa agaagtgctc 46020
ctgagtccag ccacggaagg agatgtggct tagttctcct tctctgccat ttctccaggc 46080
tcctaccagg cactctcggg actggttatt tccagaaatg gaatgtaaaa tgagcctttt 46140
cctccccacc caccctttgt tttagtgtgt gcatgcgtgc tctggagagg ttagggaaga 46200
gcgtcgaagt cttgcttaaa gacttcaacc tcccttcttt tagacaggac ctctcgctcg 46260
actcgaagct cacgatttta gctaggttgg ctggctggca aactcacagg atcctgactg 46320
tgcaggtcaa cattggggtt ccgggcacac acagccaacc tgtcaatgcc gaggactcga 46380
actcacatct tcatgcctgg gcagccagtg ctcttatgca cttagccacc caagtggctc 46440
attgttttaa attttcacct attatatgca tgtgtttgtg gaggggagga aaggacaact 46500
tttgggagtt gattctccct ccccaccatg gatagggttc caaccaagtt gtcaggtctg 46560
aatagaaggc ctttttacct gctaagccat cgtttcaacc ctgaaccata ggtctttatg 46620
ttttgttttt gttggttagt tggtttgggg gttgtgtttg tttgtttgtt tgtttgttgt 46680
ttgttttttg agacagggtt tctctgtata gccctggctg tcctggaact cactctgtag 46740
accaggctgg cctcgaactc agaaatctgc ctgtctctgc ctcgcaagtg ctgtgggttt 46800
tttgtttgtt tgtttgtttg tttgttttat gtgacaaaaa gtttagagga tctttgagca 46860
gatatcctcc tgcactttgc ttattggtgt tgctgccatc tctctcagaa acattgtaca 46920
cagctctatc tcattggacc gcagagtcca tgaaacattg ttggatgata tgaaagtcta 46980
gcctgttgta caagttatag ctttgaagta agtctaacaa aagaaacgat gtaagagaaa 47040
aatcagagcg aactctaatg tctttggacc cacctttttag cagttacgtg ttacagtgtt 47100
acaacatata ctttcccaac tcaaaacaaa ctacagactc attacttagg caagtggagt 47160
tttgtatacc tcagagttca aacgcctaaa aaataccagg cttagcgtta gggccagttt 47220
cttctttact tagcagcaca cttcctttga ttttcacagt aggctgcagt gtgtgggaat 47280
gttggggagg aagcctccgc gctgagaact ccaggctgag tcgggccaca gttgagattc 47340
atatcacagg aaacaaaccg aaacaatagc tttacgatac ttgcttccac actggcccag 47400
gaggacagaa cacactgtgg cgggaacatg ggtggaaata tcacttgatt gtcttaaatc 47460
cagatgaacc ctgcgctctg gggctgaagt ggagtcgctt ctgcgtccca agagctttag 47520
accgcagtaa atgtatagaa tgtgcattcg ccccaattct gatttgaggc ttcccagact 47580
catatgtaaa aaaatcaaat tctcattact gcagagttgg agatcagcac aaagccaggt 47640

-continued ttctagacat aaatgtcaag tttatttttg attattttga tttgaatttg tttatgtttt 47700
attcctggca tttgcctagt gaagtcacac agtctgctca ggatatgatt ctccgatccc 47760
tgagacatta aaatccagga catggtttta aagctttcac catgacttct caggaaaagt 47820
gggacaaagg ggacagaatt acagcagcag atgtgatttc tgtgccctcc tatgccttgt 47880
ggtaagacct gttttccctg gttttcagcc caattgtttt actgtcccac ctcccccggc 47940
cccacctata ctcaaaatca aggccttttc tgtcctgttt ggaaggaggc cagtaagatg 48000
attcatgcca ggatgttact ggctgagagc agccagcggt cccttcaaga aagtctaacc 48060
ttgcttatag cattctctta aagcaaagag tctggccagt cagcgacagt cactgactgt 48120
agcgccccat agcattttat gaaggctagc gcagcaagca agggtggggg agcaggtgtg 48180
aaaagaacaa aataaaaatc tccaatgctg gacttgtggg gcacaccagg agagcagcag 48240
caaggccagc tgagatctat cactctgcag aaagtgtgag atagccccag cctgctcaca 48300
gtgcggcata aggcacagta agtggcccac actctttatg tttgccgtca gtatgcccgg 48360
aagacgcgtg cacagccttt gaaaggaaag accctgcgga gataactaag tagcaagcac 48420
cagggaagta ggaaacctgt atcggagctt gttaggaaca aggagtttct tgaagatgga 48480
aacatctaga aggatcatcc gggtgaagta agaaagcagc agccttacgg ctggcacagc 48540
caggcctcaa agacccagtt agaagccacc tgctctgcca cctgctagtt cacacaaggc 48600
aagtggctct accatactgg tgtgccaccc aacatgggcg gtgctgccta aaggaaatga 48660
gcagtgctcc ggaaaaggcc ctccacagcc ttctcagcgg cacatatcct ggcggtggga 48720
gccatcaaag cctgtttact ggggctattt ttagcattaa agaatttcgt ggtccttctc 48780
aaaggagaca gttcgtctat accagttctt tgagattcga accctgacag attctgggaa 48840
gcaaatggcc aggatgtaga acctgagcta tttagaccac ccagcccagt tccttagcaa 48900
gcacctactt tattttgtac caatggtttg ctctccgttg ttatcagcat ccccaggagg 48960
ggcttaggct cttcgacaga tgtcttcctg gcagtttgtt ggttcctgaa ttgcaccctt 49020
ccttgcagta tccccagctc tccctgagac aggactgagt gtgtaatgag tgctgtgagc 49080
cagggaagcc atggaggaaa agccttagta actgcaggga gggagggagg tctggtgtgc 49140
gcagccgcca ggcatagcag tttttagcag aattgtgaca ggaggctcag ggctctgggt 49200
gcagcagggg gatgtctgcc tccctcttgg ctgggagtga cctagccaag ttccttcaga 49260
gactcccagg aggacaagca ggtgctaaaa gagcaaatag ttccactgaa ggaaggggcc 49320
acacccaagc tgggctgctc tagggtcgca gggaaggggt gggggagggt gctattggcc 49380
attgtgactt cagtctcaag atgttccatg tctgtggccc cagacaccct tctccctcct 49440
ctctaaaggg cagtccacct gccactgtag ccaatttcgc cacctcctgg aagtaagcgt 49500
gctggacagt tcggaaaggc cgcttggctg tgccgggcct gttaaaaaca ggaaacttta 49560
agcagaacta ttttctctgg gtctagttaa ccccgatagg ttgtcttggg attactccag 49620
attttgaagt cagtgttgcc actgagatca aagaagctga agtgaaaata aattctcagt 49680
aggcctcagc actagcctct gtctgtctgg agaaagtagc cacctcgccc tataacccaa 49740
atgcagctga aaccttctcc gggcatgttt ccggggtcag gcaccctttg cccagactgg 49800
ctggttttcc tgacgtgggg gatagtcttc agcacgtggt ctctggagcg acagctttga 49860
caccctctga acacttttttg ttgatgttgt tgttgttgtt aaaggaagaa aaggcacttt 49920
ttcagcttcc ctgaattagg aaggaagcct gggaggaggt agaaccttcc agcaccaccc 49980
tgggtggggt gcggcctcct cgtactagcc aggtcttggg ctctgagctc agcttaaatt 50040

-continued ttcagcagag ggttccacgt ttttatttta ctttgcacaa atcccgcaag ttgcatagca 50100
gtcctgggcc cgccagaggt cctggcccac ccactcagcc ttggctagac ttgaactcac 50160
tatgtagacc aagatggcct ggaattcaca gagatctacc tgcctctgcc tcctgatagc 50220
tgggattaaa gacctgctct aacacacctg gttaaatcca gatttctaaa gcacacacat 50280
atttgacatt aaataatgaa caagaagagg gcatagcctg tggtctgagg ataacagcca 50340
ggagccggaa caagagctga gcttagattg cagaggtgga cttggtagtc caggacacac 50400
agagtgcatg gttgggggta gagttccccc acaacgcccc ctagtgtctg cctcttgtcc 50460
ctcacggctt tgtgcctcta agttccattc tctttcgact attctatgtg ctatctatcc 50520
ccggacttat gtccccaaag tggtgctctg agaagccacc tctctgcccc ttgactggaa 50580
gagaagcttt gggacactgg gctcccttat tgtcccagtc tctgatattg ggccatggat 50640
cttctgcctc tagctggcct cttgtctgtc ctgggaggaa ggctgtctgt gtgtcctgca 50700
gtggtggccc aatcctgtcc agttgcctga cagacctctc tttccatact catgtgaact 50760
cacattccag gtgaattagc aaattgctct ttctaactct atgaagaatg gagctggaat 50820
tttgctgggg attgtgttga atctgtagaa tgctttcggc aagatggcca ttctcactat 50880
cttaatcctg ccaatccatg agtgtgggag atatttcatg tttcctctcc atcctatgtc 50940
ttctttttta gagtcatctc tcctctgact gctggagctt gtgctctctg taccccttct 51000
ttggtacccc atggtaatgt gcgtgagggc ttatttagct ttgtgaggtt gtgagccacg 51060
aactcgccac cttggctctg atttgagata gtaatggtgt cttagaggag ggagcagatg 51120
aggtagagct tgtagtcgtt gatatcactt taagcagtta atttacttaa ccttacaatt 51180
catgaagatg ggaatcgcta tcctggtttg ctggtggagg actccagcgt tcaatcgtta 51240
cccaaagtca taagcaagtg ggaagcagat gtaggaatag atacaacatt tgactccgaa 51300
gcttgtgagg tggttgaacg tggccctgca cttagctcct ggggcttcct aacattctag 51360
acatcatagc ctttggaaaa atggcttgac tcagaagtct tgcactataa aatgagactg 51420
caaatggtac atgccttgtg cgttattgaa aagccaatgt agagtgttta atgctgggtc 51480
tgtctgtggt tgatgttcca cttacgttag cagctaaaat aactgctgct gctgctgcga 51540
ggtctagcat tctatctgta gcctctaccc ccagccttcc tattggtaca gcaaattctg 51600
ctaccacaga aaccacgctg tcccacagtc attgtcaatg tggcctgggt gttccaccag 51660
gcatgtggca aatgttagat ggttggtagt gtgcctttcc ctgtgccctg gagccatgcc 51720
tgtcccctcg gtcatgtctg ttttaacact cgtgcccctg ttgttcattc ccctctctct 51780
ccagtctgct ctgaaaatga atctgaagct gaggccgacc agcaaatgga taacttgtac 51840
ctgaaagcct tggagggttt cattgctgtg gtgacccaag acggtgacat gatctttctg 51900
tcggaaaaca tcagcaagtt catgggactt actcaggtga caccctctgc ctcgttcagt 51960
aggaaaaaca tgtctttatt tggggataga cactaacggg gggtcctagg catagtctta 52020
cttgactttt ccttatgcat tcccatatga tgatgacagt ccttaggact tcccaatgtc 52080
atggggcttg acattccttg tggctgccct gacaggtctc ttctagctag attaacttgg 52140
caaaagtata aatcaagccc ttgttgccat caacattgct ctgatacgtc tgtaagtcca 52200
tagacccaat attgactgga gactattgat aaccactcag ttcatccccc tgcctgtctc 52260
tgaatgcaga cattatccta gcttcctctt ggagtccgaa tgacttcatc actaggagta 52320
acagcatctg gccttgcttt tgaaacaggt agaactaaca ggacacagca tctttgactt 52380

-continued

```
cactcatcct tgcgaccatg aggagatccg tgagaacctg actctcaaaa acggtaaagt  52440
gttcttcttt gtttgcattc ttctcatgac ccccaaagcc tgcacaaata gcccaaatgg  52500
attatgttcc atagatacag ttggactagc ttctgggtga gtatgcagct gttgagatga  52560
ggcccagcac atagaatagc tcctaatggc ccatccatga tgcctgatgt cacactacga  52620
ggtcagggtg ccatctctag gacatttcat catcacctga gatcaatcat ctccgccaag  52680
cgacaccacc caaaccaata gcttcatcta tgcctgatta tttatgggag ctacaggtgc  52740
cttttgtcgt gtatcaagcc acccaacaca caggcttaag caatctccca catttctggg  52800
gattctgtgg gcaggtctct agctcaatgt gacatcagct ggattgcagc catcaggggc  52860
taaactaggt tgaagtgatt aagatggctc acctggtgtg ctgctgggac agtgaccaca  52920
gctctcagtc tatggagcct cccggtagcc ttcttcatat gaagactcca gagcaaccat  52980
cttgtatgac agctcaggcc atgcatcttc cttctcccct gtaaagtgca gctgcagaag  53040
cctacagacc atcctaggcc ctagccctga aataggcatg tcaccacttc taaccctatt  53100
cggctggcga gggaaaggtt caggcttgcc ctgtgtctca ggtccgtgtc aagaggcatg  53160
gcccttagga ttaccactga agagcagcta tgacgggaat gtggagattt tcagaagaac  53220
taaaactttg gtgctggaga gctggctctg tggttaagaa tactggctat tcttctgagg  53280
acctaagttg acctcccagg ttctttgact ggtggtaggt cacaactcca gcttcaggga  53340
gatccagggt cctcccctaa cctctgcagg tatctgcaca aatatgccca taaacacaaa  53400
ggtacaaact tcagcaaatc tttccaaacc acacgaaagg agccatcgct gtaggcagca  53460
gtggcttcca atgactggtg agatcctctt gaacttgaga atctatcacc agtctggaca  53520
gactgcccac atcaacatct tgtaaatctg tcacctgtca ctactatggg gtgtgtgctc  53580
atccaacctg aatagcaaag gcagtgatgc cacgcctgcg aggcgtgttc tcgttgcctt  53640
gtgtgctgca aaaggggagg ctttgttggc tcacctctcc tgttggtaca gagtactgta  53700
atccacactc agacttacaa agctttgtaa aattataacc acctcccttt ccaatgctgc  53760
cccagcctct catctgcatt gctgcttcct atccaaagac cttggtcaac tggcttccag  53820
agtacatagg ctggggacca ccatgagttt atttgtcttg cctgtggtgc caagaaaccc  53880
taggctaagc cacccaacac atagaatgat tggttcttga tggtgaaggg gctattgatc  53940
acagacctgc gccaccatac ttggctttca gaagcacttc ctaaatcggt gtctctcgtt  54000
gcttctcttc tagagaacac tgctccctgg gttctttgtc tcaactcaac tgctgaccaa  54060
aacctttgtt tgagcatctg tgagctgaac taagaatctc actcctgtgc tgttcaaagt  54120
ctttcttttc aaatcgatgg caaaagatga ggccaaatct aggatctttt tgcttttagg  54180
tttctctgac tcatagctga gtgtcctcca cttatctgag gaaaactcag gtctttagat  54240
tcatgaatgg ggatttgaga tcaagcagac tcagccaatc agcaagtcct tgctgaaggt  54300
ttcaggctgc atagactcat ggtctaaaag caaggggtcc gtgtggattc ctggaagaag  54360
aaaaggttgg gagacgggct gtggaatgct ttgatggtga gtggaaagcc tcaaactggg  54420
tcctgcaaac agtcaaaggc tgttgaagat gtttaagctg aggtgatact atcagatgtc  54480
agaatgggga gactccagtg attagcaagt taggagccca caattacaac ccagactatt  54540
aatcacaaat gaatattgag ctccctcatt cctaaatcct ggggggggct ctctcagtac  54600
agttataact catcatatac aaactccacc taataactaa aattataaga agcctaatta  54660
tgggagagac agtttataag aacaacattc aagctgtcac ttaatgggtt ctgcagaaga  54720
tgtttaaatc cagttcaagg atgccagttc ttttgataca cagctgtttt agactgtgtc  54780
```

-continued

```
ggtcaaatca atgttcctta gaggtgtggg tgcagaggtt ggcagcttct cttagagcag  54840
tgtgactact tgttggaaag ttctgaattg ctctgtgatg ctgggcctgt ggaggccaag  54900
gatgaagatg gcggtgtagc cacagtttag acaccgttgg actcatgttt tctgttctgc  54960
ataacaagaa gcagaaaacc tggacaggct ttggagattt gtactaaagg aaagaagccg  55020
tatgttcctt gtctcggtga tttatttaat cctaaatgaa aggtcatcta attgatcttt  55080
atcaagaaca tcgttaagat agacttgtct acccagttcc agttaaaaac aaggggtgtg  55140
tgtgtgtgtg tgtgtgtgtg tgtgtgtgtg agtgtgtatg tgtgagtgtg tgagtgtgtg  55200
tgtgtgttca ttcccctccc ctcccctcct tgacatgtgt caccttagga ggaaactgat  55260
gaatggtaca ttatccaaag catagtcatt cgaggattca ggtaggatat tggttgctca  55320
cattcctgag agacaggcta gcgagagcag agaggagtgt ccaaggataa ttctaactag  55380
acagacttat gtccttggag caaccatggt cactctcagg tttcctgcta gagacccaag  55440
gcctgactgg ggagagacat ctaaaactgt ggtgtagcct cacagctctc aggtgacaaa  55500
caggtacagt gtgtagcaaa catggcacag ctcctgcctt ccaggccttc ctgctcctgg  55560
gaatgcagtc acacaggagc ttctactcag ccatcctcca agaaatctaa cttctgcagg  55620
ggagcagctt tctcccagga gtccctccac tgtgagtctc caccaacctg gtgttagctc  55680
atagtccctg ggtgggactg gccatcacta gaagttttgt aaaaaacctt ccttgacata  55740
tttctgtcct ctagttctga ccacaattga gccaggactc aaggcacagc aacaaaggga  55800
caccattagt atttaagcca tgagggcctc tctgcccatg gcaggctaca cgcactctac  55860
tacaaaccac aggagacaca aatacaagtt gcccagaaac attgtaattt ggattaattt  55920
aactggctcc cacgcccttc cccactcagg ctctggtttt gggaagaaga gcaaagacgt  55980
gtccaccgag cgtgacttct tcatgaggat gaagtgcacg gtcaccaaca gaggccggac  56040
tgtcaacctc aagtcggcca cctggaaggt aggattcgtg gagtctcaag aaagagccag  56100
gagcaggagg tgcctgaggc ctctccctct tctcggccgt ctcggccttg tcttacttct  56160
gtgctttgac cccaggtcct gcactgcacc gggcaagtga gagtctacaa caactgcccc  56220
cctcacagta gcctctgtgg ctccaaggag cccctgctgt cctgccttat catcatgtgt  56280
gagccaatcc agcacccatc ccacatggac atccccctgg acagcaagac tttcctgagc  56340
cgccacagca tggacatgaa gttcacctac tgtgacgaca ggtggggtgt tgggacaggg  56400
tgggtcttac cagtgtgcat ctgtgagagt gtgacagcgc agggacggga ctaggacatg  56460
gtgtgggact gctggctgca agtttgtaga aggtagcctc cttccatgtg aagactttaa  56520
aatgaagaga gctaggttag actctaaccc tcagttccaa agcaactgga cgttctcttg  56580
ggagtggggg gcacagaaac aataaagact gtggacttgg actagagaac ctagcagagt  56640
catctgtggt cagtgtaggc tgctgttctt accttcatta aaggggagac cacagagggt  56700
gcacaggaag gcatgctgtg tggttgtcag tacatgcaag gtttgtatag actacaccac  56760
agttcctatc cacttgtgct gctgctgttg ggatggagat gtggaggaca acggtgagaa  56820
cgagttgtga tgtgcagtgg cttgcaccag ggtgagggaa gccaggtgag aggctgcact  56880
gggcgtgcat gcctagcctg agtgaaaggc atcactcact gtgcctgact acttcaccca  56940
tcgtaagctc agctctgccg tgtctctctg agcagaagat agatcggagg tacgccctct  57000
gcagttttca gagagacccc gaaagtcccg gtgccagatc catgacaccg gctttgaggt  57060
gcagtggcac ttgggatgct tgtgcagaaa cccaggagtg gtcagggatg tgggtgacag  57120
```

-continued

```
gagggagttg ctctgaagca ggaaaaccaa accctcacct gccatctcct gaaagcagaa  57180
aagagactgt aaaaaggagc tggcaggtga gggaactatc tcccagaaag gttcatttgc  57240
tgttaatttc cattcattat tgtggtttga gtgggtttca ggtaaaaggg ctagccttgg  57300
gttaagggca gaaggggaca gtcacaagaa atgggcagcc taaagggaca aagatgccat  57360
gtgcacgcac acagaggtac catggtgacg tccttaggtt ggctcagtac ggcgggtggg  57420
gtggggttca tactcacagg aaggatcctg ggatttagag atgtggctcg tcgtgcacag  57480
ggagatgccg cttagggtgg cttaggacac acagtatttt cagcatactc ttgccttcca  57540
aggaagctga ttgcatggcc ggcccaacgt gaattctgtt ctgctaggga gccgactgca  57600
gagggatgca aacacagagt gccccacgga gcgtttaacc gattagcaga ttagttaacc  57660
agggtacaga taggacagtt agtgaagggg ctattttaag tgtttaatcc cttggtgtta  57720
tttctcgatt gctttgggtt gggggagagg cttgttctgt ttgcatgtgt tgagatgtgg  57780
agcagtgtgt gtgtgtgtgt gtgtgtgtgt gtgtgtgtgt aagaggggaa gggagagaga  57840
gagagagaga gagagagaga gagagagaga atacatacac taacatgacc ttctgagaga  57900
tgtgctctaa atccagagcc tacatgtgag agccagtgta gagcagggct cccccatttt  57960
actcagtgaa ttatttggtt tggtgacatc tgacacaaag gggattgtgt cccctaacag  58020
aagcagggaa agaatctgaa gagaggaatt ttgagtccac aatcagattt gagcgagttt  58080
gatactttcc tctgattatg cttgtatgtg tgtgatatgt ttctatatat gaatatatgt  58140
atatatgtat atgtatttga ttattaatta tgagtcagtg aatactttaa accctccaat  58200
agtgtctgtc attttcatat atgtataggg cacagttatg gcttagacag tattgcttat  58260
ctgaaaatct tggaactaaa ctcgtttctc attttcgagt ttgggggaaa ttttgcgtaa  58320
actgtcctca agtgaatcta gaaattcaac atccaaactg ctctagaatc tgaagttttt  58380
aagtgtaatg taggcacact ttgggcatca gattttcaga tgaagagtgc ccgcctgtgg  58440
actgctgtgg ctctggcaac aggagtcttc acttgcttgg ccaggcaaaa gaaaaatctc  58500
gtcttcctct agcccccacc ctctcaaggc tggcccatga tttgcagcaa tcctcctgcc  58560
ccagcatcct gagtgctgag gatgtcttta ttgtccgagt aattaatgtc ctcctctgct  58620
gtgcactcaa acataaaagt tgcagtctgt ctgtttccta acattcttag ggactaatcc  58680
atgagctgtc actggggaac agctgccata aactgttgtg tcacggggga aagaaacaag  58740
tcctggtgcc tgagggtttg ggcttgagat ccgagcagct tagtgaaacc acagggaatt  58800
tgtaggacag aacagaacgt gccattcatc ctggaggaag acccaagcca ttctgaaatc  58860
ctttaaaagg gttgggtttt taaattcacg tgagatgcca tctagtggcc aaatagaata  58920
actgtgaagg aagccaactc atcaagatga ggttttctta gaaaaatcac atgtaatctc  58980
agtgtgattt tgtgagtctt ctgtaacttt gaaagatgta tgaaaattat agtaagcatt  59040
taaaactcat aagtaaaacc atttaaagaa taaaccacac aaaaagaatt tgagagcacc  59100
atgttccatc aaaacaatac aggacatagc caagagttag gtttgtaagt taggaagact  59160
tgtgtataat gctcctgcag agaccccacc ccatacacat aattacagct acctgtagct  59220
ctacttacag ggacttgggc ctctggcctc tgagggcaca cgtacacggg cacaaacacg  59280
tgcgcctata tgcatacatg cacacacgtg ttatcacgca cacgtactta aatctttggg  59340
gaaaaagatg tatggtggat tcattcaaag aacttaggaa cagtaagaca gcttgagtga  59400
gagaaggctt gagggccatg gaaagaatgt ccgtgaagtc ctgggctgct gagatggctc  59460
agcaaataga ggaacttgcc gccaagcctg ggaaaccgag tttgaccccc agaaccagta  59520
```

-continued tggacagagc tgatttgctg acttcacaag tagtcctctg accacacaca cacacacaca 59580
cacacacaca ctatggcatg tacactcaca caaataaatg catttttaaa gaggaaatta 59640
taaagaacca taaagtgtga ggccaggcgt gtgtgaagac agctagaagg tgtgtcaagt 59700
ccaagagtaa agcagactgg tttaagcaaa ttcgttgtaa aataatatgt tccctttttgc 59760
acattggaga tgattaataa actttgctgc tttttgtaat gggtggtatc gccttaattt 59820
cagggtgatc ttttgcaagc accgtgaatg tattttggtc tcatatataa ttgattccaa 59880
gtgctttagc aggcctgtac attgcctttc tccagacatc tcagttaggg gttatccaat 59940
gcttctttag atcctgaagt tagactctaa cgtgctctgc gtgtccttat gtccgctcag 60000
ctgacagtat tctggaatca gccctagcca tgtttgaatg tgtaataaca actactcaca 60060
tgttgtcctg aaacacctgg tctgttggaa atgctctgca gactccctgt agtttatatc 60120
agagtttatt gcatgatggg gttcctacca cggattagtc acttctcaca ttccttctca 60180
ctgttggggg ttttgtcgac ggagctggtg gcatgcagga tagcactggt ccaggctacc 60240
ttctggtgta taacttcacc ctaccaacaa cacatctcac agagaccata gatcccatag 60300
agaactgtta accatagagc tggggtatag acttcatata actgggcagt attcggggtg 60360
tgtgtgcaag acttaagggc tgttgcttga agcaagtctg gcccagataa aaatatatta 60420
aaatgattag gtcttgaaat ctgagtagtg aataatctag atatcattaa agaaatgcac 60480
tgccagtgct tataaatata cagaaaataa aaaccaagtg tctgggggtc gttaaagcac 60540
acaaggaaag agccagtgag aatacacatt gattaatgat agcgttcttg ggaaggcaag 60600
tacgtggcta aaaagtgctc agtactttca tcttcacgca gagttcagat actccctaga 60660
cactgtgttt acatgattaa ctcagcaaac cctgggcctc tgaagggagg gagcagcgat 60720
agaattggca ctagggggct gcagcctggg agggatggca tgtggctgat tctgctgtct 60780
ctagagggga cagcatgcag aagaccattt ccttcctgac cattccatat aacacaccta 60840
cacgtgtctt taacatgcca cacttcattc tgtgtgtgtt tgtatataca tgcgtatatg 60900
ggctcccttg gtctgcctgc atgcttctga aggtcagata tcagcactgg gtgtcttcct 60960
cttccattct ctactttgtt tttttgagac aggctcttgc aatgagctca gaacttactg 61020
ttttggctaa agtaactgat cagcaagctc ttgggatctg cctgctatgc cactgccatc 61080
cactggcccc acccactggc tccacccact ggccccaccc actggccccc agcatttgcc 61140
ccacccactg gcccagcact gggcttgcag acatcttctg ccatgcagca ggctgaggct 61200
ggggatctga actcagatct ttatgcttgg atagtgagca ctttgagcca tttcctcact 61260
cgtgcttgta gactatctcc agaacaaaga gcagttgtgg acagtgaata aatcacctca 61320
gattttacct tcacgcctca ctctgaaggc caaagccaga gtctggtctg acttcagaac 61380
aaagataccc ttcttccatt cattgtctgt ttcctctctt tcttcctctc ctgcctcctc 61440
ataggcttgc tccgtcctct ttggagtctc acttctttat ctgcttgtta ttaaagcatg 61500
cactcggtcc ccagctttga aatccgacag atctttttac gtttcccccct cctctcgtgc 61560
agtctcgagt tgacttttaa gtttacgggt gaccccaaat gattcttctt ccagcgagtc 61620
aaggatctct aattatgaag agcaaagtgg tccctctccc ctgatggaga gcacggatgg 61680
cactcttatc tgccgcagcc agggaaatga gcagggaagg ccccgggggc cataacagcg 61740
agtctataaa caagttcggt tccttaacct ccctatggcg tcggtgtgcc tgcggatggg 61800
ggcaaacggt cattagctgt aacttggggc ttcctggctt tgtgaagtct tgagaacccg 61860

-continued

```
catggtctgc gattgtgttc gggccgtgcg catttcccag ttttttactg tagtctgttt  61920
aaaggaatga agagggaaac attaaatatt tattttggct gacaagataa ctgaaagctg  61980
ctagcgggaa gataactggc aagtctgaaa tctgggtttg tttgtcttct agaacatgcc  62040
cattgtgtgt ctttgaaagg atgatacggt cattaggcaa aaacatctta ttatgaggtt  62100
gattataata tttactcgaa gccttttgat ggcaagatcc taatcgtgaa aggaaatggg  62160
atttcttcag gaaagatgat cacatccttc ctagaaggcc agtggtaaaa gtttgtagaa  62220
aattttgcat cggctcagtc cggctggcaa gtgagcaacc ctgtgagtgg ctctgctgtc  62280
cctggttctg gttctgattc ccagggagtt tgaggtgcag ttggcttctc gggaatgctg  62340
tatggctagg tacaggcatt gctccactcc tcattccccc cagctttata tcagcgggag  62400
tgtctgtggg taccagctcc agggtccgaa atcaagtggg gacaaatcct cttgtggtaa  62460
ggatggccag ctggcactag tgctctgcca gcctcacagg actgaattag ccatacttag  62520
aggttatgtc agtgggccta acctttgctc tgcaaagact tgggcctcca gcatcgcgtc  62580
tggtcagaaa acttgccttt tctctgctaa cataagagca ggtagtatac agaatggaag  62640
ggcagactga agactgtgat gagctgctag aggtgctcct gtgggtacac acatgtgcac  62700
gtacgtgtaa acacatgtga acacgtgtgc actgagatgg ttaatcatgc ttaaggaaag  62760
tagatcgtga cccgggttcc taagtggggc tggattgtca gcatgacttc cctcactgtg  62820
gggaggcagg aggagaaggc ccacggtgta agagtccagt acatccttcc tagggcccgg  62880
gcacatggcc tttaggcctc tgcaagagaa gaaggaattg gagggggttc ggtggagaag  62940
gagaggcctg cggtgactct gggagagaaa ctggttgcag atggctggtg gggagagtac  63000
atgacaccct gcaagttagc tgaaaatcag atttcttaca agcaaagact ggattctggg  63060
gagatctaga accagggcag tttgccccag ccaagagagt agctggccta agacgagtag  63120
ctggcttgag aaggactggg tctaacagcc acatgccatt acgattggat ggaatgaata  63180
cagagacagt cactcgagca agcagagctt tttattttcc ttgtccttag cctctgtcca  63240
gagggcacag aacacagctg tgccccaagg cagtgtgctc caaggaggat ggtcataccg  63300
agctgctccc gtcagctctg gcttgtgatg agcaaagtgt gaggcatcta cgatagagga  63360
ctcgtgggac tcacagcaga atgacatgcg actcacaagg tggccggtgc agtgattcta  63420
gggcaggctt ttgttcactt aaatgtctcc acacagaaag cttccatgcg tcttcgtggc  63480
tctctccata ttggcttttt cctgtccagt tctcaaccaa aactagacca tccagaggga  63540
acacatctac acgcggcgca ctcatgccat tttctggctt cgctgcttgt ttacctgcca  63600
ggactgattt ttatgttgct tccccttagc agcctctgtc cttctccctc atggagatgg  63660
gaagagacaa gctgctggag acacatctag ggtcatagat ggcagctgag cagcatccag  63720
gggtgacacc ggagagaaaa cttcctccct ggctcttcct cgccttccct tctgggacac  63780
aggatttcca tctaaacatt cctcagcttc aactagaatg agcttgagat gctagctagg  63840
aggcctcagc gcttgttcct gtctgaactg ggcacttgtg tggccatcaa gccaattctg  63900
tcctctctca gatctccact tacacagatg aactgggagg tggagccatg tgacccctcc  63960
tgaccccagg acctcttaga tactaggcag tagagtcctc tgagatagaa cttcaggaag  64020
ggcaggagag tgggggacgg gggcagatcc acagttgcag ctgagtctga tgggtttttt  64080
ttaaattagg tatttatttc atttacattt ccaatgttat cccaaaagtc ccccacacgc  64140
tcccacttct tggccctggc attcccctgt actgaggcat ataaagtttg cacaatcaat  64200
gggcctctct ttccagtgat ggccgactag gccatcttct gattcatatg cagctagaga  64260
```

-continued

```
catgagctcc ggggttactg gttagttcat attgttgttc cacctatagg gttgcagatc  64320
cctttagctc cttgggtact ttctctagct cctccattgg gggggccctg tgatccatcc  64380
aatagctgac tgtgagcatc cacttctgtg tttgttaggc cccagcatag tctcacaaga  64440
gacagctata tctgggtcct ttcagcaaaa tcttgctagt gtatgcaatg gtgtcagcgt  64500
ttggaagctt attatgggat ggatccctgg ctatggcagt ctctagatgg cccatccttt  64560
cgtctcagct ccaaactttg tctctgtaac tccttccttg ggtgttttgt tcccaattct  64620
aagaaggggc aaagtgtcca cactttggtc tttattcttc ttgagtttca tgtgtttagc  64680
aaattgtatc ttatatcttg ggtattctaa gttcctgggc taatatccac ttatcagtga  64740
gtacatattg tgtgagttcg tttgtgattg ggttacctca ctcaggatga tgccctcctg  64800
atggggtttt gcttgagtaa agaaatggtg tgatgaggtg tgacgatact tgatacattc  64860
accttagatc ctgaagtctc tgatcgcatg ctgtgccaag gctgtttggt cttttgtcct  64920
cacctgctgc ttccttttta attcagaatc ttggaactga ttggttacca ccccgaggag  64980
ctacttggac gctctgccta tgagttctac catgccctgg attcggagaa catgaccaaa  65040
agtcaccaga actgtgagtt cctagatacc ctgtgtcctc gacgtctgcc cttgagggta  65100
tgattgacaa gacacggcct tggttacttc ctcccagagt taccatcttg ggtggcagat  65160
aaggtagata ccttcaagat ggtcagagac tcaccgatgc caccagcccc taaatggcgt  65220
ttatgcaaat taagaaaaag actcttgagt cctcgcagat ggttaacatt ctatgcaacc  65280
ctcaggggca gtcttgaaga gcagctaaaa gtgggtgtgt aaccagcttg ggctgcact   65340
agatcggcaa gcacctcggc atagaagagg gcctgggaag gttccaacga gagttggctt  65400
gcactgaatc agtttccatg gtagagagga tggggctaac cagaggaaga ggtaagagag  65460
ggggctgcct gtgcagcagc acactgtgtg catgcgggag agcctgcaca gcgaaggagt  65520
tcaggaacag agctgtccag tagtagagcc tctatcacag aaacatcctg tgccttcata  65580
ggccacacaa gacctaggta gtacttgcag tgtgtctggt gcattgagaa atgtctttaa  65640
acttaagttt taaatgattt aagtagcttt tcttggcact tggctacctt attggactga  65700
gtggttctgt ggtgttccct tggccacgtt tccaattcgg tctttccatt tatggatgct  65760
ccagggtaat tttgaatacg taaaacccat caacatgtaa gaaactggac ttggtcctct  65820
gaggactagg gattggtaga cttgatctct accctaagga gtctttgttt tggaagaaaa  65880
gggagcctgg ctcccagaaa ctgggtgacc tttaacctta gcatctctca tagcatcgtg  65940
gtaatacaaa cagcaggtga atgataatct cataaacaga ctatatttag gaaagagatc  66000
atccaagcag gacactggta cagacagggc tgccgagggg ataggctagg agtcttcaaa  66060
taggaaaccc tgagaagcca cctagcagcc atactggcaa tgtaggaaac agaagtgtag  66120
ctttctgttc caagtctgat tctgcccgac actcctctgt ttacagtcgg gagagctcga  66180
gctcagcttc actaactgtg cagcaactcc acaagctgtg cacagcatgg ggggggggga  66240
gggagagaga gagagagaga gagagggagg gagggaggga gggagggagg gagggaatat  66300
gagaattcaa actcacccct ctgtttcctc cctgggagct ttgggtttca tctgatctaa  66360
taatacagca ggggccatta tggcatctca gacaagtctc ttactgtctc tctggcataa  66420
aaacaaaaat atccaaatag actaccccag gggtggcagg acactccctg atgctctcag  66480
ggagatgacc cagccagaga ctccaaggta tggtgtcagc cttctcttgg agggccccca  66540
atgcttttgt gctccctagg ggttccccac ccccaaggcc gattggtaga gacacacaac  66600
```

-continued tgtattctgc tcagctctgg cctagctcac cagctagtgt ctctgggtct ggcttccttt 66660
tttttcttgg ccttctaagc caatggggtc tgtcaacaca gccgggaaaa tatcttcatt 66720
ttaagtacct gggaattctt ggagggtagt gttatacttt gtctcctggg gagggccgtt 66780
agagagctca gtggccatgt ggaaagaaga cggctccctg tttagagctc cctcatctat 66840
aaagagggat agcaaggaag ctggtcctac cggtttgcag ctgactcctg ggggaaatac 66900
gttggaaaaa cgttttggtt ggatattgtt tttacttaat ccatatattt aaccccccag 66960
cacacctaag gataactcac agtccaaata gaaagtacag actcttgatt ttctgggttt 67020
tgtttatttt tttcccccag tggagttagg aaaagctgcc ctgagcacag aggcctgtat 67080
ttaaccaaga ggcctgcatc aagcaaagtc tttccgccct atccccctac aagtacagtt 67140
ccattctaga tcccctgcca gtgtgtgggg tctctgattc accatgtgtg tcacagcttg 67200
tgtgtgtttc ccatccaaac gcctggagaa gctccgtcct cagccagatt tagataattg 67260
aaagtcatca tttccaaatg ggctaataat ctatacactg tcactctcag aggggaagag 67320
ttgggctggt ttctctttgt tgtgctctta ggaaaacaag attaaaggcc ataaaaagcc 67380
tccctctctc tcctggagtg gcaggccctt caccaaggct ggcattaatg agaggaatgg 67440
gagtggtgtg acttagaggt gactgataca gcaggcccgc gcctgcactt aacagaagtg 67500
cagctcaaac ctccgctcag cgaacttctt cgtgaaaaag actaagaaca ctgaatgtgg 67560
caagcaataa gaactatgta aatgagctaa ttccaggctt gatgtcatgc aagaattgcg 67620
tcactgcagc caggtggcct ccatgtcacc cagaaagcga cagcagaaaa gataaaggtt 67680
ccttctctgg ccaaggagtc catgatggtt aacaacatgg ccttagcccg tttttttttt 67740
ttttttcttt ctcacttctt tctggctcaa cataatgtag tcagagagga tccatggccc 67800
ctggaatcaa aagaccgatg atctaaacac tatgactgtt attctgtgca aagtgaagca 67860
aacacagcct tcctaggctg cgtttccttg tgttagaggg tgctgtctct cctccctcct 67920
gcacaggagt ccatttaaaa gattagatga agataagaca atcaaagtgg caaaacaatc 67980
tgactacttc tgataataaa aacatggtct tcagcagata atctagaagt ttcttacctt 68040
gttacacccc catgaaaaag aaagccacgt tcttttggat gtggatttgg atacagatgt 68100
ctattgcact tttattcaca acgggaaact caaacatcca ggtcaaagga ataaactggc 68160
catggtacac ccagggagac acttctctcc cacgaatcac agaaacaccc acaacctcag 68220
gaacacgatg ctcaaggata atgaagccaa actcaagaaa gtctactccc atagacgtct 68280
agaaaggaca ggagacggtg ccggggaaag atcggtgatc gtctggaatc agaagtcaga 68340
actaggagga ggagttaggc acgtgggcca tggggcaggt tcagatgaag tttttggtcc 68400
ctctgctgtg gtgatggcta cttaggtgtt tacgtttgtc aaaactcact gtactatatg 68460
cgtgaaatag ttacctctcc atgggattaa ttaaaattaa ttaattaaaa ttaaaattaa 68520
ttaaaataca ataaagcttg ttgtagagag gaaaatgtgt ctaatctaga ctctcaagcc 68580
tgagactgtg caagctggca atcatgttta gccaaaggac tctttcaagg gctgcagtcg 68640
ctgtcgatgg gaagcaggag tttcacacac tggtaaccca caccaagcaa ggcagccatg 68700
acactgaact ccacaggtgc actatgtaat gactgtcaca gggacttgaa tttacctctc 68760
aaggcagcgg tggctctgct gagcaatgcg cacatgtaat tctccatcat tcctgctcct 68820
cgctgctgtg tgttaagata tccaagaggg taagatgtgc caaggcagaa ggactgtgac 68880
tggtgtgact atgaacaagg ccatccctca tcagaccatg caggactgat gaggtggccc 68940
acgagctgac tggtagatcc aaggagactg cctacaggga acatagctgt tctctcctag 69000

-continued aaccccagga caattgccgt aaacaattcc tagtaacata actggcacag tacctaagca 69060
ctaggcattg atagcttgtg gaagaggaaa ttcctaaaca gtgtttgtgt agccgatgag 69120
gcaggcaagt ccatttgatc tgcaaacagc agtagccttc tggacagtta gaaatgacag 69180
tgatggacat gagaggaaac cacaccagga ttgttactta cccaaagtcc ccaagccagc 69240
aagacttcct gagcctccca tcattcctct tcagttctct gtgacctggg cacttctggg 69300
ctggagctct gaacaatcat ttggaggggg ggggggtga aagtcagtgg acagtttaag 69360
aagctaacag acatttctaa aatcagcaga catgactgaa aaggagccct tgagagctct 69420
ttcacaaaaa taaaaatgca tttggaaatg gggaagaaga caaactagtg tgtgggacac 69480
cccttggtgt ttttagactg tgaaattgac tacttagaat ggcctaggag aggaaagaaa 69540
ctctaagctg gcagtctcac ggggcagttg gcaagtttaa agaccttcca gtggctgagg 69600
ccctgaatta acagtacagg cctttcccta ctccagataa atagagcagt agtttctctc 69660
aaattgtatc tggctcctaa ggtagcagaa agttcaaggg acacaaagtt taaaaaacaa 69720
acttcagctg ggtcttgtga cacagctctt gagttgagtc ccagttattc aggggctaa 69780
ggcagaagaa tggtttaagg cccgcctaga cttcagaggg agttcaagga caacctgact 69840
aatgcatcaa aataacagaa aggactgggg ctggagctcc gtggacgagc acttgcccag 69900
ccctgttctg tcctccacag tcagggaatg ggacggggct gcagccctgc ggtccacctt 69960
ccagatgtgg tctgctacct tcaggaggtg aagtcagtag ggtgctgctc cctggttgac 70020
tgggagtcac tcctgcactg ggcaggcaaa catctgcttt ccttcagaac tcctattccc 70080
attttttgaa acgaagagtt ggctgaaatg atctcccccct cccccaaccc tctcactgtt 70140
cctggccttg gcatccatct ggcagctctg tccatccccc tccccgggca ggtgacactt 70200
cctgtggggt tagagtgtgt gctgcacacc actcctgcac ctctcttacc tctggctcct 70260
ttcttcacta gtgtgcacca aggggcaggt ggtatctggc cagtaccgga tgctagccaa 70320
acacggagga tatgtgtggc tggagaccca ggggacggtc atctacaacc cccgcaacct 70380
gcagcctcag tgtatcatgt gtgtcaacta tgtgctgagg tgagtcgagg agggagcagc 70440
cagcctctcg ggaccctggg cagtacctcc acatgctggc tgtggtgtgg atccttctaa 70500
ctgggagggc tctatattga ggtcttagga acagagctct agcgtgtttc tttttcattt 70560
gtcagctatg gtatcatgtc tctgacttgt gctgaggggg gagaagatgg catagagtaa 70620
tgcttgatgt tgtgtgaatg ggagacagtg ctctcctggg taagctgttt tgggaagatg 70680
tggatgttat accctctccc ctccacccct ggaaagacta tgagcggctg ccattgataa 70740
tatgaaggaa actaacatag gaatccagga cttttgtgtg cctacagctt gagcacaggg 70800
agcgagcgaa cagcccacag gttgaggcta acctcaccgt ctctgcttct gtggctcaca 70860
gaattggatt gtttgtgttt ctgcctaaca cttctctgag aggtttatct accaggcttc 70920
tgacatgtct ggggcgggag agccaaaggc ttttgctaaa agatgcagat actctgagcc 70980
gctctctctt cccatcagtg agatcgagaa gaacgacgtg gtgttctcca tggaccagac 71040
cgaatccctg ttcaagccac acctgatggc catgaacagc atctttgaca gcagtgacga 71100
tgtggctgta actgagaaga gcaactacct gttcaccaaa ctgaaggagg agcccgagga 71160
actggcccag ttggccccca ccccaggaga tgccattatt tctctcgatt tcggtgcgta 71220
cttcctagcc ctggttgaac ccacagaacc ctcatggact ggcggacagt tcttgttatg 71280
acaagcctcc ctggccacag cttccctaaa ccacagatgc actcgggcct tgctgatcac 71340

-continued

```
tgtgcgtggt caggttctgc taggtagaga agaagcacag actcatggcc actgagttat  71400
aagtcctcat gaagggtaaa gaggtaggca aggagagggc tccctctcga ggggcccatc  71460
ctctacctgg cttgagagtc tgagttgagg cgtgtgtctc agggagtgtc ctctaactta  71520
agcgaaaggc tgagtcagaa cagcgccaga accagtagcc gagaggagac tgagggcgag  71580
gatgaagccc tcggtggctg cctgcgttag aatgtctgcc catcttcctg gaagagaagt  71640
ccttttggtc ctgagctctc ctctgacacc cggaactgtc cagggagagg cctcttccgg  71700
tctgcaccct ctccagccca gctctgactg ctcccctttg caatcaaatc cccctttgat  71760
aatgtgcatc tgagaggcca caggaaaatg gacacctcag agaaccagaa agggcaatga  71820
gccctcttgc acgagataac cttgtaaccc cccagctcca tgttggtact gaggcaaatg  71880
gcccaattct cctctgataa cttcctcagc tctgttctgg aaggctctgc aggaaacaac  71940
tgcttctatc tagtaagctc ggtctctgaa tgccaaatgc tgctggagat tgctctcttt  72000
ataggaagtc cccagattga atcatagttc tggtcctatc taggctccac agtactgagg  72060
gtgtcaactt caggccctct tttaggacct tttgtgaact ttctgggctt atccaccctg  72120
gggtgagccc agatctcacg aatgctcctc aagcaagcct tgtctttaca ggaagccaga  72180
acttcgatga accctcagcc tatggcaagg ccatccttcc cccgggccag ccatgggtct  72240
cggggctgag gagccacagt gcccagagcg agtccgggag cctgccagcc ttcactgtgc  72300
cccaggcaga caccccaggg aacactacac ccagtgcttc aagcagcagt agctgctcca  72360
cggtgagccc ccaccctcca ggagagcaca cagggctcat gggcccctca agctctgctg  72420
ccagatgact ggacagaccc cctgagaagt actgcctccc ttgggtgtta cagtgcccct  72480
aaggatggct cagatactcc gagagacact agagctgact accggctctt agcatctgtc  72540
ttccaccctt atccacgtcg tgactcttga aatcacagca agaacctagg caggtctctg  72600
caaaccaaag gcttcaacca cagagccctg ctggccacag cctctatcca gtttgcacat  72660
caagacacac aggacaagta gctcacaacc cgtggtacac aaatccctct atttgacggg  72720
agaaatcgaa caagcctttc acagggtcac ctagatcatc agaaaacaca gaaattcact  72780
ttataattca taactgtagc caaattactg ttttgaggtt gggggtcagc acagcatgag  72840
gaactggagg gctgcagcat caggaaagtt aaggaccact gatctaggaa gtgatccaag  72900
cctctcctta gagggagacg aaggttcaga gaggttgatg agctgagctg cttcacacag  72960
cttgtaaata gtagtcccct tcacagatgc ttggtagaac ggggcagagt gcagaaccat  73020
gcttgtctgt tctcaatgga ctcctggcga gacaggcccc gtgttcttac ttggtctcgt  73080
ccttcctggt ctccagccca gcagccctga ggactactat tcatccttgg agaatccctt  73140
gaagatcgaa gtgattgaga agcttttcgc catggacacg gagccgaggg acccgggcag  73200
tacccaggtg ggccccgcgc gtgggtgaca gagggctcct ttgcagagac ccccggtgtg  73260
ctgcgcaaag cttcggggtc aggaagcttg tgagtggcgc gctcccttcc tactgtgtcc  73320
ctgctcagcc ccacactcct gtctaactgt tgaccccatc tctgtcttgc acaaatggtg  73380
taagtggtgg tggtggaggt gggcgagggt ggtgatgaga atctccaggg gcgatcctca  73440
cacctccctt tgattgtctc agcctgagtt ctccacccca gcttccacat tgttctttag  73500
tgtgtggcct tatcctatcc tgcagaacct cttgttgttt ctgtgcatgt ctttttcctc  73560
tgtgtgtgtg tgtgtgtacg cgcgcgcgtg tgcctgtgac acttcttagc acaagcaggc  73620
acacttcctt cagtaccagt cttgggtaca aagatctatc tgtagtgagg ggtcattggc  73680
tgaccgaccg cggctgaagc ttgtgtcttt gcttatgagt attctgttgt gaccatgggt  73740
```

-continued gtccctgagt atctactggt gagtgagaac agcagtccct gtgggggaga tgaagattag 73800
ctggtacaaa taggataaag gagcagtgca acagaggcca gaagttggcc tggctaaaag 73860
agaaagagaa ggctgcaggt caaaagtgga gaaagctcac tgaacctgta caggatgaag 73920
ggacagatgc aggttatatc ccaacagcaa tccttgtacc ctcaatggca aatctgagca 73980
gttccagcag aggtatttga atggaggact gacagtttca aaaggcctag gcagggcagg 74040
gctgggccag ccactatgta ccctttgctc tgtgtctcct cagacggact tcagtgaact 74100
ggatttggag accttggcac cctacatccc tatggacggc gaggacttcc agctgagccc 74160
catctgccca gaggagccgc tcatgccaga gagcccccag cccacccccc agcactgctt 74220
cagtaccatg accagcatct tccagccgct caccccgggg gccacccacg gccccttctt 74280
cctcgataag tacccgcagc agttggaaag caggaagaca gagtctgagc actggcccat 74340
gtcttccatc ttctttgatg ctgggagcaa agggtccctg tctccatgct gtggccaggc 74400
cagcacccct ctctcttcta tgggaggcag atccaacacg cagtggcccc cggatccacc 74460
attacatttc ggccctacta agtggcctgt gggtgatcag agtgctgaat ccctgggagc 74520
cctgccggtg gggtcatcgc agttggaacc tccgagcgcc ccgcctcatg tctccatgtt 74580
caagatgagg ttagtgacag atgtctggct ggaggggaca tactgggcag ggcgagtaca 74640
tgtacacacc tgcttatgaa ggctctagag ggtcacatca gcttcccgct gaccatatcc 74700
cctcactgta tgtgtaggca gctggcactt ttcctagtcc tcctctgata tgtgagagcc 74760
agaccccagc agatagaaga aggggctttt ttaagtgatg tctgtctacc tttggacaca 74820
gataggtatt atggtatttc ctccatagtc ctgtactttc catctgcctg gagcctctgt 74880
ggggtgcaca caggcaccag cattttcctg tcttcccagt aggctgcagt cccataagct 74940
gatgtgtctt gtctatagta cgtacccttt atagagcacc ccagatggtc ctctggaagg 75000
aaggcattca gcagaaatcc ttctagagac tgttgtcatc tagctgggca ggacccctga 75060
gggcaggact gaggtggaca ggtgtgcgga gagaggcgca ggtgacagaa ctcttgagca 75120
tcttacagaa ggaagagctg agctgccgcc gctcaagccc tttagcattc tgccctccat 75180
agatcgcctg agtcataagt gttagattct gatgaagaca ccaggcagcg ggaggctgta 75240
gatgcctcac acccaccact gtcttctctt ggcattggca ggtctgcaaa ggacttcggg 75300
gcccgaggtc catacatgat gagcccagcc atgatcgccc tgtccaacaa gctgaagcta 75360
aagcggcagc tggagtatga ggagcaagcc ttccaagaca caagcggggt aagccatgtc 75420
tgtgaacgaa cagcctactg gacaggaagg agatgaggct agggtagaga tgcagacagc 75480
tagatctggt agtgagcacc tgcccctgct gggtctgtgt gctacccacc ctactccacc 75540
ctggcccact tcctccaact acacatcacc tctgcagggg gaccctccag gcaccagcag 75600
ttcacacttg atgtggaaac gtatgaagag cctcatgggc gggacctgtc ctttgatgcc 75660
tgacaagacc atcagtgcga acatggcccc cggtaagcag gcctggccca ggggtctggt 75720
ggagggttga aggctcagag cacattccct gagccttgtt agaatgggtt atatccatgc 75780
catgagcagg atcccggttc agaggtctct acatgacttc tgaaaaagaa agcaggctga 75840
gagcgctatt gtctgcccta atgacagcac cacagttcac tctctggctt ggatcctcca 75900
gatgaattca cccaaaaatc tatgagaggc ctgggccagc cactgagaca cctgccacct 75960
ccccagccac catctaccag gagctcaggg gagaacgcca agactgggtt cccgccacag 76020
tgctatgcct cccagttcca ggactacggt cctccaggag ctcaaaaggt gtcaggtgag 76080

-continued

```
tgctttggaa ctcccaccat agccagggtc tgatgcaaac aggtggcctg gctggccaga  76140
gagctgagag gcagccactt gcaggaagca actctgcgtt tggacaagac tgccttcaga  76200
gcccctgctc aggtctgatg cgactgctta cagtccatag ggctcttcat cagccaagct  76260
gcatgagatg gtttaggcag gaccaagtct cctctttatt ccagagcctg catggtacca  76320
ggcccagaaa ggatttgaca atgacttgtt caaagtacaa ggaaggccca ggagggtgca  76380
ggctcctcat tgatgagctg agattgtgtg agaaagtaag aaaggcctct ttggctgttg  76440
tccctgagaa agggcagagc cacggttact tctggccaag caggctcccc agaaggtggg  76500
tctcaggctg gggaagcttt ggtagaagga agcggctggt atggcaaggg ccccagggct  76560
gtggtggact tctgagcaag acaagctcgc tgccctggaa aggcaggctg gaagattgtg  76620
cacggctctg gaagggatcg tccagtaatc agtcagatca catccgggct cttggccccg  76680
caagaccaag agtctacatc tttcctcagc tgctcattgc ctgaagtgta tacacatacc  76740
gtaacaagct ttctctgaaa ggttgcacag gggactcact gatgggaggg tagcctggtg  76800
atccagtaag ttcagctatt gccactgaaa cacacaagtg ttcccataga cgcctttgct  76860
cggcacaaac aatctgtggt ttgagaaaga aaattccaga gccttgtcta cagtagcaga  76920
gttgggggaaa atttatagtt gtgttcttag aattccatct gaagaaccca aaagccctgg  76980
gctgatattt cagttctgtt gtttaccagc aggtgggctt gcaagccaga agtcttaaaa  77040
gagaaagttt aaagtttaaa gagaggacca cacatcactc acccccggta tacacatctg  77100
ggcagctgta gtcagcaaat gacaggtttc cccagctgtt gaatgcgaag caaaactaat  77160
ttcaacatag atcgtttctg cccatagacc gaaaggaggt gaatttaaga agggcagggc  77220
atctgttggt aggagtgcag gcaacgggaa gtgtggaccc cagaagggag agcacactgg  77280
gacccagctc tgtctctaaa ctgagagagc tctgctctcg ctccagccat ctttggatct  77340
caccactgct gtggcatgtc ctcttctggc tccgtcctct gaacagggga tggagcccca  77400
gggccagagt gctgctgcat cggaagttgc tggaagctgg agacacagtt gtttgcatgc  77460
atgccctttc ctctggtcat ctacagccag cggagcaggt gtgtgccagt cctctaaaac  77520
accctcctct ccctcctctc aggcgtggcc agtcgactgc tggggccatc gttcgagcct  77580
tacctgttgc cggaactgac cagatatgac tgtgaggtga acgtgcccgt gcctggaagc  77640
tccacactcc tgcaggggag agaccttctc agagctctgg accaggccac ctgagccagg  77700
gcctctggcc gggcatgccc ctgcctgccc cgccgtcttg acctgccagc ttcacttcca  77760
tctgtgttgc tattaggtat ctctaacacc agcacacttc ttacgagatg tactcaacct  77820
ggcctactgg ccaggtcacc aagcagtggc ctttatctga catgctcact ttattatcca  77880
tgttttaaaa atacatagtt gttgtacctg ctatgtttta ccgttgatga aagtgttctg  77940
aaattttata agatttcccc ctccctccct cccttgaatt acttctaatt tatattcccc  78000
aaaggttttt ctctctctca ttcatatcca tactaacaag catggtggct ggtgcctctc  78060
cctaggaaag ctttggcgtc attcaactca agtgttcttg ttcttgttgc caaagagaaa  78120
aggattttcc tccactgtgg attctccctc tcccccaccc ccacatacac acacacacac  78180
acacacccct acacacatat acacacatgc acgtatgcgt gcacacacac acacacacac  78240
acacacacac acacacaccc ctacacacac acacacacac acacatatac acacacacac  78300
acacacacac acacacccct acacacatat acacacatgc acgtatgcgt gcacacacac  78360
acacacacac acacacaccc ctacacacat atacacacat gcacgtatgc gtgcacacac  78420
acacacacac acacacatct aatcaccata ttgtaaaatt ttgtgttttt aaagccaact  78480
```

-continued

```
ctttgctccg gttttttcat acgacttagt atggggcaaa aaagcaatgt gaagaatcaa  78540

ctctagggtt acctgtgaag ccacgcggtg gtgttcgaag ctgtctggta atgcccccat  78600

ctctccccgg gtccagtgga tttttttaac tattattcaa aagcaaaact gagttttgtt  78660

ttgtttggtt ttttaagaag aatttatatc cgggt                             78695
```

<210> SEQ ID NO 258
<211> LENGTH: 379
<212> TYPE: DNA
<213> ORGANISM: mus musculus
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<300> PUBLICATION INFORMATION:
<301> AUTHORS: Aizawa et al.
<302> TITLE: Computational Analysis Of Full-Length Mouse cDNAs Compared With Human Genome Sequences
<303> JOURNAL: Mamm. Genome.
<304> VOLUME: 12
<306> PAGES: 673-677
<307> DATE: 2001
<308> DATABASE ACCESSION NUMBER: BY229956.1
<309> DATABASE ENTRY DATE: 2002-12-10
<313> RELEVANT RESIDUES: (1)..(379)

<400> SEQUENCE: 258

```
gattcgagag cggccggtgt acagctccgg agtccgcagc gctccgctcc agctctcctg     60

aggcggccgt acaatcctcg gcagtgtcct gagactgtat ggtcatctca gcggccgcac    120

tcgcttgccc ccggattttt ttccaacttg ctctcttcga gccatttttt tttctttttt    180

tctttttctt tttttctttt tctttttggg tgggttggtt tggatttgtc agatcccaga    240

aaagtgactc ctgttcgggg ctaaacggaa ctccaggtcc cttgtgctgc tctctctctc    300

tttgggcgtc ttacaacctc ctcccactcc tttccccggc cccgnctcct cctgcaggtt    360

cctcccngtc atcccccta                                                  379
```

<210> SEQ ID NO 259
<211> LENGTH: 2730
<212> TYPE: DNA
<213> ORGANISM: mus musculus
<300> PUBLICATION INFORMATION:
<301> AUTHORS: Carninci et al.
<302> TITLE: High-Efficiency Full-Length cDNA Cloning
<303> JOURNAL: Meth. Enzymol.
<304> VOLUME: 303
<306> PAGES: 19-44
<307> DATE: 1999
<308> DATABASE ACCESSION NUMBER: AK087208.01
<309> DATABASE ENTRY DATE: 2004-04-03
<313> RELEVANT RESIDUES: (1)..(2730)

<400> SEQUENCE: 259

```
gaccatcgta aaaatgtttg ctacttaact gcactccctg tgtagcacac aggaagtgct     60

gtgtgggacc tgcacagtgt tttgaggaca tgattgccct ctgttgcgga taggttgtct    120

tttcatggac agattgttgc taatgtttct ttatagtgga atgtgcccag gactaaaagt    180

ttcacataaa taaatggtca cagtatgtcc tcacagttac tggttactga tgcgacactt    240

aggcagcttc atggtagaat ctgacgagtt agcaggcaga tactctgact tttaaactta    300

cccgtgttag tacgtgatat ggactttgta cgaagaccgt gtttctttag gatctctgga    360
```

-continued

```
aagaggcagg tttgggtgtc agtttgtcct ttccttccca ttctgcaaca aagaagagtc    420
agtctggcac ctcaggctgg caaggatggc acccactgca gctaccaccc ttggaggtct    480
ttgcttctgg attgcaaatg gaggcgtgtt gtccgcctca tgttctcttg gcctttactg    540
atgtctccag actctaacct gtcgtctctc agatcagaaa cagggtctta ggtaagccag    600
ggcctggtct gaccgtagct tcttcgccct tctctttcca ttggtgccct ttgaccctgt    660
cctcaaactt tgttcattag tttaattaaa tctttgctaa cgctacccac gtgaagccca    720
gttctggctc ctgcaagaat acagaagaaa gcaatttgag aagacaccaa tgcgcaaaag    780
cagagtcaat accaaaaggt ggcttgctca tagctcccct gggctgagcc agatgggttc    840
agtgggagaa ttgactcact gtgggggtga gtgggtcact accgagagtg tgaatggatg    900
acgtccacat tccaggacta acccctcgtt tcttcatgta ggagcagctc agagctgagg    960
aaggagaaat cccgtgatgc cgcgaggtgc cggcgcagca aggagacgga ggtcttctat   1020
gagttggctc atgagttgcc cctgcctcac agtgtgagct cccacctgga caaagcctcc   1080
atcatgcgcc tggccatcag cttccttcgg acacataagc tcctgtcctc aggtaaggct   1140
tgacaggtcc tgcccccaag ctggcatcta cctaggcctc gctccaagac acatctacca   1200
atatccactc acagaagctg gcacatggcc tttagtgtta catttattta gttgcgtgtg   1260
agggtatgca tgtgggtcag aggacagcct ttgggagtcc attctgttct cttcttccat   1320
catctgggat ctgggacttg aacttgggtc ctcaggctta gcagcaaatg cctctagcca   1380
ctggaccttc ttgctggccc tgttccttca ttttagcatc tcccctctgg caatgatctt   1440
ctcatgagtt cacccaggga agagaccaag gacagactca agtgagagtg tgaggtgctc   1500
ccagagagtg tgaggtgctc ccagagagtg tgaggtgctc caaggggttg gagagccgag   1560
agcagcttct cctggaagcc catccagtac ctctggacct ctggcgagag tcccgctcca   1620
cactgtgttg actctgcagg aagcctttta tccttgtctt ccagctacat ctctaggaca   1680
tcagaaatgg tgatgtccct tgtgatctat ctctcagaac cttggtttcc ttgcctacaa   1740
actggaatta gccaggcata ctgcctggga ggataagggg taggaaatgg ggggggggga   1800
ttattagggc actataggaa tgagtggaga ccgcgggtca gctgtattcg ttcttgctgg   1860
ggctagcccc ccccatagag gacagcctcg ggcacctctc cctgggtcag ccgatgcgtt   1920
cttctttccc gcatatctct tcacccacca accgttcata acgaatgctt tctttccttt   1980
gtcagagtta catccctcaa aaatcatttc ctgttaggcc tcaccaggaa gaggcagcct   2040
gggggttcca ctttcacatc ctatgtgcag tcttgtcaga cttatcagtt ctgtaaggaa   2100
actgggcagc atatagctgc caggctggca ctacagcagg gcagtgtccg aggcatgagc   2160
aagggaggca ggcaggcaag ggggaaagag atcccctggc tcattttgag ttttcctgag   2220
tgagtgtgtc actctggaga tgactcctta catggctatt ctgggaaaga gccccctgca   2280
cagaggggtc cagaatgagg cggggaagcc agactagcct gtgctattct gggcccctgt   2340
gcacaggaag gatatatggg aaagaccttc ggaggttaga atggctgctc atcccatcgt   2400
cctcctctaa cccccaggct ggaggctaag cctgggctgc aaggctgagg tgaccgtgct   2460
gttacagaaa tgagcagaga gtggagaaag caagggcgga gccgctgcac acacagcagg   2520
gcaacagcaa ttactcagat ttagacggtg aaaatggttg agggaagctc aggctaagga   2580
cttgtaaagc ctggactgct aaataaaaag gcagactcgg aggtgtctca cccatgcccc   2640
atgcatgcct tcattttaca gaggattgtc ctcttggaga aatgaggacg acagttcggt   2700
```

-continued gatttgtagg attttgcaaa gcctgtcagg 2730

<210> SEQ ID NO 260
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 260
ggttccttaa ccccgtaggg 20

<210> SEQ ID NO 261
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 261
acctgggttc cttaaccccg 20

<210> SEQ ID NO 262
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 262
ggagcacctg ggttccttaa 20

<210> SEQ ID NO 263
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 263
ttgtcagctg tcattgtcgc 20

<210> SEQ ID NO 264
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 264
tctccttgtc agctgtcatt 20

<210> SEQ ID NO 265
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 265
gaagacctcc gtctccttgc 20

<210> SEQ ID NO 266
<211> LENGTH: 20
<212> TYPE: DNA
<213> ORGANISM: Artificial Sequence -continued
<220> FEATURE:
<223> OTHER INFORMATION: Oligonucleotide primer

<400> SEQUENCE: 266
caggtgggag ctcacactgt 20

<210> SEQ ID NO 267
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 267
aagctgatgg ccaggcgcat 20

<210> SEQ ID NO 268
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 268
ttcaggtaca agttatccat 20

<210> SEQ ID NO 269
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 269
aaggctttca ggtacaagtt 20

<210> SEQ ID NO 270
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 270
aatgaaaccc tccaaggctt 20

<210> SEQ ID NO 271
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 271
atgaacttgc tgatgttttc 20

<210> SEQ ID NO 272
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 272
gtcccatgaa cttgctgatg 20

-continued

<210> SEQ ID NO 273
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 273
acctgggtaa gtcccatgaa 20

<210> SEQ ID NO 274
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 274
tgttagttct acctgggtaa 20

<210> SEQ ID NO 275
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 275
gtcaaagatg ctgtgtcctg 20

<210> SEQ ID NO 276
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 276
ggatgagtga agtcaaagat 20

<210> SEQ ID NO 277
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 277
atgaagaagt cacgctcggt 20

<210> SEQ ID NO 278
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 278
ttcatcctca tgaagaagtc 20

<210> SEQ ID NO 279
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 279
tgcacttcat cctcatgaag 20

<210> SEQ ID NO 280
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 280
tgacagtccg gcctctgttg 20

<210> SEQ ID NO 281
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 281
actctcactt gcccggtgca 20

<210> SEQ ID NO 282
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 282
gttgttgtag actctcactt 20

<210> SEQ ID NO 283
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 283
attggctcac acatgatgat 20

<210> SEQ ID NO 284
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 284
tgggtgctgg attggctcac 20

<210> SEQ ID NO 285
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 285
atgctgtggc ggctcaggaa 20

<210> SEQ ID NO 286

-continued

<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 286
gggtggtaac caatcagttc 20

<210> SEQ ID NO 287
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 287
gtgcacaagt tctggtgact 20

<210> SEQ ID NO 288
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 288
ccttggtgca caagttctgg 20

<210> SEQ ID NO 289
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 289
gtcccctggg tctccagcca 20

<210> SEQ ID NO 290
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 290
tgaccgtccc ctgggtctcc 20

<210> SEQ ID NO 291
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 291
gtagatgacc gtcccctggg 20

<210> SEQ ID NO 292
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 292

-continued gggttgtaga tgaccgtccc 20

<210> SEQ ID NO 293
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 293
catagttgac acacatgata 20

<210> SEQ ID NO 294
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 294
tccatggaga acaccacgtc 20

<210> SEQ ID NO 295
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 295
tctggtccat ggagaacacc 20

<210> SEQ ID NO 296
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 296
aaagatgctg ttcatggcca 20

<210> SEQ ID NO 297
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 297
tggtgaacag gtagttgctc 20

<210> SEQ ID NO 298
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 298
agctcctcgg gctcctcctt 20

<210> SEQ ID NO 299
<211> LENGTH: 20
<212> TYPE: DNA

-continued

<213> ORGANISM: Artificial Sequence
<220> FEATURE:
<223> OTHER INFORMATION: Oligonucleotide primer

<400> SEQUENCE: 299
ggccttgcca taggctgagg 20

<210> SEQ ID NO 300
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 300
aggatggcct tgccataggc 20

<210> SEQ ID NO 301
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 301
ctgctgggcg tggagcagct 20

<210> SEQ ID NO 302
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 302
tgaagtccgt ctgggtactg 20

<210> SEQ ID NO 303
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 303
tccaactgct gcgggtactt 20

<210> SEQ ID NO 304
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 304
ttgctcccag catcaaagaa 20

<210> SEQ ID NO 305
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 305
cagggaccct ttgctcccag 20

-continued

<210> SEQ ID NO 306
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 306
gtgctggcct ggccacagca 20

<210> SEQ ID NO 307
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 307
cttgaacatg gagacatgag 20

<210> SEQ ID NO 308
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 308
cagacctcat cttgaacatg 20

<210> SEQ ID NO 309
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 309
ctttgcagac ctcatcttga 20

<210> SEQ ID NO 310
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 310
ttcagcttgt tggacagggc 20

<210> SEQ ID NO 311
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 311
gtgaactgct ggtgcctgga 20

<210> SEQ ID NO 312
<211> LENGTH: 20
<212> TYPE: DNA
<213> ORGANISM: Artificial Sequence
<220> FEATURE:

-continued

<223> OTHER INFORMATION: Oligonucleotide primer

<400> SEQUENCE: 312
cacatcaagt gtgaactgct 20

<210> SEQ ID NO 313
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 313
ccgcccatga ggctcttcat 20

<210> SEQ ID NO 314
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 314
aggacaggtc ccgcccatga 20

<210> SEQ ID NO 315
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 315
caggcatcaa aggacaggtc 20

<210> SEQ ID NO 316
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 316
gatttttggg tgaattcatc 20

<210> SEQ ID NO 317
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 317
ctggccacgc ctgacacctt 20

<210> SEQ ID NO 318
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 318
gatggcccca gcagtcgact 20

-continued

<210> SEQ ID NO 319
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 319
cgaacgatgg ccccagcagt 20

<210> SEQ ID NO 320
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 320
aggtaaggct cgaacgatgg 20

<210> SEQ ID NO 321
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 321
cagtcatatc tggtcagttc 20

<210> SEQ ID NO 322
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 322
cctcacagtc atatctggtc 20

<210> SEQ ID NO 323
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 323
gttcacctca cagtcatatc 20

<210> SEQ ID NO 324
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 324
ggcacgttca cctcacagtc 20

<210> SEQ ID NO 325
<211> LENGTH: 20
<212> TYPE: DNA
<213> ORGANISM: Artificial Sequence
<220> FEATURE:
<223> OTHER INFORMATION: Oligonucleotide primer -continued

<400> SEQUENCE: 325
gcacgggcac gttcacctca 20

<210> SEQ ID NO 326
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 326
tctctcccct gcaggagtgt 20

<210> SEQ ID NO 327
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 327
tctgagaagg tctctcccct 20

<210> SEQ ID NO 328
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 328
ggtccagagc tctgagaagg 20

<210> SEQ ID NO 329
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 329
gctcaggtgg cctggtccag 20

<210> SEQ ID NO 330
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 330
ggccctggct caggtggcct 20

<210> SEQ ID NO 331
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 331
agaacaagaa cacttgagtt 20

<210> SEQ ID NO 332
<211> LENGTH: 20

-continued

<212> TYPE: DNA
<213> ORGANISM: Artificial Sequence
<220> FEATURE:
<223> OTHER INFORMATION: Oligonucleotide primer

<400> SEQUENCE: 332
aacagttgag acatgacagt 20

<210> SEQ ID NO 333
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 333
tgtcactaac ctcatcttga 20

<210> SEQ ID NO 334
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 334
acaggagtca cttttctggg 20

<210> SEQ ID NO 335
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 335
catacagtct caggacactg 20

<210> SEQ ID NO 336
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 336
aatctgtcca tgaaaagaca 20

<210> SEQ ID NO 337
<211> LENGTH: 20
<212> TYPE: DNA
<213> ORGANISM: Homo sapiens

<400> SEQUENCE: 337
cagcgacaat gacagctgac 20

<210> SEQ ID NO 338
<211> LENGTH: 20
<212> TYPE: DNA
<213> ORGANISM: Homo sapiens

<400> SEQUENCE: 338
caggccacct gagccaggcc 20

<210> SEQ ID NO 339

-continued

<211> LENGTH: 20
<212> TYPE: DNA
<213> ORGANISM: Homo sapiens

<400> SEQUENCE: 339
tagactccga gaacatgacc 20

<210> SEQ ID NO 340
<211> LENGTH: 20
<212> TYPE: DNA
<213> ORGANISM: Homo sapiens

<400> SEQUENCE: 340
agcagcagca gctgctccac 20

<210> SEQ ID NO 341
<211> LENGTH: 20
<212> TYPE: DNA
<213> ORGANISM: Homo sapiens

<400> SEQUENCE: 341
ccactgagcg caaatgtacc 20

<210> SEQ ID NO 342
<211> LENGTH: 20
<212> TYPE: DNA
<213> ORGANISM: Homo sapiens

<400> SEQUENCE: 342
agaagagtaa cttcctattc 20

<210> SEQ ID NO 343
<211> LENGTH: 20
<212> TYPE: DNA
<213> ORGANISM: Homo sapiens

<400> SEQUENCE: 343
atggacgggg aagacttcca 20

<210> SEQ ID NO 344
<211> LENGTH: 20
<212> TYPE: DNA
<213> ORGANISM: Homo sapiens

<400> SEQUENCE: 344
ttaccaccct gaggagctgc 20

<210> SEQ ID NO 345
<211> LENGTH: 20
<212> TYPE: DNA
<213> ORGANISM: Homo sapiens

<400> SEQUENCE: 345
agcctatgaa ttctaccatg 20

<210> SEQ ID NO 346
<211> LENGTH: 20
<212> TYPE: DNA
<213> ORGANISM: Homo sapiens

<400> SEQUENCE: 346
cgacctgaag attgaagtga 20

-continued

<210> SEQ ID NO 347
<211> LENGTH: 20
<212> TYPE: DNA
<213> ORGANISM: Homo sapiens

<400> SEQUENCE: 347
gtgcccgtgc tgggaagctc 20

<210> SEQ ID NO 348
<211> LENGTH: 20
<212> TYPE: DNA
<213> ORGANISM: Homo sapiens

<400> SEQUENCE: 348
tgggagcctg cctgccttca 20

<210> SEQ ID NO 349
<211> LENGTH: 20
<212> TYPE: DNA
<213> ORGANISM: Homo sapiens

<400> SEQUENCE: 349
gctgtggcca ggccagcacc 20

<210> SEQ ID NO 350
<211> LENGTH: 20
<212> TYPE: DNA
<213> ORGANISM: Homo sapiens

<400> SEQUENCE: 350
tgcgaccatg aggagattcg 20

<210> SEQ ID NO 351
<211> LENGTH: 20
<212> TYPE: DNA
<213> ORGANISM: Homo sapiens

<400> SEQUENCE: 351
cctgatggcc atgaacagca 20

<210> SEQ ID NO 352
<211> LENGTH: 20
<212> TYPE: DNA
<213> ORGANISM: Homo sapiens

<400> SEQUENCE: 352
ggccaaggac caatgcagta 20

<210> SEQ ID NO 353
<211> LENGTH: 20
<212> TYPE: DNA
<213> ORGANISM: Homo sapiens

<400> SEQUENCE: 353
acccagagcg aggctgggag 20

<210> SEQ ID NO 354
<211> LENGTH: 20
<212> TYPE: DNA
<213> ORGANISM: Homo sapiens

<400> SEQUENCE: 354
ctgggaagct ccacgctcct 20

-continued

<210> SEQ ID NO 355
<211> LENGTH: 20
<212> TYPE: DNA
<213> ORGANISM: Homo sapiens

<400> SEQUENCE: 355
aagcaaagac atgtccacag 20

<210> SEQ ID NO 356
<211> LENGTH: 20
<212> TYPE: DNA
<213> ORGANISM: Homo sapiens

<400> SEQUENCE: 356
gagctggact tggagacact 20

<210> SEQ ID NO 357
<211> LENGTH: 20
<212> TYPE: DNA
<213> ORGANISM: Homo sapiens

<400> SEQUENCE: 357
aactgccctc ctcacaatag 20

<210> SEQ ID NO 358
<211> LENGTH: 20
<212> TYPE: DNA
<213> ORGANISM: Homo sapiens

<400> SEQUENCE: 358
ggtggcagca cctcacattt 20

<210> SEQ ID NO 359
<211> LENGTH: 20
<212> TYPE: DNA
<213> ORGANISM: Homo sapiens

<400> SEQUENCE: 359
agcagctgct ccacgcccaa 20

<210> SEQ ID NO 360
<211> LENGTH: 20
<212> TYPE: DNA
<213> ORGANISM: Homo sapiens

<400> SEQUENCE: 360
agagttcttg ggagcagcgc 20

<210> SEQ ID NO 361
<211> LENGTH: 20
<212> TYPE: DNA
<213> ORGANISM: Homo sapiens

<400> SEQUENCE: 361
atttgagtcc tacctgctgc 20

<210> SEQ ID NO 362
<211> LENGTH: 20
<212> TYPE: DNA
<213> ORGANISM: Homo sapiens

<400> SEQUENCE: 362
gacccacctg gtggcagcac 20

-continued

<210> SEQ ID NO 363
<211> LENGTH: 20
<212> TYPE: DNA
<213> ORGANISM: Homo sapiens

<400> SEQUENCE: 363
agactccgag aacatgacca 20

<210> SEQ ID NO 364
<211> LENGTH: 20
<212> TYPE: DNA
<213> ORGANISM: Homo sapiens

<400> SEQUENCE: 364
ttctccatgg accagactga 20

<210> SEQ ID NO 365
<211> LENGTH: 20
<212> TYPE: DNA
<213> ORGANISM: Homo sapiens

<400> SEQUENCE: 365
ccatgaggag attcgtgaga 20

<210> SEQ ID NO 366
<211> LENGTH: 20
<212> TYPE: DNA
<213> ORGANISM: Homo sapiens

<400> SEQUENCE: 366
tttggataac gacctgaaga 20

<210> SEQ ID NO 367
<211> LENGTH: 20
<212> TYPE: DNA
<213> ORGANISM: Homo sapiens

<400> SEQUENCE: 367
ctcctgcaag gaggggacct 20

<210> SEQ ID NO 368
<211> LENGTH: 20
<212> TYPE: DNA
<213> ORGANISM: Homo sapiens

<400> SEQUENCE: 368
gtgttctatg agctggccca 20

<210> SEQ ID NO 369
<211> LENGTH: 20
<212> TYPE: DNA
<213> ORGANISM: Homo sapiens

<400> SEQUENCE: 369
tggcagcacc tcacatttga 20

<210> SEQ ID NO 370
<211> LENGTH: 20
<212> TYPE: DNA
<213> ORGANISM: Homo sapiens

<400> SEQUENCE: 370

-continued ccgaagctga ccagcagatg 20

<210> SEQ ID NO 371
<211> LENGTH: 20
<212> TYPE: DNA
<213> ORGANISM: Homo sapiens

<400> SEQUENCE: 371
ggaccagact gaatccctgt 20

<210> SEQ ID NO 372
<211> LENGTH: 20
<212> TYPE: DNA
<213> ORGANISM: Mus musculus

<400> SEQUENCE: 372
ccctacgggg ttaaggaacc 20

<210> SEQ ID NO 373
<211> LENGTH: 20
<212> TYPE: DNA
<213> ORGANISM: Mus musculus

<400> SEQUENCE: 373
cggggttaag gaacccaggt 20

<210> SEQ ID NO 374
<211> LENGTH: 20
<212> TYPE: DNA
<213> ORGANISM: Mus musculus

<400> SEQUENCE: 374
ttaaggaacc caggtgctcc 20

<210> SEQ ID NO 375
<211> LENGTH: 20
<212> TYPE: DNA
<213> ORGANISM: Mus musculus

<400> SEQUENCE: 375
gcgacaatga cagctgacaa 20

<210> SEQ ID NO 376
<211> LENGTH: 20
<212> TYPE: DNA
<213> ORGANISM: Mus musculus

<400> SEQUENCE: 376
aatgacagct gacaaggaga 20

<210> SEQ ID NO 377
<211> LENGTH: 20
<212> TYPE: DNA
<213> ORGANISM: Mus musculus

<400> SEQUENCE: 377
gcaaggagac ggaggtcttc 20

<210> SEQ ID NO 378
<211> LENGTH: 20
<212> TYPE: DNA
<213> ORGANISM: Mus musculus

<400> SEQUENCE: 378
acagtgtgag ctcccacctg 20

<210> SEQ ID NO 379
<211> LENGTH: 20
<212> TYPE: DNA
<213> ORGANISM: Mus musculus

<400> SEQUENCE: 379
atgcgcctgg ccatcagctt 20

<210> SEQ ID NO 380
<211> LENGTH: 20
<212> TYPE: DNA
<213> ORGANISM: Mus musculus

<400> SEQUENCE: 380
atggataact tgtacctgaa 20

<210> SEQ ID NO 381
<211> LENGTH: 20
<212> TYPE: DNA
<213> ORGANISM: Mus musculus

<400> SEQUENCE: 381
aacttgtacc tgaaagcctt 20

<210> SEQ ID NO 382
<211> LENGTH: 20
<212> TYPE: DNA
<213> ORGANISM: Mus musculus

<400> SEQUENCE: 382
aagccttgga gggtttcatt 20

<210> SEQ ID NO 383
<211> LENGTH: 20
<212> TYPE: DNA
<213> ORGANISM: Mus musculus

<400> SEQUENCE: 383
catcagcaag ttcatgggac 20

<210> SEQ ID NO 384
<211> LENGTH: 20
<212> TYPE: DNA
<213> ORGANISM: Mus musculus

<400> SEQUENCE: 384
ttcatgggac ttacccaggt 20

<210> SEQ ID NO 385
<211> LENGTH: 20
<212> TYPE: DNA
<213> ORGANISM: Mus musculus

<400> SEQUENCE: 385
ttacccaggt agaactaaca 20

<210> SEQ ID NO 386
<211> LENGTH: 20
<212> TYPE: DNA
<213> ORGANISM: Mus musculus -continued

<400> SEQUENCE: 386
caggacacag catctttgac 20

<210> SEQ ID NO 387
<211> LENGTH: 20
<212> TYPE: DNA
<213> ORGANISM: Mus musculus

<400> SEQUENCE: 387
atctttgact tcactcatcc 20

<210> SEQ ID NO 388
<211> LENGTH: 20
<212> TYPE: DNA
<213> ORGANISM: Mus musculus

<400> SEQUENCE: 388
accgagcgtg acttcttcat 20

<210> SEQ ID NO 389
<211> LENGTH: 20
<212> TYPE: DNA
<213> ORGANISM: Mus musculus

<400> SEQUENCE: 389
gacttcttca tgaggatgaa 20

<210> SEQ ID NO 390
<211> LENGTH: 20
<212> TYPE: DNA
<213> ORGANISM: Mus musculus

<400> SEQUENCE: 390
cttcatgagg atgaagtgca 20

<210> SEQ ID NO 391
<211> LENGTH: 20
<212> TYPE: DNA
<213> ORGANISM: Mus musculus

<400> SEQUENCE: 391
caacagaggc cggactgtca 20

<210> SEQ ID NO 392
<211> LENGTH: 20
<212> TYPE: DNA
<213> ORGANISM: Mus musculus

<400> SEQUENCE: 392
tgcaccgggc aagtgagagt 20

<210> SEQ ID NO 393
<211> LENGTH: 20
<212> TYPE: DNA
<213> ORGANISM: Mus musculus

<400> SEQUENCE: 393
aagtgagagt ctacaacaac 20

<210> SEQ ID NO 394
<211> LENGTH: 20
<212> TYPE: DNA
<213> ORGANISM: Mus musculus -continued

<400> SEQUENCE: 394
atcatcatgt gtgagccaat 20

<210> SEQ ID NO 395
<211> LENGTH: 20
<212> TYPE: DNA
<213> ORGANISM: Mus musculus

<400> SEQUENCE: 395
gtgagccaat ccagcaccca 20

<210> SEQ ID NO 396
<211> LENGTH: 20
<212> TYPE: DNA
<213> ORGANISM: Mus musculus

<400> SEQUENCE: 396
ttcctgagcc gccacagcat 20

<210> SEQ ID NO 397
<211> LENGTH: 20
<212> TYPE: DNA
<213> ORGANISM: Mus musculus

<400> SEQUENCE: 397
gaactgattg gttaccaccc 20

<210> SEQ ID NO 398
<211> LENGTH: 20
<212> TYPE: DNA
<213> ORGANISM: Mus musculus

<400> SEQUENCE: 398
agtcaccaga acttgtgcac 20

<210> SEQ ID NO 399
<211> LENGTH: 20
<212> TYPE: DNA
<213> ORGANISM: Mus musculus

<400> SEQUENCE: 399
ccagaacttg tgcaccaagg 20

<210> SEQ ID NO 400
<211> LENGTH: 20
<212> TYPE: DNA
<213> ORGANISM: Mus musculus

<400> SEQUENCE: 400
tggctggaga cccaggggac 20

<210> SEQ ID NO 401
<211> LENGTH: 20
<212> TYPE: DNA
<213> ORGANISM: Mus musculus

<400> SEQUENCE: 401
ggagacccag gggacggtca 20

<210> SEQ ID NO 402
<211> LENGTH: 20
<212> TYPE: DNA

<213> ORGANISM: Mus musculus

<400> SEQUENCE: 402
cccaggggac ggtcatctac 20

<210> SEQ ID NO 403
<211> LENGTH: 20
<212> TYPE: DNA
<213> ORGANISM: Mus musculus

<400> SEQUENCE: 403
gggacggtca tctacaaccc 20

<210> SEQ ID NO 404
<211> LENGTH: 20
<212> TYPE: DNA
<213> ORGANISM: Mus musculus

<400> SEQUENCE: 404
gacgtggtgt tctccatgga 20

<210> SEQ ID NO 405
<211> LENGTH: 20
<212> TYPE: DNA
<213> ORGANISM: Mus musculus

<400> SEQUENCE: 405
ggtgttctcc atggaccaga 20

<210> SEQ ID NO 406
<211> LENGTH: 20
<212> TYPE: DNA
<213> ORGANISM: Mus musculus

<400> SEQUENCE: 406
tggccatgaa cagcatcttt 20

<210> SEQ ID NO 407
<211> LENGTH: 20
<212> TYPE: DNA
<213> ORGANISM: Mus musculus

<400> SEQUENCE: 407
gagcaactac ctgttcacca 20

<210> SEQ ID NO 408
<211> LENGTH: 20
<212> TYPE: DNA
<213> ORGANISM: Mus musculus

<400> SEQUENCE: 408
aaggaggagc ccgaggagct 20

<210> SEQ ID NO 409
<211> LENGTH: 20
<212> TYPE: DNA
<213> ORGANISM: Mus musculus

<400> SEQUENCE: 409
cctcagccta tggcaaggcc 20

<210> SEQ ID NO 410
<211> LENGTH: 20

-continued

<212> TYPE: DNA
<213> ORGANISM: Mus musculus

<400> SEQUENCE: 410
gcctatggca aggccatcct 20

<210> SEQ ID NO 411
<211> LENGTH: 20
<212> TYPE: DNA
<213> ORGANISM: Mus musculus

<400> SEQUENCE: 411
agctgctcca cgcccagcag 20

<210> SEQ ID NO 412
<211> LENGTH: 20
<212> TYPE: DNA
<213> ORGANISM: Mus musculus

<400> SEQUENCE: 412
cagtacccag acggacttca 20

<210> SEQ ID NO 413
<211> LENGTH: 20
<212> TYPE: DNA
<213> ORGANISM: Mus musculus

<400> SEQUENCE: 413
aagtacccgc agcagttgga 20

<210> SEQ ID NO 414
<211> LENGTH: 20
<212> TYPE: DNA
<213> ORGANISM: Mus musculus

<400> SEQUENCE: 414
ctgggagcaa agggtccctg 20

<210> SEQ ID NO 415
<211> LENGTH: 20
<212> TYPE: DNA
<213> ORGANISM: Mus musculus

<400> SEQUENCE: 415
tgctgtggcc aggccagcac 20

<210> SEQ ID NO 416
<211> LENGTH: 20
<212> TYPE: DNA
<213> ORGANISM: Mus musculus

<400> SEQUENCE: 416
ctcatgtctc catgttcaag 20

<210> SEQ ID NO 417
<211> LENGTH: 20
<212> TYPE: DNA
<213> ORGANISM: Mus musculus

<400> SEQUENCE: 417
catgttcaag atgaggtctg 20

<210> SEQ ID NO 418

-continued

<211> LENGTH: 20
<212> TYPE: DNA
<213> ORGANISM: Mus musculus

<400> SEQUENCE: 418
tcaagatgag gtctgcaaag 20

<210> SEQ ID NO 419
<211> LENGTH: 20
<212> TYPE: DNA
<213> ORGANISM: Mus musculus

<400> SEQUENCE: 419
gccctgtcca acaagctgaa 20

<210> SEQ ID NO 420
<211> LENGTH: 20
<212> TYPE: DNA
<213> ORGANISM: Mus musculus

<400> SEQUENCE: 420
tccaggcacc agcagttcac 20

<210> SEQ ID NO 421
<211> LENGTH: 20
<212> TYPE: DNA
<213> ORGANISM: Mus musculus

<400> SEQUENCE: 421
atgaagagcc tcatgggcgg 20

<210> SEQ ID NO 422
<211> LENGTH: 20
<212> TYPE: DNA
<213> ORGANISM: Mus musculus

<400> SEQUENCE: 422
tcatgggcgg gacctgtcct 20

<210> SEQ ID NO 423
<211> LENGTH: 20
<212> TYPE: DNA
<213> ORGANISM: Mus musculus

<400> SEQUENCE: 423
gacctgtcct ttgatgcctg 20

<210> SEQ ID NO 424
<211> LENGTH: 20
<212> TYPE: DNA
<213> ORGANISM: Mus musculus

<400> SEQUENCE: 424
aaggtgtcag gcgtggccag 20

<210> SEQ ID NO 425
<211> LENGTH: 20
<212> TYPE: DNA
<213> ORGANISM: Mus musculus

<400> SEQUENCE: 425
agtcgactgc tggggccatc 20

-continued

<210> SEQ ID NO 426
<211> LENGTH: 20
<212> TYPE: DNA
<213> ORGANISM: Mus musculus

<400> SEQUENCE: 426
actgctgggg ccatcgttcg 20

<210> SEQ ID NO 427
<211> LENGTH: 20
<212> TYPE: DNA
<213> ORGANISM: Mus musculus

<400> SEQUENCE: 427
ccatcgttcg agccttacct 20

<210> SEQ ID NO 428
<211> LENGTH: 20
<212> TYPE: DNA
<213> ORGANISM: Mus musculus

<400> SEQUENCE: 428
gaactgacca gatatgactg 20

<210> SEQ ID NO 429
<211> LENGTH: 20
<212> TYPE: DNA
<213> ORGANISM: Mus musculus

<400> SEQUENCE: 429
gaccagatat gactgtgagg 20

<210> SEQ ID NO 430
<211> LENGTH: 20
<212> TYPE: DNA
<213> ORGANISM: Mus musculus

<400> SEQUENCE: 430
gatatgactg tgaggtgaac 20

<210> SEQ ID NO 431
<211> LENGTH: 20
<212> TYPE: DNA
<213> ORGANISM: Mus musculus

<400> SEQUENCE: 431
gactgtgagg tgaacgtgcc 20

<210> SEQ ID NO 432
<211> LENGTH: 20
<212> TYPE: DNA
<213> ORGANISM: Mus musculus

<400> SEQUENCE: 432
tgaggtgaac gtgcccgtgc 20

<210> SEQ ID NO 433
<211> LENGTH: 20
<212> TYPE: DNA
<213> ORGANISM: Mus musculus

<400> SEQUENCE: 433
acactcctgc aggggagaga 20

-continued

<210> SEQ ID NO 434
<211> LENGTH: 20
<212> TYPE: DNA
<213> ORGANISM: Mus musculus

<400> SEQUENCE: 434
aggggagaga ccttctcaga 20

<210> SEQ ID NO 435
<211> LENGTH: 20
<212> TYPE: DNA
<213> ORGANISM: Mus musculus

<400> SEQUENCE: 435
ccttctcaga gctctggacc 20

<210> SEQ ID NO 436
<211> LENGTH: 20
<212> TYPE: DNA
<213> ORGANISM: Mus musculus

<400> SEQUENCE: 436
ctggaccagg ccacctgagc 20

<210> SEQ ID NO 437
<211> LENGTH: 20
<212> TYPE: DNA
<213> ORGANISM: Mus musculus

<400> SEQUENCE: 437
aactcaagtg ttcttgttct 20

<210> SEQ ID NO 438
<211> LENGTH: 20
<212> TYPE: DNA
<213> ORGANISM: Mus musculus

<400> SEQUENCE: 438
actgtcatgt ctcaactgtt 20

<210> SEQ ID NO 439
<211> LENGTH: 20
<212> TYPE: DNA
<213> ORGANISM: Mus musculus

<400> SEQUENCE: 439
tcaagatgag gttagtgaca 20

<210> SEQ ID NO 440
<211> LENGTH: 20
<212> TYPE: DNA
<213> ORGANISM: Mus musculus

<400> SEQUENCE: 440
cccagaaaag tgactcctgt 20

<210> SEQ ID NO 441
<211> LENGTH: 20
<212> TYPE: DNA
<213> ORGANISM: Mus musculus

<400> SEQUENCE: 441
cagtgtcctg agactgtatg 20

-continued

<210> SEQ ID NO 442
<211> LENGTH: 20
<212> TYPE: DNA
<213> ORGANISM: Artificial Sequence
<220> FEATURE:
<223> OTHER INFORMATION: Synthetic Construct

<400> SEQUENCE: 442
ttcgcggctg gacgattcag 20

<210> SEQ ID NO 443
<211> LENGTH: 20
<212> TYPE: DNA
<213> ORGANISM: Artificial Sequence
<220> FEATURE:
<223> OTHER INFORMATION: Synthetic Construct

<400> SEQUENCE: 443
cctcatggtc gcagggatga 20

<210> SEQ ID NO 444
<211> LENGTH: 20
<212> TYPE: DNA
<213> ORGANISM: Artificial Sequence
<220> FEATURE:
<223> OTHER INFORMATION: Synthetic Construct

<400> SEQUENCE: 444
tctcctcatg gtcgcaggga 20

<210> SEQ ID NO 445
<211> LENGTH: 20
<212> TYPE: DNA
<213> ORGANISM: Artificial Sequence
<220> FEATURE:
<223> OTHER INFORMATION: Synthetic Construct

<400> SEQUENCE: 445
tcatggtcac atggatgagt 20

<210> SEQ ID NO 446
<211> LENGTH: 20
<212> TYPE: DNA
<213> ORGANISM: Artificial Sequence
<220> FEATURE:
<223> OTHER INFORMATION: Synthetic Construct

<400> SEQUENCE: 446
cctcatggtc acatggatga 20

<210> SEQ ID NO 447
<211> LENGTH: 20
<212> TYPE: DNA
<213> ORGANISM: Artificial Sequence
<220> FEATURE:
<223> OTHER INFORMATION: Synthetic Construct

<400> SEQUENCE: 447
ctcatggtca catggatgag 20

<210> SEQ ID NO 448
<211> LENGTH: 20
<212> TYPE: DNA
<213> ORGANISM: Artificial Sequence
<220> FEATURE:

-continued

<223> OTHER INFORMATION: Synthetic Construct

<400> SEQUENCE: 448
atttcctcat ggtcacatgg 20

<210> SEQ ID NO 449
<211> LENGTH: 20
<212> TYPE: DNA
<213> ORGANISM: Artificial Sequence
<220> FEATURE:
<223> OTHER INFORMATION: Synthetic Construct

<400> SEQUENCE: 449
aaaccctcca aggctttcag 20

<210> SEQ ID NO 450
<211> LENGTH: 20
<212> TYPE: DNA
<213> ORGANISM: Artificial Sequence
<220> FEATURE:
<223> OTHER INFORMATION: Synthetic Construct

<400> SEQUENCE: 450
tcctcatggt cgcagggatg 20

<210> SEQ ID NO 451
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: n = inosine
<220> FEATURE:
<221> NAME/KEY: misc_feature
<222> LOCATION: (15)..(15)
<223> OTHER INFORMATION: n = pseudouridine

<400> SEQUENCE: 451
tcctcatggt cncanggatg 20

<210> SEQ ID NO 452
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: n = inosine
<220> FEATURE:
<221> NAME/KEY: misc_feature
<222> LOCATION: (14)..(14)
<223> OTHER INFORMATION: n = pseudouridine

<400> SEQUENCE: 452
cctcatggtc ncanggatga 20

<210> SEQ ID NO 453
<211> LENGTH: 20
<212> TYPE: DNA
<213> ORGANISM: Artificial Sequence
<220> FEATURE:
<223> OTHER INFORMATION: Control Oligonucleotide
<220> FEATURE:
<221> NAME/KEY: misc_feature -continued
<222> LOCATION: (1)..(20)
<223> OTHER INFORMATION: equal mixture of the bases A, C, G and T

<400> SEQUENCE: 453
nnnnnnnnnn nnnnnnnnnn 20

<210> SEQ ID NO 454
<211> LENGTH: 20
<212> TYPE: DNA
<213> ORGANISM: Artificial Sequence
<220> FEATURE:
<223> OTHER INFORMATION: Control Oligonucleotide

<400> SEQUENCE: 454
ccttccctga aggttcctcc 20

<210> SEQ ID NO 455
<211> LENGTH: 19
<212> TYPE: DNA
<213> ORGANISM: Artificial Sequence
<220> FEATURE:
<223> OTHER INFORMATION: Synthetic Construct

<400> SEQUENCE: 455
cgagaggcgg acgggaccg 19

<210> SEQ ID NO 456
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine

<400> SEQUENCE: 456
cgagaggcgg acgggaccgt t 21

<210> SEQ ID NO 457
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine

<400> SEQUENCE: 457
cggtcccgtc cgcctctcgt t 21

<210> SEQ ID NO 458
<211> LENGTH: 19
<212> TYPE: DNA
<213> ORGANISM: Artificial Sequence
<220> FEATURE:
<223> OTHER INFORMATION: Synthetic Construct

<400> SEQUENCE: 458
cggtcccgtc cgcctctcg 19

MODULATION OF HIF1α AND HIF2α EXPRESSION

CROSS-REFERENCE TO RELATED APPLICATIONS

This application is a continuation-in-part of U.S. Ser. No. 10/304,126 filed Nov. 23, 2002 now U.S. Pat. No. 7,144,999.

FIELD OF THE INVENTION

The present invention provides compositions and methods for modulating the expression of HIF1α (HIF1α) and hypoxia-inducible factor 2 alpha (HIF2α). In particular, this invention relates to compounds, particularly oligonucleotide compounds, which, in preferred embodiments, hybridize with nucleic acid molecules encoding HIF1α and HIF2α. Such compounds are shown herein to modulate the expression of HIF1α and HIF2α.

BACKGROUND OF THE INVENTION

Oxygen homeostasis is an essential cellular and systemic function; hypoxia leads to metabolic demise, but this must be balanced by the risk of oxidative damage to cellular lipids, nucleic acids, and proteins resulting from hyperoxia. As a result, cellular and systemic oxygen concentrations are tightly regulated via response pathways that affect the activity and expression of a multitude of cellular proteins. This balance is disrupted in heart disease, cancer, cerebrovascular disease, and chronic obstructive pulmonary disease (Semenza, *Genes Dev.,* 2000, 14, 1983–1991) (Semenza, G., 2001, *Trends Mol. Med.,* 7, 345–350. Cells are typically cultured in the laboratory at an ambient oxygen concentration of 21%, but cells in the human body are exposed to much lower oxygen concentrations ranging from 16% in the lungs to less than 6% in most other organs of the body often significantly less in tumors. Semenza G., 2001, *Trends Mol. Med.,* 7, 345–350.

Solid tumor growth depends on a continuous supply of oxygen and nutrients through neovascularization (angiogenesis). Tumors often become hypoxic, often because new blood vessels are aberrant and have poor blood flow. Cancer cells make adaptive changes that allow them to proliferate even at hypoxia. These changes include an increase in glycolysis and an increase in production of angiogenic factors. Hypoxia in tumors is associated with resistance to radio- and chemotherapy, and thus is an indicator of poor survival.

The transcriptional complex, hypoxia inducible factor (HIF), is a key regulator of oxygen homeostasis. Hypoxia induces the expression of genes participating in many cellular and physiological processes, including oxygen transport and iron metabolism, erythropoiesis, angiogenesis, glycolysis and glucose uptake, transcription, metabolism, pH regulation, growth-factor signaling, response to stress and cell adhesion. These gene products participate in either increasing oxygen delivery to hypoxic tissues or activating an alternative metabolic pathway (glycolysis) which does not require oxygen. Hypoxia-induced pathways, in addition to being required for normal cellular processes, can also aid tumor growth by allowing or aiding angiogenesis, immortalization, genetic instability, tissue invasion and metastasis (Harris, *Nat. Rev. Cancer,* 2002, 2, 38–47; Maxwell et al., *Curr. Opin. Genet. Dev.,* 2001, 11, 293–299).

HIF is a heterodimer composed of an alpha subunit complexed with a beta subunit, both of which are basic helix-loop-helix transcription factors. The beta subunit of HIF is a constitutive nuclear protein. The alpha subunit is the regulatory subunit specific to the oxygen response pathway, and can be one of three subunits, HIF1α, 2 alpha or 3 alpha (HIF-1α, HIF-2α and HIF-3α, respectively) (Maxwell et al., *Curr. Opin. Genet. Dev.,* 2001, 11, 293–299; Safran and Kaelin, *J. Clin. Invest.,* 2003, 111, 779–783).

The transcription factor hypoxia-inducible factor 1 (HIF-1) plays an essential role in homeostatic responses to hypoxia by binding to the DNA sequence 5'-TACGTGCT-3' and activating the transcription of dozens of genes in vivo under hypoxic conditions (Wang and Semenza, *J. Biol. Chem.,* 1995, 270, 1230–1237). These gene products participate in either increasing oxygen delivery to hypoxic tissues or activating an alternative metabolic pathway (glycolysis) which does not require oxygen. This list includes: aldolase C, enolase 1, glucose transporter 1, glucose transporter 3, glyceraldehyde-3-phosphate dehydrogenase, hexokinase 1, hexokinase 2, insulin-like growth factor-2 (IGF-2), IGF binding protein 1, IGF binding protein 3, lactate dehydrogenase A, phosphoglycerate kinase 1, pyruvate kinase M, p21, transforming growth factor B3, ceruloplasmin, erythropoietin, transferrin, transferrin receptor, a1b-adrenergic receptor, adrenomedullin, endothelin-1, heme oxygenase 1, nitric oxide synthase 2, plasminogen activator inhibitor 1, vascular endothelial growth factor (VEGF), VEGF receptor FTL-1, and p35 (Semenza, *Genes Dev.,* 2000, 14, 1983–1991). Expression of HIF1α is also sensitive to oxygen concentration: increased levels of protein are detected in cells exposed to 1% oxygen and these decay rapidly upon return of the cells to 20% oxygen (Wang et al., *Proc. Natl. Acad. Sci. U.S.A.,* 1995, 92, 5510–5514).

Hypoxia-inducible factor-1 alpha is a heterodimer composed of a 120 kDa alpha subunit complexed with a 91 to 94 kDa beta subunit, both of which contain a basic helix-loop-helix (Wang and Semenza, *J. Biol. Chem.,* 1995, 270, 1230–1237). The gene encoding hypoxia-inducible factor-1 alpha (HIF1α, also called HIF-1 alpha, HIF1A, HIF-1A, HIF1-A, and MOP1) was cloned in 1995 (Wang et al., *Proc. Natl. Acad. Sci. U.S.A.,* 1995, 92, 5510–5514). A nucleic acid sequence encoding HIF1α is disclosed and claimed in U.S. Pat. No. 5,882,914, as are expression vectors expressing the recombinant DNA, and host cells containing said vectors (Semenza, 1999).

HIF1α expression and HIF-1 transcriptional activity are precisely regulated by cellular oxygen concentration. The beta subunit is a constitutive nuclear protein, while the alpha subunit is the regulatory subunit. HIF1α mRNA is expressed at low levels in tissue culture cells, but it is markedly induced by hypoxia or ischemia in vivo (Yu et al., *J. Clin. Invest.,* 1999, 103, 691–696). HIF1α protein is negatively regulated in non-hypoxic cells by ubiquitination and proteasomal degradation (Huang et al., *Proc. Natl. Acad. Sci. U.S.A.,* 1998, 95, 7987–7992). Under hypoxic conditions, the degradation pathway is inhibited, HIF1α protein levels increase dramatically, and the fraction that is ubiquitinated decreases. HIF1α then translocates to the nucleus and dimerizes with a beta subunit (Sutter et al., *Proc. Natl. Acad. Sci. U.S.A.,* 2000, 97, 4748–4753).

A natural antisense transcript that is complementary to the 3' untranslated region of HIF1α mRNA has been discovered and is named "aHIF" (Thrash-Bingham and Tartof, *J. Natl. Cancer Inst.,* 1999, 91, 143–151). This is the first case of overexpression of a natural antisense transcript exclusively associated with a specific human malignant disease. aHIF is specifically overexpressed in nonpapillary clear-cell renal carcinoma under both normoxic and hypoxic conditions, but not in papillary renal carcinoma. Although aHIF is not further induced by hypoxia in nonpapillary disease, it can be induced in lymphocytes where there is a concomitant decrease in HIF1α mRNA.

HIF1α plays an important role in promoting tumor progression and is overexpressed in common human cancers, including breast, colon, lung, and prostate carcinoma. Overexpression of HIFs is sometimes observed in cancers, such as clear cell renal cell carcinoma, even at normoxia. Mutations that inactivate tumor suppressor genes or activate oncogenes have, as one of their consequences, upregulation of HIF1α activity, either through an increase in HIF1α protein expression, HIF1α transcriptional activity, or both (Semenza, *Pediatr. Res.,* 2001, 49, 614–617).

Until a tumor establishes a blood supply, the hypoxic conditions limit tumor growth. Subsequent increases in HIF1α activity result in increased expression of target genes such as vascular endothelial growth factor (VEGF). VEGF expression is essential for vascularization and the establishment of angiogenesis in most solid tumors (Iyer et al., *Genes Dev.,* 1998, 12, 149–162). A significant association between hypoxia-inducible factor-1 alpha, VEGF overexpression and tumor grade is also seen in human glioblastoma multiforme, the highest grade glioma in which mean patient survival time is less than one year. The rapidly proliferating tumor outgrows its blood supply, resulting in extensive necrosis, and these regions express high levels of HIF1α protein and VEGF mRNA, suggesting a response of the tumor to hypoxia (Zagzag et al., *Cancer,* 2000, 88, 2606–2618).

The action of the von Hippel-Landau (VHL) tumor suppressor gene product is implicated in hypoxic gene regulation, in both normal and diseased cells. Individuals with VHL disease are predisposed to renal cysts, clear cell renal carcinoma, phaeochromocytoma, haemangioblastomas of the central nervous system, angiomas of the retina, islet cell tumors of the pancreas, and endolymphatic sac tumors (Pugh and Ratcliffe, *Semin. Cancer. Biol.,* 2003, 13, 83–89). The VHL gene product participates in ubiquitin-mediated proteolysis by acting as the recognition component of the E3-ubiquitin ligase complex involved in the degradation of hypoxia-inducible factor alpha subunits (Cockman et al., *J. Biol. Chem.,* 2000, 275, 25733–25741; Ohh et al., *Nat. Cell Biol.,* 2000, 2, 423–427). In normal cells, VHL/HIF complexes form and target HIF alpha subunits for destruction (Maxwell et al., *Nature,* 1999, 399, 271–275). This is proposed to occur through hydroxylation of the oxygen-dependent domain of HIF2α and subsequent recognition by the VHL gene product, as recognition of a homologous oxygen-dependent domain is the mechanism by which the VHL protein recognizes HIF1α (Maxwell et al., *Nature,* 1999, 399, 271–275). HIF2α is in fact hydroxylated by the enzyme prolyl 4-hydroxylases in vitro (Hirsila et al., *J. Biol. Chem.,* 2003).

The p53 tumor suppressor also targets HIF1α for degradation by the proteasome. Loss of p53 activity occurs in the majority of human cancers and indicates that amplification of normal HIF1α levels contributes to the angiogenic switch during tumorigenesis (Ravi et al., *Genes Dev.,* 2000, 14, 34–44).

A mouse model of pulmonary hypertension has shown that local inhibition of HIF1α activity in the lung might represent a therapeutic strategy for treating or preventing pulmonary hypertension in at risk individuals. In pulmonary hypertension hypoxia-induced vascular remodeling leads to decreased blood flow, which leads to progressive right heart failure and death. This hypoxia-induced vascular remodeling is markedly impaired in mice that are partially HIF1α deficient (Yu et al., *J. Clin. Invest.,* 1999, 103, 691–696). Decreased vascular density and retarded solid tumor growth is also seen in mouse embryonic stem cells which are deficient for HIF1α (Ryan et al., *Embo J,* 1998, 17, 3005–3015).

During hypoxia, cells shift to a glycolytic metabolic mode for their energetic needs and HIF1α is known to upregulate the expression of many glycolytic genes. HIF1α may play a pivotal role in the Warburg effect in tumors, a paradoxical situation in which tumor cells growing under normoxic conditions show elevated glycolytic rates, which enhances tumor growth and expansion. HIF1α mediates the expression of 6-phosphofructo-2-kinase/fructose-2,6-bisphosphatase-3, a gene whose protein product maintains levels of the key regulator of glycolytic flux, fructose-2,6-bisphosphate (Minchenko et al., *J. Biol. Chem.,* 2001, 14, 14).

Currently, there are no known therapeutic agents which effectively inhibit the synthesis of HIF1α and to date, investigative strategies aimed at modulating HIF1α function have involved the use of antisense expression vectors and oligonucleotides. These studies have served to define the involvement of HIF1α in disease progression and to identify novel roles of HIF1α in vivo including unique roles for HIF1α as a transcription factor under non-hypoxic conditions and as an inhibitor of gene expression.

Gene transfer of an antisense HIF1α plasmid has been shown to enhance the efficacy of cancer immunotherapy. Antisense therapy was shown to slow, but not eradicate, the growth of EL-4 tumors established in mice. In addition, endogenously expression of HIF1α was almost completely inhibited in these tumors. When antisense therapy was combined with T-cell costimulator B7-1 immunotherapy, the tumors completely and rapidly regressed within 1 week. Furthermore, when these tumor-free mice were rechallenged with EL-4 cells, no tumors emerged, indicating that systemic antitumor immunity had been achieved (Sun et al., *Gene Ther.,* 2001, 8, 638–645).

Activation of HIF1α is thought to aggravate heart failure by upregulation of cardiac ET-1, a gene product involved in heart failure and whose inhibition improves the survival rate of rats with heart failure. In a failing heart, a metabolic switch occurs, and HIF1α activates the expression of glycolytic enzymes as compensation for impaired b-oxidation of fatty acid. Another consequence of increased HIF1α activity is that in rat cardiomyocytes, HIF1α was shown to bind to the 5'-promoter region of the ET-1 gene and increase ET-1 expression. In vitro, an antisense oligonucleotide targeted to hypoxia-inducible factor-1 alpha largely inhibited the increased gene expression of ET-1, confirming the role of HIF1α in heart failure (Kakinuma et al., *Circulation,* 2001, 103, 2387–2394). This antisense oligonucleotide is comprised of 20 nucleotides and targets bases 11 to 31 of the rat HIF1α with GenBank accession number AF_057308 incorporated herein by reference.

Preeclampsia is a disorder of unknown etiology that is the leading cause of fetal and maternal morbidity and mortality. Defective downregulation of HIF1α may play a major role in the pathogenesis of preeclampsia. For most of the first trimester, the human fetus develops under hypoxic conditions but at 10–12 weeks the intervillous space opens, the fetus is exposed to maternal blood and at this stage the trophoblast cells invade the maternal decidua. The switch of the trophoblasts from a proliferative to an invasive phenotype is controlled by cellular oxygen concentration. The proliferative, non-invasive trophoblast phenotype appears to be maintained by HIF1α mediated expression of TGFbeta3 because treatment of human villous explants with an antisense oligonucleotide against HIF1α or TGF beta 3 induces invasion under hypoxic conditions. In this case the HIF1α antisense oligonucleotide was comprised of phosphorothioate oligonucleotides, 16 nucleotides in length, and targeted to the AUG codon (Caniggia et al., *J. Clin. Invest.,* 2000, 105, 577–587.; Caniggia et al., *Placenta,* 2000, 21 *Suppl A*, S25–30).

The human intestinal trefoil factor (ITF) gene product protects the epithelial barrier during episodes of intestinal hypoxia. The ITF gene promoter bears a bindingsite for hypoxia-inducible factor-1 alpha, and the function of HIF1α as a transcription factor for ITF was confirmed in vitro. T84 colonic epithelial cells were treated with a phosphorothioate antisense oligonucleotide, 15 nucleotides in length and targeted to the AUG codon of HIF1α and this resulted in a loss of ITF hypoxia inducibility (Furuta et al., *J. Exp. Med.,* 2001, 193, 1027–1034).

Human epidemiological and animal studies have associated inhalation of nickel dusts with an increased incidence of pulmonary fibrosis. Nickel transcriptionally activates plasminogen activator inhibitor (PAI-1), an inhibitor of fibrinolysis, through the HIF1α signaling pathway. This was evidenced by decreases in PAI-1 mRNA levels when human airway epithelial cells were treated with an antisense oligonucleotide directed against HIF1α identical to the one used in the preeclampsia study discussed above. These data may be critical for understanding the pathology of pulmonary fibrosis and other diseases associated with nickel exposure (Andrew et al., *Am J Physiol Lung Cell Mol Physiol,* 2001, 281, L607–615).

HIF1α is constitutively expressed in cerebral neurons under normoxic conditions. A second dimerization partner for HIF1α is ARNT2, a cerebral translocator homologous to hypoxia-inducible factor-1 beta. One splice variant of HIF1α found in rat neurons dimerizes with ARNT2 more avidly than it does with HIF1b, and the resulting hypoxia-inducible factor-1 alpha-ARNT2 heterodimer does not recognize the HIF1α binding site of the erythropoietin gene. This suggests that transcription of a different set of genes is controlled by the hypoxia-inducible factor-1 alpha-ARNT2 heterodimer controls in neurons under nonhypoxic conditions than the hypoxia-inducible factor-1 alpha-HIF1α heterodimer controls under hypoxic conditions. This was evidenced by antisense oligonucleotide downregulation of HIF1α expression in which the antisense oligonucleotide consisted of 16 phosphorothioate nucleotides targeted to bases 38 to 54 of the rat hypoxia-inducible factor-1 with GenBank accession number AF_057308 (Drutel et al., *Eur. J. Neurosci.,* 2000, 12, 3701–3708).

A role for HIF1α in mediating a down-regulatory pathway was recently discovered using antisense oligonucleotide depletion of hypoxia-inducible factor-1 alpha. The peroxisome proliferator-activated receptors (PPARS) are a nuclear hormone-binding proteins that regulate transcriptional activities. Ligands which bind the PPAR-gamma isoform man amplify or inhibit the expression of inflammation-related gene products and may regulate the duration of inflammatory response. Hypoxia elicits a down-regulation of PPAR-gamma in intestinal epithelial cells which is effected through a binding site for HIF1α on the antisense strand of the PPAR-gamma gene. The expression of PPAR-gamma was upregulated in hypoxic cells when treated with an antisense oligonucleotide targeted to HIF1α identical to the one used in the preeclampsia study discussed above (Narravula and Colgan, *J. Immunol.,* 2001, 166, 7543–7548).

The gene encoding hypoxia-inducible factor 2 alpha (HIF2α; also called HIF-2 alpha, endothelial PAS domain protein 1, EPAS1, MOP2, hypoxia-inducible factor 2, HIF-related factor, HRF, HIF1 alpha-like factor, HLF) was initially identified as a transcription factor expressed in endothelial cells (Ema et al., *Proc. Natl. Acad. Sci. U.S.A.,* 1997, 94, 4273–4278; Flamme et al., *Mech. Dev.,* 1997, 63, 51–60; Hogenesch et al., *J. Biol. Chem.,* 1997, 272, 8581–8593; Tian et al., *Genes Dev.,* 1997, 11, 72–82). A nucleic acid sequence encoding human HIF2α is disclosed and claimed in U.S. Pat. No. 5,695,963 (McKnight et al., 1997).

HIF2α mRNA is primarily expressed in highly vascularized adult tissues, such as lung, heart and liver, and in the placenta and endothelial cells of the embryonic and adult mouse (Hogenesch et al., *J. Biol. Chem.,* 1997, 272, 8581–8593). Comparison of normal human tissues and cancers reveals that HIF2α protein is not detectable in normal tissue, but is easily visualized in malignant tissues (Talks et al., *Am. J. Pathol.,* 2000, 157, 411–421). The requirement for expression of HIF2α in development is demonstrated by the abnormalities observed in HIF2α gene deficient mouse embryos, which include the disruption of catecholamine homeostasis and lack of protection against heart failure observed (Tian et al., *Genes Dev.,* 1998, 12, 3320–3324). Targeted disruption of the HIF2α gene and generation of embryos deficient for HIF2α is disclosed in the PCT publication WO 02/086497 (Compernolle et al., 2002). This publication also discloses antisense oligodeoxyribonucleotides for use in inhibiting HIF2α expression targeted to the translation initiation codon of HIF2α (Compernolle et al., 2002).

HIF2α expression and HIF transcriptional activity are precisely regulated by cellular oxygen concentration. Whereas changes in oxygen levels do not affect HIF1-beta protein levels, the abundance of the alpha subunits is markedly increased upon exposure of cells to hypoxia, primarily due to stabilization of the alpha subunit protein (Safran and Kaelin, *J. Clin. Invest.,* 2003, 111, 779–783). HIF2α mRNA and protein is expressed at low levels in tissue culture cells, but protein expression is markedly induced by exposure to 1% oxygen, a hypoxic state (Wiesener et al., *Blood,* 1998, 92, 2260–2268). The hypoxia-inducible factor 2 alpha/hypoxia-inducible factor 1 beta heterodimer protein binds to the hypoxic response element, which contains the core recognition sequence 5'-TACGTG-3' and is found in the cis-regulatory regions of hypoxia-regulated genes (Ema et al., *Proc. Natl. Acad. Sci. U.S.A.,* 1997, 94, 4273–4278; Hogenesch et al., *J. Biol. Chem.,* 1997, 272, 8581–8593). Binding of the heterodimer to the HRE induces gene expression. Upon return to normoxic conditions, HIF2α protein is rapidly degraded (Wiesener et al., *Blood,* 1998, 92, 2260–2268).

The mitogen-activated protein kinase (MAPK) pathway is critical for HIF2α activation. Inhibition of a dual specificity protein kinase that directly phosphorylates MAPK prevents HIF2α trans-activation during hypoxia (Conrad 1999; Conrad, 2001). However, the inhibitor does not prevent HIF2α phosphorylation, thus, while the MAPK pathway regulates the activity of hypoxia-inducible factor 2 alpha, it does not directly phosphorylate the protein (Conrad et al., *Comp. Biochem. Physiol. B. Biochem. Mol Biol.,* 2001, 128, 187–204; Conrad et al., *J. Biol. Chem.,* 1999, 274, 33709–33713). The Src family kinase pathway is also implicated in regulation of hypoxia-inducible factor 2 alpha. A specific inhibitor of the Src family of kinases abolishes the hypoxia-induced expression of HIF2α mRNA in human lung adenocarcinoma cells (Sato et al., *Am. J. Respir. Cell Mol. Biol.,* 2002, 26, 127–134).

The maintenance of oxygen homeostasis, in addition to being required in physiological development, is also required in tumor growth. Tumor cells experience hypoxia because blood circulates poorly through the aberrant blood vessel that tumors establish. Although hypoxia is toxic to cancer cells, they survive as a result of genetic and adaptive changes that allow them to thrive in a hypoxic environment. One such adaptation is an increase in the expression of the angiogenic growth factor named vascular endothelial growth factor (VEGF). VEGF is a key angiogenic factor secreted by cancer cells, as well as normal cells, in response to hypoxia (Harris, *Nat. Rev. Cancer,* 2002, 2, 38–47; Maxwell et al., *Curr. Opin. Genet. Dev.,* 2001, 11, 293–299).

Hemangioblastomas, the most frequent manifestation of VHL gene mutations, exhibit overexpression of VEGF mRNA in their associated stromal cells. The VEGF mRNA overexpression is highly correlated with elevated expression of HIF2α mRNA. This finding suggests a relationship between loss of function of the VHL gene, and transcriptional activation of the VEGF gene, possibly through HIF2α activity in VEGF-dependent vascular growth (Flamme et al., *Am. J. Pathol.,* 1998, 153, 25–29).

The tumor suppressive activity of the VHL gene product can be overridden by the activation of HIF target genes in human renal carcinoma cells in vivo. VHL gene product mutants lose the ability to target HIF for ubiquitin-mediated destruction, suggesting that down regulation of HIF and VHL tumor suppressor function are intimately linked (Kondo et al., *Cancer Cell,* 2002, 1, 237–246). In contrast to human renal cell carcinoma, the product of the tuberous sclerosis complex-2 (Tsc-2) gene, product rather than VHL gene, is the primary target for rodent renal cell carcinoma (Liu et al., *Cancer Res.,* 2003, 63, 2675–2680). Rat RCC cells lacking Tsc-2 function exhibit stabilization of HIF2α protein and upregulation of VEGF, and were highly vascularized (Liu et al., *Cancer Res.,* 2003, 63, 2675–2680).

A link between elevated HIF2α activity and angiogenesis has also been demonstrated by experiments that show how HIF activity regulates VEGF expression. Normal human kidney cells typically have low levels of hypoxia-inducible factor 2 alpha, but upon introduction of a vector encoding HIF2α into these cells, VEGF mRNA and protein levels increase significantly (Xia et al., *Cancer,* 2001, 91, 1429–1436). When HIF2α was inhibited, VEGF expression was significantly decreased, thus demonstrating a direct link between HIF2αactivity and VEGF expression (Xia et al., *Cancer,* 2001, 91, 1429–1436). Similarly, a dose-dependent increase in VEGF mRNA is observed when human umbilical vein cells are transduced with a virus encoding HIF2α (Maemura et al., *J. Biol. Chem.,* 1999, 274, 31565–31570). Expression of a mutated HIF2α that lacks a transactivation domain inhibits the induction of VEGF mRNA during hypoxia, a finding that further suggests that HIF2α is an important regulator of VEGF expression (Maemura et al., *J. Biol. Chem.,* 1999, 274, 31565–31570).

A correlation between HIF activity and VEGF expression is also observed in malignant cells and tissues. HIF2α can be readily detected in renal cell carcinoma (RCC) cell lines in the absence of a vector encoding HIF2α (Xia et al., *Cancer,* 2001, 91, 1429–1436). Significant increases in HIF2α and VEGF mRNA in renal cell carcinoma tissue samples, compared to normal tissue, suggest that abnormal activation of HIF2α may be involved in the angiogenesis of RCC (Xia et al., *Cancer,* 2001, 91, 1429–1436).

In addition to RCC, the expression of HIF2α in other malignancies has also been reported. HIF2α is expressed at the levels of mRNA and protein in human bladder cancers, especially in those with an invasive phenotype (Xia et al., *Urology,* 2002, 59, 774–778). Another example of overexpression of HIF2α is seen in squamous cell head-and-neck cancer (SCHNC). Higher levels of HIF2α were associated with locally aggressive behavior of SCHNC, as well as intensification of angiogenesis (Koukourakis et al., *Int. J. Radiat. Oncol. Biol. Phys.,* 2002, 53, 1192–1202). These findings also demonstrated a link between overexpression of HIF2α and resistance to chemotherapy. Yet another correlation between overexpression of HIF2α and cancer is seen in malignant pheochromocytomas, which exhibit a higher level of HIF2α and an induced VEGF pathway, when compared to benign counterparts (Favier et al., *Am. J. Pathol.,* 2002, 161, 1235–1246). HIF2α overexpression is also a common event in non-small-cell lung cancer (NSCLC) and is related to the up-regulation of multiple angiogenic factors and overexpression of angiogenic receptors by cancer cells. HIF2α overexpression in NSCLC is an indicator of poor prognosis (Giatromanolaki et al., *Br. J. Cancer,* 2001, 85, 881–890). Taken together, these studies demonstrate that elevated HIF2α confers aggressive tumor behavior, and that targeting the HIF pathway may aid the treatment of several different types of cancers.

Overexpression of HIF2α has also been observed in several cancer cell lines in addition to RCC cell lines. Elevated levels of HIF2α mRNA and protein are seen in human lung adenocarcinoma cells, and exposure of these cells to hypoxia further increases HIF2α expression (Sato et al., *Am. J. Respir. Cell Mol. Biol.,* 2002, 26, 127–134). Furthermore, the hypoxia response element plays a role in constitutively upregulating an isoform of VEGF in cancer cell lines under normoxic conditions. The HRE located within a cell type-specific enhancer element in glioblastoma cells participates in the up-regulation of VEGF expression through enhanced binding of HIF2α to the HRE (Liang et al., *J. Biol. Chem.,* 2002, 277, 20087–20094). A truncated version of HIF2α that can bind to hypoxia-inducible factor 1 beta, but not to the HRE, was unable to transactivate the VEGF promoter (Liang et al., *J. Biol. Chem.,* 2002, 277, 20087–20094). This further demonstrates the capability of cancer cells to combat hypoxic conditions by enhancing expression of factors required for vascularization and angiogenesis.

Short interfering RNAs (siRNAs) have been used to specifically inhibit the expression of HIF1α and HIF2α in human breast and renal carcinoma cell lines and in a human endothelial cell line. SiRNA duplexes with dTdT overhangs at both ends were designed to target nucleotides 1521–1541 and 1510–1530 of the HIF1α mRNA sequence (NM001530) and nucleotides 1260–1280 and 328–348 of the HIF2α sequence (NM001430). It was found that in the breast carcinoma and endothelial cell lines, gene expression and cell migration patterns were critically dependent on HIF1α but not hypoxia-inducible factor-2 alpha, but critically dependent on HIF2α in the renal carcinoma cells. Sowter et al., 2003, *Cancer Res.,* 63, 6130–6134.

Defective downregulation of HIF2α may play a major role in the pathogenesis of preeclampsia. HIF2α protein levels are increased during early development, as expected in a hypoxic environment, and then decrease significantly with gestational age (Rajakumar and Conrad, *Biol. Reprod.,* 2000, 63, 559–569). However, HIF2α protein expression is significantly increased in preeclamptic relative to normal term placentas (Rajakumar et al., *Biol. Reprod.,* 2001, 64, 499–506). This result suggests that failure to down-regulate HIF2α protein expression during early pregnancy could prevent the switch of the trophoblast to an invasive phenotype and ultimately lead to preeclampsia (Rajakumar et al., *Biol. Reprod.,* 2001, 64, 499–506).

Overexpression of hypoxia-inducible factor 2 alpha, as well as hypoxia-inducible factor 1, has been observed in the inflammatory bowel diseases Crohn's disease and ulcerative colitis (Giatromanolaki et al., *J. Clin. Pathol.,* 2003, 56, 209–213). However, VEGF expression was weak in ulcerative colitis samples, and absent in Crohn's disease samples. The discordant expression of VEGF and HIF2α may lead to a reduced ability of a tissue to produce or respond to VEGF, which may in turn lead to reduced endothelial and epithelial cell viability (Giatromanolaki et al., *J. Clin. Pathol.,* 2003, 56, 209–213).

In addition to participating in adaptive changes in response to hypoxia, HIF2α may also function in an inflammatory response in cardiac myocytes. In cultured cardiac myocytes, interleukin-1 beta (IL-1beta) significantly increased both HIF2α mRNA and protein levels (Tanaka et al., *J. Mol. Cell Cardiol.,* 2002, 34, 739–748). Transduction of cardiac myocytes with adenovirus expressing HIF2α dramatically increased the levels of adrenomedullin (AM) mRNA, which is also upregulated by IL-lbeta (Tanaka et al., *J. Mol. Cell Cardiol.,* 2002, 34, 739–748). Since IL-1 beta has been implicated in the pathogenesis of heart failure, and AM is known to improve cardiac function during heart failure, these results suggest that HIF2α plays a role in the adaptation of the cardiac myocytes during heart failure (Tanaka et al., *J. Mol. Cell Cardiol.,* 2002, 34, 739–748).

Disclosed and claimed in the PCT publication WO 00/09657 is a method of inhibiting angiogenesis in a mammal through administration of a compound which inhibits the binding of human HIF2α protein to the DNA regulatory element of an angiogenic factor, wherein the compound can be an antisense nucleic acid molecule complementary to all or part of the mRNA encoding human HIF2α (Lee et al., 2000). This publication also discloses a nucleic acid encoding human hypoxia-inducible factor 2 alpha.

The PCT publication WO 01/62965 discloses and claims a differential screening method for identifying a genetic element involved in a cellular process, which method includes introducing HIF2α into cells (Kingsman, 2001). This publication also discloses the development of HIF2α agonists or antagonists.

The PCT publication WO 02/34291 claims methods and reagents, including the use of antisense oligonucleotides, for the inhibition of human HIF1α transcription (Colgan, 2002). This publication also discloses a nucleic acid encoding human hypoxia-inducible factor 2 alpha.

U.S. Pat. No. 6,395,548 claims a nucleic acid encoding a deletion mutant of human HIF2α and the use of this deletion mutant as a method of inhibiting expression of an angiogenic factor in vitro. This patent also discloses a nucleic acid encoding human hypoxia-inducible factor 2 alpha, as well as nucleic acids complementary to all or part of the human HIF2α cDNA for use in antisense treatment to inhibit the expression of HIF2α (Lee et al., 2002).

U.S. Pat. No. 6,432,927 discloses nucleic acid sequences, including sense and antisense oligonucleotides, which are derived from an HIF2α and incorporated into recombinant nucleic acid molecules for the purpose of sustaining HIF2α expression in cells (Gregory and Vincent, 2002).

The nucleic acid sequence encoding a human HIF2α and insertion of this sequence into a viral expression vector, for the purpose of driving human HIF2α expression in mammalian cells, is disclosed in the PCT publication WO 02/068466 (White et al., 2002).

The PCT publication WO 02/094862 discloses a method for introducing into a muscle cell a nucleic acid sequence encoding hypoxia-inducible factor 2 alpha, for the purpose of overexpressing HIF2α and stimulating angiogenesis or metabolic activity (Guy, 2002).

Disclosed and claimed in the US pre-grant publication 2003/0045686 is a nucleic acid encoding human hypoxia-inducible factor 2 alpha, and a method of delivering a therapeutically effective amount of this nucleic acid to a subject for the purpose of reducing or preventing hypoxia (Kaelin Jr. and Ivan, 2003). This publication also discloses and claims human HIF muteins, including HIF2α mutein, which are designed to be more stable and/or resistant to degradation.

As a consequence of HIF2α involvement in many diseases, there remains a long felt need for additional agents capable of effectively regulating HIF2α function. As such, inhibition is especially important in the treatment of cancer, given that the upregulation of expression of HIF2α is associated with so many different types of cancer.

As a consequence of HIF1α and HIF2α involvement in many diseases, there remains a long felt need for additional agents capable of effectively inhibiting HIF1α and HIF2α function.

Antisense technology is emerging as an effective means for reducing the expression of specific gene products and may therefore prove to be uniquely useful in a number of therapeutic, diagnostic, and research applications for the modulation of HIF1α and HIF2α expression.

The present invention provides compositions and methods for modulating HIF1α and HIF2α expression. In particular antisense compositions for modulating HIF1α and/or HIF2α expression are believed to be useful in treatment of abnormal proliferative conditions associated with HIF1α and/or HIF2α. Examples of abnormal proliferative conditions are hyperproliferative disorders such as cancers, tumors, hyperplasias, pulmonary fibrosis, angiogenesis, psoriasis, atherosclerosis and smooth muscle cell proliferation in the blood vessels, such as stenosis or restenosis following angioplasty. It is presently believed that inhibition of both HIF1α and HIF2α may be a particularly useful approach to treatment of such disorders.

SUMMARY OF THE INVENTION

The present invention is directed to compounds, especially nucleic acid and nucleic acid-like oligomers, which are targeted to a nucleic acid encoding HIF1α and/or HIF2α, and which modulate the expression of HIF1α and/or HIF2α. Pharmaceutical and other compositions comprising the compounds of the invention are also provided. Further provided are methods of screening for modulators of HIF1α and/or HIF2α and methods of modulating the expression of HIF1α and/or HIF2α in cells, tissues or animals comprising contacting said cells, tissues or animals with one or more of the compounds or compositions of the invention. Methods of treating an animal, particularly a human, suspected of having or being prone to a disease or condition associated with expression of HIF1α and/or HIF2α are also set forth herein. Such methods comprise administering a therapeutically or prophylactically effective amount of one or more of the compounds or compositions of the invention to the person in need of treatment.

DETAILED DESCRIPTION OF THE INVENTION

A. Overview of the Invention

The present invention employs compounds, preferably oligonucleotides and similar species for use in modulating the function or effect of nucleic acid molecules encoding HIF1α or HIF2α. This is accomplished by providing oligonucleotides which specifically hybridize with one or more nucleic acid molecules encoding HIF1α or HIF2α. Thus "target nucleic acid" refers to a nucleic acid molecule encoding HIF1α or HIF2α. As used herein, the term "nucleic acid molecule encoding HIF1α" has been used for convenience to encompass DNA encoding HIF1α, RNA (including pre-mRNA and mRNA or portions thereof) transcribed from such DNA, and also cDNA derived from such RNA. Similarly, the term "nucleic acid molecule encoding HIF2α" has been used for convenience to encompass DNA encoding HIF2α, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of HIF1α or HIF2α. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.,* 1990, 215, 403–410; Zhang and Madden, *Genome Res.,* 1997, 7, 649–656).

B. Compounds of the Invention

According to the present invention, compounds include antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995; 81, 611–620). Montgomery et al. have shown that the primary interference effects of dsRNA are posttranscriptional (Montgomery et al., *Proc. Natl. Acad. Sci. USA,* 1998, 95, 15502–15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806–811). Recently, it has been shown that it is, in fact, the single-stranded RNA oligomers of antisense polarity of the dsRNAs which are the potent inducers of RNAi (Tijsterman et al., *Science,* 2002, 295, 694–697).

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. These oligonucleotides are then tested using the methods described herein to determine their ability to inhibit expression of HIF2α mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

While oligonucleotides are a preferred form of the compounds of this invention, the present invention comprehends other families of compounds as well, including but not limited to oligonucleotide analogs and mimetics such as those described herein.

The compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the compounds of the invention are 12 to 50 nucleobases in length. One having ordinary skill in the art will appreciate that this embodies compounds of 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 15 to 30 nucleobases in length. One having ordinary skill in the art will appreciate that this embodies compounds of 15, 16, 17, 18, 19, 20, 21, 22, 23, 24, 25, 26, 27, 28, 29, or 30 nucleobases in length.

Particularly preferred compounds are oligonucleotides from about 12 to about 50 nucleobases, even more preferably those comprising from about 15 to about 30 nucleobases.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include oligonucleotide sequences that comprise at least the 8 consecutive nucleobases from the 5'-terminus of one of the illustrative preferred antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly preferred antisense compounds are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). One having skill in the art armed with the preferred antisense compounds illustrated herein will be able, without undue experimentation, to identify further preferred antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes HIF1α or HIF2α.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding HIF1α or HIF2α, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are hereinbelow referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 8–80 nucleobases in length comprising a stretch of at least eight (8) consecutive nucleobases selected from within the illustrative preferred target segments are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 8 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 8 to about 80 nucleobases). One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

D. Screening and Target Validation

In a further embodiment, the "preferred target segments" identified herein may be employed in a screen for additional compounds that modulate the expression of HIF1α or HIF2α. "Modulators" are those compounds that decrease or increase the expression of a nucleic acid molecule encoding HIF1α or HIF2α and which comprise at least an 8-nucleobase portion which is complementary to a preferred target segment. The screening method comprises the steps of contacting a preferred target segment of a nucleic acid molecule encoding HIF1α or HIF2α with one or more candidate modulators, and selecting for one or more candidate modulators which decrease or increase the expression of a nucleic acid molecule encoding HIF1α or HIF2α. Once it is shown that the candidate modulator or modulators are capable of modulating (e.g. either decreasing or increasing) the expression of a nucleic acid molecule encoding HIF1α or HIF2α, the modulator may then be employed in further investigative studies of the function of HIF1α or HIF2α, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806–811; Timmons and Fire, *Nature* 1998, 395, 854; Timmons et al., *Gene,* 2001, 263, 103–112; Tabara et al., *Science,* 1998, 282, 430–431; Montgomery et al., *Proc. Natl. Acad. Sci. USA,* 1998, 95, 15502–15507; Tuschl et al., *Genes Dev.,* 1999, 13, 3191–3197; Elbashir et al., *Nature,* 2001, 411, 494–498; Elbashir et al., *Genes Dev.* 2001, 15, 188–200). For example, such double-stranded moieties have been shown to inhibit the target by the classical hybridization of antisense strand of the duplex to the target, thereby triggering enzymatic degradation of the target (Tijsterman et al., *Science,* 2002, 295, 694–697).

The compounds of the present invention can also be applied in the areas of drug discovery and target validation. The present invention comprehends the use of the compounds and preferred target segments identified herein in drug discovery efforts to elucidate relationships that exist between HIF1α or HIF2α and a disease state, phenotype, or condition. These methods include detecting or modulating HIF1α or HIF2α comprising contacting a sample, tissue, cell, or organism with the compounds of the present invention, measuring the nucleic acid or protein level of HIF1α or HIF2α and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

E. Kits, Research Reagents, Diagnostics, and Therapeutics

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17–24; Celis, et al., *FEBS Lett.,* 2000, 480, 2–16), SAGE (serial analysis of gene expression) (Madden, et al., *Drug Discov. Today,* 2000, 5, 415–425), READS (restriction enzyme amplification of digested cDNAs) (Prashar and Weissman, *Methods Enzymol.,* 1999, 303, 258–72), TOGA (total gene expression analysis) (Sutcliffe, et al., *Proc. Natl. Acad. Sci. U.S.A.,* 2000, 97, 1976–81), protein arrays and proteomics (Celis, et al., *FEBS Lett.,* 2000, 480, 2–16; Jungblut, et al., *Electrophoresis,* 1999, 20, 2100–10), expressed sequence tag (EST) sequencing (Celis, et al., *FEBS Lett.,* 2000, 480, 2–16; Larsson, et al., *J. Biotechnol.,* 2000, 80, 143–57), subtractive RNA fingerprinting (SuRF) (Fuchs, et al., *Anal. Biochem.,* 2000, 286, 91–98; Larson, et al., *Cytometry,* 2000, 41, 203–208), subtractive cloning, differential display (DD) (Jurecic and Belmont, *Curr. Opin. Microbiol.,* 2000, 3, 316–21), comparative genomic hybridization (Carulli, et al., *J. Cell Biochem. Suppl.,* 1998, 31, 286–96), FISH (fluorescent in situ hybridization) techniques (Going and Gusterson, *Eur. J. Cancer,* 1999, 35, 1895–904) and mass spectrometry methods (To, *Comb. Chem. High Throughput Screen,* 2000, 3, 235–41).

The compounds of the invention are useful for research and diagnostics, because these compounds hybridize to nucleic acids encoding HIF1α or HIF2α. For example, oligonucleotides that are shown to hybridize with such efficiency and under such conditions as disclosed herein as to be effective HIF1α or HIF2α inhibitors will also be effective primers or probes under conditions favoring gene amplification or detection, respectively. These primers and probes are useful in methods requiring the specific detection of nucleic acid molecules encoding HIF1α or HIF2α and in the amplification of said nucleic acid molecules for detection or for use in further studies of HIF1α or HIF2α. Hybridization of the antisense oligonucleotides, particularly the primers and probes, of the invention with a nucleic acid encoding HIF1α or HIF2α can be detected by means known in the art. Such means may include conjugation of an enzyme to the oligonucleotide, radiolabelling of the oligonucleotide or any other suitable detection means. Kits using such detection means for detecting the level of HIF1α or HIF2α in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of HIF1α or HIF2α is treated by administering one or more antisense compounds in accordance with this invention. For example, in one non-limiting embodiment, the methods comprise the step of administering to the animal in need of treatment, a therapeutically effective amount of a HIF1α or HIF2α inhibitor. The HIF1α or HIF2α inhibitors of the present invention effectively inhibit the activity of the HIF target protein or inhibit the expression of the HIF1α or HIF2α protein. In one embodiment, the activity or expression of HIF1α or HIF2α in an animal is inhibited by about 10%. Preferably, the activity or expression of HIF1α or HIF2α in an animal is inhibited by about 30%. More preferably, the activity or expression of HIF1α and/or HIF2α in an animal is inhibited by 50% or more.

For example, the reduction of the expression of HIF1α may be measured in serum, adipose tissue, liver or any other body fluid, tissue or organ of the animal. Preferably, the cells contained within said fluids, tissues or organs being analyzed contain a nucleic acid molecule encoding HIF1α or HIF2α protein and/or the HIF1α or HIF2α protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

F. Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugar and Internucleoside Linkages-Mimetics

In other preferred oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Preferred embodiments of the invention are oligonucleotides with phosphorothioate backbones and oligonucleosides with heteroatom backbones, and in particular $—CH_2—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified Sugars

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-$O—CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-$O—CH_2—O—CH_2—N(CH_3)_2$, also described in examples hereinbelow.

Other preferred modifications include 2'-methoxy (2'-$O—CH_3$), 2'-aminopropoxy (2'-$OCH_2CH_2CH_2NH_2$), 2'-allyl (2'-$CH_2—CH{=}CH_2$), 2'-O-allyl (2'-$O—CH_2—CH{=}CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have. sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene ($—CH_2—)_n$ group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($—C≡C—CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications, pages* 289–302, Crooke, S. T. and Lebleu, B. ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

G. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration, includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine ara-binoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxyco-formycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teni-poside, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

H. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-$O^2$-2'-anhydro-5-methyluridine , 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O-[N,N-dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides:

Unsubstituted and substituted phosphodiester (P═O) oligonucleotides are synthesized on an automated DNA synthesizer (Applied Biosystems model 394) using standard phosphoramidite chemistry with oxidation by iodine.

Phosphorothioates (P═S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides:

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P═O or P═S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis.

Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820–11821; Matteucci, M. D. and Caruthers, M. H. *J. Am. Chem. Soc.*, 1981, 103, 3185–3191; Beaucage, S. L. and Caruthers, M. H. *Tetrahedron Lett.*, 1981, 22, 1859–1862; Dahl, B. J., et al., *Acta Chem. Scand.*, 1990, 44, 639–641; Reddy, M. P., et al., *Tetrahedrom Lett.*, 1994, 25, 4311–4314; Wincott, F. et al., *Nucleic Acids Res.*, 1995, 23, 2677–2684; Griffin, B. E., et al., *Tetrahedron*, 1967, 23, 2301–2313; Griffin, B. E., et al., *Tetrahedron*, 1967, 23, 2315–2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Example 4

Synthesis of Chimeric Oligonucleotides

Chimeric oligonucleotides, oligonucleosides or mixed oligonucleotides/oligonucleosides of the invention can be of several different types. These include a first type wherein the “gap” segment of linked nucleosides is positioned between 5' and 3' “wing” segments of linked nucleosides and a second “open end” type wherein the “gap” segment is located at either the 3' or the 5' terminus of the oligomeric compound. Oligonucleotides of the first type are also known in the art as “gapmers” or gapped oligonucleotides. Oligonucleotides of the second type are also known in the art as “hemimers” or “wingmers”.

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

D Sign and Screening of Duplexed Antisense Compounds Targeting HIF1α or HIF2α

In accordance with the present invention, a series of nucleic acid duplexes comprising the antisense compounds of the present invention and their complements can be designed to target HIF1α or HIF2α. The nucleobase sequence of the antisense strand of the duplex preferably comprises at least a portion of an oligonucleotide in Tables 1, 3, 4, 5, 6, 13, or 14. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 455) and having a two-nucleobase overhang of deoxythymidine(dT) would have the following structure:

```
  cgagaggcggacgggaccgTT    Antisense Strand
  |||||||||||||||||||
TTgctctccgcctgccctggc      Complement
```

As another example, a duplex comprising an antisense strand having the sequence CGAGAGGCGGACGG GACCG (SEQ ID NO: 455) and having no overhangs would have the following structure:

```
cgagaggcggacgggaccg   Antisense Strand
|||||||||||||||||||
gctctccgcctgccctggc   Complement
```

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 uM. Once diluted, 30 uL of each strand is combined with 15uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate HIF1● or HIF2● expression.

When cells reached 80% confluency, they are treated with duplexed antisense compounds of the invention. For cells grown in 96-well plates, wells are washed once with 200 ●L OPTI-MEM-1 reduced-serum medium (Gibco BRL) and then treated with 130 ●L of OPTI-MEM-1 containing 12 ●g/mL LIPOFECTIN (Gibco BRL) and the desired duplex antisense compound at a final concentration of 200 M. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Institute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 65–75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4–7 hours of treatment at 37° C., the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of HIF1α and/or HIF2α Expression

Antisense modulation of HIF1α and/or HIF2α expression can be assayed in a variety of ways known in the art. For example, HIF1α or HIF2α mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of HIF1α or HIF2α can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to HIF1α or HIF2α can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays and In Vivo Studies for the Use of HIF1α or HIF2α Inhibitors Phenotypic Assays Once HIF1α or HIF2α inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of HIF1α and/or HIF2α in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with HIF1α and/or HIF2α inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the HIF1α and/or HIF2α inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758–1764). Other methods for poly(A)+ mRNA isolation are routine in the art. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d(T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes, 60 μL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of HIF1α mRNA Levels

Quantitation of HIF1α mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5× PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20–200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368–374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Probes and primers to human HIF1α were designed to hybridize to a human HIF1α sequence, using published sequence information (GenBank accession number U29165.1, incorporated herein by reference and incorporated herein as SEQ ID NO:4). For human HIF1α the PCR primers were:

forward primer: CCAGTTACGTTCCTTCGATCAGT (SEQ ID NO: 5) reverse primer: TTTGAGGACTTGCGCTTTCA (SEQ ID NO: 6) and the PCR probe was: FAM-TCACCATTAGAAAGCAGTTCCGCAAGCC-TAMRA (SEQ ID NO: 7) where FAM is the fluorescent dye and TAMRA is the quencher dye. For human GAPDH the PCR primers were:

forward primer: GAAGGTGAAGGTCGGAGTC(SEQ ID NO:8) reverse primer: GAAGATGGTGATGGGATTTC (SEQ ID NO:9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Example 14

Northern Blot Analysis of HIF1α mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human HIF1α, a human HIF1α specific probe was prepared by PCR using the forward primer CCAGTTACGTTCCTTCGATCAGT (SEQ ID NO: 5) and the reverse primer TTTGAGGACTTGCGCTTTCA (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human HIF1α Expression by Chimeric Phosphorothioate Oligonucleotides Having 2'-MOE Wings and a Deoxy Gap In accordance with the present invention, a series of antisense compounds were designed to target different regions of the human HIF1α RNA, using published sequences (GenBank accession number U29165.1, incorporated herein by reference and incorporated herein as SEQ ID NO: 4, positions 82000 to 139500 of the sequence with GenBank accession number AL137129.4, incorporated herein by reference and incorporated herein as SEQ ID NO: 11, GenBank accession number AU123241.1, incorporated herein by reference and incorporated herein as SEQ ID NO: 12, and GenBank accession number AB073325.1, incorporated herein by reference and incorporated herein as SEQ ID NO: 13). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on human HIF1α mRNA levels by quantitative real-time PCR as described in other examples herein. Data are averages from three experiments in which A549 cells were treated with the antisense oligonucleotides of the present invention. If present, "N.D." indicates "no data".

TABLE 1

Inhibition of human HIF1α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175477 | Coding | 4 | 2496 | aaagtgatgtagtagctgca | 54 | 14 |
| 175478 | Coding | 4 | 854 | ggtatcatatacgtgaatgt | 73 | 15 |
| 175479 | 3'UTR | 4 | 3179 | taccacgtactgctggcaaa | 31 | 16 |
| 175480 | Coding | 4 | 2039 | tgtgctttgaggacttgcgc | 94 | 17 |
| 175481 | Coding | 4 | 583 | gaaatgtaaatcatgtcacc | 56 | 18 |
| 175482 | Coding | 4 | 1408 | tcaaagaggctacttgtatc | 75 | 19 |
| 175483 | Coding | 4 | 1674 | ttaatgcaacttcttgattg | 45 | 20 |
| 175484 | 3'UTR | 4 | 3333 | atcattattatatgattaac | 60 | 21 |
| 175485 | 5'UTR | 4 | 152 | gaaaggcaagtccagaggtg | 42 | 22 |
| 175486 | 3'UTR | 4 | 3027 | taaactccctagccaaaaat | 40 | 23 |
| 175487 | Coding | 4 | 2085 | cattagcagtaggttcttgt | 75 | 24 |
| 175488 | 3'UTR | 4 | 3101 | gatcatgatgaaaggttact | 86 | 25 |
| 175489 | Coding | 4 | 1001 | aaatttcatatccaggctgt | 85 | 26 |
| 175490 | Coding | 4 | 460 | agtttcctcacacgcaaata | 38 | 27 |
| 175491 | Coding | 4 | 1983 | actgatcgaaggaacgtaac | 87 | 28 |
| 175492 | Coding | 4 | 2404 | cgctttctctgagcattctg | 44 | 29 |
| 175493 | Coding | 4 | 649 | aaatcaaacacactgtgtcc | 79 | 30 |
| 175494 | Coding | 4 | 1139 | tcctttagtaaacatatcat | 71 | 31 |
| 175495 | Coding | 4 | 1442 | caaagttaaagcatcaggtt | 79 | 32 |
| 175496 | Coding | 4 | 1765 | ctagtgcttccatcggaagg | 37 | 33 |
| 175497 | 3'UTR | 4 | 3424 | aatgccacataccttctaga | 24 | 34 |
| 175498 | 5'UTR | 4 | 110 | tcgtgagactagagagaagc | 71 | 35 |
| 175499 | 3'UTR | 4 | 3094 | atgaaaggttactgccttct | 81 | 36 |
| 175500 | Coding | 4 | 912 | tcagcaccaagcaggtcata | 8 | 37 |
| 175501 | 3'UTR | 4 | 2841 | aagtttgtgcagtattgtag | 33 | 38 |
| 175502 | Coding | 4 | 2396 | ctgagcattctgcaaagcta | 0 | 39 |
| 175503 | Coding | 4 | 350 | ttcagattctttacttcgcc | 54 | 40 |
| 175504 | Coding | 4 | 2320 | gataacacgttagggcttct | 41 | 41 |

TABLE 1-continued

Inhibition of human HIF1α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 175505 | Coding | 4 | 2331 | tcaaagcgacagataacacg | 51 | 42 |
| 175506 | Coding | 4 | 1091 | caaagcatgataatattcat | 56 | 43 |
| 175507 | Coding | 4 | 565 | ccatcatctgtgagaaccat | 86 | 44 |
| 175508 | Coding | 4 | 2222 | atatggtgatgatgtggcac | 76 | 45 |
| 175509 | 5'UTR | 4 | 51 | ctcctcaggtggcttgtcag | 33 | 46 |
| 175510 | 3'UTR | 4 | 2931 | tgagctgtctgtgatccagc | 94 | 47 |
| 175511 | Coding | 4 | 2321 | agataacacgttagggcttc | 86 | 48 |
| 175512 | Start Codon | 4 | 248 | catggtgaatcggtccccgc | 76 | 49 |
| 175513 | Coding | 4 | 1224 | tgttatatatgacagttgct | 73 | 50 |
| 224184 | Coding | 4 | 414 | ccttatcaagatgcgaactc | 63 | 51 |
| 224185 | Coding | 4 | 480 | ccaaatcaccagcatccaga | 32 | 52 |
| 224186 | Coding | 4 | 619 | aactgagttaatcccatgta | 72 | 53 |
| 224187 | Coding | 4 | 627 | ttagttcaaactgagttaat | 31 | 54 |
| 224188 | Coding | 4 | 706 | aggccatttctgtgtgtaag | 62 | 55 |
| 224189 | Coding | 4 | 961 | ctatctaaaggaatttcaat | 10 | 56 |
| 224190 | Coding | 4 | 1036 | cccatcaattcggtaattct | 41 | 57 |
| 224191 | Coding | 4 | 1125 | tatcatgatgagttttggtc | 81 | 58 |
| 224192 | Coding | 4 | 1283 | aataataccactcacaacgt | 60 | 59 |
| 224193 | Coding | 4 | 1380 | caactttggtgaatagctga | 71 | 60 |
| 224194 | Coding | 4 | 1699 | agtgactctggatttggttc | 44 | 61 |
| 224195 | Coding | 4 | 1928 | catctccaagtctaaatctg | 36 | 62 |
| 224196 | Coding | 4 | 1995 | ctaatggtgacaactgatcg | 72 | 63 |
| 224197 | Coding | 4 | 2126 | cactgtttttaattcatcag | 65 | 64 |
| 224198 | Coding | 4 | 2457 | ataatgttccaattcctact | 31 | 65 |
| 224199 | Stop Codon | 4 | 2735 | agaaaaagctcagttaactt | 57 | 66 |
| 224200 | 3'UTR | 4 | 2828 | attgtagccaggcttctaaa | 68 | 67 |
| 224201 | 3'UTR | 4 | 3056 | atcttcttaaaaataattcg | 18 | 68 |
| 224202 | 3'UTR | 4 | 3193 | tgtgcaattgtggctaccac | 76 | 69 |
| 224203 | 3'UTR | 4 | 3316 | aacaatgtcatgttccaggt | 88 | 70 |
| 224204 | 3'UTR | 4 | 3486 | gctggcaaagtgactataga | 72 | 71 |
| 224205 | 3'UTR | 4 | 3896 | ttccacagaagatgtttatt | 30 | 72 |
| 224206 | 3'UTR | 4 | 3899 | tttttccacagaagatgttt | 14 | 73 |
| 224207 | intron | 11 | 11258 | tagagctaaacgatctagaa | 47 | 74 |
| 224208 | intron | 11 | 23630 | taactctttctggccttgaa | 93 | 75 |
| 224209 | intron | 11 | 25682 | attggccctaacagaaaatc | 19 | 76 |

TABLE 1-continued

Inhibition of human HIF1α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 224210 | intron: exon junction | 11 | 27616 | agaacttatcctacttaaca | 7 | 77 |
| 224211 | intron | 11 | 39357 | gtttccctcgtgttgctcag | 63 | 78 |
| 224212 | exon: intron junction | 11 | 39759 | ttgtacttactatcatgatg | 25 | 79 |
| 224213 | exon: intron junction | 11 | 41520 | acttacttacctcacaacgt | 9 | 80 |
| 224214 | intron: exon junction | 11 | 47989 | aatctgtgtcctttaaaaca | 35 | 81 |
| 224215 | exon | 11 | 2745 | tgtgcactgaggagctgagg | 19 | 82 |
| 224216 | exon | 4 | 296 | acgttcagaacttatctttt | 45 | 83 |
| 224217 | Stop Codon | 13 | 2221 | catgctaaataattcctact | 0 | 84 |

As shown in Table 1, SEQ ID NOs 14, 15, 17, 18, 19, 20, 21, 22, 23, 24, 25, 26, 28, 29, 30, 31, 32, 35, 36, 40, 41, 42, 43, 44, 45, 47, 48, 49, 50, 51, 53, 55, 57, 58, 59, 60, 61, 63, 64, 66, 67, 69, 70, 71, 74, 75, 78 and 83 demonstrated at least 40% inhibition of human HIF1α expression in this assay and are therefore preferred. More preferred are SEQ ID NOs 47, 48 and 25. The target regions to which these preferred sequences are complementary are herein referred to as "preferred target segments" and are therefore preferred for targeting by compounds of the present invention. These preferred target segments are shown in Table 2. The sequences represent the reverse complement of the preferred antisense compounds shown in Table 1. "Target site" indicates the first (5'-most) nucleotide number on the particular target nucleic acid to which the oligonucleotide binds. Also shown in Table 2 is the species in which each of the preferred target segments was found.

TABLE 2

Sequence and position of preferred target segments identified in HIF1α.

| SITE ID | TARGET SEQ ID NO | TARGET SITE | SEQUENCE | REV COMP OF SEQ ID | ACTIVE IN | SEQ ID NO |
|---|---|---|---|---|---|---|
| 90592 | 4 | 2496 | tgcagctactacatcacttt | 14 | *H. sapiens* | 85 |
| 90593 | 4 | 854 | acattcacgtatatgatacc | 15 | *H. sapiens* | 86 |
| 90595 | 4 | 2039 | gcgcaagtcctcaaagcaca | 17 | *H. sapiens* | 87 |
| 90596 | 4 | 583 | ggtgacatgatttacatttc | 18 | *H. sapiens* | 88 |
| 90597 | 4 | 1408 | gatacaagtagcctctttga | 19 | *H. sapiens* | 89 |
| 90598 | 4 | 1674 | caatcaagaagttgcattaa | 20 | *H. sapiens* | 90 |
| 90599 | 4 | 3333 | gttaatcatataataatgat | 21 | *H. sapiens* | 91 |
| 90600 | 4 | 152 | cacctctggacttgcctttc | 22 | *H. sapiens* | 92 |
| 90601 | 4 | 3027 | atttttggctagggagttta | 23 | *H. sapiens* | 93 |
| 90602 | 4 | 2085 | acaagaacctactgctaatg | 24 | *H. sapiens* | 94 |

TABLE 2-continued

Sequence and position of preferred target segments identified in HIF1α.

| SITE ID | TARGET SEQ ID NO | TARGET SITE | SEQUENCE | REV COMP OF SEQ ID | ACTIVE IN | SEQ ID NO |
|---|---|---|---|---|---|---|
| 90603 | 4 | 3101 | agtaacctttcatcatgatc | 25 | *H. sapiens* | 95 |
| 90604 | 4 | 1001 | acagcctggatatgaaattt | 26 | *H. sapiens* | 96 |
| 90606 | 4 | 1983 | gttacgttccttcgatcagt | 28 | *H. sapiens* | 97 |
| 90607 | 4 | 2404 | cagaatgctcagagaaagcg | 29 | *H. sapiens* | 98 |
| 90608 | 4 | 649 | ggacacagtgtgtttgattt | 30 | *H. sapiens* | 99 |
| 90609 | 4 | 1139 | atgatatgtttactaaagga | 31 | *H. sapiens* | 100 |
| 90610 | 4 | 1442 | aacctgatgctttaactttg | 32 | *H. sapiens* | 101 |
| 90613 | 4 | 110 | gcttctctctagtctcacga | 35 | *H. sapiens* | 102 |
| 90614 | 4 | 3094 | agaaggcagtaacctttcat | 36 | *H. sapiens* | 103 |
| 90618 | 4 | 350 | ggcgaagtaaagaatctgaa | 40 | *H. sapiens* | 104 |
| 90619 | 4 | 2320 | agaagccctaacgtgttatc | 41 | *H. sapiens* | 105 |
| 90620 | 4 | 2331 | cgtgttatctgtcgctttga | 42 | *H. sapiens* | 106 |
| 90621 | 4 | 1091 | atgaatattatcatgctttg | 43 | *H. sapiens* | 107 |
| 90622 | 4 | 565 | atggttctcacagatgatgg | 44 | *H. sapiens* | 108 |
| 90623 | 4 | 2222 | gtgccacatcatcaccatat | 45 | *H. sapiens* | 109 |
| 90625 | 4 | 2931 | gctggatcacagacagctca | 47 | *H. sapiens* | 110 |
| 90626 | 4 | 2321 | gaagccctaacgtgttatct | 48 | *H. sapiens* | 111 |
| 90627 | 4 | 248 | gcggggaccgattcaccatg | 49 | *H. sapiens* | 112 |
| 90628 | 4 | 1224 | agcaactgtcatatataaca | 50 | *H. sapiens* | 113 |
| 140838 | 4 | 414 | gagttcgcatcttgataagg | 51 | *H. sapiens* | 114 |
| 140840 | 4 | 619 | tacatgggattaactcagtt | 53 | *H. sapiens* | 115 |
| 140842 | 4 | 706 | cttacacacagaaatggcct | 55 | *H. sapiens* | 116 |
| 140844 | 4 | 1036 | agaattaccgaattgatggg | 57 | *H. sapiens* | 117 |
| 140845 | 4 | 1125 | gaccaaaactcatcatgata | 58 | *H. sapiens* | 118 |
| 140846 | 4 | 1283 | acgttgtgagtggtattatt | 59 | *H. sapiens* | 119 |
| 140847 | 4 | 1380 | tcagctattcaccaaagttg | 60 | *H. sapiens* | 120 |
| 140848 | 4 | 1699 | gaaccaaatccagagtcact | 61 | *H. sapiens* | 121 |
| 140850 | 4 | 1995 | cgatcagttgtcaccattag | 63 | *H. sapiens* | 122 |
| 140851 | 4 | 2126 | ctgatgaattaaaaacagtg | 64 | *H. sapiens* | 123 |
| 140853 | 4 | 2735 | aagttaactgagctttttct | 66 | *H. sapiens* | 124 |
| 140854 | 4 | 2828 | tttagaagcctggctacaat | 67 | *H. sapiens* | 125 |
| 140856 | 4 | 3193 | gtggtagccacaattgcaca | 69 | *H. sapiens* | 126 |
| 140857 | 4 | 3316 | acctggaacatgacattgtt | 70 | *H. sapiens* | 127 |
| 140858 | 4 | 3486 | tctatagtcactttgccagc | 71 | *H. sapiens* | 128 |
| 140861 | 11 | 11258 | ttctagatcgtttagctcta | 74 | *H. sapiens* | 129 |
| 140862 | 11 | 23630 | ttcaaggccagaaagagtta | 75 | *H. sapiens* | 130 |

TABLE 2-continued

Sequence and position of preferred target segments identified in HIF1α.

| SITE ID | TARGET SEQ ID NO | TARGET SITE | SEQUENCE | REV COMP OF SEQ ID | ACTIVE IN | SEQ ID NO |
|---|---|---|---|---|---|---|
| 140865 | 11 | 39357 | ctgagcaacacgagggaaac | 78 | *H. sapiens* | 131 |
| 140870 | 4 | 296 | aaaagataagttctgaacgt | 83 | *H. sapiens* | 132 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of HIF1α.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 16

Western Blot Analysis of HIF1α or HIF2α Prot in Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to HIF1α or HIF2α is used, with a radiolabeled or fluorescently labeled secondary antibody directed against the primary antibody species. Bands are visualized using a PHOSPHORIMAGER™ (Molecular Dynamics, Sunnyvale Calif.).

Example 17

Additional Antisense Oligonucleotides Against Human HIF1α

A series of antisense compounds were designed to target different regions of the human HIF1α RNA, using published sequences (GenBank accession number U29165.1, incorporated herein by reference and incorporated herein as SEQ ID NO: 133). The compounds are shown in Table 3. "Target site" indicates the first (5'-most) nucleotide number on the particular target sequence to which the compound binds. All compounds in Table 3 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on human HIF1α mRNA levels by quantitative real-time PCR as described in other examples herein. Data are averages from three experiments in which A549 cells were treated with the antisense oligonucleotides of the present invention. "Species" indicates the animal species of HIF1α nucleic acid to which the compounds are fully complementary (H=human, M=mouse, R=rat). As noted many of the compounds are fully complementary to more than one species.

TABLE 3

Inhibition of human HIF1α mRNA levels by additional chimeric phosphorothioate oligonucleotides having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298690 | Coding | 133 | 373 | tgatgagcaagctcataaaa | 51 | 134 | H, M, R |
| 298691 | Coding | 133 | 378 | gcaactgatgagcaagctca | 77 | 135 | H, M, R |
| 298692 | Coding | 133 | 385 | ggaagtggcaactgatgagc | 62 | 136 | H, M, R |
| 298693 | Coding | 133 | 631 | ccagttagttcaaactgagt | 79 | 137 | H, M, R |
| 298694 | Coding | 133 | 636 | tgtgtccagttagttcaaac | 79 | 138 | H, M, R |
| 298695 | Coding | 133 | 641 | cacactgtgtccagttagtt | 79 | 139 | H, M, R |
| 298696 | Coding | 133 | 663 | cacatggatgagtaaaatca | 69 | 140 | H, M |

TABLE 3-continued

Inhibition of human HIF1α mRNA levels by additional chimeric phosphorothioate oligonucleotides having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298697 | Coding | 133 | 673 | tcctcatggtcacatggatg | 84 | 141 | H, M, R |
| 298698 | Coding | 133 | 682 | tctctcatttcctcatggtc | 80 | 142 | H, M, R |
| 298699 | Coding | 133 | 687 | gcatttctctcatttcctca | 73 | 143 | H, M, R |
| 298700 | Coding | 133 | 695 | gtgtgtaagcatttctctca | 67 | 144 | H, M, R |
| 298701 | Coding | 133 | 705 | ggccatttctgtgtgtaagc | 78 | 145 | H, M, R |
| 298702 | Coding | 133 | 865 | tggttactgttggtatcata | 85 | 146 | H, M |
| 298703 | Coding | 133 | 919 | tcacaaatcagcaccaagca | 57 | 147 | H, M, R |
| 298704 | Coding | 133 | 924 | tgggttcacaaatcagcacc | 71 | 148 | H, M, R |
| 298705 | Coding | 133 | 931 | tgaggaatgggttcacaaat | 69 | 149 | H, M, R |
| 298706 | Coding | 133 | 967 | gtcttgctatctaaaggaat | 58 | 150 | H, M |
| 298707 | Coding | 133 | 1078 | tattcataaattgagcggcc | 80 | 151 | H, M |
| 298708 | Coding | 133 | 1084 | tgataatattcataaattga | 13 | 152 | H, M, R |
| 298709 | Coding | 133 | 1117 | tgagttttggtcagatgatc | 64 | 153 | H, M, R |
| 298710 | Coding | 133 | 1144 | acttgtcctttagtaaacat | 58 | 154 | H, M, R |
| 298711 | Coding | 133 | 1149 | tggtgacttgtcctttagta | 75 | 155 | H, M, R |
| 298712 | Coding | 133 | 1154 | tcctgtggtgacttgtcctt | 76 | 156 | H, M, R |
| 298713 | Coding | 133 | 1159 | tactgtcctgtggtgacttg | 62 | 157 | H, M, R |
| 298714 | Coding | 133 | 1164 | tcctgtactgtcctgtggtg | 83 | 158 | H, M, R |
| 298715 | Coding | 133 | 1171 | gcaagcatcctgtactgtcc | 67 | 159 | H, M, R |
| 298716 | Coding | 133 | 1192 | cagacatatccacctctttt | 56 | 160 | H, M, R |
| 298717 | Coding | 133 | 1198 | tcaacccagacatatccacc | 53 | 161 | H, M, R |
| 298718 | Coding | 133 | 1217 | tatgacagttgcttgagttt | 64 | 162 | H, M |
| 298719 | Coding | 133 | 1222 | ttatatatgacagttgcttg | 69 | 163 | H, M |
| 298720 | Coding | 133 | 1308 | gaagggagaaaatcaagtcg | 46 | 164 | H, M, R |
| 298721 | Coding | 133 | 1320 | attctgtttgttgaagggag | 43 | 165 | H, M, R |
| 298722 | Coding | 133 | 1354 | ttcatatctgaagattcaac | 53 | 166 | H, M, R |
| 298723 | Coding | 133 | 1387 | tctgattcaactttggtgaa | 59 | 167 | H, M |
| 298724 | Coding | 133 | 1549 | attacatcattatataatgg | 39 | 168 | H, M |
| 298725 | Coding | 133 | 1639 | ctacttcgaagtggctttgg | 77 | 169 | H, M, R |
| 298726 | Coding | 133 | 1645 | tcagcactacttcgaagtgg | 80 | 170 | H, M, R |
| 298727 | Coding | 133 | 1771 | ctttgtctagtgcttccatc | 73 | 171 | H, M, R |
| 298728 | Coding | 133 | 1955 | atcatccattgggatatagg | 74 | 172 | H, M, R |
| 298729 | Coding | 133 | 1996 | tctaatggtgacaactgatc | 78 | 173 | H, M, R |
| 298730 | Coding | 133 | 2421 | catcatgttccatttttcgc | 69 | 174 | H, M, R |
| 298731 | Coding | 133 | 2632 | gtcagctgtggtaatccact | 69 | 175 | H, M, R |
| 298732 | Coding | 133 | 2638 | taactggtcagctgtggtaa | 58 | 176 | H, M, R |

TABLE 3-continued

Inhibition of human HIF1α mRNA levels by additional chimeric phosphorothioate oligonucleotides having 2'-MOE wings and a deoxy gap

| ISIS # | REGION | TARGET seq id no | TARGET site | Sequence | % INHIB | SEQ ID NO | Species |
|---|---|---|---|---|---|---|---|
| 298733 | Coding | 133 | 2659 | ggagcattaacttcacaatc | 39 | 177 | H, M, R |
| 298734 | Coding | 133 | 2680 | aggtttctgctgccttgtat | 65 | 178 | H, M, R |
| 298735 | Coding | 133 | 2689 | ccctgcagtaggtttctgct | 63 | 179 | H, M, R |
| 298736 | Coding | 133 | 2694 | cttcaccctgcagtaggttt | 76 | 180 | H, M, R |
| 298737 | Coding | 133 | 2699 | taattcttcaccctgcagta | 71 | 181 | H, M, R |
| 298738 | Coding | 133 | 2704 | ctgagtaattcttcaccctg | 77 | 182 | H, M, R |
| 298739 | Coding | 133 | 2709 | aagctctgagtaattcttca | 84 | 183 | H, M, R |
| 298740 | Coding | 133 | 2714 | atccaaagctctgagtaatt | 66 | 184 | H, M, R |
| 298741 | Coding | 133 | 2719 | acttgatccaaagctctgag | 72 | 185 | H, M, R |
| 298742 | Stop codon | 133 | 2728 | gctcagttaacttgatccaa | 80 | 186 | H, M, R |
| 298743 | 3'UTR | 133 | 2770 | tgagccaccagtgtccaaaa | 85 | 187 | H, M, R |
| 298744 | 3'UTR | 133 | 2821 | ccaggcttctaaaattagat | 68 | 188 | H, M |
| 298745 | 3'UTR | 133 | 2835 | gtgcagtattgtagccaggc | 78 | 189 | H, M |
| 298746 | 3'UTR | 133 | 2840 | agtttgtgcagtattgtagc | 74 | 190 | H, M |
| 298747 | 3'UTR | 133 | 3004 | taaataaaaaggtgcatttt | 0 | 191 | H, M, R |
| 298749 | 3'UTR | 133 | 3110 | actgcctatgatcatgatga | 74 | 192 | H, M |
| 298750 | 3'UTR | 133 | 3194 | ttgtgcaattgtggctacca | 79 | 193 | H, M, R |
| 298751 | 3'UTR | 133 | 3199 | atatattgtgcaattgtggc | 0 | 194 | H, M, R |
| 298752 | 3'UTR | 133 | 3204 | agaaaatatattgtgcaatt | 31 | 195 | H, M, R |
| 298753 | 3'UTR | 133 | 3264 | cttaaaaactagttttataa | 21 | 196 | H, M, R |
| 298754 | 3'UTR | 133 | 3382 | atgtaaatggctttacccat | 68 | 197 | H, M, R |
| 298755 | 3'UTR | 133 | 3437 | ttttatccaaataaatgcca | 59 | 198 | H, M, R |
| 298756 | 3'UTR | 133 | 3443 | tgagaattttatccaaataa | 44 | 199 | H, M, R |
| 298757 | 3'UTR | 133 | 3701 | taatagcgacaaagtgcata | 81 | 200 | H, M, R |
| 298758 | 3'UTR | 133 | 3706 | gatgttaatagcgacaaagt | 54 | 201 | H, M, R |
| 298759 | 3'UTR | 133 | 3711 | aaaaggatgttaatagcgac | 77 | 202 | H, M, R |
| 298760 | 3'UTR | 133 | 3752 | aatgcttctaaaattactca | 62 | 203 | H, M, R |
| 298761 | 3'UTR | 133 | 3766 | tatattcctaaaataatgct | 30 | 204 | H, M |
| 298762 | 3'UTR | 133 | 3892 | acagaagatgtttatttgat | 44 | 205 | H, M, R |

In Table 3, SEQ ID NO 134, 135, 136, 137, 138, 139, 140, 141, 142, 143, 144, 145, 146, 147, 148, 149, 150, 151, 153, 154, 155, 156, 157, 158, 159, 160, 161, 162, 163, 166, 167, 169, 170, 171, 172, 173, 174, 175, 176, 178, 179, 180, 181, 182, 184, 185, 186, 187, 188, 189, 190, 192, 193, 197, 198, 200, 201, 202 and 203 demonstrated at least 50% inhibition of HIF1α expression and are therefore preferred.

Example 18

Antisense Inhibition of Mouse HIF1α Expression by Chimeric Phosphorothioate Oligonucleotides Having 2'-MOE Wings and a Deoxy Gap In accordance with the present invention, a series of antisense compounds were designed to target different regions of the mouse HIF1α RNA, using published sequences (GenBank accession number NM_010431.1, incorporated herein by reference and incorporated herein as SEQ ID NO: 206. The compounds are shown in Table 4. "Target site" indicates the first (5'-most) nucleotide number on the particular target sequence to which the compound binds. All compounds in Table 4 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines. The compounds were analyzed for their effect on mouse HIF1α mRNA levels by quantitative real-time PCR as described in other examples herein. Unlike previous examples, the oligonucleotide concentration in this experiment is 50 nM. Data are averages from three experiments in which b.END cells were treated with the antisense oligonucleotides of the present invention. In Table 4, "Species" indicates the animal species of HIF1α nucleic acid to which the compounds are fully complementary (H=human, M=mouse, R=rat). As noted many of the compounds are fully complementary to more than one species.

TABLE 4

Inhibition of mouse HIF1α mRNA levels by chimeric phosphorothioate oligonucleotides having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298690 | Coding | 206 | 366 | tgatgagcaagctcataaaa | 32 | 134 | H, M, R |
| 298691 | Coding | 206 | 371 | gcaactgatgagcaagctca | 67 | 135 | H, M, R |
| 298692 | Coding | 206 | 378 | ggaagtggcaactgatgagc | 33 | 136 | H, M, R |
| 298693 | Coding | 206 | 624 | ccagttagttcaaactgagt | 58 | 137 | H, M, R |
| 298694 | Coding | 206 | 629 | tgtgtccagttagttcaaac | 39 | 138 | H, M, R |
| 298695 | Coding | 206 | 634 | cacactgtgtccagttagtt | 71 | 139 | H, M, R |
| 298696 | Coding | 206 | 656 | cacatggatgagtaaaatca | 60 | 140 | H, M |
| 298697 | Coding | 206 | 666 | tcctcatggtcacatggatg | 56 | 141 | H, M, R |
| 298698 | Coding | 206 | 675 | tctctcatttcctcatggtc | 69 | 142 | H, M, R |
| 298699 | Coding | 206 | 680 | gcatttctctcatttcctca | 70 | 143 | H, M, R |
| 298700 | Coding | 206 | 688 | gtgtgtaagcatttctctca | 64 | 144 | H, M, R |
| 298701 | Coding | 206 | 698 | ggccatttctgtgtgtaagc | 46 | 145 | H, M, R |
| 298702 | Coding | 206 | 858 | tggttactgttggtatcata | 69 | 146 | H, M |
| 298703 | Coding | 206 | 912 | tcacaaatcagcaccaagca | 45 | 147 | H, M, R |
| 298704 | Coding | 206 | 917 | tgggttcacaaatcagcacc | 34 | 148 | H, M, R |
| 298705 | Coding | 206 | 924 | tgaggaatgggttcacaaat | 64 | 149 | H, M, R |
| 298706 | Coding | 206 | 960 | gtcttgctatctaaaggaat | 42 | 150 | H, M |
| 298707 | Coding | 206 | 1071 | tattcataaattgagcggcc | 64 | 151 | H, M |
| 298708 | Coding | 206 | 1077 | tgataatattcataaattga | 0 | 152 | H, M, R |
| 298709 | Coding | 206 | 1110 | tgagttttggtcagatgatc | 26 | 153 | H, M, R |
| 298710 | Coding | 206 | 1137 | acttgtcctttagtaaacat | 47 | 154 | H, M, R |
| 298711 | Coding | 206 | 1142 | tggtgacttgtcctttagta | 64 | 155 | H, M, R |
| 298712 | Coding | 206 | 1147 | tcctgtggtgacttgtcctt | 58 | 156 | H, M, R |

TABLE 4-continued

Inhibition of mouse HIF1α mRNA levels by chimeric phosphorothioate oligonucleotides having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298713 | Coding | 206 | 1152 | tactgtcctgtggtgacttg | 48 | 157 | H, M, R |
| 298714 | Coding | 206 | 1157 | tcctgtactgtcctgtggtg | 61 | 158 | H, M, R |
| 298715 | Coding | 206 | 1164 | gcaagcatcctgtactgtcc | 70 | 159 | H, M, R |
| 298716 | Coding | 206 | 1185 | cagacatatccacctctttt | 43 | 160 | H, M, R |
| 298717 | Coding | 206 | 1191 | tcaacccagacatatccacc | 55 | 161 | H, M, R |
| 298718 | Coding | 206 | 1210 | tatgacagttgcttgagttt | 39 | 162 | H, M |
| 298719 | Coding | 206 | 1215 | ttatatatgacagttgcttg | 42 | 163 | H, M |
| 298720 | Coding | 206 | 1301 | gaagggagaaaatcaagtcg | 23 | 164 | H, M, R |
| 298721 | Coding | 206 | 1313 | attctgtttgttgaagggag | 30 | 165 | H, M, R |
| 298722 | Coding | 206 | 1347 | ttcatatctgaagattcaac | 5 | 166 | H, M, R |
| 298723 | Coding | 206 | 1380 | tctgattcaactttggtgaa | 52 | 167 | H, M |
| 298724 | Coding | 206 | 1542 | attacatcattatataatgg | 29 | 168 | H, M |
| 298725 | Coding | 206 | 1629 | ctacttcgaagtggctttgg | 57 | 169 | H, M, R |
| 298726 | Coding | 206 | 1635 | tcagcactacttcgaagtgg | 59 | 170 | H, M, R |
| 298727 | Coding | 206 | 1761 | ctttgtctagtgcttccatc | 46 | 171 | H, M, R |
| 298728 | Coding | 206 | 1987 | atcatccattgggatatagg | 29 | 172 | H, M, R |
| 298729 | Coding | 206 | 2028 | tccaatggtgacaactgatc | 19 | 173 | H, M, R |
| 298730 | Coding | 206 | 2444 | catcatgttccatttttcgc | 55 | 174 | H, M, R |
| 298731 | Coding | 206 | 2655 | gtcagctgtggtaatccact | 59 | 175 | H, M, R |
| 298732 | Coding | 206 | 2661 | taactggtcagctgtggtaa | 62 | 176 | H, M, R |
| 298733 | Coding | 206 | 2682 | ggagcattaacttcacaatc | 32 | 177 | H, M, R |
| 298734 | Coding | 206 | 2703 | aggtttctgctgccttgtat | 50 | 178 | H, M, R |
| 298735 | Coding | 206 | 2712 | ccctgcagtaggtttctgct | 53 | 179 | H, M, R |
| 298736 | Coding | 206 | 2717 | cttcaccctgcagtaggttt | 46 | 180 | H, M, R |
| 298737 | Coding | 206 | 2722 | taattcttcaccctgcagta | 42 | 181 | H, M, R |
| 298738 | Coding | 206 | 2727 | ctgagtaattcttcaccctg | 62 | 182 | H, M, R |
| 298739 | Coding | 206 | 2732 | aagctctgagtaattcttca | 44 | 183 | H, M, R |
| 298740 | Coding | 206 | 2737 | atccaaagctctgagtaatt | 42 | 184 | H, M, R |
| 298741 | Coding | 206 | 2742 | acttgatccaaagctctgag | 47 | 185 | H, M, R |
| 298742 | Stop codon | 206 | 2751 | gctcagttaacttgatccaa | 67 | 186 | H, M, R |
| 298743 | 3'UTR | 206 | 2853 | tgagccaccagtgtccaaaa | 56 | 187 | H, M, R |
| 298744 | 3'UTR | 206 | 2895 | ccaggcttctaaaattagat | 48 | 188 | H, M |
| 298745 | 3'UTR | 206 | 2909 | gtgcagtattgtagccaggc | 72 | 189 | H, M |
| 298746 | 3'UTR | 206 | 2914 | agtttgtgcagtattgtagc | 62 | 190 | H, M |
| 298747 | 3'UTR | 206 | 3067 | taaataaaaaggtgcatttt | 4 | 191 | H, M, R |

TABLE 4-continued

Inhibition of mouse HIF1α mRNA levels by chimeric phosphorothioate oligonucleotides having 2'-MOE wings and a deoxy gap

| ISIS # | REGION | TARGET SEQ ID | TARGET SITE | Sequence | % INHIB | SEQ ID NO | Species |
|---|---|---|---|---|---|---|---|
| 298748 | 3'UTR | 206 | 3162 | gatcatgatgagaatttact | 56 | 207 | M |
| 298749 | 3'UTR | 206 | 3171 | actgcctatgatcatgatga | 64 | 192 | H, M, |
| 298750 | 3'UTR | 206 | 3253 | ttgtgcaattgtggctacca | 74 | 193 | H, M, R |
| 298751 | 3'UTR | 206 | 3258 | atatattgtgcaattgtggc | 67 | 194 | H, M, R |
| 298752 | 3'UTR | 206 | 3263 | agaaaatatattgtgcaatt | 24 | 195 | H, M, R |
| 298753 | 3'UTR | 206 | 3322 | cttaaaaactagttttataa | 0 | 196 | H, M, R |
| 298754 | 3'UTR | 206 | 3428 | atgtaaatggctttacccat | 51 | 197 | H, M, R |
| 298755 | 3'UTR | 206 | 3483 | ttttatccaaataaatgcca | 28 | 198 | H, M, R |
| 298756 | 3'UTR | 206 | 3489 | tgagaattttatccaaataa | 14 | 199 | H, M, R |
| 298757 | 3'UTR | 206 | 3739 | taatagcgacaaagtgcata | 43 | 200 | H, M, R |
| 298758 | 3'UTR | 206 | 3744 | gatgttaatagcgacaaagt | 23 | 201 | H, M, R |
| 298759 | 3'UTR | 206 | 3749 | aaaaggatgttaatagcgac | 45 | 202 | H, M, R |
| 298760 | 3'UTR | 206 | 3789 | aatgcttctaaaattactca | 30 | 203 | H, M, R |
| 298761 | 3'UTR | 206 | 3803 | tatattcctaaaataatgct | 0 | 204 | H, M |
| 298762 | 3'UTR | 206 | 3928 | acagaagatgtttatttgat | 21 | 205 | H, M, R |

In Table 4, SEQ ID NOs 134, 135, 136, 137, 138, 139, 140, 141, 142, 143, 144, 145, 146, 147, 148, 149, 150, 151, 154, 155, 156, 157, 158, 159, 160, 161, 162, 163, 167, 169, 170, 171, 174, 175, 176, 177, 178, 179, 180, 181, 182, 183, 184, 185, 186, 187, 188, 189, 190, 207, 192, 193, 194, 197, 200, and 202 demonstrated at least 32% inhibition of HIF1α expression and are therefore preferred.

Example 19

Real-Time Quantitative PCR Analysis of HIF2α mRNA Levels

Quantitation of HIF2α mRNA levels was accomplished by real-time quantitative PCR using the ABI PRISM™ 7600, 7700, or 7900 Sequence Detection System (PE-Applied Biosystems, Foster City, Calif.) as described in previous examples.

Probes and primers to human HIF2α were designed to hybridize to a human HIF2α sequence, using published sequence information (GenBank accession number NM_001430.1, incorporated herein by reference and incorporated herein as SEQ ID NO: 208). For human HIF2α the PCR primers were:

forward primer: AAGCCTTGGAGGGTTTCATTG (SEQ ID NO: 209) reverse primer: TGCTGATGTTTTCTGACAGAAAGAT (SEQ ID NO: 210) and the PCR probe was: FAM-CGTGGTGACCCAAGATGGCGACA-TAMRA (SEQ ID NO: 211) where FAM is the fluorescent dye and TAMRA is the quencher dye. For human GAPDH the PCR primers and probe were those listed in previous examples (SEQ ID NOs: 8, 9, 10).

Probes and primers to mouse HIF2α were designed to hybridize to a mouse HIF2α sequence, using published sequence information (GenBank accession number NM_010137.1, incorporated herein by reference and incorporated herein as SEQ ID NO: 212). For mouse HIF2α the PCR primers were:

forward primer: GGCCATCGTTCGAGCCTTA (SEQ ID NO: 213) reverse primer: GGCACGGGCACGTTCA (SEQ ID NO: 214) and the PCR probe was: FAM-CTGTTGCCGGAACTGACCAGATATGACTG-TAMRA (SEQ ID NO: 215) where FAM is the fluorescent reporter dye and TAMRA is the quencher dye. For mouse GAPDH the PCR primers were:

forward primer: GGCAAATTCAACGGCACAGT(SEQ ID NO: 216) reverse primer: GGGTCTCGCTCCTGGAAGAT (SEQ ID NO: 217) and the PCR probe was: 5'JOE-AGGCCGAGAATGGGAAGCTTGTCATC-TAMRA 3' (SEQ ID NO: 218) where JOE is the fluorescent reporter dye and TAMRA is the quencher dye.

Example 20

Northern Blot Analysis of HIF2α mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Electrophoresis and blotting was performed as described in previous examples.

To detect human HIF2α, a human HIF2α specific probe was prepared by PCR using the forward primer AAGCCTTGGAGGGTTTCATTG (SEQ ID NO: 209) and the reverse primer TGCTGATGTTTTCTGACAGAAAGAT (SEQ ID NO: 210). To normalize for variations in loading and transfer efficiency membranes were stripped and probed for human glyceraldehyde-3-phosphate dehydrogenase (GAPDH) RNA (Clontech, Palo Alto, Calif.).

To detect mouse HIF2α, a mouse HIF2α specific probe was prepared by PCR using the forward primer GGCCATCGTTCGAGCCTTA (ID NO: 213) and the reverse primer GGCACGGGCACGTTCA (SEQ ID NO: 214). To normalize for variations in loading and transfer efficiency membranes were stripped and probed for mouse glyceraldehyde-3-phosphate dehydrogenase (GAPDH) RNA (Clontech, Palo Alto, Calif.).

Example 21

Antisense Inhibition of Human HIF2α Expression by Chimeric Phosphorothioate Oligonucleotides Having 2'-MOE Wings and a Deoxy Gap In accordance with the present invention, a series of antisense compounds were designed to target different regions of the human HIF2α RNA, using published sequences (GenBank accession number NM_001430.1, incorporated herein by reference and incorporated herein as SEQ ID NO: 208). The compounds are shown in Table 5. "Target site" indicates the first (5'-most) nucleotide number on the particular target sequence to which the compound binds. All compounds in Table 5 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human HIF2α mRNA levels by quantitative real-time PCR as described in other examples herein. Data are averages from three experiments in which A549 cells were treated with the antisense oligonucleotides of the present invention.

TABLE 5

Inhibition of human HIF2α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 221985 | Start Codon | 208 | 142 | gtcagctgtcattgtcgctg | 74 | 219 |
| 221987 | Stop Codon | 208 | 2751 | ggcctggctcaggtggcctg | 54 | 220 |
| 221989 | Coding | 208 | 1000 | ggtcatgttctcggagtcta | 82 | 221 |
| 221991 | Coding | 208 | 1572 | gtggagcagctgctgctgct | 80 | 222 |
| 221993 | Coding | 208 | 2412 | ggtacatttgcgctcagtgg | 76 | 223 |
| 221995 | Coding | 208 | 2206 | tgggcctcgagccccaaaac | 15 | 224 |
| 221997 | Coding | 208 | 1300 | gaataggaagttactcttct | 51 | 225 |
| 221999 | Coding | 208 | 1752 | tggaagtcttccccgtccat | 69 | 226 |
| 222001 | Coding | 208 | 947 | gcagctcctcagggtggtaa | 82 | 227 |
| 222003 | Coding | 208 | 977 | catggtagaattcataggct | 82 | 228 |
| 222005 | Coding | 208 | 1631 | tcacttcaatcttcaggtcg | 55 | 229 |
| 222007 | Coding | 208 | 2691 | gagcttcccagcacgggcac | 79 | 230 |
| 222009 | Coding | 208 | 1502 | tgaaggcaggcaggctccca | 77 | 231 |
| 222011 | Coding | 208 | 2008 | ggtgctggcctggccacagc | 72 | 232 |
| 222013 | Coding | 208 | 561 | cgaatctcctcatggtcgca | 89 | 233 |
| 222015 | Coding | 208 | 1247 | tgctgttcatggccatcagg | 78 | 234 |
| 222017 | Coding | 208 | 1679 | tactgcattggtccttggcc | 78 | 235 |
| 222019 | Coding | 208 | 1488 | ctcccagcctcgctctgggt | 63 | 236 |
| 222021 | Coding | 208 | 2700 | aggagcgtggagcttcccag | 59 | 237 |
| 222023 | Coding | 208 | 623 | ctgtggacatgtctttgctt | 79 | 238 |
| 222025 | Coding | 208 | 1716 | agtgtctccaagtccagctc | 84 | 239 |
| 222027 | Coding | 208 | 759 | ctattgtgaggagggcagtt | 75 | 240 |
| 222029 | Coding | 208 | 237 | tcatagaacacctccgtctc | 37 | 241 |

TABLE 5-continued

Inhibition of human HIF2α mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 222031 | Coding | 208 | 2334 | aaatgtgaggtgctgccacc | 67 | 242 |
| 222033 | Coding | 208 | 1578 | ttgggcgtggagcagctgct | 54 | 243 |
| 222035 | Coding | 208 | 2126 | gcgctgctcccaagaactct | 89 | 244 |
| 222037 | Coding | 208 | 2639 | gcagcaggtaggactcaaat | 64 | 245 |
| 222039 | Coding | 208 | 2325 | gtgctgccaccaggtgggtc | 79 | 246 |
| 222041 | Coding | 208 | 1001 | tggtcatgttctcggagtct | 82 | 247 |
| 222043 | Coding | 208 | 1209 | tcagtctggtccatggagaa | 80 | 248 |
| 222045 | Coding | 208 | 566 | tctcacgaatctcctcatgg | 68 | 249 |
| 222047 | Coding | 208 | 1622 | tcttcaggtcgttatccaaa | 56 | 250 |
| 222049 | Coding | 208 | 2715 | aggtcccctccttgcaggag | 66 | 251 |
| 222051 | Coding | 208 | 246 | tgggccagctcatagaacac | 82 | 252 |
| 222053 | Coding | 208 | 2336 | tcaaatgtgaggtgctgcca | 73 | 253 |
| 222055 | Coding | 208 | 391 | catctgctggtcagcttcgg | 85 | 254 |
| 222057 | Coding | 208 | 1217 | acagggattcagtctggtcc | 84 | 255 |

As shown in Table 5, SEQ ID NOs 219, 220, 221, 211, 223, 225, 226, 227, 228, 229, 230, 231, 232, 233, 234, 235, 236, 237, 238, 239, 240, 242, 243, 244, 245, 246, 247, 248, 249, 250, 251, 252, 253, 254 and 255 demonstrated at least 40% inhibition of HIF2α expression and are therefore preferred. More preferred are SEQ ID NOs 233, 239 and 244. The target regions to which these preferred sequences are complementary are herein referred to as "preferred target segments" and are therefore preferred for targeting by compounds of the present invention. These preferred target segments are shown in Table 7. These sequences are shown to contain thymine (T) but one of skill in the art will appreciate that thymine (T) is generally replaced by uracil (U) in RNA sequences. The sequences represent the reverse complement of the preferred antisense compounds shown in Table 5. "Target site" indicates the first (5'-most) nucleotide number on the particular target nucleic acid to which the oligonucleotide binds. Also shown in Table 7 is the species in which each of the preferred target segments was found.

Example 22

Antisense Inhibition of Mouse HIF2α Expression by Chimeric Phosphorothioate Oligonucleotides Having 2'-MOE Wings and a Deoxy Gap In accordance with the present invention, a second series of antisense compounds were designed to target different regions of the mouse HIF2α RNA, using published sequences (GenBank accession number NM_010137.1, incorporated herein by reference and incorporated herein as SEQ ID NO: 212, nucleotides 20468925 to 20547619 of the sequence with GenBank accession number NW_000133.1, incorporated herein by reference and incorporated herein as SEQ ID NO: 257, GenBank accession number BY229956.1, incorporated herein by reference and incorporated herein as SEQ ID NO: 258, and GenBank accession number AK087208.1, incorporated herein by reference and incorporated herein as SEQ ID NO: 259). The compounds are shown in Table 6. "Target site" indicates the first (5'-most) nucleotide number on the particular target nucleic acid to which the compound binds. All compounds in Table 6 are chimeric oligonucleotides ("gapmers") 20 nucleotides in length, composed of a central "gap" region consisting of ten 2'-deoxynucleotides, which is flanked on both sides (5' and 3'-directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse HIF2α mRNA levels by quantitative real-time PCR as described in other examples herein. Data are averages from three experiments in which b.END cells were treated with the antisense oligonucleotides of the present invention.

TABLE 6

Inhibition of mouse HIF2α mRNA levels by chimeric phosphorothioate oligonucleotides having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 320972 | 5'UTR | 212 | 130 | ggttccttaaccccgtaggg | 70 | 260 |
| 320973 | 5'UTR | 212 | 135 | acctgggttccttaaccccg | 61 | 261 |
| 320974 | 5'UTR | 212 | 140 | ggagcacctgggttccttaa | 70 | 262 |
| 320975 | Start Codon | 212 | 178 | ttgtcagctgtcattgtcgc | 72 | 263 |
| 320976 | Start Codon | 212 | 183 | tctccttgtcagctgtcatt | 84 | 264 |
| 320977 | Coding | 212 | 266 | gaagacctccgtctccttgc | 83 | 265 |
| 320978 | Coding | 212 | 317 | caggtgggagctcacactgt | 76 | 266 |
| 320979 | Coding | 212 | 352 | aagctgatggccaggcgcat | 64 | 267 |
| 320980 | Coding | 212 | 442 | ttcaggtacaagttatccat | 78 | 268 |
| 320981 | Coding | 212 | 448 | aaggctttcaggtacaagtt | 73 | 269 |
| 320982 | Coding | 212 | 461 | aatgaaaccctccaaggctt | 87 | 270 |
| 320983 | Coding | 212 | 520 | atgaacttgctgatgttttc | 29 | 271 |
| 320984 | Coding | 212 | 525 | gtcccatgaacttgctgatg | 57 | 272 |
| 320985 | Coding | 212 | 535 | acctgggtaagtcccatgaa | 63 | 273 |
| 320986 | Coding | 212 | 545 | tgttagttctacctgggtaa | 62 | 274 |
| 320987 | Coding | 212 | 563 | gtcaaagatgctgtgtcctg | 83 | 275 |
| 320988 | Coding | 212 | 574 | ggatgagtgaagtcaaagat | 50 | 276 |
| 320989 | Coding | 212 | 673 | atgaagaagtcacgctcggt | 63 | 277 |
| 320990 | Coding | 212 | 682 | ttcatcctcatgaagaagtc | 53 | 278 |
| 320991 | Coding | 212 | 687 | tgcacttcatcctcatgaag | 58 | 279 |
| 320992 | Coding | 212 | 714 | tgacagtccggcctctgttg | 52 | 280 |
| 320993 | Coding | 212 | 766 | actctcacttgcccggtgca | 87 | 281 |
| 320994 | Coding | 212 | 776 | gttgttgtagactctcactt | 64 | 282 |
| 320995 | Coding | 212 | 850 | attggctcacacatgatgat | 76 | 283 |
| 320996 | Coding | 212 | 860 | tgggtgctggattggctcac | 75 | 284 |
| 320997 | Coding | 212 | 913 | atgctgtggcggctcaggaa | 87 | 285 |
| 320998 | Coding | 212 | 970 | gggtggtaaccaatcagttc | 76 | 286 |
| 320999 | Coding | 212 | 1057 | gtgcacaagttctggtgact | 50 | 287 |
| 321000 | Coding | 212 | 1062 | ccttggtgcacaagttctgg | 74 | 288 |
| 321001 | Coding | 212 | 1135 | gtcccctgggtctccagcca | 78 | 289 |
| 321002 | Coding | 212 | 1140 | tgaccgtcccctgggtctcc | 63 | 290 |
| 321003 | Coding | 212 | 1145 | gtagatgaccgtcccctggg | 68 | 291 |
| 321004 | Coding | 212 | 1150 | gggttgtagatgaccgtccc | 62 | 292 |
| 321005 | Coding | 212 | 1191 | catagttgacacacatgata | 37 | 293 |
| 321006 | Coding | 212 | 1234 | tccatggagaacaccacgtc | 76 | 294 |
| 321007 | Coding | 212 | 1239 | tctggtccatggagaacacc | 83 | 295 |

TABLE 6-continued

Inhibition of mouse HIF2α mRNA levels by chimeric phosphorothioate oligonucleotides having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 321008 | Coding | 212 | 1286 | aaagatgctgttcatggcca | 51 | 296 |
| 321009 | Coding | 212 | 1338 | tggtgaacaggtagttgctc | 64 | 297 |
| 321010 | Coding | 212 | 1363 | agctcctcgggctcctcctt | 83 | 298 |
| 321011 | Coding | 212 | 1454 | ggccttgccataggctgagg | 49 | 299 |
| 321012 | Coding | 212 | 1459 | aggatggccttgccataggc | 53 | 300 |
| 321013 | Coding | 212 | 1612 | ctgctgggcgtggagcagct | 40 | 301 |
| 321014 | Coding | 212 | 1725 | tgaagtccgtctgggtactg | 58 | 302 |
| 321015 | Coding | 212 | 1939 | tccaactgctgcgggtactt | 82 | 303 |
| 321016 | Coding | 212 | 2002 | ttgctcccagcatcaaagaa | 0 | 304 |
| 321017 | Coding | 212 | 2012 | cagggaccctttgctcccag | 81 | 305 |
| 321018 | Coding | 212 | 2038 | gtgctggcctggccacagca | 66 | 306 |
| 321019 | Coding | 212 | 2216 | cttgaacatggagacatgag | 65 | 307 |
| 321020 | Coding | 212 | 2226 | cagacctcatcttgaacatg | 72 | 308 |
| 321021 | Coding | 212 | 2231 | ctttgcagacctcatcttga | 73 | 309 |
| 321022 | Coding | 212 | 2296 | ttcagcttgttggacagggc | 51 | 310 |
| 321023 | Coding | 212 | 2376 | gtgaactgctggtgcctgga | 79 | 311 |
| 321024 | Coding | 212 | 2386 | cacatcaagtgtgaactgct | 0 | 312 |
| 321025 | Coding | 212 | 2413 | ccgcccatgaggctcttcat | 70 | 313 |
| 321026 | Coding | 212 | 2423 | aggacaggtcccgcccatga | 85 | 314 |
| 321027 | Coding | 212 | 2433 | caggcatcaaaggacaggtc | 55 | 315 |
| 321028 | Coding | 212 | 2482 | gatttttgggtgaattcatc | 38 | 316 |
| 321029 | Coding | 212 | 2647 | ctggccacgcctgacacctt | 65 | 317 |
| 321030 | Coding | 212 | 2665 | gatggccccagcagtcgact | 64 | 318 |
| 321031 | Coding | 212 | 2670 | cgaacgatggccccagcagt | 48 | 319 |
| 321032 | Coding | 212 | 2680 | aggtaaggctcgaacgatgg | 65 | 320 |
| 321033 | Coding | 212 | 2707 | cagtcatatctggtcagttc | 78 | 321 |
| 321034 | Coding | 212 | 2712 | cctcacagtcatatctggtc | 83 | 322 |
| 321035 | Coding | 212 | 2717 | gttcacctcacagtcatatc | 66 | 323 |
| 321036 | Coding | 212 | 2722 | ggcacgttcacctcacagtc | 81 | 324 |
| 321037 | Coding | 212 | 2727 | gcacgggcacgttcacctca | 90 | 325 |
| 321038 | Coding | 212 | 2758 | tctctcccctgcaggagtgt | 79 | 326 |
| 321039 | Coding | 212 | 2768 | tctgagaaggtctctcccct | 51 | 327 |
| 321040 | Coding | 212 | 2778 | ggtccagagctctgagaagg | 73 | 328 |
| 321041 | Stop Codon | 212 | 2791 | gctcaggtggcctggtccag | 69 | 329 |
| 321042 | Stop Codon | 212 | 2798 | ggccctggctcaggtggcct | 12 | 330 |

TABLE 6-continued

Inhibition of mouse HIF2α mRNA levels by chimeric phosphorothioate oligonucleotides having 2'-MOE wings and a deoxy gap

| ISIS # | REGION | TARGET SEQ ID NO: | TARGET SITE | SEQUENCE | % INHIB | SEQ ID NO |
|---|---|---|---|---|---|---|
| 321043 | 3'UTR | 212 | 3199 | agaacaagaacacttgagtt | 66 | 331 |
| 321044 | intron | 257 | 12633 | aacagttgagacatgacagt | 67 | 332 |
| 321045 | exon: intron junction | 257 | 74580 | tgtcactaacctcatcttga | 45 | 333 |
| 321046 | 5'UTR | 258 | 235 | acaggagtcacttttctggg | 43 | 334 |
| 321047 | 5'UTR | 258 | 82 | catacagtctcaggacactg | 47 | 335 |
| 321048 | Genomic | 259 | 116 | aatctgtccatgaaaagaca | 33 | 336 |

As shown in Table 6, SEQ ID NO, 260, 261, 262, 263, 264, 265, 266, 267, 268, 269, 270, 272, 273, 274, 275, 276, 277, 278, 279, 280, 281, 282, 283, 284, 285, 286, 287, 288, 289, 290, 291, 292, 294, 295, 296, 297, 298, 299, 300, 301, 302, 303, 305, 306, 307, 308, 309, 310, 311, 313, 314, 315, 317, 318, 319, 320, 321, 322, 323, 324, 325, 326, 327, 328, 329, 331, 332, 333, 334 and 335 demonstrated at least 40% inhibition of mouse HIF2α expression in this experiment and are therefore preferred. More preferred are SEQ ID NOs 270, 281 and 285. The target regions to which these preferred sequences are complementary are herein referred to as "preferred target segments" and are therefore preferred for targeting by compounds of the present invention. These preferred target segments are shown in Table 7. These sequences are shown to contain thymine (T) but one of skill in the art will appreciate that thymine (T) is generally replaced by uracil (U) in RNA sequences. The sequences represent the reverse complement of the preferred antisense compounds shown in Tables 5 and 6. "Target site" indicates the first (5'-most) nucleotide number on the particular target nucleic acid to which the oligonucleotide binds. Also shown in Table 3 is the species in which each of the preferred target segments was found.

TABLE 7

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 138730 | 208 | 142 | cagcgacaatgacagctgac | 291 | *H. sapiens* | 337 |
| 138731 | 208 | 2751 | caggccacctgagccaggcc | 292 | *H. sapiens* | 338 |
| 138732 | 208 | 1000 | tagactccgagaacatgacc | 293 | *H. sapiens* | 339 |
| 138733 | 208 | 1572 | agcagcagcagctgctccac | 294 | *H. sapiens* | 340 |
| 138734 | 208 | 2412 | ccactgagcgcaaatgtacc | 295 | *H. sapiens* | 341 |
| 138736 | 208 | 1300 | agaagagtaacttcctattc | 297 | *H. sapiens* | 342 |
| 138737 | 208 | 1752 | atggacggggaagacttcca | 298 | *H. sapiens* | 343 |
| 138738 | 208 | 947 | ttaccaccctgaggagctgc | 299 | *H. sapiens* | 344 |
| 138739 | 208 | 977 | agcctatgaattctaccatg | 300 | *H. sapiens* | 345 |
| 138740 | 208 | 1631 | cgacctgaagattgaagtga | 301 | *H. sapiens* | 346 |
| 138741 | 208 | 2691 | gtgcccgtgctgggaagctc | 302 | *H. sapiens* | 347 |
| 138742 | 208 | 1502 | tgggagcctgcctgccttca | 303 | *H. sapiens* | 348 |
| 138743 | 208 | 2008 | gctgtggccaggccagcacc | 304 | *H. sapiens* | 349 |
| 138744 | 208 | 561 | tgcgaccatgaggagattcg | 305 | *H. sapiens* | 350 |
| 138745 | 208 | 1247 | cctgatggccatgaacagca | 306 | *H. sapiens* | 351 |

TABLE 7-continued

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 138746 | 208 | 1679 | ggccaaggaccaatgcagta | 307 | *H. sapiens* | 352 |
| 138747 | 208 | 1488 | acccagagcgaggctgggag | 308 | *H. sapiens* | 353 |
| 138748 | 208 | 2700 | ctgggaagctccacgctcct | 309 | *H. sapiens* | 354 |
| 138749 | 208 | 623 | aagcaaagacatgtccacag | 310 | *H. sapiens* | 355 |
| 138750 | 208 | 1716 | gagctggacttggagacact | 311 | *H. sapiens* | 356 |
| 138751 | 208 | 759 | aactgccctcctcacaatag | 312 | *H. sapiens* | 357 |
| 138753 | 208 | 2334 | ggtggcagcacctcacattt | 314 | *H. sapiens* | 358 |
| 138754 | 208 | 1578 | agcagctgctccacgcccaa | 315 | *H. sapiens* | 359 |
| 138755 | 208 | 2126 | agagttcttgggagcagcgc | 316 | *H. sapiens* | 360 |
| 138756 | 208 | 2639 | atttgagtcctacctgctgc | 317 | *H. sapiens* | 361 |
| 138757 | 208 | 2325 | gacccacctggtggcagcac | 318 | *H. sapiens* | 362 |
| 138758 | 208 | 1001 | agactccgagaacatgacca | 319 | *H. sapiens* | 363 |
| 138759 | 208 | 1209 | ttctccatggaccagactga | 320 | *H. sapiens* | 364 |
| 138760 | 208 | 566 | ccatgaggagattcgtgaga | 321 | *H. sapiens* | 365 |
| 138761 | 208 | 1622 | tttggataacgacctgaaga | 322 | *H. sapiens* | 366 |
| 138762 | 208 | 2715 | ctcctgcaaggaggggacct | 323 | *H. sapiens* | 367 |
| 138763 | 208 | 246 | gtgttctatgagctggccca | 324 | *H. sapiens* | 368 |
| 138764 | 208 | 2336 | tggcagcacctcacatttga | 325 | *H. sapiens* | 369 |
| 138765 | 208 | 391 | ccgaagctgaccagcagatg | 326 | *H. sapiens* | 370 |
| 138766 | 208 | 1217 | ggaccagactgaatccctgt | 327 | *H. sapiens* | 371 |
| 237138 | 212 | 130 | ccctacggggttaaggaacc | 332 | *M. musculus* | 372 |
| 237139 | 212 | 135 | cggggttaaggaacccaggt | 333 | *M. musculus* | 373 |
| 237140 | 212 | 140 | ttaaggaacccaggtgctcc | 334 | *M. musculus* | 374 |
| 237141 | 212 | 178 | gcgacaatgacagctgacaa | 335 | *M. musculus* | 375 |
| 237142 | 212 | 183 | aatgacagctgacaaggaga | 336 | *M. musculus* | 376 |
| 237143 | 212 | 266 | gcaaggagacggaggtcttc | 337 | *M. musculus* | 377 |
| 237144 | 212 | 317 | acagtgtgagctcccacctg | 338 | *M. musculus* | 378 |
| 237145 | 212 | 352 | atgcgcctggccatcagctt | 339 | *M. musculus* | 379 |
| 237146 | 212 | 442 | atggataacttgtacctgaa | 340 | *M. musculus* | 380 |
| 237147 | 212 | 448 | aacttgtacctgaaagcctt | 341 | *M. musculus* | 381 |
| 237148 | 212 | 461 | aagccttggagggtttcatt | 342 | *M. musculus* | 382 |
| 237150 | 212 | 525 | catcagcaagttcatgggac | 344 | *M. musculus* | 383 |
| 237151 | 212 | 535 | ttcatgggacttacccaggt | 345 | *M. musculus* | 384 |
| 237152 | 212 | 545 | ttacccaggtagaactaaca | 346 | *M. musculus* | 385 |
| 237153 | 212 | 563 | caggacacagcatctttgac | 347 | *M. musculus* | 386 |
| 237154 | 212 | 574 | atctttgacttcactcatcc | 348 | *M. musculus* | 387 |

TABLE 7-continued

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 237155 | 212 | 673 | accgagcgtgacttcttcat | 349 | *M. musculus* | 388 |
| 237156 | 212 | 682 | gacttcttcatgaggatgaa | 350 | *M. musculus* | 389 |
| 237157 | 212 | 687 | cttcatgaggatgaagtgca | 351 | *M. musculus* | 390 |
| 237158 | 212 | 714 | caacagaggccggactgtca | 352 | *M. musculus* | 391 |
| 237159 | 212 | 766 | tgcaccgggcaagtgagagt | 353 | *M. musculus* | 392 |
| 237160 | 212 | 776 | aagtgagagtctacaacaac | 354 | *M. musculus* | 393 |
| 237161 | 212 | 850 | atcatcatgtgtgagccaat | 355 | *M. musculus* | 394 |
| 237162 | 212 | 860 | gtgagccaatccagcaccca | 356 | *M. musculus* | 395 |
| 237163 | 212 | 913 | ttcctgagccgccacagcat | 357 | *M. musculus* | 396 |
| 237164 | 212 | 970 | gaactgattggttaccaccc | 358 | *M. musculus* | 397 |
| 237165 | 212 | 1057 | agtcaccagaacttgtgcac | 359 | *M. musculus* | 398 |
| 237166 | 212 | 1062 | ccagaacttgtgcaccaagg | 360 | *M. musculus* | 399 |
| 237167 | 212 | 1135 | tggctggagacccaggggac | 361 | *M. musculus* | 400 |
| 237168 | 212 | 1140 | ggagacccaggggacggtca | 362 | *M. musculus* | 401 |
| 237169 | 212 | 1145 | cccaggggacggtcatctac | 363 | *M. musculus* | 402 |
| 237170 | 212 | 1150 | gggacggtcatctacaaccc | 364 | *M. musculus* | 403 |
| 237172 | 212 | 1234 | gacgtggtgttctccatgga | 366 | *M. musculus* | 404 |
| 237173 | 212 | 1239 | ggtgttctccatggaccaga | 367 | *M. musculus* | 405 |
| 237174 | 212 | 1286 | tggccatgaacagcatcttt | 368 | *M. musculus* | 406 |
| 237175 | 212 | 1338 | gagcaactacctgttcacca | 369 | *M. musculus* | 407 |
| 237176 | 212 | 1363 | aaggaggagcccgaggagct | 370 | *M. musculus* | 408 |
| 237177 | 212 | 1454 | cctcagcctatggcaaggcc | 371 | *M. musculus* | 409 |
| 237178 | 212 | 1459 | gcctatggcaaggccatcct | 372 | *M. musculus* | 410 |
| 237179 | 212 | 1612 | agctgctccacgcccagcag | 373 | *M. musculus* | 411 |
| 237180 | 212 | 1725 | cagtacccagacggacttca | 374 | *M. musculus* | 412 |
| 237181 | 212 | 1939 | aagtacccgcagcagttgga | 375 | *M. musculus* | 413 |
| 237183 | 212 | 2012 | ctgggagcaaagggtccctg | 377 | *M. musculus* | 414 |
| 237184 | 212 | 2038 | tgctgtggccaggccagcac | 378 | *M. musculus* | 415 |
| 237185 | 212 | 2216 | ctcatgtctccatgttcaag | 379 | *M. musculus* | 416 |
| 237186 | 212 | 2226 | catgttcaagatgaggtctg | 380 | *M. musculus* | 417 |
| 237187 | 212 | 2231 | tcaagatgaggtctgcaaag | 381 | *M. musculus* | 418 |
| 237188 | 212 | 2296 | gccctgtccaacaagctgaa | 382 | *M. musculus* | 419 |
| 237189 | 212 | 2376 | tccaggcaccagcagttcac | 383 | *M. musculus* | 420 |
| 237191 | 212 | 2413 | atgaagagcctcatgggcgg | 385 | *M. musculus* | 421 |
| 237192 | 212 | 2423 | tcatgggcgggacctgtcct | 386 | *M. musculus* | 422 |
| 237193 | 212 | 2433 | gacctgtcctttgatgcctg | 387 | *M. musculus* | 423 |

TABLE 7-continued

Sequence and position of preferred target segments identified in hypoxia-inducible factor 2 alpha.

| SITE ID | TARGET SEQ ID NO | TARGET SITE | SEQUENCE | REV COMP OF SEQ ID | ACTIVE IN | SEQ ID NO |
|---|---|---|---|---|---|---|
| 237195 | 212 | 2647 | aaggtgtcaggcgtggccag | 389 | *M. musculus* | 424 |
| 237196 | 212 | 2665 | agtcgactgctggggccatc | 390 | *M. musculus* | 425 |
| 237197 | 212 | 2670 | actgctggggccatcgttcg | 391 | *M. musculus* | 426 |
| 237198 | 212 | 2680 | ccatcgttcgagccttacct | 392 | *M. musculus* | 427 |
| 237199 | 212 | 2707 | gaactgaccagatatgactg | 393 | *M. musculus* | 428 |
| 237200 | 212 | 2712 | gaccagatatgactgtgagg | 394 | *M. musculus* | 429 |
| 237201 | 212 | 2717 | gatatgactgtgaggtgaac | 395 | *M. musculus* | 430 |
| 237202 | 212 | 2722 | gactgtgaggtgaacgtgcc | 396 | *M. musculus* | 431 |
| 237203 | 212 | 2727 | tgaggtgaacgtgcccgtgc | 397 | *M. musculus* | 432 |
| 237204 | 212 | 2758 | acactcctgcaggggagaga | 398 | *M. musculus* | 433 |
| 237205 | 212 | 2768 | aggggagagaccttctcaga | 399 | *M. musculus* | 434 |
| 237206 | 212 | 2778 | ccttctcagagctctggacc | 400 | *M. musculus* | 435 |
| 237207 | 212 | 2791 | ctggaccaggccacctgagc | 401 | *M. musculus* | 436 |
| 237209 | 212 | 3199 | aactcaagtgttcttgttct | 403 | *M. musculus* | 437 |
| 237210 | 257 | 12633 | actgtcatgtctcaactgtt | 404 | *M. musculus* | 438 |
| 237211 | 257 | 74580 | tcaagatgaggttagtgaca | 405 | *M. musculus* | 439 |
| 237212 | 258 | 235 | cccagaaaagtgactcctgt | 406 | *M. musculus* | 440 |
| 237213 | 258 | 82 | cagtgtcctgagactgtatg | 407 | *M. musculus* | 441 |

As these "preferred target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these preferred target segments and consequently inhibit the expression of HIF2α.

According to the present invention, antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

Example 23

Expression of HIF1α and HIF2α in Various Human Cell Lines

U87-MG human glioblastoma, PC-3 human prostate cancer, JEG-3 human choriocarcinoma, HeLa human cervix cancer, SK-N-BE(2) neuroblastoma, MCF-7 human breast cancer, 786-O human clear-cell renal cell carcinoma, Calu-1 human lung cancer, and Hep3B human hepatocellular carcinoma cells were purchased from American Type Culture Collection (ATCC; Manassas, Va.) and cultured according to ATCC directions. Human umbilical endothelial cells (HUVEC) were obtained from Cascade Biologics (Portland Oreg.). Hypoxic treatments of cells (0.5–0.8×$10^6$/60 mm dish or 1–2×$10^6$/100 mm dish) were performed at 1% $O_2$ in a chamber controlled by ProOx oxygen sensor (BioSpherix, Redfield, N.Y.) for 16 h. To achieve the optimal hypoxic induction, 3 or 6 ml of medium was used for 60 mm and 100 mm dish culture, respectively during incubation. $CoCl_2$ (150 μM) was added to the cells to mimic hypoxic condition in some experiments.

Cultured cells at normoxia, hypoxia, or with $CoCl_2$ were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde, and 400 nM epoxomicin were separated on 12% SDS-PAGE and transferred to PVDF membranes (Amersham Biosciences). Typically, 35–50 μg of proteins were loaded per lane. Immunoblotting was performed with the following antibodies: anti-HIF-1α (BD Transduction Laboratories) at 1:250 (v/v); anti-HIF-2α (EPAS1) (Santa Cruz Biotechnology Inc) at 1:150; anti-HIF-1β (BD Transduction Laboratories) at 1:1000; anti-VHL (BD Transduction Laboratories) at 1:500; anti-GLUT-1 (Alpha Diagnostic International) at 1:600, and anti-α-tubulin (Sigma) at 1:2000 in 0.05% Tween-20/Tris-buffered saline (T-TBS) blocking buffer containing 5% nonfat skim milk at 4° C. overnight, followed by washing with T-TBS for 30 min. Goat anti-mouse or rabbit IgGs coupled with HRP (BioRad) were used as secondary antibodies at 1:3000.

Immunospecific bands were detected by enhanced chemiluminescence plus (ECL-Plus) detection kit (Amersham Biosciences).

Hif1α expression was shown to be increased in hypoxic conditions and in the presence of $CoCl_2$ (which mimics hypoxia) in U87-MG human glioblastoma, PC-3 human prostate cancer, JEG-3 human choriocarcinoma, HeLa human cervix cancer, SK-N-BE(2) neuroblastoma, MCF-7 human breast cancer, Calu-1 human lung cancer, and Hep3B human hepatocellular carcinoma cells but not 786-O human clear-cell renal cell carcinoma cells.

Hif2α expression was shown to be increased in hypoxic (1% $O_2$) conditions and in the presence of $CoCl_2$ in U87-MG human glioblastoma, PC-3 human prostate cancer, JEG-3 human choriocarcinoma, MCF-7 human breast cancer, 786-O human clear-cell renal cell carcinoma, Calu-1 human lung cancer, Hep3B human hepatocellular carcinoma cells and HUVECs.

Example 24

Antisense Modulation of HIF1α mRNA Expression in Cancer Cells (Dose Response)

HeLa, Hep3B, or U87-MG cells were plated in 96-well plates (8–10,000/well) 16 h prior to transfection. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

The transfection medium was switched to complete growth medium (120 μl/well) 4 h after transfection. Sixty microliters of medium was removed from the well 3 h after media switch and the cells were further incubated at normoxia or hypoxia for 16–20 h.

TABLE 8

HIF1α mRNA expression in antisense treated HeLa cells
Shown as percent inhibition relative to control oligonucleotide

| Oligonucleotide and conditions: | Normoxia or Hypoxia | Percent inhibition of HIF1α mRNA expression after treatment with oligonucleotide at concentrations shown: 0 | 6.25 nM | 25 nM | 100 nM | 200 nM |
|---|---|---|---|---|---|---|
| 129688 | N | 0 | 0 | 0 | 30 | 47 |
| 129688 | H | 1 | 1 | 10 | 30 | 57 |
| 175510 | N | 0 | 24 | 77 | 94 | 94 |
| 175510 | H | 1 | 39 | 82 | 95 | 96 |
| 298697 | N | 0 | 44 | 72 | 91 | 93 |
| 298697 | H | 3 | 30 | 75 | 92 | 93 |
| 222035 | N | 0 | 0 | 0 | 1 | 24 |
| 222035 | H | 3 | 3 | 0 | 11 | 35 |
| 10/35 | N | 0 | 33 | 82 | 94 | 94 |
| 10/35 | H | 3 | 35 | 85 | 94 | 95 |
| 97/35 | N | 0 | 16 | 66 | 84 | 85 |
| 97/35 | H | 3 | 34 | 79 | 88 | 89 |

N = Normoxia (21% $O_2$)
H = Hypoxia (1% $O_2$)

It can be seen that the HIF1α antisense oligonucleotides ISIS 175510 and 298697 specifically inhibited HIF1α and not HIF2α. Similar results were obtained in Hep3b human hepatocellular carcinoma cells and in U87-MG human glioblastoma cells.

Example 25

Antisense Modulation of HIF2α mRNA expression in cancer cells (Dose Response)

HeLa, Hep3B, or U87-MG cells were plated in 96-well plates (8–10,000/well) 16 h prior to transfection. The following antisense oligonucleotides were delivered into cells by lipofectin (3 μg/ml per 100 nM oligonucleotide) in Opti-Mem media (Invitrogen) at the indicated concentration: ISIS (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides). The transfection medium was switched to complete growth medium (120 μl/well) 4 h after transfection. Sixty microliters of medium was removed from the well 3 h after media switch and the cells were further incubated at normoxia or hypoxia for 16–20 h.

TABLE 9

HIF2α mRNA expression in ASO treated HeLa cells
Shown as percent inhibition relative to control oligonucleotide

| Oligonucleotide and conditions: | Normoxia or Hypoxia | Percent inhibition of HIF1α mRNA expression after treatment with oligonucleotide at concentrations shown: 0 | 6.25 nM | 25 nM | 100 nM | 200 nM |
|---|---|---|---|---|---|---|
| 129688 | N | 0 | 0 | 16 | 12 | 21 |
| 129688 | H | 0 | 0 | 4 | 12 | 50 |
| 175510 | N | 0 | 1 | 0 | 0 | 0 |
| 175510 | H | 0 | 8 | 0 | 4 | 0 |
| 298697 | N | 0 | 0 | 10 | 48 | 65 |
| 298697 | H | 0 | 0 | 11 | 52 | 58 |
| 222035 | N | 0 | 0 | 62 | 93 | 96 |
| 222035 | H | 0 | 19 | 73 | 94 | 96 |
| 10/35 | N | 0 | 0 | 77 | 96 | 96 |
| 10/35 | H | 0 | 21 | 78 | 94 | 95 |
| 97/35 | N | 0 | 0 | 63 | 89 | 95 |
| 97/35 | H | 0 | 34 | 79 | 96 | 96 |

N = Normoxia (21% $O_2$)
H = Hypoxia (1% $O_2$)

It can be seen that the HIF2α antisense oligonucleotide ISIS 222035 specifically inhibited HIF2α relative to HIF1α. The oligonucleotide ISIS 298697, designed to target human HIF1α, showed some ability to inhibit HIF2α expression as well. This oligonucleotide has perfect complementarity to the HIF1α target sequence and was found to have only two mismatches to the human HIF2α. Similar results were seen in U87-MG human glioblastoma cells and HepG3 hepatocellular carcinoma cells.

Example 26

HIF2α Plays a Major Role in the Induction of VEGF by Hypoxia in U87-MG Cells Genes whose products are dramatically induced by hypoxia (or $CoCl_2$, a mimic of hypoxia) include erythropoietin (Epo), glucose transporter-1 (Glut-1), vascular endothelial growth factor (VEGF) and Phosphofructokinase-L (PFK-L). They are induced by hypoxia to varying extents in various cell lines. As shown in previous examples, VEGF expression is induced by hypoxia in U87-MG cells. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α and HIF2α inhibitory oligonucleotides).

TABLE 10

HIF2α plays a major role in the induction of VEGF by hypoxia in U87-MG cells

| Oligonucleotide and conditions: | Normoxia or Hypoxia | Relative VEGF mRNA expression after treatment with oligonucleotide at concentrations shown: 0 | 6.25 nM | 25 nM | 100 nM | 200 nM |
|---|---|---|---|---|---|---|
| 129688 | N | 100 | 103 | 111 | 73 | 81 |
| 129688 | H | 372 | 378 | 346 | 363 | 383 |
| 175510 | N | 100 | 86 | 65 | 61 | 62 |
| 175510 | H | 372 | 397 | 407 | 338 | 392 |
| 298697 | N | 100 | 111 | 81 | 56 | 73 |
| 298697 | H | 372 | 413 | 342 | 312 | 275 |
| 222035 | N | 100 | 94 | 69 | 48 | 45 |
| 222035 | H | 372 | 399 | 257 | 131 | 108 |
| 10/35 | N | 100 | 81 | 48 | 45 | 44 |
| 10/35 | H | 372 | 431 | 254 | 110 | 80 |
| 97/35 | N | 100 | 119 | 63 | 45 | 47 |
| 97/35 | H | 372 | 409 | 289 | 124 | 85 |

ISIS 175510, which specifically inhibits HIF1α and not HIF2α, was found to have no effect on VEGF induction by hypoxia in U87-MG cells. In contrast, ISIS 222035, which specifically inhibits HIF2α and not HIF1α, caused a dose-dependent decrease in VEGF induction. ISIS 298697, which was designed to target HIF1α but was found to have crossreactivity with HIF2α, also interfered with VEGF induction by hypoxia. Thus HIF2α plays a major role in the induction of VEGF by hypoxia in U87-MG cells.

Example 27

HIF2α Plays a Major Role in the Induction of Epo by Hypoxia in Hep3B Cells

Genes whose products are dramatically induced by hypoxia (or $CoCl_2$, a mimic of hypoxia) include Epo, Glut-1, VEGF and PFK-L. They are induced by hypoxia to varying extents in various cell lines. Epo (erythropoietin) expression is induced by hypoxia in Hep3B cells. The following antisense oligonucleotides were delivered into Hep3B cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGACGATTCAG; SEQ ID NO: 442) is an unrelated control. 10/35 is an equal mixture of ISIS 175510 and 222035 (HIF1α and HIF2α inhibitory oligonucleotides). ISIS 97/35 is an equal mixture of ISIS 298697 and ISIS 222035 (HIF1α HIF2α inhibitory oligonucleotides).

TABLE 11

HIF2α plays a major role in the induction of Epo by hypoxia in Hep3B cells

| Oligonucleotide and conditions: | Normoxia or Hypoxia | Relative Epo mRNA expression after treatment with oligonucleotide at concentrations shown: Shown as -Fold induction over control 0 | 6.25 nM | 25 nM | 100 nM | 200 nM |
|---|---|---|---|---|---|---|
| 129688 | N | 1 | 1 | 0 | 3 | 11 |
| 129688 | H | 531 | 586 | 433 | 261 | 128 |
| 175510 | N | 1 | 8 | 3 | 3 | 2 |
| 175510 | H | 531 | 577 | 542 | 326 | 144 |
| 298697 | N | 1 | 9 | 11 | 12 | 3 |
| 298697 | H | 531 | 436 | 326 | 52 | 6 |
| 222035 | N | 1 | 3 | 3 | 2 | 1 |
| 222035 | H | 531 | 302 | 101 | 2 | 2 |
| 10/35 | N | 1 | 2 | 0 | 0 | 3 |
| 10/35 | H | 531 | 212 | 30 | 0 | 1 |
| 97/35 | N | 1 | 2 | 0 | 1 | 4 |
| 97/35 | H | 531 | 194 | 29 | 2 | 1 |

ISIS 175510, which specifically inhibits HIF1● and not HIF2●, was found to have no effect on Epo induction by hypoxia in Hep3B cells. In contrast, ISIS 222035, which specifically inhibits HIF2● and not HIF1●, caused a dose-dependent decrease in Epo induction. ISIS 298697, which was designed to target HIF1● but was found to have crossreactivity with HIF2●, also interfered with Epo induction by hypoxia. Thus HIF2a plays a major role in the induction of Epo by hypoxia in Hep3B cells.

Example 28

Both HIF1α and HIF2α Play a Major Role in the Induction of VEGF by Hypoxia in HeLa Cells Genes whose products are dramatically induced by hypoxia (or $CoCl_2$) include Epo (erythropoietin), Glut-1, VEGF and Phosphofructokinase (PFK)-L. They are induced by hypoxia to varying extents in various cell lines. VEGF expression is induced by hypoxia in HeLa cells. The following antisense oligonucleotides were delivered into cells by lipofectin (3 μg/ml per 100 nM oligonucleotide) in Opti-Mem media (Invitrogen) at the indicated concentration: ISIS 175510 (SEQ ID NO: 47) and ISIS 298697 (SEQ ID NO: 141) are targeted to human HIF-1α ASOs; ISIS 222035 (SEQ ID NO: 244) is targeted to human HIF-2α; and ISIS 129688 (TTCGCGGCTGGATTCAG; SEQ ID NO: 442) is an unrelated control. 10/35 is an equal mixture of ISIS 175510 and 222035 (HIF1● and HIF2● inhibitory oligonucleotides). ISIS 97/35 is an equal mixture of ISIS 298697 and ISIS 222035 (HIF1● and HIF2● inhibitory oligonucleotides).

TABLE 12

| HIF1α and HIF2α play a major role in the induction of VEGF by hypoxia in HeLa cells | | | | | | |
|---|---|---|---|---|---|---|
| Oligo-nucleotide and conditions: | Normoxia or Hypoxia | Relative VEGF mRNA expression after treatment with oligonucleotide at concentrations shown: 0 | 6.25 nM | 25 nM | 100 nM | 200 nM |
| 129688 | N | 100 | 119 | 100 | 85 | 93 |
| 129688 | H | 284 | 283 | 289 | 234 | 209 |
| 175510 | N | 100 | 95 | 132 | 110 | 113 |
| 175510 | H | 284 | 249 | 157 | 113 | 106 |
| 298697 | N | 100 | 84 | 105 | 93 | 93 |
| 298697 | H | 284 | 211 | 144 | 106 | 108 |
| 222035 | N | 100 | 111 | 114 | 92 | 67 |
| 222035 | H | 284 | 260 | 209 | 144 | 77 |
| 10/35 | N | 100 | 94 | 97 | 76 | 58 |
| 10/35 | H | 284 | 214 | 104 | 74 | 70 |
| 97/35 | N | 100 | 106 | 80 | 65 | 56 |
| 97/35 | H | 284 | 207 | 108 | 73 | 60 |

In this experiment all oligonucleotides except for the control (129688) interfered with induction of VEGF by hypoxia in HeLa cells. Thus both HIF1α and HIF2α play a major role in the induction of VEGF by hypoxia in HeLa cells. Because the relative role of HIF1α and HIF2α in hypoxic induction depends both on cell type and by induced gene (e.g., VEGF vs Epo), it is believed to be preferred to target both HIF1α and HIF2α for antisense inhibition. This may be achieved by a single cross-HIF antisense compound (such as ISIS 298697) or by a combination of one or more antisense compounds targeted to HIF1α and one or more antisense compounds targeted to HIF2α. Compounds administered in combination may be given simultaneously or sequentially.

Example 29

Designing and Testing HIF1●/HIF2● Cross-Reacting Antisense Compounds

The human HIF1α and HIF2α target sequences were compared for regions of identity but none were found to be as long as 20 nucleotides. However, based on the somewhat limited sequence homology between the human HIF1α and HIF2α target sequences, a series of antisense sequences were designed which were perfectly complementary to either HIF1α or HIF2α and which had no more than 4 mismatches to the other HIFα. These compounds are shown in Table 13. The primary target sequence (perfect complementarity) is shown in the "target" column and the number of mismatches against the other HIF is shown in subsequent columns. "Target site" refers to position on the primary target sequence.

TABLE 13

| HIF1α/HIF2α crossreacting antisense sequences | | | | | | | | |
|---|---|---|---|---|---|---|---|---|
| ISIS NO | OLIGO_SEQ | SEQ ID NO | Target | #Mis-match vs HIF1α | # Mis-matches vs HIF2α | Target site | HIF1α~EC50 | HIF2α~EC50 |
| 129688 | TTCGCGGCTGGACGATTCAG | 442 | Control | | | | | |
| 330460 | CCTCATGGTCGCAGGGATGA | 443 | HIF2α | 2 (G-A, G-U) | | 554 | | |
| 330462 | TCTCCTCATGGTCGCAGGGA | 444 | HIF2α | 3 (G-A, G-U, C-A) | | 557 | | |
| 222013 | CGAATCTCCTCATGGTCGCA | 233 | HIF2α | 4 (G-U, C-A, A-G, G-A) | | 561 | | |
| 298697 | TCCTCATGGTCACATGGATG | 141 | HIF1α | | 2 (A-C, T-C) | 673 | 5 | 30 |
| 330447 | TCATGGTCACATGGATGAGT | 445 | HIF1α | | 2 A-C, T-C) | 670 | 8 | 50 |
| 330449 | CCTCATGGTCACATGGATGA | 446 | HIF1α | | 2 A-C, T-C) | 672 | 5 | 30 |
| 330448 | CTCATGGTCACATGGATGAG | 447 | HIF1α | | 2 (A-C, T-C) | 671 | | |
| 330452 | ATTTCCTCATGGTCACATGG | 448 | HIF1α | | 3 (A-C, T-C, G-T) | 676 | | |
| 330470 | AAACCCTCCAAGGCTTTCAG | 449 | HIF2α | 2 (G-U, C-U) | | 423 | 45 | 20 |
| 326743 | TCCTCATGGTCGCAGGGATG | 450 | HIF2α | 2 G-A, G-U) | | 555 | 40 | 10 |

Thus it is possible to inhibit both HIF1α and HIF2α with a single crossreacting oligonucleotide, although the relative antisense efficacy is not equal for the two forms because of imperfect homology to one HIFα or the other.

Example 30

Crossr Acting HIF1α/HIF2α Antisense Compounds Containing "Universal" Bases

In order to try to get antisense compounds that were highly potent against both HIF1α and HIF2α targets, the nucleobases at the sites of the mismatches against one or the other HIF were replaced with the "universal bases" inosine or 3'nitro-pyrrole. Inosine has the ability to pair with G, U or C. If there was an A at the particular position of either of the sequences, we used 3-nitropyrrole. This is a base that does not have binding affinity to any of the bases, but also does not cause steric hindrance of the duplex. These oligos were screened and found to be active against both targets with an intermediate potency. This is shown in Table 14. In the table, "I" indicates inosine and "P" indicates 3-nitropyrrole.

(2002) Cancer Research 62:2034–42), which supports the use of in vitro tube formation as an endpoint for angiogenesis.

Angiogenesis, or neovascularization, is the formation of new capillaries from existing blood vessels. In adult organisms this process is typically controlled and short-lived, for example in wound repair and regeneration. However, aberrant capillary growth can occur and this uncontrolled growth plays a causal and/or supportive role in many pathologic conditions such as tumor growth and metastasis. In the context of this invention "aberrant angiogenesis" refers to unwanted or uncontrolled angiogenesis. Angiogenesis inhibitors are being evaluated for use as antitumor drugs. Other diseases and conditions associated with angiogenesis include arthritis, cardiovascular diseases, skin conditions, and aberrant wound healing. Aberrant angiogenesis can also occur in the eye, causing loss of vision. Examples of ocular conditions involving aberrant angiogenesis include macular degeneration, diabetic retinopathy and retinopathy of prematurity.

The tube formation assay is performed using an in vitro Angiogenesis Assay Kit (Chemicon International, Temecula, Calif.), or growth factor reduced Matrigel (BD Biosciences, Bedford, Mass.). HUVECs were plated at 4000 cells/well in 96-well plates. One day later, cells were transfected with antisense and control oligonucleotides according to standard published procedures (Monia et al., (1993) J Biol Chem. 1993 Jul. 5;268(19):14514–22) using 75 nM oligonucleotide in lipofectin (Gibco, Grand Island, N.Y.). Approximately fifty hours post-transfection, cells were transferred to 96-well plates coated with ECMatrix™ (Chemicon International) or growth factor depleted Matrigel. Under these conditions, untreated HUVECs form tube-like structures. After an overnight incubation at 37° C., treated and untreated cells were inspected by light microscopy. Individual wells were assigned discrete scores from 1 to 5 depending on the extent of tube formation. A score of 1 refers to a well with no tube formation while a score of 5 is given to wells where all cells are forming an extensive tubular network.

TABLE 14

HIF1α/HIF2α crossreacting antisense compounds containing universal bases

| ISIS NO | OLIGO_SEQ | SEQ ID NO | Target | # Mismatch vs HIF1α | # Mismatch vs HIF2α | Target site | HIF1α~EC50 | HIF2α~EC50 |
|---|---|---|---|---|---|---|---|---|
| 326743 | TCCTCATGGTCGCAGGGATG | 450 | HIF2α | 2 (G-A, G-U) | | 555 | 40 | 10 |
| 298697 | TCCTCATGGTCACATGGATG | 141 | HIF1α | | 2 (A-C, T-C) | 673 | 5 | 30 |
| 330449 | CCTCATGGTCAPCATGGATGA | 446 | HIF1α | | 2 (A-C, T-C) | 672 | 5 | 30 |
| 337223 | TCCTCATGGTCICAPGGATG | 451 | HIF1α and HIF2α | 2 (I-T, P-A) | 2 (I-C, P-C) | 673 | 25 | 15 |
| 337224 | CCTCATGGTCICAPGGATGA | 452 | HIF1α and HIF2α | 2 (I-T, P-A) | 2 (I-C, P-C) | 672 | 25 | 15 |

Introduction of universal bases into the antisense compounds at the site of mismatches resulted in a more equal inhibitory effect for both HIF1α and HIF2α.

Example 31

Tube Formation Assay to Determine Effect of HIF1α and HIF2α Antisense Inhibitors on Angiogenesis Angiogenesis is stimulated by numerous factors that promote interaction of endothelial cells with each other and with extracellular matrix molecules, resulting in the formation of capillary tubes. This process can be reproduced in tissue culture by the formation of tube-like structures by endothelial cells. Loss of tube formation in vitro has been correlated with the inhibition of angiogenesis in vivo (Carmeliet et al., (2000) Nature 407:249–257; and Zhang et al., Table 15

Effect of HIF1α and HIF2α Antisense Oligonucleotides on Angiogenic Tube Formation ISIS 29848 (NNNNNNNNNNNNNNNNNNNN; SEQ ID NO: 453) is a control oligonucleotide containing an equal mixture of the bases A, C, G and T at every position. ISIS 298695 (SEQ ID NO: 139) and ISIS 298750 (Seq; SEQ ID NO: 193) are targeted to HIF1α; ISIS 330447 (Seq; SEQ ID NO: 445) is a cross-HIF oligonucleotide having perfect complementarity to HIF1α target and imperfect complementarity (and thus less inhibitory effect) for HIF2α; ISIS 222035 (SEQ ID NO: 244) and 222025 (SEQ ID NO: 239) are targeted to HIF2α and ISIS 326743 is a cross-HIF oligonucleotide having perfect complementarity to HIF2α target and imperfect complementarity (and thus less inhibitory effect) for HIF1α.

| ISIS # | Target | 0 | 10 nM | 35 nM | 75 nM |
|---|---|---|---|---|---|
| 29848 | control | 5 | 5 | 4.75 | 4.375 |
| 298695 | HIF1α | 5 | 5 | 5 | 3.75 |
| 298750 | HIF1α | 5 | 5 | 4.75 | 3.25 |
| 330447 | HIF 1α/2α | 5 | 5 | 4.25 | 3 |
| 222035 | HIF2α | 5 | 5 | 3.75 | 1.75 |
| 222025 | HIF2α | 5 | 5 | 3.5 | 1.75 |
| 326743 | HIF2α/1α | 5 | 5 | 4.75 | 5 |

As calculated from the assigned discrete scores, it is apparent that HUVEC tube formation is inhibited by reduction of HIF2α and HIF1α, singly or in combination.

Example 32

Inhibition of HIF1α Expression In Vivo

C57B1/6 mice are maintained on a standard rodent diet and are used as control (lean) animals. Seven-week old male C57B1/6 mice are injected subcutaneously with oligonucleotides at a dose of 25 mg/kg two times per week for 4 weeks. Saline-injected animals serve as a control. After the treatment period, mice are sacrificed and target levels are evaluated in liver, using RNA isolation and target mRNA expression level quantitation (RT-PCR) as described in other examples herein.

Oligonucleotides used in this experiment were ISIS 298695 (SEQ ID NO: 139), ISIS 298697 (SEQ ID NO: 141), and ISIS 298750, (SEQ ID NO: 193), all targeted to mouse HIF1● and crossreactive to human HIF1● ISIS 141923 (CCTTCCCTGAAGGTTCCTCC; SEQ ID NO: 454) is an unrelated negative control oligonucleotide. Results are shown in Table 16.

TABLE 16

| Antisense inhibition of HIF1• expression in mouse liver by antisense to HIF1• | |
|---|---|
| ISIS # | % inhib. of HIF1• |
| Saline | 0 |
| ISIS 298695 | 76 |
| ISIS 298697 | 70 |
| ISIS 298750 | 74 |
| ISIS 141923 (control) | 0 |

The effect of inhibiting HIF1α on levels of VEGF and GLUT1 in mouse liver was also determined. These are both hypoxia-inducible targets. Results are shown in Table 17 and 18.

TABLE 17

| Effect of Antisense inhibition of HIF1• on VEGF expression in mouse liver | |
|---|---|
| ISIS # | % inhib. of VEGF |
| Saline | 0 |
| ISIS 298695 | 12 |
| ISIS 298697 | 4 |
| ISIS 298750 | 0 |
| ISIS 141923 (control) | 0 |

TABLE 18

| Effect of antisense inhibition of HIF1• on GLUT1 expression in mouse liver | |
|---|---|
| ISIS # | % inhib. of VEGF |
| Saline | 0 |
| ISIS 298695 | 0 |
| ISIS 298697 | 15 |
| ISIS 298750 | 0 |
| ISIS 141923 (control) | 22 |

Example 33

Antisense Inhibition of HIF1α in a Mouse Model of Hepatocellular Carcinoma (HCC)

An HCC mouse model (C57BL/6-TgN(CRP-TagSV40) 60-4, Taconic, Germantown N.Y.) for hepatocellular carcinoma was used in which transgenic male mice express SV40 T-antigen (Tag) in their livers, which leads to spontaneous development of well-differentiated hepatocellular carcinoma (HCC) carcinomas (Ruther et al., 1993, *Oncogene* 8, 87–93). HCC mice were treated with ISIS 298695, ISIS 298697 or ISIS 298750, all targeted to HIF1● or with an unrelated control oligonucleotide. HCC and wild type mice were also treated with saline alone. Results are shown in Table 19.

TABLE 19

| Antisense inhibition of HIF1• in HCC mouse liver | | |
|---|---|---|
| ISIS # | SEQ ID NO | % inhib. of HIF1• |
| Saline | | 0 |
| ISIS 298695 | 139 | 43 |
| ISIS 298697 | 141 | 33 |
| ISIS 298750 | 193 | 40 |

TABLE 19-continued

| Antisense inhibition of HIF1• in HCC mouse liver | | |
|---|---|---|
| ISIS # | SEQ ID NO | % inhib. of HIF1• |
| ISIS 141923 (control) | 454 | 11 |
| C57BL6/saline | | 43 |

The effect of HIF1● inhibition on GLUT1 expression in HCC mice was also evaluated. Results are shown in Table 20.

TABLE 20

| Effect of antisense inhibition of HIF1• on GLUT1 levels in HCC mouse liver | | |
|---|---|---|
| ISIS # | SEQ ID NO | % inhib. of GLUT1 |
| Saline | | 0 |
| ISIS 298695 | 139 | 0 |
| ISIS 298697 | 141 | 0 |
| ISIS 298750 | 193 | 13 |
| ISIS 141923 (control) | 454 | 18 |
| C57BL6/saline | | 2 |

Example 34

Inhibition of HIF2α Expression in Tumor Cells by Wild-Type p53 Under Hypoxia in T47D Tumor Cells T47D breast adenocarcinoma cells were obtained from the American Type Culture Collection (ATCC) (Manassas, Va.). Cells were cultured in Gibco DMEM High glucose media supplemented with 10% FBS. p53 is a tumor suppressor gene product which is inactive or aberrant in approximately 50% of human tumors. T47D cells are p53 null, i.e. they contain inactive mutant p53. These cells express high levels of HIF2● even in normoxic conditions. Hypoxia or $CoCl_2$ induces even higher levels of HIF2● expression. In contrast, T47D cells which have been transfected with a plasmid expressing p53, thus restoring p53 function in these cells, express extremely low levels of HIF2●, even in hypoxic conditions or in $CoCl_2$ simulation of hypoxia. This increase in HIF2● in cells with aberrant p53 is believed to be a novel observation and is believed to indicate a link between p53 and the HIF pathway.

Example 35

Effects of Antisense Inhibition of HIF1α and/or HIF2α on Cancer Cell Proliferation Under Hypoxia/Glucose Deprivation PC-3 human prostate cancer cells were cultured as described in previous examples. Cells were electroporated with oligonucleotide at concentrations described below and grown for 16 hours at normoxia and 0.45 g/l glucose. The medium was then replaced with either glucose (4.5 g/l glucose) or low-glucose medium (no added glucose) and cells were then kept at hypoxia (1% $O_2$) or normoxia (21% $O_2$) for another 48 hours. The effect of antisense treatment on cell proliferation was measured. Oligonucleotides were ISIS 129688 (unrelated control), ISIS 175510 (HIF1α), ISIS 222035 (HIF2α) and ISIS 298697 (HIF1α with some cross-reactivity to HIF2α). Results are shown in the tables below, one table for each culture condition.

TABLE 21

| Effect of HIF antisense on proliferation of PC-3 cancer cells Normoxia/Glucose | | | | |
|---|---|---|---|---|
| | Cell proliferation as percent of saline control | | | |
| ISIS # | 0 nM | 10 nM | 20 nM | SEQ ID NO |
| 129688 | 100 | 103 | 103 | 442 |
| 175510 | 100 | 126 | 93 | 47 |
| 222035 | 100 | 130 | 116 | 244 |
| 298697 | 100 | 118 | 86 | 141 |

TABLE 22

| Effect of HIF antisense on proliferation of PC-3 cancer cells Hypoxia/Glucose | | | | |
|---|---|---|---|---|
| | Cell proliferation as percent of saline control | | | |
| ISIS # | 0 nM | 10 nM | 20 nM | SEQ ID NO |
| 129688 | 100 | 104 | 99 | 442 |
| 175510 | 100 | 113 | 105 | 47 |
| 222035 | 100 | 106 | 91 | 244 |
| 298697 | 100 | 113 | 83 | 141 |

TABLE 23

| Effect of HIF antisense on proliferation of PC-3 cancer cells Normoxia/Low Glucose | | | | |
|---|---|---|---|---|
| | Cell proliferation as percent of saline control | | | |
| ISIS # | 0 nM | 10 nM | 20 nM | SEQ ID NO |
| 129688 | 100 | 107 | 105 | 442 |
| 175510 | 100 | 96 | 89 | 47 |
| 222035 | 100 | 91 | 68 | 244 |
| 298697 | 100 | 91 | 88 | 141 |

TABLE 24

| Effect of HIF antisense on proliferation of PC-3 cancer cells Hypoxia/Low Glucose | | | | |
|---|---|---|---|---|
| | Cell proliferation as percent of saline control | | | |
| ISIS # | 0 nM | 10 nM | 20 nM | SEQ ID NO |
| 129688 | 100 | 105 | 103 | 442 |
| 175510 | 100 | 90 | 85 | 47 |
| 222035 | 100 | 88 | 80 | 244 |
| 298697 | 100 | 88 | 61 | 141 |

Example 36

Effect of Antisense Inhibitors of HIFs on Human Tumor Cell Xenografts in Mice

Nude mice are injected in the flank with approximately $10^6$ U87-MG human glioblastoma cells. Mice are dosed with antisense compound beginning the day after tumor inoculation and continuing every other day. Oligonucleotides used are ISIS 129688 (unrelated control), ISIS 175510 (HIF1α), ISIS 222035 (HIF2α) and ISIS 298697 (HIF1α with some crossreactivity to HIF2α). Tumor volume is measured every few days beginning 10 days after inoculation.

Similar xenograft studies are performed with MDA-MB231 human breast cancer cells, which are p53-deficient. Nude mice are injected in the flank with approximately $10^6$ MDA-MB231 human breast cancer cells. Mice are dosed with antisense compound beginning the day after tumor inoculation and continuing every other day. Oligonucleotides used are ISIS 129688 (unrelated control), ISIS 175510 (HIF1α), ISIS 222035 (HIF2α) and ISIS 298697 (HIF1α with some crossreactivity to HIF2α). Tumor volume is measured every few days beginning 10 days after inoculation.

Example 37

Effect of Antisense Inhibitors of HIFs on Angiogenic Conditions in the Eye

It is believed that antisense inhibitors of HIF2α and possibly HIF1α will be useful in treatment of angiogenic conditions, because of their effect on endothelial tube formation in an in vitro model for angiogenesis (see previous examples).

A pig model of ocular neovascularization, the branch retinal vein occlusion (BVO) model, is used to study ocular neovascularization. Male farm pigs (8–10 kg) are subjected to branch retinal vein occlusions (BVO) by laser treatment in both eyes. The extent of BVO is determined by indirect opthalmoscopy after a 2 week period. Intravitreous injections (10 ●M) of ISIS 129688 (unrelated control), ISIS 175510 (HIF1α), ISIS 222035 (HIF2α) or ISIS 298697 (HIF1α with some crossreactivity to HIF2α) are started on the day of BVO induction and are repeated at weeks 2, 6, and 10 after BVO (Right eye—vehicle, Left eye—antisense molecule). Stereo fundus photography and fluorescein angiography are performed at baseline BVO and at weeks 1, 6 and 12 following intravitreous injections to measure the neovascular response. In addition capillary gel electrophoresis analysis of the eye sections containing sclera, choroid, and the retina are performed to determine antisense concentrations, and gross and microscopic evaluations are performed to determine eye histopathology.

What is claimed is:

1. An antisense oligonucleotide 15 to 30 nucleobases in length targeted to a nucleic acid molecule encoding HIF1α (SEQ ID NO: 133), wherein said compound comprises at least 8 consecutive nucleobases of SEQ ID NO:446.

2. The antisense oligonucleotide of claim 1 wherein said antisense oligonucleotide is a DNA oligonucleotide.

3. The antisense oligonucleotide of claim 1 wherein said antisense oligonucleotide is an RNA oligonucleotide.

4. The antisense oligonucleotide of claim 1 wherein said antisense oligonucleotide is a chimeric oligonucleotide.

5. The antisense oligonucleotide of claim 1 comprising at least one modified internucleoside linkage, sugar moiety, or nucleobase.

6. The antisense oligonucleotide of claim 1 comprising at least one 2'-O-methoxyethyl sugar moiety.

7. The antisense oligonucleotide of claim 1 comprising at least one phosphorothioate internucleoside linkage.

8. The antisense oligonucleotide of claim 1 comprising at least one 5-methylcytosine.

9. A method of inhibiting the expression of HIF1α in a cell in vitro comprising contacting said cell with the antisense oligonucleotide of claim 1.

10. A kit or assay device comprising the antisense oligonucleotide of claim 1.

11. A composition comprising the antisense oligonucleotide of claim 1 in a pharmaceutically acceptable carrier.

12. An antisense oligonucleotide with a nucleotide sequence consisting of SEQ ID NO: 446.

13. The antisense oligonucleotide of claim 1 having 100% complementarity with the nucleic acid molecule encoding HIF1α.

14. An antisense oligonucleotide 16, 17, 18, 19, 20, 21, 22, 23, 24 or 25 nucleobases in length targeted to a nucleic acid molecule encoding HIF1-alpha (SEQ ID NO: 133), wherein said antisense oligonucleotide has at least 80% identity with SEQ ID NO: 446.

15. The antisense oligonucleotide of claim 14 which is 18, 19, 20, 21 or 22 nucleobases in length and has at least 90% identity with SEQ ID NO: 446.

16. The antisense oligonucleotide of claim 15 which is 19, 20 or 21 nucleobases in length and has at least 95% identity with SEQ ID NO: 446.

17. The antisense oligonacleotide of claim 12 comprising a central region of ten 2'-deoxynucleotides which is flanked on each side by five 2'-O-methoxyethyl nucleotides, wherein the internucleoside linkages of said oligonucleotide are phosphorothioate throughout the oligonucleotide and the cytidine residues are 5-niethylcytidines.

18. A pharmaceutical composition comprising the antisense oligonucleotide of claim 17.

* * * * *

UNITED STATES PATENT AND TRADEMARK OFFICE

CERTIFICATE OF CORRECTION

PATENT NO. : 7,217,572 B2
APPLICATION NO. : 10/719370
DATED : May 15, 2007
INVENTOR(S) : Donna T. Ward et al.

It is certified that error appears in the above-identified patent and that said Letters Patent is hereby corrected as shown below:

1) Column 366, Claim 17, line 18, please delete "oligonacleotide" and insert therefor --oligonucleotide--;

2) Column 366, Claim 17, line 23, please delete "5-niethylcytidines" and insert therefor --5-methylcytidines--.

Signed and Sealed this

Third Day of July, 2007

JON W. DUDAS
*Director of the United States Patent and Trademark Office*

UNITED STATES PATENT AND TRADEMARK OFFICE

CERTIFICATE OF CORRECTION

PATENT NO. : 7,217,572 B2
APPLICATION NO. : 10/719370
DATED : May 15, 2007
INVENTOR(S) : Ward et al.

It is certified that error appears in the above-identified patent and that said Letters Patent is hereby corrected as shown below:

Title Page; item (56);
First Page, Col. 2 (Other Publications), line 6, Delete "pates" and insert -- pages --, therefor.
First Page, Col. 2 (Other Publications), line 9, Delete "inhibitor-1"" and insert -- inhibitor-1," --, therefor.
Page 2, Col. 1 (Other Publications), line 14, Delete "hypoxia inducible" and insert -- hypoxia-inducible --, therefor.
Page 2, Col. 1 (Other Publications), line 34, Delete "Hypoxia Inducible" and insert -- Hypoxia-Inducible --, therefor.
Page 2, Col. 1 (Other Publications), line 57, Delete "hypoxia inducible" and insert -- hypoxia-inducible --, therefor.
Page 2, Col. 1 (Other Publications), line 61, Delete "Hypoxia inducible" and insert -- Hypoxia-inducible --, therefor.
Page 2, Col. 2 (Other Publications), line 1, Delete "s" and insert -- a --, therefor.
Page 2, Col. 2 (Other Publications), line 72, Delete "Endotelial" and insert -- Endothelial --, therefor.
Page 3, Col. 2 (Other Publications), line 6, Delete "Investigtion," and insert -- Investigation, --, therefor.
Col. 1, line 52, Delete "hypoxia inducible" and insert -- hypoxia-inducible --, therefor.
Col. 5, line 13, (Approx.), Delete "bindingsite" and insert -- binding site --, therefor. (Consider Space)
Col. 5, line 57, Delete "(PPARS)" and insert -- (PPARs) --, therefor.
Col. 7, line 51, (Approx.), Delete "HIF2αactivity" and insert -- HIF2α activity --, therefor. (Consider Space)
Col. 23, line 51, (Approx.), Delete "B.ed.," and insert -- B.,ed., --, therefor.
Col. 26, line 39, Delete "administration," and insert -- administration --, therefor.
Col, 28, line 63, Delete "ara-binoside," and insert -- arabinoside, --, therefor.
Col. 29, line 3, Delete "deoxyco-formycin," and insert -- deoxycoformycin, --, therefor.
Col. 29, line 8, Delete "teni-poside," and insert -- teniposide, --, therefor.
Col. 33, line 15, Delete "Tetrahedrom" and insert -- Tetrahedron --, therefor.
Col. 34, line 62, (Approx.), After "Strand" insert -- (SEQ ID NO: 456) --.
Col, 34, line 63, (Approx.), After "Complement" insert -- (SEQ ID NO: 457) --.
Col. 35, line 5, After "Strand" insert -- (SEQ ID NO: 455) --.

UNITED STATES PATENT AND TRADEMARK OFFICE
CERTIFICATE OF CORRECTION

PATENT NO. : 7,217,572 B2
APPLICATION NO. : 10/719370
DATED : May 15, 2007
INVENTOR(S) : Ward et al.

It is certified that error appears in the above-identified patent and that said Letters Patent is hereby corrected as shown below:

Col. 35, line 6, (Approx.), After "Complement" insert -- (SEQ ID NO: 458) --.
Col. 35, line 25, Delete "HIF1● or HIF2●" and insert -- HIF1α or HIF2α --, therefor.
Col. 35, line 29, Delete "200 ●L" and insert -- 200 µL --, therefor.
Col. 35, line 31, Delete "130 ●L" and insert --130 µL --, therefor.
Col. 35, line 32, Delete "●g/mL" and insert -- µg/mL --, therefor.
Col. 35, line 33, Delete "200 M." and insert -- 200 nM. --, therefor.
Col. 39, line 61, (Approx.), Delete "minutes," and insert -- minutes. --, therefor.
Col. 59, line 22, Col. 4 (Table 4), Delete "tccaatggtgacaactgatc" and insert -- tctaatggtgacaactgatc --, therefor.
Col. 62, lines 48-49, Delete "AGGCCGAGAATGGGAAGCTTGTCATC" and insert -- AAGGCCGAGAATGGGAAGCTTGTCATC --, therefor.
Col. 66, line 57, Delete "3'-directions)" and insert -- 3' directions) --, therefor.
Col. 79, line 4, Delete "Hif1α" and insert -- HIF1α --, therefor.
Col. 79, line 11 (Approx.), Delete "Hif2α" and insert -- HIF2α --, therefor.
Col. 82, lines 34-35, Delete "HIF1● and not HIF2●" and insert -- HIF1α and not HIF2α --, therefor.
Col. 82, line 37, Delete "HIF2● and not HIF1●" and insert -- HIF2α and not HIF1α --, therefor.
Col. 82, line 39, Delete "HIF1●" and insert -- HIF1α --, therefor.
Col. 82, line 40, Delete "HIF2●" and insert -- HIF2α --, therefor.
Col. 82, line 62, (Approx.), Delete "(TTCGCGGCTGGATTCAG;" and insert -- (TTCGCGGCTGGACGATTCAG; --, therefor.
Col. 82, line 64, Delete "HIF1● and HIF2●" and insert -- HIF1α and HIF2α --, therefor.
Col. 82, line 66, Delete "HIF1● and HIF2●" and insert -- HIF1α and HIF2α --, therefor.
Col. 83-84, lines 2-3, Col. 6 (Table 13), Delete "Mismatches" and insert -- Mismatch --, therefor.
Col. 84, line 11, (Approx.), Delete "HIF1●/HIF2●" and insert -- HIF1α/HIF2α--, therefor.
Col. 85, line 8, (Approx.), Delete "Crossr Acting" and insert -- Crossreacting --, therefor.
Col. 87, lines 1-5, (Approx.), Delete "Table 15 Effect of HIF1α and HIF2α antisense oligonucleotides on angiogenic tube formation".
Col. 87, line 20, Insert -- Table 15 Effect of HIF1α and HIF2α antisense oligonucleotides on angiogenic tube formation --.
Col. 87, line 53, Delete "HIF1● and crossreactive to human HIF1● " and insert -- HIF1α and crossreactive to human HIF1α --, therefor.

UNITED STATES PATENT AND TRADEMARK OFFICE

CERTIFICATE OF CORRECTION

PATENT NO. : 7,217,572 B2 
APPLICATION NO. : 10/719370
DATED : May 15, 2007
INVENTOR(S) : Ward et al.

It is certified that error appears in the above-identified patent and that said Letters Patent is hereby corrected as shown below:

Col. 87, lines 60-61, (Approx.), Delete "HIF1● expression in mouse liver by antisense to HIF1●" and insert -- HIF1α expression in mouse liver by antisense to HIF1α --, therefor.
Col. 87, line 62, (Approx.), Delete "HIF1●" and insert -- HIF1α --, therefor.
Col. 88, lines 3-4, (Approx.), Delete "HIF1● expression in mouse liver by antisense to HIF1●" and insert -- HIF1α expression in mouse liver by antisense to HIF1α --, therefor.
Col. 88, line 6, (Approx.), Delete "HIF1●" and insert -- HIF1α --, therefor.
Col. 88, line 17, (Approx.), Delete "HIF1●" and insert -- HIF1α --, therefor.
Col. 88, line 31, (Approx.), Delete "HIF1●" and insert -- HIF1α --, therefor.
Col. 88, line 54, Delete "HIF1●" and insert -- HIF1α --, therefor.
Col. 88, line 61, (Approx.), Delete "HIF1●" and insert -- HIF1α --, therefor.
Col. 88, line 63, (Approx.), Delete "HIF1●" and insert -- HIF1α --, therefor.
Col. 89, line 4, (Approx.), Delete "HIF1●" and insert -- HIF1α --, therefor.
Col. 89, line 5, (Approx.), Delete "HIF1●" and insert --HIF1α --, therefor.
Col. 89, line 11, (Approx.), Delete "HIF1●" and insert -- HIF1α --, therefor.
Col. 89, line 17, (Approx.), Delete "HIFI●" and insert -- HIF1α --, therefor.
Col. 89, line 42, Delete "HIF2●" and insert -- HIF2α --, therefor.
Col. 89, line 43, Delete "HIF2●" and insert -- HIF2α --, therefor.
Col. 89, line 46, Delete "HIF2●" and insert -- HIF2α --, therefor.
Col. 89, line 47, Delete "HIF2●" and insert -- HIF2α --, therefor.
Col. 92, line 11, Delete "10 ●M" and insert -- 10 μM --, therefor.
In the Claims:
Col. 366, line 18, (Approx.), In Claim 17, delete "oligonacleotide" and insert -- oligonucleotide --, therefor.
Col. 366, line 23, (Approx.), In Claim 17, delete "5-niethylcytidines." and insert -- 5-methylcytidines. --, therefor.

Signed and Sealed this

Twenty-fifth Day of November, 2008

JON W. DUDAS
*Director of the United States Patent and Trademark Office*